(12) United States Patent
Aspnes et al.

(10) Patent No.: US 11,802,121 B2
(45) Date of Patent: *Oct. 31, 2023

(54) GLP-1 RECEPTOR AGONISTS AND USES THEREOF

(71) Applicant: Pfizer Inc., New York, NY (US)

(72) Inventors: Gary Erik Aspnes, Biberach an der Riss (DE); Scott W. Bagley, Voluntown, CT (US); John M. Curto, Mystic, CT (US); Matthew S. Dowling, Old Lyme, CT (US); David Edmonds, Basel (CH); Mark E. Flanagan, Gales Ferry, CT (US); Kentaro Futatsugi, Sharon, MA (US); David A. Griffith, Sudbury, MA (US); Kim Huard, Berkeley, CA (US); Gajendra Ingle, New Haven, CT (US); Wenhua Jiao, Salem, CT (US); Chris Limberakis, Pawcatuck, CT (US); Alan M. Mathiowetz, Waltham, MA (US); David W. Piotrowski, Waterford, CT (US); Roger B. Ruggeri, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/049,052

(22) Filed: Oct. 24, 2022

(65) Prior Publication Data

US 2023/0124938 A1    Apr. 20, 2023

Related U.S. Application Data

(63) Continuation of application No. 17/085,534, filed on Oct. 30, 2020, now Pat. No. 11,512,070, which is a continuation of application No. 16/861,646, filed on Apr. 29, 2020, now Pat. No. 10,851,081, which is a continuation of application No. 16/220,184, filed on Dec. 14, 2018, now Pat. No. 10,669,259, which is a continuation of application No. 15/839,901, filed on Dec. 13, 2017, now Pat. No. 10,208,019.

(60) Provisional application No. 62/435,533, filed on Dec. 16, 2016.

(51) Int. Cl.
| | | |
|---|---|---|
| A61K 31/496 | (2006.01) | |
| A61K 31/4545 | (2006.01) | |
| C07D 401/14 | (2006.01) | |
| C07D 487/04 | (2006.01) | |
| A61P 3/00 | (2006.01) | |
| A61P 15/10 | (2006.01) | |
| A61P 17/06 | (2006.01) | |
| A61P 9/10 | (2006.01) | |
| A61P 19/06 | (2006.01) | |
| A61P 25/28 | (2006.01) | |
| A61P 25/30 | (2006.01) | |
| A61P 43/00 | (2006.01) | |
| A61P 1/16 | (2006.01) | |
| A61P 25/02 | (2006.01) | |
| A61P 3/04 | (2006.01) | |
| A61P 19/02 | (2006.01) | |
| A61P 3/10 | (2006.01) | |
| A61P 13/12 | (2006.01) | |
| A61P 25/18 | (2006.01) | |
| A61P 1/00 | (2006.01) | |
| A61P 15/00 | (2006.01) | |
| A61P 25/16 | (2006.01) | |
| C07D 405/14 | (2006.01) | |
| C07D 413/14 | (2006.01) | |
| C07D 471/04 | (2006.01) | |

(52) U.S. Cl.
CPC ........ *C07D 401/14* (2013.01); *A61K 31/4545* (2013.01); *A61K 31/496* (2013.01); *A61P 1/00* (2018.01); *A61P 1/16* (2018.01); *A61P 3/00* (2018.01); *A61P 3/04* (2018.01); *A61P 3/10* (2018.01); *A61P 9/10* (2018.01); *A61P 13/12* (2018.01); *A61P 15/00* (2018.01); *A61P 15/10* (2018.01); *A61P 17/06* (2018.01); *A61P 19/02* (2018.01); *A61P 19/06* (2018.01); *A61P 25/02* (2018.01); *A61P 25/16* (2018.01); *A61P 25/18* (2018.01); *A61P 25/28* (2018.01); *A61P 25/30* (2018.01); *A61P 43/00* (2018.01); *C07D 405/14* (2013.01); *C07D 413/14* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | |
|---|---|---|
| 10,208,019 B2 | 2/2019 | Aspnes et al. |
| 10,669,259 B2 | 6/2020 | Aspnes et al. |
| 10,851,081 B2 | 12/2020 | Aspnes et al. |
| 2004/0127504 A1 | 7/2004 | Cowart et al. |
| 2008/0280933 A1 | 11/2008 | Efremov et al. |
| 2009/0264426 A1 | 10/2009 | Sakuraba et al. |
| 2013/0123237 A1 | 5/2013 | Anand et al. |
| 2018/0170908 A1 | 6/2018 | Aspnes et al. |

FOREIGN PATENT DOCUMENTS

| | | |
|---|---|---|
| WO | 2002/074752 | 9/2002 |
| WO | 2011/143365 | 11/2011 |

*Primary Examiner* — Samantha L Shterengarts
(74) *Attorney, Agent, or Firm* — Feng Shao

(57) ABSTRACT

Provided herein are 6-carboxylic acids of benzimidazoles and 4-aza-, 5-aza-, 7-aza- and 4,7-diaza-benzimidazoles as GLP-1R agonists, processes to make said compounds, and methods comprising administering said compounds to a mammal in need thereof.

20 Claims, No Drawings

GLP-1 RECEPTOR AGONISTS AND USES THEREOF

This application is a continuation of U.S. patent application Ser. No. 17/085,534, filed Oct. 30, 2020, which in turn is a continuation of U.S. patent application Ser. No. 16/861, 646 filed Apr. 29, 2020, issued as U.S. Pat. No. 10,851,081, which in turn is a continuation of U.S. patent application Ser. No. 16/220,184 filed Dec. 14, 2018, issued as U.S. Pat. No. 10,669,259, which in turn is a continuation of U.S. patent application Ser. No. 15/839,901, filed Dec. 13, 2017, issued as U.S. Pat. No. 10,208,019, which in turn claims the benefit of priority to U.S. Provisional Application Ser. No. 62/435, 533, filed Dec. 16, 2016, the disclosure of each of the foregoing applications is hereby incorporated by reference in its entirety.

FIELD OF INVENTION

Provided herein are 6-carboxylic acids of benzimidazoles and 4-aza-, 5-aza-, 7-aza-, and 4,7-diaza-benzimidazoles as GLP-1R agonists, processes to make said compounds, and methods comprising administering said compounds to a mammal in need thereof.

BACKGROUND OF THE INVENTION

Diabetes is a major public health concern because of its increasing prevalence and associated health risks. The disease is characterized by high levels of blood glucose resulting from defects in insulin production, insulin action, or both. Two major forms of diabetes are recognized, Type 1 and Type 2. Type 1 diabetes (T1D) develops when the body's immune system destroys pancreatic beta cells, the only cells in the body that make the hormone insulin that regulates blood glucose. To survive, people with Type 1 diabetes must have insulin administered by injection or a pump. Type 2 diabetes mellitus (referred to generally as T2DM) usually begins with either insulin resistance or when there is insufficient production of insulin to maintain an acceptable glucose level.

Currently, various pharmacological approaches are available for treating hyperglycemia and subsequently, T2DM (Hampp, C. et al. *Use of Antidiabetic Drugs in the U.S., 2003-2012, Diabetes Care* 2014, 37, 1367-1374). These may be grouped into six major classes, each acting through a different primary mechanism: (A) Insulin secretogogues, including sulphonyl-ureas (e.g., glipizide, glimepiride, glyburide), meglitinides (e.g., nateglidine, repaglinide), dipeptidyl peptidase IV (DPP-IV) inhibitors (e.g., sitagliptin, vildagliptin, alogliptin, dutogliptin, linagliptin, saxogliptin), and glucagon-like peptide-1 receptor (GLP-1R) agonists (e.g., liraglutide, albiglutide, exenatide, lixisenatide, dulaglutide, semaglutide), which enhance secretion of insulin by acting on the pancreatic beta-cells. Sulphonyl-ureas and meglitinides have limited efficacy and tolerability, cause weight gain and often induce hypoglycemia. DPP-IV inhibitors have limited efficacy. Marketed GLP-1R agonists are peptides administered by subcutaneous injection. Liraglutide is additionally approved for the treatment of obesity. (B) Biguanides (e.g., metformin) are thought to act primarily by decreasing hepatic glucose production. Biguanides often cause gastrointestinal disturbances and lactic acidosis, further limiting their use. (C) Inhibitors of alpha-glucosidase (e.g., acarbose) decrease intestinal glucose absorption. These agents often cause gastrointestinal disturbances. (D) Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. (E) Insulin is used in more severe cases, either alone or in combination with the above agents, and frequent use may also lead to weight gain and carries a risk of hypoglycemia. (F) sodium-glucose linked transporter cotransporter 2 (SGLT2) inhibitors (e.g., dapagliflozin, empagliflozin, canagliflozin, ertugliflozin) inhibit reabsorption of glucose in the kidneys and thereby lower glucose levels in the blood. This emerging class of drugs may be associated with ketoacidosis and urinary tract infections.

However, with the exception of GLP-1R agonists and SGLT2 inhibitors, the drugs have limited efficacy and do not address the most important problems, the declining β-cell function and the associated obesity.

Obesity is a chronic disease that is highly prevalent in modern society and is associated with numerous medical problems including hypertension, hypercholesterolemia, and coronary heart disease. It is further highly correlated with T2DM and insulin resistance, the latter of which is generally accompanied by hyperinsulinemia or hyperglycemia, or both. In addition, T2DM is associated with a two to fourfold increased risk of coronary artery disease. Presently, the only treatment that eliminates obesity with high efficacy is bariatric surgery, but this treatment is costly and risky. Pharmacological intervention is generally less efficacious and associated with side effects. There is therefore an obvious need for more efficacious pharmacological intervention with fewer side effects and convenient administration.

Although T2DM is most commonly associated with hyperglycemia and insulin resistance, other diseases associated with T2DM include hepatic insulin resistance, impaired glucose tolerance, diabetic neuropathy, diabetic nephropathy, diabetic retinopathy, obesity, dyslipidemia, hypertension, hyperinsulinemia and nonalcoholic fatty liver disease (NAFLD).

NAFLD is the hepatic manifestation of metabolic syndrome, and is a spectrum of hepatic conditions encompassing steatosis, non-alcoholic steatohepatitis (NASH), fibrosis, cirrhosis and ultimately hepatocellular carcinoma. NAFLD and NASH are considered the primary fatty liver diseases as they account for the greatest proportion of individuals with elevated hepatic lipids. The severity of NAFLD/NASH is based on the presence of lipid, inflammatory cell infiltrate, hepatocyte ballooning, and the degree of fibrosis. Although not all individuals with steatosis progress to NASH, a substantial portion does.

GLP-1 is a 30 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of beta-cells. In non-clinical experiments GLP-1 promotes continued beta-cell competence by stimulating transcription of genes important for glucose-dependent insulin secretion and by promoting beta-cell neogenesis (Meier, et al. *Biodrugs.* 2003; 17 (2): 93-102).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption. In people with T2DM, the normal post-prandial rise in GLP-1 is absent or reduced (Vilsboll T, et al. *Diabetes*. 2001. 50; 609-613).

Holst (*Physiol. Rev.* 2007, 87, 1409) and Meier (*Nat. Rev. Endocrinol.* 2012, 8, 728) describe that GLP-1 receptor agonists, such as GLP-1, liraglutide and exendin-4, have 3 major pharmacological activities to improve glycemic control in patients with T2DM by reducing fasting and post-prandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

There remains a need for an easily-administered prevention and/or treatment for cardiometabolic and associated diseases.

DETAILED DESCRIPTION OF THE INVENTION

The present invention concerns compounds of Formula I

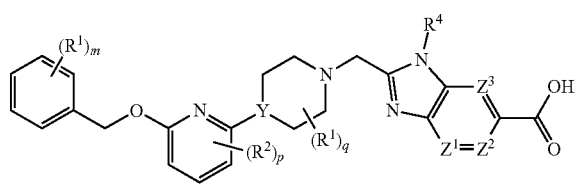

I or a pharmaceutically acceptable salt thereof, wherein
each $R^1$ is independently halogen, —CN, —$C_{1-3}$alkyl, or —$OC_{1-3}$alkyl, wherein the alkyl of $C_{1-3}$alkyl and $OC_{1-3}$alkyl is substituted with 0 to 3 F atoms;
m is 0, 1, 2, or 3;
each $R^2$ is independently F, Cl, or —CN;
p is 0, 1 or 2;
each $R^3$ is independently F, —OH, —CN, —$C_{1-3}$alkyl, —$OC_{1-3}$alkyl, or —$C_{3-4}$cycloalkyl, or 2 $R^3$s may together cyclize to form —$C_{3-4}$spirocycloalkyl, wherein the alkyl of $C_{1-3}$alkyl and $OC_{1-3}$alkyl, cycloalkyl, or spirocycloalkyl may be substituted as valency allows with 0 to 3 F atoms and with 0 to 1 —OH;
q is 0, 1, or 2;
Y is CH or N;
$R^4$ is —$C_{1-3}$alkyl, —$C_{0-3}$alkylene-$C_{3-6}$cycloalkyl, —$C_{0-5}$alkylene-$R^5$, or —$C_{1-3}$alkylene-$R^6$,
wherein said alkyl may be substituted as valency allows with 0 to 3 substituents independently selected from 0 to 3 F atoms and 0 to 1 substituent selected from —$C_{0-1}$alkylene-CN, —$C_{0-1}$alkylene-$OR^O$, and —$N(R^N)_2$, and
wherein said alkylene and cycloalkyl may be independently substituted as valency allows with 0 to 2 substituents independently selected from 0 to 2 F atoms and 0 to 1 substituent selected from —$C_{0-1}$alkylene-CN, —$C_{0-1}$alkylene-$OR^O$, and —$N(R^N)_2$;
$R^5$ is a 4- to 6-membered heterocycloalkyl, wherein said heterocycloalkyl may be substituted with 0 to 2 substituents as valency allows independently selected from:

0 to 1 oxo (=O),
0 to 1 —CN,
0 to 2 F atoms, and
0 to 2 substituents independently selected from —$C_{1-3}$alkyl and —$OC_{1-3}$alkyl, wherein the alkyl of $C_{1-3}$alkyl and $OC_{1-3}$alkyl may be substituted with 0 to 3 substituents as valency allows independently selected from:
0 to 3 F atoms,
0 to 1 —CN, and
0 to 1 —$OR^O$;
$R^6$ is a 5- to 6-membered heteroaryl, wherein said heteroaryl may be substituted with 0 to 2 substituents as valency allows independently selected from:
0 to 2 halogens,
0 to 1 substituent selected from —$OR^O$ and —$N(R^N)_2$, and
0 to 2 —$C_{1-3}$alkyl, wherein the alkyl may be substituted with 0 to 3 substituents as valency allows independently selected from:
0 to 3 F atoms, and
0 to 1 —$OR^O$;
each $R^O$ is independently H, or —$C_{1-3}$alkyl, wherein $C_{1-3}$alkyl may be substituted with 0 to 3 F atoms;
each $R^N$ is independently H, or —$C_{1-3}$alkyl;
$Z^1$ is CH or N; $Z^2$ and $Z^3$ are each independently —$CR^Z$ or N, provided that when $Z^1$ or $Z^3$ is N, $Z^2$ is —$CR^Z$; and
each $R^Z$ is independently H, F, Cl, or —$CH_3$.

Another embodiment concerns compounds of Formula II

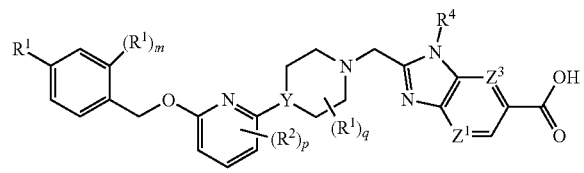

II or a pharmaceutically acceptable salt thereof, wherein
m is 0 or 1;
$R^2$ is F;
p is 0, or 1; and
q is 0 or 1.

Another embodiment concerns compounds of Formulas I or II, wherein
m is 0 or 1;
q is 0 or 1; and
$R^3$ is —F, —$CH_3$, —$CH_2CH_3$, —$CH_2OH$, —$CF_3$, isopropyl, or cyclopropyl, or a pharmaceutically acceptable salt thereof.

Another embodiment concerns compounds of Formula III

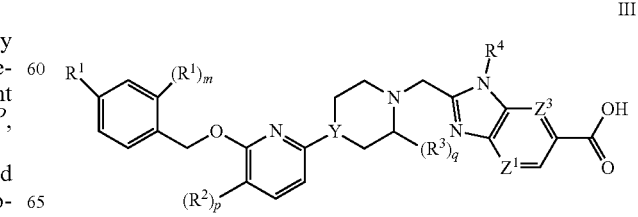

III or a pharmaceutically acceptable salt thereof, wherein
m is 0 or 1;
R² is F;
p is 0, or 1;
R³ is —C$_{1-2}$alkyl, wherein —C$_{1-2}$alkyl may be substituted as valency allows with 0 to 3 F atoms; and
q is 0 or 1.

Another embodiment concerns compounds of Formulas I, II, or III, wherein each R¹ is independently F, Cl, —CN, —CH₃, or —CF₃, or a pharmaceutically acceptable salt thereof.

Another embodiment concerns compounds of Formulas I, II, or III, wherein
R³ is —CH₃;
q is 0 or 1; and
R⁴ is —CH₂CH₂OCH₃, C$_{1-3}$alkylene-R⁵, or C$_{1-3}$alkylene-R⁶, or a pharmaceutically acceptable salt thereof.

Another embodiment concerns compounds of Formulas I, II, or III, wherein
R⁴ is —CH₂—R⁵, wherein R⁵ is the 4- to 5-membered heterocycloalkyl, wherein said heterocycloalkyl may be substituted with 0 to 2 substituents as valency allows independently selected from:
  0 to 2 F atoms, and
  0 to 1 substituent selected from —OCH₃ and —CH₂OCH₃;
or a pharmaceutically acceptable salt thereof.

Another embodiment concerns compounds of Formulas I, II, or III, wherein the heterocycloalkyl of R⁵ is a monovalent radical of wherein the heterocycloalkyl may be substituted with 0 to 2 substituents as valency allows, e.g., replacing hydrogen, independently selected from:
  0 to 1 oxo (O=),
  0 to 1 —CN,
  0 to 2 F atoms, and
  0 to 2 substituents independently selected from —C$_{1-3}$alkyl and —OC$_{1-3}$alkyl, wherein the alkyl of C$_{1-3}$alkyl and OC$_{1-3}$alkyl may be independently substituted with 0 to 3 substituents as valency allows independently selected from:
    0 to 3 F atoms,
    0 to 1 —CN, and
    0 to 1 —OR$^O$,
or a pharmaceutically acceptable salt thereof.

Another embodiment concerns compounds of Formulas I, II, or III, wherein the heterocycloalkyl of R⁵ is a monovalent radical of wherein the heterocycloalkyl may be substituted with 0 to 2 substituents as valency allows, e.g., replacing hydrogen, independently selected from:
  0 to 1 —CN,
  0 to 2 F atoms, and
  0 to 2 substituents independently selected from —C$_{1-3}$alkyl and —OC$_{1-3}$alkyl, wherein the alkyl of C$_{1-3}$alkyl and OC$_{1-3}$alkyl may be independently substituted with 0 to 3 substituents as valency allows independently selected from:
    0 to 3 F atoms,
    0 to 1 —CN, and
    0 to 1 —OR$^O$, or a pharmaceutically acceptable salt thereof.

Another embodiment concerns compounds of Formulas I, II, or III, wherein the heterocycloalkyl of R⁵ is a monovalent radical of wherein the heterocycloalkyl may be substituted with 0 to 1 substituent as valency allows, e.g., replacing hydrogen, selected from:
  —CN,
  F atom, and
  0 to 1 substituent independently selected from —C$_{1-3}$alkyl and —OC$_{1-3}$alkyl, wherein the alkyl of C$_{1-3}$alkyl and OC$_{1-3}$alkyl may be substituted with 0 to 3 substituents as valency allows independently selected from:
    0 to 3 F atoms,
    0 to 1 —CN, and
    0 to 1 —OR$^O$, or a pharmaceutically acceptable salt thereof.

Another embodiment concerns compounds of Formulas I, II, or III, wherein the heterocycloalkyl of R⁵ is

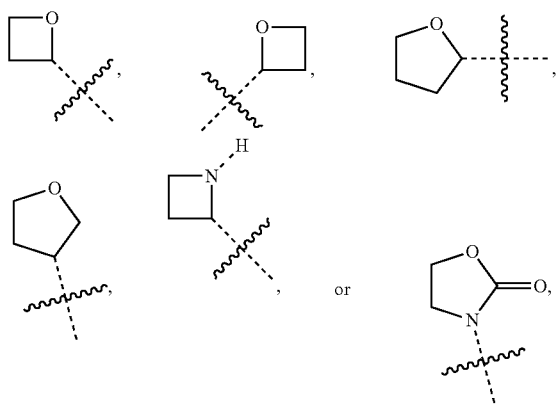

and wherein the heterocycloalkyl may be substituted with 0 to 1 substituent as valency allows, e.g., replacing hydrogen, selected from:
— CN,
F atom, and
0 to 1 substituent independently selected from —$C_{1-3}$alkyl and —$OC_{1-3}$alkyl, wherein the alkyl of $C_{1-3}$alkyl and $OC_{1-3}$alkyl may be substituted with 0 to 3 substituents as valency allows with:
0 to 3 F atoms,
0 to 1 —CN, or
0 to 1 —$OR^O$, or a pharmaceutically acceptable salt thereof.

Another embodiment concerns compounds of Formulas I, II, or III, wherein the heterocycloalkyl of $R^5$ is

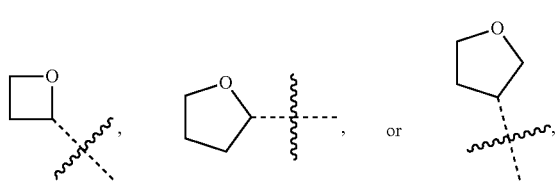 [SMILES: *[C@@H]1CCO1 ; *[C@@H]1CCCO1 ; *[C@@H]1CCOC1]

and wherein the heterocycloalkyl may be substituted as valency allows with 0 to 1 methyl, wherein said methyl may be substituted with 0 to 3 F atoms, or a pharmaceutically acceptable salt thereof.

Another embodiment concerns compounds independently selected from one or any combination of the following:

2-[(4-{6-[(4-chloro-2-fluorobenzyl)oxy]pyridin-2-yl}piperidin-1-yl)methyl]-1-[(2S)-oxetan-2-ylmethyl]-1H-benzimidazole-6-carboxylic acid;

2-[(4-{6-[(4-cyano-2-fluorobenzyl)oxy]pyridin-2-yl}piperazin-1-yl)methyl]-1-[(2S)-oxetan-2-ylmethyl]-1H-benzimidazole-6-carboxylic acid;

2-[(4-{6-[(4-cyano-2-fluorobenzyl)oxy]pyridin-2-yl}piperidin-1-yl)methyl]-1-[oxetan-2-ylmethyl]-1H-benzimidazole-6-carboxylic acid;

2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid;

2-[(4-{6-[(4-cyano-2-fluorobenzyl)oxy]pyridin-2-yl}piperidin-1-yl)methyl]-1-[(2R)-oxetan-2-ylmethyl]-1H-benzimidazole-6-carboxylic acid;

2-{[4-(6-{[(4-cyano-2-fluorophenyl)(methyl-d2)]oxy}pyridin-2-yl)piperidin-1-yl]methyl}-1-[(2S)-oxetan-2-ylmethyl]-1H-benzimidazole-6-carboxylic acid;

2-[(4-{6-[(4-cyano-2-fluorobenzyl)oxy]-5-fluoropyridin-2-yl}piperidin-1-yl)methyl]-1-[(2S)-oxetan-2-ylmethyl]-1H-benzimidazole-6-carboxylic acid;

2-[(4-{6-[(4-cyano-2-fluorobenzyl)oxy]pyridin-2-yl}piperidin-1-yl)methyl]-3-[(2S)-oxetan-2-ylmethyl]-3H-imidazo[4,5-b]pyridine-5-carboxylic acid;

2-{[(2S)-4-{6-[(4-cyano-2-fluorobenzyl)oxy]pyridin-2-yl}-2-methylpiperazin-1-yl]methyl}-1-[(2S)-oxetan-2-ylmethyl]-1H-benzimidazole-6-carboxylic acid;

2-[(4-{6-[(4-chloro-2-fluorobenzyl)oxy]pyridin-2-yl}piperidin-1-yl)methyl]-1-[(2S)-tetrahydrofuran-2-ylmethyl]-1H-benzimidazole-6-carboxylic acid;

2-[(4-{6-[(2,4-difluorobenzyl)oxy]pyridin-2-yl}piperidin-1-yl)methyl]-1-[(2S)-oxetan-2-ylmethyl]-1H-benzimidazole-6-carboxylic acid;

2-[(4-{6-[(2,4-difluorobenzyl)oxy]pyridin-2-yl}piperidin-1-yl)methyl]-3-[(2S)-oxetan-2-ylmethyl]-3H-imidazo[4,5-b]pyridine-5-carboxylic acid;

2-[(4-{6-[(4-chloro-2-fluorobenzyl)oxy]pyridin-2-yl}piperazin-1-yl)methyl]-1-[(2S)-oxetan-2-ylmethyl]-1H-benzimidazole-6-carboxylic acid;

2-[(4-{6-[(4-chloro-2-fluorobenzyl)oxy]pyridin-2-yl}piperazin-1-yl)methyl]-3-[(2S)-oxetan-2-ylmethyl]-3H-imidazo[4,5-b]pyridine-5-carboxylic acid;

2-[(4-{6-[(4-chloro-2-fluorobenzyl)oxy]pyridin-2-yl}piperidin-1-yl)methyl]-1-[(3R)-tetrahydrofuran-3-ylmethyl]-1H-benzimidazole-6-carboxylic acid;

2-[(4-{6-[(4-chloro-2-fluorobenzyl)oxy]pyridin-2-yl}piperidin-1-yl)methyl]-3-[(2S)-oxetan-2-ylmethyl]-3H-imidazo[4,5-b]pyridine-5-carboxylic acid;

2-[(4-{6-[(4-cyano-2-fluorobenzyl)oxy]pyridin-2-yl}piperazin-1-yl)methyl]-3-[(2S)-oxetan-2-ylmethyl]-3H-imidazo[4,5-b]pyridine-5-carboxylic acid;

2-[(4-{6-[(4-cyano-2-fluorobenzyl)oxy]pyridin-2-yl}piperidin-1-yl)methyl]-1-[(2S)-tetrahydrofuran-2-ylmethyl]-1H-benzimidazole-6-carboxylic acid;

2-[(4-{6-[(4-cyano-2-fluorobenzyl)oxy]pyridin-2-yl}piperidin-1-yl)methyl]-1-[(3R)-tetrahydrofuran-3-ylmethyl]-1H-benzimidazole-6-carboxylic acid;

2-[(4-{6-[(4-cyano-2-fluorobenzyl)oxy]pyridin-2-yl}piperidin-1-yl)methyl]-1-[(3S)-tetrahydrofuran-3-ylmethyl]-1H-benzimidazole-6-carboxylic acid;

2-[(4-{6-[(4-cyanobenzyl)oxy]-5-fluoropyridin-2-yl}piperidin-1-yl)methyl]-1-[(2S)-oxetan-2-ylmethyl]-1H-benzimidazole-6-carboxylic acid;

2-[(4-{6-[(4-cyanobenzyl)oxy]-5-fluoropyridin-2-yl}piperidin-1-yl)methyl]-1-[(2S)-tetrahydrofuran-2-ylmethyl]-1H-benzimidazole-6-carboxylic acid;

2-[(4-{6-[(4-cyanobenzyl)oxy]-5-fluoropyridin-2-yl}piperidin-1-yl)methyl]-1-[(2R)-tetrahydrofuran-2-ylmethyl]-1H-benzimidazole-6-carboxylic acid;

2-[(4-{6-[(4-cyanobenzyl)oxy]pyridin-2-yl}piperidin-1-yl)methyl]-1-[(2S)-oxetan-2-ylmethyl]-1H-benzimidazole-6-carboxylic acid;

2-[(4-{6-[(4-cyanobenzyl)oxy]pyridin-2-yl}piperidin-1-yl)methyl]-1-[(2S)-tetrahydrofuran-2-ylmethyl]-1H-benzimidazole-6-carboxylic acid;

2-[(4-{6-[(4-cyanobenzyl)oxy]pyridin-2-yl}piperidin-1-yl)methyl]-1-[(2R)-tetrahydrofuran-2-ylmethyl]-1H-benzimidazole-6-carboxylic acid;

2-{[(2S)-4-{6-[(2,4-difluorobenzyl)oxy]-5-fluoropyridin-2-yl}-2-methylpiperazin-1-yl]methyl}-1-[(2S)-oxetan-2-ylmethyl]-1H-benzimidazole-6-carboxylic acid;

2-{[(2S)-4-{6-[(2,4-difluorobenzyl)oxy]pyridin-2-yl}-2-methylpiperazin-1-yl]methyl}-1-[(2S)-oxetan-2-ylmethyl]-1H-benzimidazole-6-carboxylic acid;

2-{[(2S)-4-{6-[(4-chloro-2-fluorobenzyl)oxy]pyridin-2-yl}-2-methylpiperazin-1-yl]methyl}-1-[(2S)-oxetan-2-ylmethyl]-1H-benzimidazole-6-carboxylic acid;

2-{[(2S)-4-{6-[(4-chloro-2-fluorobenzyl)oxy]pyridin-2-yl}-2-methylpiperazin-1-yl]methyl}-3-[(2S)-oxetan-2-ylmethyl]-3H-imidazo[4,5-b]pyridine-5-carboxylic acid;

2-{[(2S)-4-{6-[(4-cyano-2-fluorobenzyl)oxy]pyridin-2-yl}-2-methylpiperazin-1-yl]methyl}-3-[(2S)-oxetan-2-ylmethyl]-3H-imidazo[4,5-b]pyridine-5-carboxylic acid; or 2-{[(2S)-4-{6-[(4-cyanobenzyl)oxy]pyridin-2-yl}-2-methylpiperazin-1-yl]methyl}-1-[(2S)-oxetan-2-ylmethyl]-1H-benzimidazole-6-carboxylic acid;

or a pharmaceutically acceptable salt thereof.

Another embodiment concerns a compound that is 2-[(4-{6-[(4-chloro-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

Another embodiment concerns a compound that is 2-[(4-{6-[(4-cyano-2-fluorobenzyl)oxy]pyridin-2-yl}piperazin-1-yl)methyl]-1-[(2S)-oxetan-2-ylmethyl]-1H-benzimidazole-6-carboxylic acid, or a pharmaceutically acceptable salt thereof.

Another embodiment concerns a compound that is 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

Another embodiment is the tris salt of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid.

Another embodiment is the free acid of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid.

Another embodiment concerns a compound that is 2-{[4-(6-{[(4-cyano-2-fluorophenyl)(methyl-d2)]oxy}pyridin-2-yl)piperidin-1-yl]methyl}-1-[(2S)-oxetan-2-ylmethyl]-1H-benzimidazole-6-carboxylic acid, or a pharmaceutically acceptable salt thereof.

Another embodiment concerns a compound that is 2-[(4-{6-[(4-cyano-2-fluorobenzyl)oxy]-5-fluoropyridin-2-yl}piperidin-1-yl)methyl]-1-[(2S)-oxetan-2-ylmethyl]-1H-benzimidazole-6-carboxylic acid, or a pharmaceutically acceptable salt thereof.

Another embodiment concerns compounds of Formulas I, II, or III, wherein

R$_4$ is —CH$_2$—R$^6$, wherein R$^6$ is the 5-membered heteroaryl, wherein said heteroaryl may be substituted with 0 to 2 substituents as valency allows independently selected from:
  0 to 2 halogens, wherein the halogen is independently selected from F and Cl,
  0 to 1 —OCH$_3$, and
  0 to 1 —CH$_3$, —CH$_2$CH$_3$, —CF$_3$, or —CH$_2$CH$_2$OCH$_3$;

or a pharmaceutically acceptable salt thereof.

Another embodiment concerns compounds of Formulas I, II, or III, wherein the heteroaryl of R$^6$ is a monovalent radical of

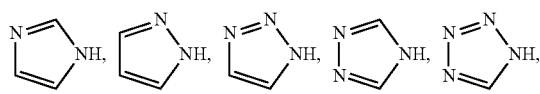

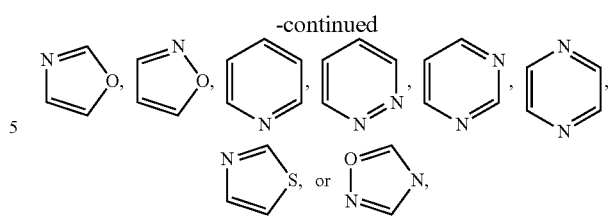

wherein said heteroaryl may be substituted with 0 to 2 substituents as valency allows, e.g., replacing hydrogen, independently selected from:
  0 to 2 halogens, wherein the halogen is independently selected from F and Cl,
  0 to 1 substituent selected from —OR$^O$ and —N(R$^N$)$_2$, or
  0 to 2 —C$_{1-3}$alkyl, wherein the alkyl may be substituted with 0 to 3 substituents as valency allows independently selected from:
    0 to 3 F atoms, and
    0 to 1 —OR$^O$;

or a pharmaceutically acceptable salt thereof.

Another embodiment concerns compounds of Formulas I, II, or III, wherein the heteroaryl of R$^6$ is a monovalent radical of

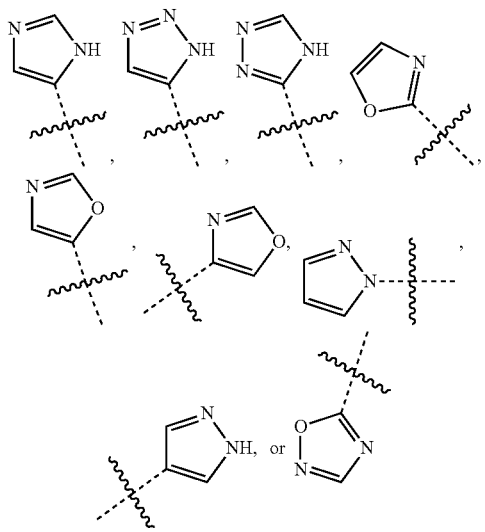

wherein said heteroaryl may be substituted with 0 to 2 substituents as valency allows, e.g., replacing hydrogen, independently selected from:
  0 to 2 halogens, wherein the halogen is independently selected from F and C,
  0 to 1 substituent selected from —OR$^O$ and —N(R$^N$)$_2$, or
  0 to 2 —C$_{1-3}$alkyl, wherein the alkyl may be substituted with 0 to 3 substituents as valency allows independently selected from:
    0 to 3 F atoms, and
    0 to 1 —OR$^O$;

or a pharmaceutically acceptable salt thereof.

Another embodiment concerns compounds of Formulas I, II, or III, wherein the heteroaryl is

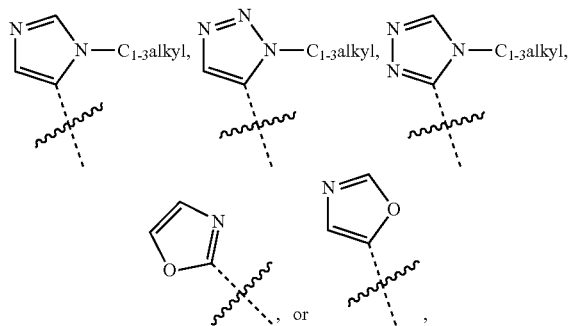

wherein C$_{1-3}$ alkyl on said heteroaryl may be substituted with 0 to 3 substituents as valency allows, e.g., replacing hydrogen, independently selected from:
  0 to 3 F atoms, and
  0 to 1 —OR$^O$;
or a pharmaceutically acceptable salt thereof.

Another embodiment concerns compounds independently selected from one or any combination of the following:
2-[(4-{6-[(4-cyano-2-fluorobenzyl)oxy]pyridin-2-yl}piperidin-1-yl)methyl]-1-(1,3-oxazol-2-ylmethyl)-1H-benzimidazole-6-carboxylic acid;
2-[(4-{6-[(4-cyano-2-fluorobenzyl)oxy]pyridin-2-yl}piperazin-1-yl)methyl]-1-(1,3-oxazol-2-ylmethyl)-1H-benzimidazole-6-carboxylic acid;
2-[(4-{6-[(4-cyano-2-fluorobenzyl)oxy]pyridin-2-yl}piperidin-1-yl)methyl]-1-(1,3-oxazol-5-ylmethyl)-1H-benzimidazole-6-carboxylic acid;
2-[(4-{6-[(4-cyano-2-fluorobenzyl)oxy]pyridin-2-yl}piperazin-1-yl)methyl]-1-(1,3-oxazol-5-ylmethyl)-1H-benzimidazole-6-carboxylic acid;
2-[(4-{6-[(4-chloro-2-fluorobenzyl)oxy]pyridin-2-yl}piperidin-1-yl)methyl]-1-[(1-methyl-1H-imidazol-5-yl)methyl]-1H-benzimidazole-6-carboxylic acid;
2-[(4-{6-[(4-chloro-2-fluorobenzyl)oxy]pyridin-2-yl}piperidin-1-yl)methyl]-1-[(1-methyl-1H-1,2,3-triazol-5-yl)methyl]-1H-benzimidazole-6-carboxylic acid;
2-[(4-{6-[(4-chloro-2-fluorobenzyl)oxy]pyridin-2-yl}piperidin-1-yl)methyl]-1-(1,3-oxazol-5-ylmethyl)-1H-benzimidazole-6-carboxylic acid;
2-{[(2S)-4-{6-[(4-cyano-2-fluorobenzyl)oxy]pyridin-2-yl}-2-methylpiperazin-1-yl]methyl}-1-(1,3-oxazol-2-ylmethyl)-1H-benzimidazole-6-carboxylic acid;
2-{[(2S)-4-{6-[(4-chloro-2-fluorobenzyl)oxy]pyridin-2-yl}-2-methylpiperazin-1-yl]methyl}-1-(1,3-oxazol-5-ylmethyl)-1H-benzimidazole-6-carboxylic acid;
2-{[(2S)-4-{6-[(4-chloro-2-fluorobenzyl)oxy]pyridin-2-yl}-2-methylpiperazin-1-yl]methyl}-1-(1,3-oxazol-2-ylmethyl)-1H-benzimidazole-6-carboxylic acid;
2-[(4-{6-[(2,4-difluorobenzyl)oxy]pyridin-2-yl}piperidin-1-yl)methyl]-1-(1,3-oxazol-2-ylmethyl)-1H-benzimidazole-6-carboxylic acid;
2-[(4-{6-[(2,4-difluorobenzyl)oxy]pyridin-2-yl}piperidin-1-yl)methyl]-1-[(1-ethyl-1H-imidazol-5-yl)methyl]-1H-benzimidazole-6-carboxylic acid;
2-[(4-{6-[(4-chloro-2-fluorobenzyl)oxy]pyridin-2-yl}piperazin-1-yl)methyl]-1-(1,3-oxazol-2-ylmethyl)-1H-benzimidazole-6-carboxylic acid;
2-[(4-{6-[(4-cyano-2-fluorobenzyl)oxy]pyridin-2-yl}piperazin-1-yl)methyl]-1-[(1-ethyl-1H-imidazol-5-yl)methyl]-1H-benzimidazole-6-carboxylic acid;
2-[(4-{6-[(4-chloro-2-fluorobenzyl)oxy]pyridin-2-yl}piperazin-1-yl)methyl]-1-[(1-methyl-1H-imidazol-5-yl)methyl]-1H-benzimidazole-6-carboxylic acid;
2-[(4-{6-[(4-cyano-2-fluorobenzyl)oxy]pyridin-2-yl}piperazin-1-yl)methyl]-1-[(1-methyl-1H-imidazol-5-yl)methyl]-1H-benzimidazole-6-carboxylic acid;
2-[(4-{6-[(4-chloro-2-fluorobenzyl)oxy]pyridin-2-yl}piperidin-1-yl)methyl]-1-(1,3-oxazol-4-ylmethyl)-1H-benzimidazole-6-carboxylic acid;
2-[(4-{6-[(4-chloro-2-fluorobenzyl)oxy]pyridin-2-yl}piperidin-1-yl)methyl]-1-(1,3-oxazol-2-ylmethyl)-1H-benzimidazole-6-carboxylic acid;
2-[(4-{6-[(2,4-difluorobenzyl)oxy]pyridin-2-yl}piperidin-1-yl)methyl]-1-(1,3-oxazol-5-ylmethyl)-1H-benzimidazole-6-carboxylic acid;
2-[(4-{6-[(4-chloro-2-fluorobenzyl)oxy]pyridin-2-yl}piperazin-1-yl)methyl]-1-(1,3-oxazol-5-ylmethyl)-1H-benzimidazole-6-carboxylic acid;
2-[(4-{6-[(4-cyano-2-fluorobenzyl)oxy]pyridin-2-yl}piperazin-1-yl)methyl]-1-[(1-ethyl-1H-1,2,3-triazol-5-yl)methyl]-1H-benzimidazole-6-carboxylic acid;
2-[(4-{6-[(4-chloro-2-fluorobenzyl)oxy]pyridin-2-yl}piperidin-1-yl)methyl]-1-(1,2-oxazol-5-ylmethyl)-1H-benzimidazole-6-carboxylic acid;
2-[(4-{6-[(4-cyano-2-fluorobenzyl)oxy]pyridin-2-yl}piperidin-1-yl)methyl]-1-(1,2-oxazol-3-ylmethyl)-1H-benzimidazole-6-carboxylic acid;
2-[(4-{6-[(4-cyano-2-fluorobenzyl)oxy]pyridin-2-yl}piperidin-1-yl)methyl]-1-[(1-ethyl-1H-imidazol-5-yl)methyl]-1H-benzimidazole-6-carboxylic acid;
2-{[(2S)-4-{6-[(4-chloro-2-fluorobenzyl)oxy]pyridin-2-yl}-2-methylpiperazin-1-yl]methyl}-1-[(1-ethyl-1H-imidazol-5-yl)methyl]-1H-benzimidazole-6-carboxylic acid;
2-[(4-{6-[(4-cyano-2-fluorobenzyl)oxy]pyridin-2-yl}piperidin-1-yl)methyl]-1-[(1-ethyl-1H-1,2,3-triazol-5-yl)methyl]-1H-benzimidazole-6-carboxylic acid;
2-[(4-{6-[(4-chloro-2-fluorobenzyl)oxy]pyridin-2-yl}piperidin-1-yl)methyl]-1-[(1-ethyl-1H-imidazol-5-yl)methyl]-1H-benzimidazole-6-carboxylic acid;
2-[(4-{6-[(4-cyano-2-fluorobenzyl)oxy]pyridin-2-yl}piperidin-1-yl)methyl]-1-[(1-methyl-1H-imidazol-5-yl)methyl]-1H-benzimidazole-6-carboxylic acid;
2-[(4-{6-[(4-chloro-2-fluorobenzyl)oxy]pyridin-2-yl}piperidin-1-yl)methyl]-3-(1,3-oxazol-2-ylmethyl)-3H-imidazo[4,5-b]pyridine-5-carboxylic acid; or
2-[(4-{6-[(4-cyano-2-fluorobenzyl)oxy]pyridin-2-yl}piperidin-1-yl)methyl]-3-(1,3-oxazol-2-ylmethyl)-3H-imidazo[4,5-b]pyridine-5-carboxylic acid;
or a pharmaceutically acceptable salt thereof.

Another embodiment concerns compounds independently selected from one or any combination of the following:
2-[(4-{6-[(4-cyano-2-fluorobenzyl)oxy]pyridin-2-yl}piperidin-1-yl)methyl]-1-(1,3-oxazol-2-ylmethyl)-1H-benzimidazole-6-carboxylic acid;
2-[(4-{6-[(4-cyano-2-fluorobenzyl)oxy]pyridin-2-yl}piperazin-1-yl)methyl]-1-(1,3-oxazol-2-ylmethyl)-1H-benzimidazole-6-carboxylic acid;
2-[(4-{6-[(4-cyano-2-fluorobenzyl)oxy]pyridin-2-yl}piperidin-1-yl)methyl]-1-(1,3-oxazol-5-ylmethyl)-1H-benzimidazole-6-carboxylic acid; or
2-[(4-{6-[(4-cyano-2-fluorobenzyl)oxy]pyridin-2-yl}piperazin-1-yl)methyl]-1-(1,3-oxazol-5-ylmethyl)-1H-benzimidazole-6-carboxylic acid;
or a pharmaceutically acceptable salt thereof.

Another embodiment concerns compounds independently selected from one or any combination of the following:

2-[(4-{6-[(4-cyanobenzyl)oxy]pyridin-2-yl}piperidin-1-yl)
methyl]-7-fluoro-1-(2-methoxyethyl)-1H-benzimidazole-
6-carboxylic acid;

2-[(4-{6-[(4-chloro-2-fluorobenzyl)oxy]pyridin-2-
yl}piperidin-1-yl)methyl]-7-fluoro-1-(2-methoxyethyl)-
1H-benzimidazole-6-carboxylic acid;

2-[(4-{6-[(4-cyanobenzyl)oxy]pyridin-2-yl}piperazin-1-yl)
methyl]-1-(2-methoxyethyl)-1H-benzimidazole-6-car-
boxylic acid;

2-{[(2S)-4-{6-[(4-cyanobenzyl)oxy]pyridin-2-yl}-2-meth-
ylpiperazin-1-yl]methyl}-1-(2-methoxyethyl)-1H-benz-
imidazole-6-carboxylic acid;

2-{[(2S)-4-{6-[(4-cyano-2-fluorobenzyl)oxy]pyridin-2-yl}-
2-methylpiperazin-1-yl]methyl}-1-(2-methoxyethyl)-1H-
benzimidazole-6-carboxylic acid;

2-{[(2S)-4-{6-[(4-chloro-2-fluorobenzyl)oxy]-5-fluoropyri-
din-2-yl}-2-methylpiperazin-1-yl]methyl}-1-(2-
methoxyethyl)-1H-benzimidazole-6-carboxylic acid;

2-{[(2S)-4-{6-[(4-cyanobenzyl)oxy]-5-fluoropyridin-2-yl}-
2-methylpiperazin-1-yl]methyl}-1-(2-methoxyethyl)-1H-
benzimidazole-6-carboxylic acid;

2-[(4-{6-[(4-chloro-2-fluorobenzyl)oxy]pyridin-2-
yl}piperidin-1-yl)methyl]-1-(2-methoxyethyl)-1H-benz-
imidazole-6-carboxylic acid; or 2-[(4-{6-[(4-chloro-2-fluorobenzyl)oxy]pyridin-2-
yl}piperidin-1-yl)methyl]-1-[(1-methoxycyclobutyl)
methyl]-1H-benzimidazole-6-carboxylic;

or a pharmaceutically acceptable salt thereof.

Another embodiment concerns compounds of other embodiments herein, e.g., compounds of Formulas I, II, or III, wherein $Z^1$, $Z^2$, and $Z^3$ are each $CR^Z$, or a pharmaceutically acceptable salt thereof.

Another embodiment concerns compounds of other embodiments herein, e.g., compounds of Formulas I, II, or III, wherein $R^Z$ is H, or a pharmaceutically acceptable salt thereof.

Another embodiment concerns compounds of other embodiments herein, e.g., compounds of Formulas I, II, or III, wherein $Z^1$, $Z^2$, and $Z^3$ are each CH, or a pharmaceutically acceptable salt thereof.

Another embodiment concerns compounds of other embodiments herein, e.g., compounds of Formulas I, II, or III, wherein p is 0 or 1; and $R^2$ is F.

Another embodiment concerns compounds of other embodiments herein, e.g., compounds of Formulas I, II, or III, wherein $R^3$ is —$CH_3$, or —$CF_3$; and q is 1, or a pharmaceutically acceptable salt thereof.

Another embodiment concerns compounds of other embodiments herein, e.g., compounds of Formulas I, II, or III, wherein each $R^1$ is independently F, Cl, or —CN, or a pharmaceutically acceptable salt thereof.

Another embodiment concerns compounds of other embodiments herein, e.g., compounds of Formulas I, II, or III, wherein $R_4$ is —$CH_2$—$R^5$, or a pharmaceutically acceptable salt thereof.

Another embodiment concerns compounds of other embodiments herein, e.g., compounds of Formulas I, II, or III, wherein $R_4$ is —$CH_2$—$R^6$, or a pharmaceutically acceptable salt thereof.

Another embodiment concerns compounds of other embodiments herein, e.g., compounds of Formula I, II, or III, wherein the compound is the free acid.

In another embodiment, the invention provides a pharmaceutical composition comprising a compound of Formulas I, II, or III, or a pharmaceutically acceptable salt thereof, as defined in any of the embodiments described herein, in admixture with at least one pharmaceutically acceptable excipient.

The invention also includes the following embodiments:

a compound of Formulas I, II, or III, or a pharmaceutically acceptable salt thereof, as defined in any of the embodiments described herein, for use as a medicament;

a compound of Formulas I, II, or III, or a pharmaceutically acceptable salt thereof, as defined in any of the embodiments described herein, for use in the prevention and/or treatment of cardiometabolic and associated diseases discussed herein, including T2DM, pre-diabetes, NASH, and cardiovascular disease;

a method of treating a disease for which an agonist of GLP-1R is indicated, in a subject in need of such prevention and/or treatment, comprising administering to the subject a therapeutically effective amount of a compound of Formulas I, II, or III, or a pharmaceutically acceptable salt thereof, as defined in any of the embodiments described herein;

the use of a compound of Formulas I, II, or III, or a pharmaceutically acceptable salt thereof, as defined in any of the embodiments described herein, for the manufacture of a medicament for treating a disease or condition for which an agonist of the GLP-1R is indicated;

a compound of Formulas I, II, or III, or a pharmaceutically acceptable salt thereof, as defined in any of the embodiments described herein, for use in the treatment of a disease or condition for which an agonist of GLP-1R is indicated; or a pharmaceutical composition for the treatment of a disease or condition for which an agonist of the GLP-1R is indicated, comprising a compound of Formulas I, II, or III, or a pharmaceutically acceptable salt thereof, as defined in any of the embodiments described herein.

Every Example or pharmaceutically acceptable salt thereof may be claimed individually or grouped together in any combination with any number of each and every embodiment described herein.

The invention also relates to a pharmaceutical composition comprising a compound of Formulas I, II, or III, or a pharmaceutically acceptable salt thereof, as defined in any of the embodiments described herein, for use in the treatment and/or prevention of cardiometabolic and associated diseases discussed herein, including T2DM, pre-diabetes, NASH, and cardiovascular disease.

Another embodiment of the invention concerns a compound of Formulas I, II, or III, or a pharmaceutically acceptable salt thereof, as defined in any of the embodiments described herein, for use in the treatment and/or treatment for cardiometabolic and associated diseases including diabetes (T1D and/or T2DM, including pre-diabetes), idiopathic T1D (Type 1b), latent autoimmune diabetes in adults (LADA), early-onset T2DM (EOD), youth-onset atypical diabetes (YOAD), maturity onset diabetes of the young (MODY), malnutrition-related diabetes, gestational diabetes, hyperglycemia, insulin resistance, hepatic insulin resistance, impaired glucose tolerance, diabetic neuropathy, diabetic nephropathy, kidney disease (e.g., acute kidney disorder, tubular dysfunction, proinflammatory changes to the proximal tubules), diabetic retinopathy, adipocyte dysfunction, visceral adipose deposition, sleep apnea, obesity (including hypothalamic obesity and monogenic obesity) and related comorbidities (e.g., osteoarthritis and urine incontinence), eating disorders (including binge eating syndrome, bulimia nervosa, and syndromic obesity such as Prader-Willi and Bardet-Biedl syndromes), weight gain from use of other agents (e.g., from use of steroids and antipsychotics), excessive sugar craving, dyslipidemia (including hyperlipidemia, hypertriglyceridemia, increased total cholesterol, high LDL cholesterol, and low HDL cholesterol), hyperinsulinemia, NAFLD (including related diseases such as steatosis, NASH, fibrosis, cirrhosis, and hepatocellular carcinoma), cardiovascular disease, atherosclerosis (including coronary artery disease), peripheral vascular disease, hypertension, endothelial dysfunction, impaired vascular compliance, congestive heart failure, myocardial infarction (e.g. necrosis and apoptosis), stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome, Crohn's disease, colitis, irritable bowel syndrome, prevention or treatment of Polycystic Ovary Syndrome and treatment of addiction (e.g., alcohol and/or drug abuse).

Abbreviations used herein are as follows:

The term "alkyl", as used herein, means a straight or branched chain monovalent hydrocarbon group of formula —$C_nH_{(2n+1)}$. Non-limiting examples include methyl, ethyl, propyl, butyl, 2-methyl-propyl, 1,1-dimethylethyl, pentyl and hexyl.

The term "alkylene", as used herein, means a straight or branched chain divalent hydrocarbon group of formula —$C_nH_{2n}$—. Non-limiting examples include ethylene, and propylene.

The term "cycloalkyl", as used herein, means a cyclic, monovalent hydrocarbon group of formula —$C_nH_{(2n-1)}$ containing at least three carbon atoms. Non-limiting examples include cyclopropyl, cyclobutyl, cyclopentyl and cyclohexyl.

The term "halogen", as used herein, refers to fluoride, chloride, bromide, or iodide.

The term "heterocycloalkyl", as used herein, refers to a cycloalkyl group in which one or more of the ring methylene groups (—$CH_2$—) has been replaced with a group selected from —O—, —S— or nitrogen, wherein the nitrogen may provide a point of attachment or may be substituted as provided within each embodiment. Where nitrogen provides a point of attachment, a structural drawing of a heterocycloalkyl would have an hydrogen on said nitrogen. Generally, the heterocycloalkyl may be substituted with 0 to 2 substituents as valency allows independently selected from oxo, —CN, halogen, alkyl and —Oalkyl and the alkyl may be further substituted. One will note that when there is 0 substitution, the heterocycloalkyl is unsubstituted.

The term "heteroaryl", as used herein, refers to a monocyclic aromatic hydrocarbon containing from 5 to 6 carbon atoms in which at least one of the ring carbon atoms has been replaced with a heteroatom selected from oxygen, nitrogen and sulfur. Such a heteroaryl group may be attached through a ring carbon atom or, where valency permits, through a ring nitrogen atom. Generally, the heteroaryl may be substituted with 0 to 2 substituents as valency allows independently selected from halogen, OH, alkyl, O-alkyl, and amino (e.g., $NH_2$, NHalkyl, N(alkyl)$_2$), and the alkyl may be further substituted. One will note that when there is 0 substitution the heteroaryl is unsubstituted.

Room temperature: RT.
Methanol: MeOH.
Ethanol: EtOH.
Isopropanol: iPrOH.
Ethyl acetate: EtOAc.
Tetrahydrofuran: THF.
Toluene: PhCH$_3$.
Cesium carbonate: Cs$_2$CO$_3$.
Lithium bis(trimethylsilyl)amide: LiHMDS.
Sodium t-butoxide: NaOtBu.
Potassium t-butoxide: KOtBu.
Lithium diisopropylamide: LDA.
Triethylamine: Et$_3$N.
N,N-diisopropylethyl amine: DIPEA.
Potassium carbonate: K$_2$CO$_3$.
Dimethyl formamide: DMF.
Dimethyl acetamide: DMAc.
Dimethyl sulfoxide: DMSO.
N-Methyl-2-pyrrolidinone: NMP.
Sodium hydride: NaH.
Trifluoroacetic acid: TFA.
Trifluoroacetic anhydride: TFAA.
Acetic anhydride: Ac$_2$O.
Dichloromethane: DCM.
1,2-Dichloroethane: DCE.
Hydrochloric acid: HCl.
1,8-Diazabicyclo[5.4.0]undec-7-ene: DBU.
Borane-dimethylsulfide complex: BH$_3$-DMS.
Borane-tetrahydrofuran complex: BH$_3$-THF.
Lithium aluminum hydride: LAH.
Acetic acid: AcOH.
Acetonitrile: MeCN.
p-Toluenesulfonic acid: pTSA.
Dibenzylidine acetone: DBA.
2,2'-Bis(diphenylphosphino)-1,1'-binaphthalene: BINAP.
1,1'-Ferrocenediyl-bis(diphenylphosphine): dppf.
1,3-Bis(diphenylphosphino)propane: DPPP.
3-Chloroperbenzoic acid: m-CPBA.
Tert-Butyl methyl ether: MTBE.
Methanesulfonyl: Ms.
N-Methylpyrrolidinone: NMP.
Thin layer chromatography: TLC.
Supercritical fluid chromatography: SFC.
4-(Dimethylamino)pyridine: DMAP.
Tert-Butyloxycarbonyl: Boc.
1-[Bis(dimethylamino)methylene]-1H-1,2,3-triazolo[4,5-b]pyridinium 3-oxidhexafluorophosphate: HATU.
Petroleum ether: PE.
2-(1H-Benzotriazole-1-yl)-1,1,3,3-tetramethyluronium hexafluorophosphate: HBTU.
2-Amino-2-(hydroxymethyl)propane-1,3-diol: tris.
tris(dibenzylideneacetone)dipalladium: Pd$_2$(dba)$_3$ $^1$H Nuclear magnetic resonance (NMR) spectra were in all cases consistent with the proposed structures. Characteristic chemical shifts (δ) are given in parts-per-million relative to the residual proton signal in the deuterated solvent (CHCl$_3$ at 7.27 ppm; CD$_2$HOD at 3.31 ppm; MeCN at 1.94 ppm; DMSO at 2.50 ppm) and are reported using conventional abbreviations for designation of major peaks: e.g. s, singlet; d, doublet; t, triplet; q, quartet; m, multiplet; br, broad. $^1$H NMR spectra were obtained with field strengths of 400 or 600 MHz if not stated.

As used herein, a wavy line, "⌇" denotes a point of attachment of a substituent to another group.

The compounds and intermediates described below were named using the naming convention provided with ChemBioDraw Ultra, Version 13.0 (CambridgeSoft Corp., Cambridge, Mass.) or ACD/Labs, Version 12 (Advanced Chemistry Development, Inc., Toronto, Ontario). The naming conventions provided with ChemBioDraw Ultra, Version 13.0 and ACD/Labs, Version 12 are well known by those skilled in the art and it is believed that the naming conventions provided with ChemBioDraw Ultra, Version 13.0 and ACD/Labs, Version 12 generally comports with the IUPAC (International Union for Pure and Applied Chemistry) recommendations on Nomenclature of Organic Chemistry and the CAS Index rules. One will note that the chemical names may have only parentheses or may have parentheses and brackets. The stereochemical descriptors may also be placed different locations within the name itself, depending on the naming convention. One of ordinary skill in the art will recognize these formatting variations and understand they provide the same chemical structure.

Pharmaceutically acceptable salts of the compounds of Formula I include acid addition and base salts.

Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, 1,5-naphathalenedisulfonic acid and xinafoate salts.

Suitable base salts are formed from bases which form non-toxic salts. Examples include the aluminium, arginine, benzathine, calcium, choline, diethylamine, bis(2-hydroxyethyl)amine (diolamine), glycine, lysine, magnesium, meglumine, 2-aminoethanol (olamine), potassium, sodium, 2-Amino-2-(hydroxymethyl)propane-1,3-diol (tris or tromethamine) and zinc salts.

Hemisalts of acids and bases may also be formed, for example, hemisulfate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of compounds of Formula I may be prepared by one or more of three methods:
(i) by reacting the compound of Formula I with the desired acid or base;
(ii) by removing an acid- or base-labile protecting group from a suitable precursor of the compound of Formula I or by ring-opening a suitable cyclic precursor, for example, a lactone or lactam, using the desired acid or base; or
(iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of Formula I, and pharmaceutically acceptable salts thereof, may exist in unsolvated and solvated forms. The term 'solvate' is used herein to describe a molecular complex comprising the compound of Formula I, or a pharmaceutically acceptable salt thereof, and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see *J Pharm Sci*, 64 (8), 1269-1288, by Haleblian (August 1975).

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of Formula I may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'.

Compounds that have the potential to form lyotropic mesophases are described as 'amphiphilic' and consist of molecules which possess an ionic (such as —COO—Na$^+$, —COO—K$^+$, or —SO$_3$—Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

The compounds of Formula I may exhibit polymorphism and/or one or more kinds of isomerism (e.g. optical, geometric or tautomeric isomerism). The compounds of Formula I may also be isotopically labelled. Such variation is implicit to the compounds of Formula I defined as they are by reference to their structural features and therefore within the scope of the invention.

Compounds of Formula I containing one or more asymmetric carbon atoms can exist as two or more stereoisomers. Where a compound of Formula I contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds which contain an aromatic moiety. It follows that a single compound may exhibit more than one type of isomerism.

The pharmaceutically acceptable salts of compounds of Formula I may also contain a counterion which is optically active (e.g. d-lactate or l-lysine) or racemic (e.g. dl-tartrate or dl-arginine).

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of Formula I (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present invention are known in the art (see, for example, Smith, Roger M., Loughborough University, Loughborough, UK; Chromatographic Science Series (1998), 75 (Supercritical Fluid Chromatography with Packed Columns), pp. 223-249 and references cited therein). In some relevant examples herein, columns were obtained from Chiral Technologies, Inc, West Chester, Pa., USA, a subsidiary of *Daicel® Chemical Industries*, Ltd., Tokyo, Japan.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

It must be emphasised that the compounds of Formula I have been drawn herein in a single tautomeric form, all possible tautomeric forms are included within the scope of the invention.

The present invention includes all pharmaceutically acceptable isotopically-labeled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of Formula I, for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of Formula I can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

One way of carrying out the invention is to administer a compound of Formula I in the form of a prodrug. Thus, certain derivatives of a compound of Formula I which may have little or no pharmacological activity themselves can, when administered into or onto the body, be converted into a compound of Formula I having the desired activity, for example by hydrolytic cleavage, particularly hydrolytic cleavage promoted by an esterase or peptidase enzyme. Such derivatives are referred to as 'prodrugs'. Further information on the use of prodrugs may be found in 'Pro-drugs as Novel Delivery Systems', Vol. 14, *ACS Symposium Series* (T. Higuchi and W. Stella) and 'Bioreversible Carriers in Drug Design', Pergamon Press, 1987 (Ed. E. B. Roche, American Pharmaceutical Association). Reference can also be made to Nature Reviews/Drug Discovery, 2008, 7, 355 and *Current Opinion in Drug Discovery and Development*, 2007, 10, 550.

Prodrugs in accordance with the invention can, for example, be produced by replacing appropriate functionalities present in the compounds of Formula I with certain moieties known to those skilled in the art as 'pro-moieties' as described, for example, in 'Design of Prodrugs' by H. Bundgaard (Elsevier, 1985) and Y. M. Choi-Sledeski and C. G. Wermuth, 'Designing Prodrugs and Bioprecursors' in Practice of Medicinal Chemistry, (Fourth Edition), Chapter 28, 657-696 (Elsevier, 2015).

Thus, a prodrug in accordance with the invention is (a) an ester or amide derivative of a carboxylic acid in a compound of Formula I; (b) an ester, carbonate, carbamate, phosphate or ether derivative of a hydroxyl group in a compound of Formula I; (c) an amide, imine, carbamate or amine derivative of an amino group in a compound form Formula I; (d) an oxime or imine derivative of a carbonyl group in a compound of Formula I; or (e) a methyl, primary alcohol or aldehyde group that can be metabolically oxidized to a carboxylic acid in a compound of Formula I.

Some specific examples of prodrugs in accordance with the invention include:

(i) where the compound of Formula I contains a carboxylic acid functionality (—COOH), an ester thereof, such as a compound wherein the hydrogen of the carboxylic acid functionality of the compound of Formula I is replaced by $C_1$-$C_8$ alkyl (e.g. ethyl) or ($C_1$-$C_8$ alkyl)C(=O)OCH$_2$— (e.g. $^tBuC$(=O)OCH$_2$—);

(ii) where the compound of Formula I contains an alcohol functionality (—OH), an ester thereof, such as a compound wherein the hydrogen of the alcohol functionality of the compound of Formula I is replaced by —CO($C_1$-$C_8$ alkyl) (e.g. methylcarbonyl) or the alcohol is esterified with an amino acid;

(iii) where the compound of Formula I contains an alcohol functionality (—OH), an ether thereof, such as a compound wherein the hydrogen of the alcohol functionality of the compound of Formula I is replaced by ($C_1$-$C_8$ alkyl)C(=O)OCH$_2$— or —CH$_2$OP(=O)(OH)$_2$;

(iv) where the compound of Formula I contains an alcohol functionality (—OH), a phosphate thereof, such as a compound wherein the hydrogen of the alcohol functionality of the compound of Formula I is replaced by —P(=O)(OH)$_2$ or —P(=O)(ONa)$_2$ or —P(=O)(O$^-$)$_2$Ca$^{2+}$;

(v) where the compound of Formula I contains a primary or secondary amino functionality (—NH$_2$ or —NHR where R≠H), an amide thereof, for example, a compound wherein, as the case may be, one or both hydrogens of the amino functionality of the compound of Formula I is/are replaced by ($C_1$-$C_{10}$)alkanoyl, —COCH$_2$NH$_2$ or the amino group is derivatised with an amino acid;

(vi) where the compound of Formula I contains a primary or secondary amino functionality (—NH$_2$ or —NHR where R≠H), an amine thereof, for example, a compound wherein, as the case may be, one or both hydrogens of the amino functionality of the compound of Formula I is/are replaced by —CH$_2$OP(=O)(OH)$_2$;

(vii) where the carboxylic acid group within compound of Formula I is replaced by a methyl group, a —CH$_2$OH group or an aldehyde group.

Certain compounds of Formula I may themselves act as prodrugs of other compounds of Formula I. It is also possible for two compounds of Formula I to be joined together in the form of a prodrug. In certain circumstances, a prodrug of a compound of Formula I may be created by internally linking two functional groups in a compound of Formula I, for instance by forming a lactone.

References to compounds of Formula I are taken to include the compounds themselves and prodrugs thereof. The invention includes such compounds of Formula I as well as pharmaceutically acceptable salts of such compounds and pharmaceutically acceptable solvates of said compounds and salts.

Administration and Dosing

Typically, a compound of the invention is administered in an amount effective to treat a condition as described herein. The compounds of the invention can be administered as compound per se, or alternatively, as a pharmaceutically acceptable salt. For administration and dosing purposes, the compound per se or pharmaceutically acceptable salt thereof will simply be referred to as the compounds of the invention.

The compounds of the invention are administered by any suitable route in the form of a pharmaceutical composition adapted to such a route, and in a dose effective for the treatment intended. The compounds of the invention may be administered orally, rectally, vaginally, parenterally, or topically.

The compounds of the invention may be administered orally. Oral administration may involve swallowing, so that the compound enters the gastrointestinal tract, or buccal or sublingual administration may be employed by which the compound enters the bloodstream directly from the mouth.

In another embodiment, the compounds of the invention may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds of the invention and/or compositions containing said compounds is based on a variety of factors, including the type, age, weight, sex and medical condition of the patient; the severity of the condition; the route of administration; and the activity of the particular compound employed. Thus the dosage regimen may vary widely. In one embodiment, the total daily dose of a compound of the invention is typically from about 0.001 to about 100 mg/kg (i.e., mg compound of the invention per kg body weight) for the treatment of the indicated conditions discussed herein. In another embodiment, total daily dose of the compound of the invention is from about 0.01 to about 30 mg/kg, and in another embodiment, from about 0.03 to about 10 mg/kg, and in yet another embodiment, from about 0.1 to about 3. It is not uncommon that the administration of the compounds of the invention will be repeated a plurality of times in a day (typically no greater than 4 times). Multiple doses per day typically may be used to increase the total daily dose, if desired.

For oral administration, the compositions may be provided in the form of tablets containing 0.1, 0.5, 1.0, 2.5, 5.0, 10.0, 15.0, 25.0, 30.0 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the invention include mammalian subjects. In one embodiment, humans are suitable subjects. Human subjects may be of either gender and at any stage of development.

Pharmaceutical Compositions

In another embodiment, the invention comprises pharmaceutical compositions. Such pharmaceutical compositions comprise a compound of the invention presented with a pharmaceutically acceptable carrier. Other pharmacologically active substances can also be present. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Pharmaceutically acceptable substances such as wetting agents or minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g. intravenous, subcutaneous, intraperitoneal, intramuscular). In another embodiment, the antibody is administered by intravenous infusion or injection. In yet another embodiment, the antibody is administered by intramuscular or subcutaneous injection.

Oral administration of a solid dose form may be, for example, presented in discrete units, such as hard or soft capsules, pills, cachets, lozenges, or tablets, each containing a predetermined amount of at least one compound of the invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the invention comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, B. C. Finnin and T. M. Morgan, J. Pharm. Sci., vol. 88, pp. 955-958, 1999.

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

Co-Administration

The compounds of the invention can be used alone, or in combination with other therapeutic agents. The invention provides any of the uses, methods or compositions as defined herein wherein the compound of any embodiment of Formula I herein, or pharmaceutically acceptable salt thereof, or pharmaceutically acceptable solvate of said compound or salt, is used in combination with one or more other therapeutic agent discussed herein.

The administration of two or more compounds "in combination" means that all of the compounds are administered closely enough in time that each may generate a biological effect in the same time frame. The presence of one agent may alter the biological effects of the other compound(s). The two or more compounds may be administered simultaneously, concurrently or sequentially. Additionally, simultaneous administration may be carried out by mixing the compounds prior to administration or by administering the compounds at the same point in time but as separate dosage forms at the same or different site of administration.

The phrases "concurrent administration," "co-administration," "simultaneous administration," and "administered simultaneously" mean that the compounds are administered in combination.

In another embodiment, the invention provides methods of treatment that include administering compounds of the present invention in combination with one or more other pharmaceutical agents, wherein the one or more other pharmaceutical agents may be selected from the agents discussed herein.

In one embodiment, the compounds of this invention are administered with an anti-diabetic agent including but not limited to a biguanide (e.g., metformin), a sulfonylurea (e.g., tolbutamide, glibenclamide, gliclazide, chlorpropamide, tolazamide, acetohexamide, glyclopyramide, glimepiride, or glipizide), a thiazolidinedione (e.g., pioglitazone, rosiglitazone, or lobeglitazone), a glitazar (e.g., saroglitazar, aleglitazar, muraglitazar or tesaglitazar), a meglitinide (e.g., nateglinide, repaglinide), a dipeptidyl peptidase 4 (DPP-4) inhibitor (e.g., sitagliptin, vildagliptin, saxagliptin, linagliptin, gemigliptin, anagliptin, teneligliptin, alogliptin, trelagliptin, dutogliptin, or omarigliptin), a glitazone (e.g., pioglitazone, rosiglitazone, balaglitazone, rivoglitazone, or lobeglitazone), a sodium-glucose linked transporter 2 (SGLT2) inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a GPR40 agonist (FFAR1/FFA1 agonist, e.g. fasiglifam), glucose-dependent insulinotropic peptide (GIP) and analogues thereof, an alpha glucosidase inhibitor (e.g. voglibose, acarbose, or miglitol), or an insulin or an insulin analogue, including the pharmaceutically acceptable salts of the specifically named agents and the pharmaceutically acceptable solvates of said agents and salts.

In another embodiment, the compounds of this invention are administered with an anti-obesity agent including but not limited to peptide YY or an analogue thereof, a neuropeptide Y receptor type 2 (NPYR2) agonist, a NPYR1 or NPYR5 antagonist, a cannabinoid receptor type 1 (CB1R) antagonist, a lipase inhibitor (e.g., orlistat), a human proislet peptide (HIP), a melanocortin receptor 4 agonist (e.g., setmelanotide), a melanin concentrating hormone receptor 1 antagonist, a farnesoid X receptor (FXR) agonist (e.g. obeticholic acid), zonisamide, phentermine (alone or in combination with topiramate), a norepinephrine/dopamine reuptake inhibitor (e.g., buproprion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues thereof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1R agonist, e.g., liraglutide, exenatide, dulaglutide, albiglutide, lixisenatide, or semaglutide), including the pharmaceutically acceptable salts of the specifically named agents and the pharmaceutically acceptable solvates of said agents and salts.

In another embodiment, the compounds of this invention are administered with an agent to treat NASH including but not limited to PF-05221304, an FXR agonist (e.g., obeticholic acid), a PPAR α/δ agonist (e.g., elafibranor), a synthetic fatty acid-bile acid conjugate (e.g., aramchol), a caspase inhibitor (e.g., emricasan), an anti-lysyl oxidase homologue 2 (LOXL2) monoclonal antibody (e.g., simtuzumab), a galectin 3 inhibitor (e.g., GR-MD-02), a MAPK5 inhibitor (e.g., GS-4997), a dual antagonist of chemokine receptor 2 (CCR2) and CCR5 (e.g., cenicriviroc), a fibroblast growth factor 21 (FGF21) agonist (e.g., BMS-986036), a leukotriene D4 (LTD4) receptor antagonist (e.g., tipelukast), a niacin analogue (e.g., ARI 3037MO), an ASBT inhibitor (e.g., volixibat), an acetyl-CoA carboxylase (ACC) inhibitor (e.g., NDI 010976), a ketohexokinase (KHK) inhibitor, a diacylglyceryl acyltransferase 2 (DGAT2) inhibitor, a CB1 receptor antagonist, an anti-CB1R antibody, or an apoptosis signal-regulating kinase 1 (ASK1) inhibitor, including the pharmaceutically acceptable salts of the specifically named agents and the pharmaceutically acceptable solvates of said agents and salts.

These agents and compounds of the invention can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing these agents and/or compounds of the invention are prepared by methods known in the art, such as described in U.S. Pat. Nos. 4,485,045 and 4,544,545.

Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the invention may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy, 20th Ed., Mack Publishing (2000).

Sustained-release preparations may be used. Suitable examples of sustained-release preparations include semipermeable matrices of solid hydrophobic polymers containing the compound of Formulas I, II, or III, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(-)-3-hydroxybutyric acid.

The formulations to be used for intravenous administration must be sterile. This is readily accomplished by, for example, filtration through sterile filtration membranes. Compounds of the invention are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing a compound of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Kits

Another aspect of the invention provides kits comprising the compound of Formulas I, II, or III or pharmaceutical compositions comprising the compound of Formulas I, II, or III of the invention. A kit may include, in addition to the compound of Formulas I, II, or III, of the invention or pharmaceutical composition thereof, diagnostic or therapeutic agents. A kit may also include instructions for use in a diagnostic or therapeutic method. In some embodiments, the kit includes the compound of Formulas I, II, or III, or a pharmaceutical composition thereof and a diagnostic agent. In other embodiments, the kit includes the compound of Formulas I, II, or III, or a pharmaceutical composition thereof.

In yet another embodiment, the invention comprises kits that are suitable for use in performing the methods of treatment described herein. In one embodiment, the kit contains a first dosage form comprising one or more of the compounds of the invention in quantities sufficient to carry out the methods of the invention. In another embodiment, the kit comprises one or more compounds of the invention in quantities sufficient to carry out the methods of the invention and a container for the dosage and a container for the dosage.

Preparation

The compounds of Formulas I, II, or III, may be prepared by the general and specific methods described below, using the common general knowledge of one skilled in the art of synthetic organic chemistry. Such common general knowledge can be found in standard reference books such as Comprehensive Organic Chemistry, Ed. Barton and Ollis, Elsevier; Comprehensive Organic Transformations: A Guide to Functional Group Preparations, Larock, John Wiley and Sons; and Compendium of Organic Synthetic Methods, Vol. I-XII (published by Wiley-Interscience). The starting materials used herein are commercially available or may be prepared by routine methods known in the art.

In the preparation of the compounds of Formulas I, II, or III, it is noted that some of the preparation methods described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, Protective Groups in Organic Synthesis, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl (Boc), benzyloxycarbonyl (Cbz), and 9-fluorenylmethylenoxycarbonyl (Fmoc) for amines and lower alkyl or benzyl esters for carboxylic acids) which are generally not chemically reactive under the reaction conditions described and can typically be removed without chemically altering other functionality in the Formula I compounds.

The Schemes described below are intended to provide a general description of the methodology employed in the preparation of the compounds of the present invention. Some of the compounds of the present invention may contain single or multiple chiral centers with the stereochemical designation (R) or (S). It will be apparent to one skilled in the art that all of the synthetic transformations can be conducted in a similar manner whether the materials are enantioenriched or racemic. Moreover the resolution to the desired optically active material may take place at any desired point in the sequence using well known methods such as described herein and in the chemistry literature.

In the Schemes that follow, the variables Y, $Z^1$, $Z^2$, $Z^3$, $R^1$, $R^2$, $R^3$, $R^4$, m, p, and q are as described herein for compounds of Formulas I, II, or III unless otherwise noted. For the Schemes provided below, each $X^1$, $X^2$, $X^3$, and $X^4$ can independently be a leaving group such as any alkyl or aryl sulfonate (e.g., mesylate, tosylate, or triflate), or a halogen or any other group that can be displaced by an amine or utilized in a metal mediated coupling reaction. $X^4$ may also be a protected carboxylic acid (i.e., ester). When the protecting group is identified as $Pg^1$, it can be an alkyl amine protecting group such as benzyl, benzhydryl, or the like; a carbamate protecting group such as Boc, Cbz, or the like; or an amide protecting group such trifluoroacetamide. When the protecting group is identified as $Pg^2$, it can be acid protecting group such as methyl, ethyl, benzyl, t-butyl or the like. $R^{4a}$ is $C_{1-2}$alkyl, $C_{0-2}$alkylene-$C_{3-6}$cycloalkyl, $C_{0-2}$alkylene-$R^5$, or $C_{1-2}$alkylene-$R^6$, wherein said alkyl, alkylene, or cycloalkyl may be independently substituted as valency allows with 0 to 3 F atoms and 0 to 1 substituent independently selected from $C_{0-1}$alkylene-$OR^O$ and —$N(R^N)_2$.

The substituted pyridine 6 may be prepared as discussed in Scheme 1. A 2,6-dihalopyridine (1, synthesized or purchased commercially) can be reacted with a substituted boronic acid or boronate ester (2) in the presence of a palladium catalyst and ligand complex in the manner of a Suzuki reaction (Maluenda and Navarro, Molecules, 2015, 20, 7528-7557) to provide compounds of the general formula 3. For best results in the Suzuki reaction, the $X^2$ halogen is preferably Cl, Br or I. Reduction of the olefin to provide compounds of general structure 4 would be performed under an atmosphere of hydrogen (15-100 psi $H_2$) in an alcoholic solvent such as MeOH or EtOH or alternatively an aprotic organic solvent such as EtOAc or THF in the presence of an appropriate catalyst such as palladium on carbon, $Pd(OH)_2$ on carbon (Pearlman's catalyst) or $PtO_2$ (Adams catalyst). Alternatively, the reduction may be accomplished by alternative methods know to those skilled in the art using reagents such as triethyl silane or other silanes, under acid or metallic catalysis, or metallic reductants, such as magnesium or similar. Alternatively, the olefin can be functionalized by methods known to one skilled in the art to introduce $R^3$ groups. For example, the olefin could be hydroborated to produce an alcohol that could be alkylated or further converted to a nitrile, F or alkyl group. Conversion to compounds of general structure 5 can be accomplished by such manner as a Buchwald-Hartwig C—O coupling (Lundgren and Stradiotto, Aldrich Chimica Acta, 2012, 45, 59-65) between compounds of the general structure 4 and an appropriately substituted benzyl alcohol in the presence of a palladium or copper catalyst and ligand complex. A preferred $X^1$ halogen is Cl. These reactions are generally performed between 0 and 110° C. in aprotic organic solvents such as but not limited to 1,4-dioxane and $PhCH_3$ with added base such as $Cs_2CO_3$, LiHMDS or NaOtBu. Alternatively, reaction of 4 with an appropriately substituted benzyl alcohol in an aprotic solvent such as DMF or THF in the presence of a strong base such as NaH, KOtBu or LiHMDS can deliver compounds of the general structure 5. Preferred $X^1$ substituents for this reaction include F and Cl or sulfones (e.g. $SO_2Me$). Removal of $Pg^1$ could be effected with many methods described in literature to provide amines 6.

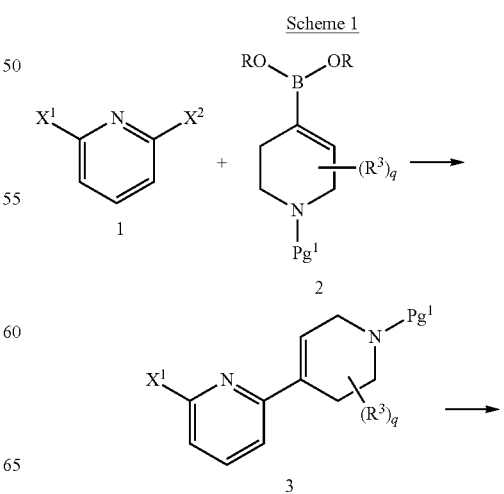

Scheme 1

-continued

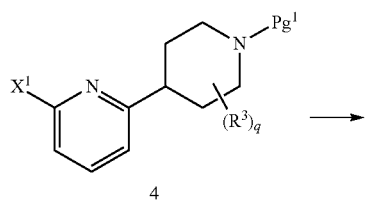

4

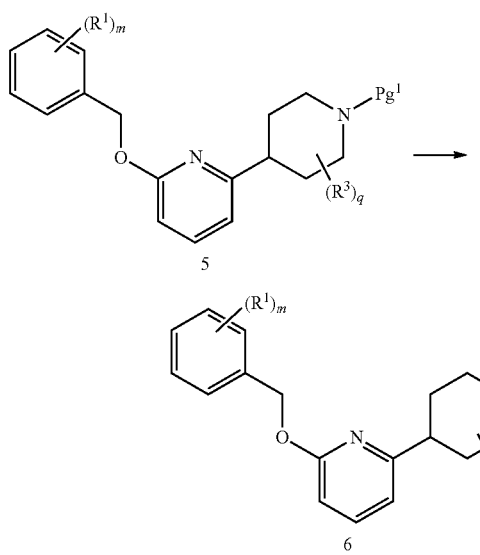

Alternatively, as shown in Scheme 2, appropriately substituted piperidine esters of general structure 7 can be reacted with 1 in the presence of strong base such as LiHMDS or LDA or other suitable base in an aprotic organic solvent such as THF to deliver compounds of the general structure 8. For best results in preparation of compounds such as 8, $X^2$ is preferably F or Cl. Removal of $Pg^2$ through ester hydrolysis to deliver carboxylic acids 9 can be performed in a traditional manner such as aqueous lithium, sodium or potassium hydroxide in a water miscible solvent such as MeOH, EtOH, THF or the like. Subjecting carboxylic acids 9 to heat (60-120° C.) in an appropriate solvent such as DCE or $PhCH_3$ will result in decarboxylation to deliver compounds of general formula 4 for use as described in Scheme 1 to obtain amines 6.

Scheme 2

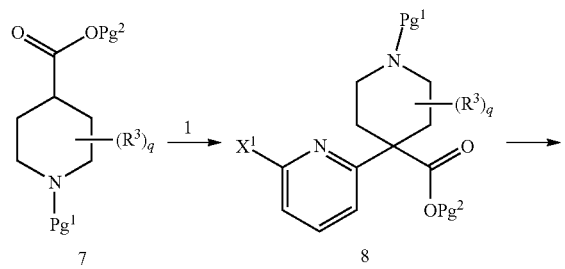

-continued

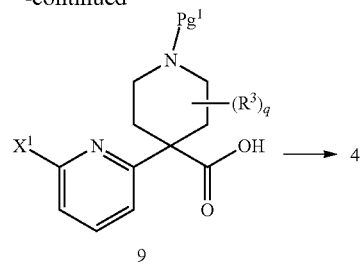

Scheme 3 provides an alternative preparation of compounds 5. Reaction of 1 with an appropriately substituted benzyl alcohol in an aprotic solvent such as DMF or THF in the presence of a strong base such as NaH, KOtBu or LiHMDS can deliver compounds of the general structure 10. Preferred $X^1$ substituents for this reaction include F and Cl, while $X^2$ substituents may include Cl, Br or I. Alternatively, Buchwald-Hartwig C—O coupling conditions similar to the preparation of 5 may be used to prepare 10 with preferred $X^1$ substituents Cl, Br or I. Suzuki reaction conditions similar to the preparation of general structure 3 may be used to prepare compounds of general structure 11 from 10. Preferred $X^2$ substituents for use in the coupling include Cl, Br or I. The olefin may be reduced via methods previously described in Scheme 1 to deliver compounds of general structure 5 that are then used to obtain amines 6.

Scheme 3

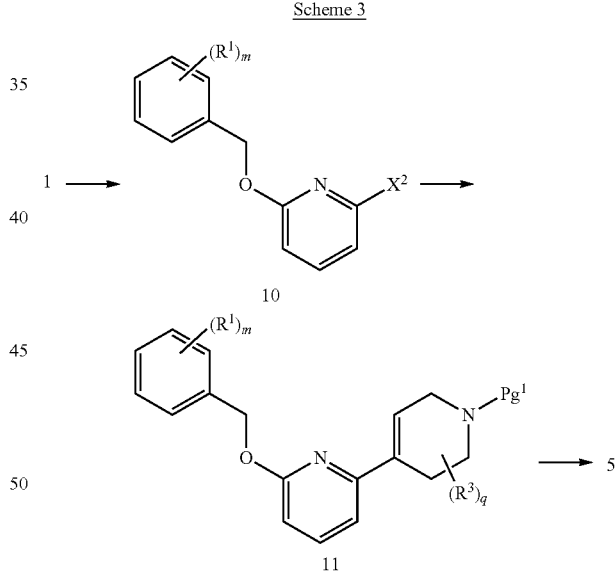

As provided in Scheme 4, conversion of 10 to compounds of general structure 12 can be accomplished by such manner as a Buchwald-Hartwig C—N coupling between compounds of the general structure 10 and an appropriately substituted and protected piperazine in the presence of a palladium or copper catalyst and ligand complex. Preferred $X^2$ substituents for use in the coupling include Cl, Br or I. These reactions are generally performed between 0 and 110° C. in aprotic organic solvents such as but not limited to 1,4-dioxane and $PhCH_3$ with added base such as $Cs_2CO_3$, LiHMDS or NaOtBu. Removal of $Pg^1$ could be effected with many methods described in literature to provide amines 13.

Scheme 4

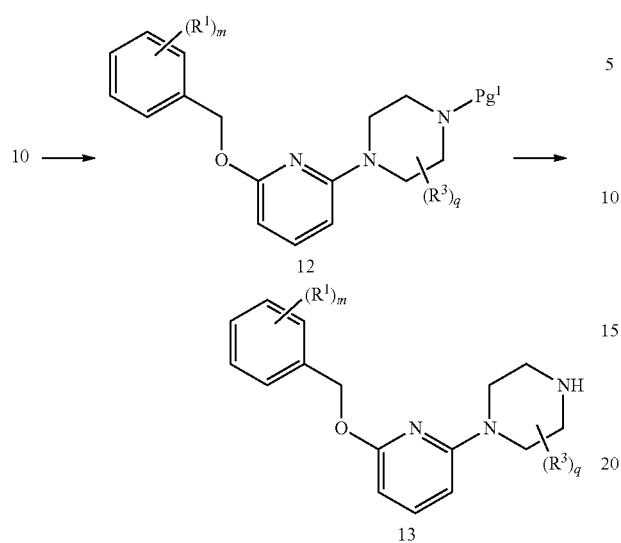

Compounds of the structure 14 (Scheme 5) may be converted to compounds of the general structure 15 through methods described previously in Scheme 1 or Scheme 2. Preferred $X^2$ substituents for use in the coupling include Cl, Br or I. Conversion of intermediates 15 into their respective N-oxides 16 can be performed with oxidants such as 3-chloroperoxybenzoic acid, Oxone® or other suitable oxidant. Rearrangement to compounds of structure 17 can be affected by treatment with an organic acid anhydride such as $Ac_2O$ or TFAA in aprotic solvents with an appropriate organic amine base such as $Et_3N$, DIPEA or other suitable base. Preparation of benzyl ethers of general structure 18 can be achieved by standard alkylation methods with appropriately substituted benzyl bromides or through standard Mitsunobu alkylation protocols (Swamy et al., Chem. Rev. 2009, 109, 2551-2651) with appropriately substituted benzyl alcohols. Removal of $Pg^1$ could be effected by many methods described in literature to provide amines 19.

Scheme 5

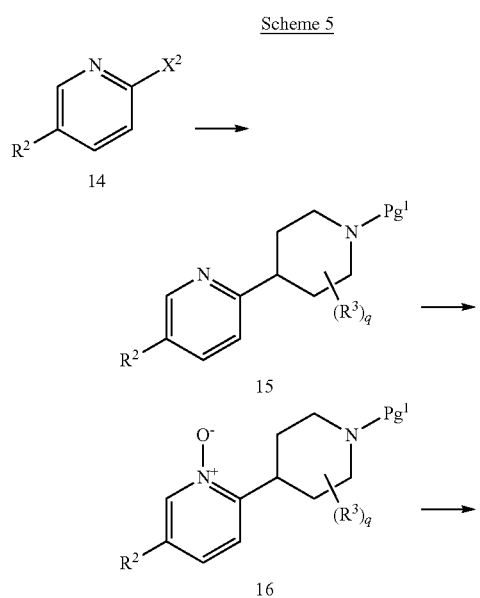

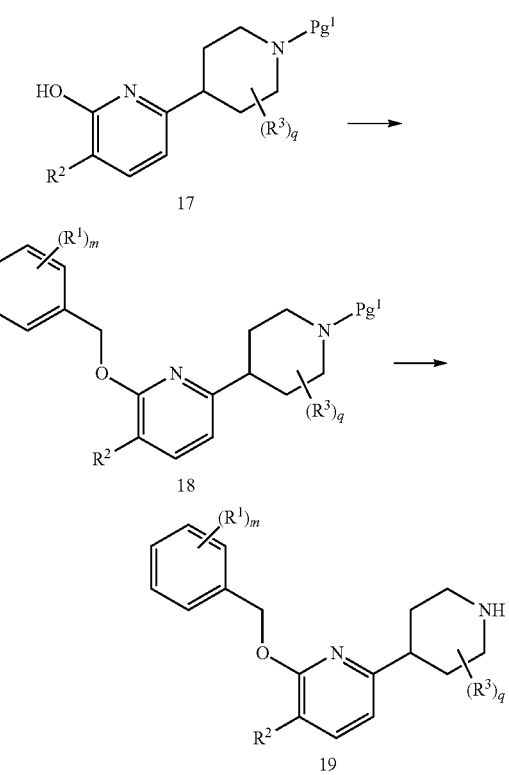

Compound 20 (Scheme 6) can be reacted with an appropriately substituted and protected piperazine in the presence of a suitable base such as $Cs_2CO_3$, $K_2CO_3$, NaH or LiHMDS or organic base such as $Et_3N$, DIPEA or DBU in a polar aprotic solvent such as but not limited to DMF, DMAc, DMSO or NMP to deliver compounds of the general structure 21. Preferred $X^1$ and $X^2$ substituents for use in the coupling include F and Cl; F is most preferred. Benzyl ethers 22 can be prepared analogously to compounds 10 in Scheme 3. Alternatively, by performing the above steps in reverse order, compounds of the general structure 25 can be prepared from the same starting material 20. Removal of $Pg^1$ could be effected by many methods described in the literature to provide amines 23 and 26.

Scheme 6

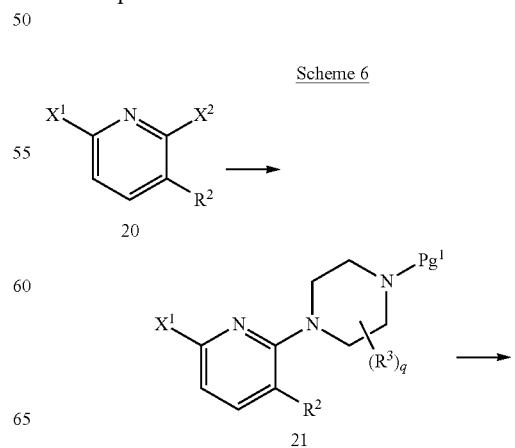

-continued

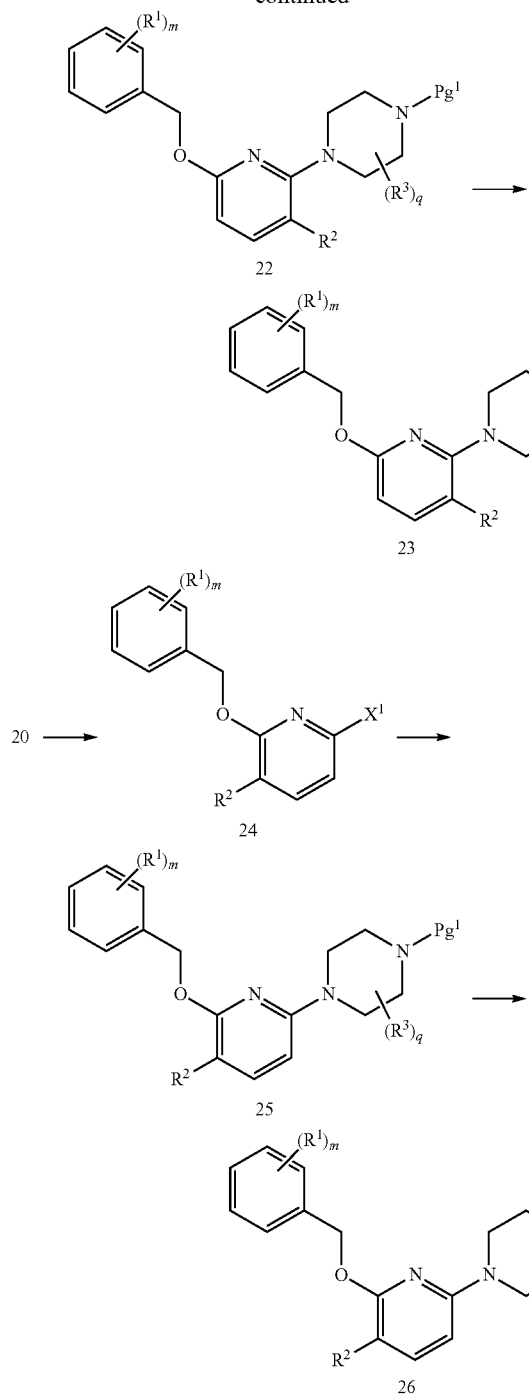

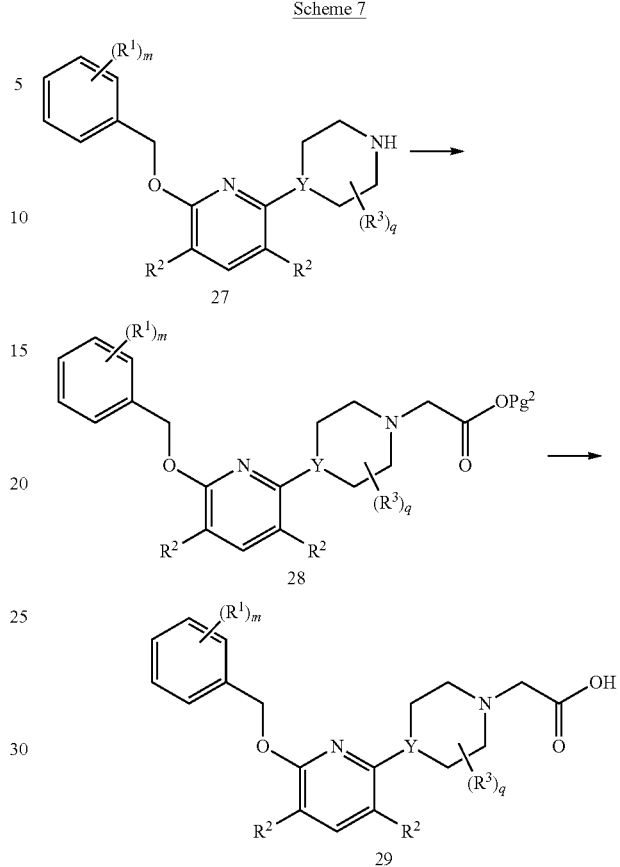

Scheme 7

Amine compounds prepared via methods described in Schemes 1-6, collectively designated as amines 27, can be alkylated with a protected 2-bromoacetate in the presence of a suitable base such as $K_2CO_3$, $Et_3N$, NaH or LiHMDS in a polar aprotic solvent such as but not limited to DMF, DMAc, DMSO or NMP to deliver compounds of the general structure 28. Standard ester hydrolysis can be performed to provide acids 29. If $Pg^2$ is t-butyl, standard acidic deprotection methods such as TFA/DCM, HCl/1,4-dioxane, HCl/EtOAc or other suitable conditions may be used to deliver acids 29.

Compounds of general structure 30 (Scheme 8) can react with amines $R^4NH_2$ in the presence of bases such as sodium-, potassium-, or cesium carbonate, -bicarbonate, hydroxide, acetate, or an organic amine base such as $Et_3N$, DIPEA, DBU, and the like in a polar aprotic solvent such as but not limited to THF, DMF, DMAc, DMSO or NMP or a protic solvent such as water, MeOH, EtOH or iPrOH or a mixture thereof to deliver compounds of the general structure 31. One will note that if an example provides an $R^4$ with a resolved enantiomeric center, the other enantiomer or a racemix mixture thereof could be obtained by selection of the appropriate starting material. Preferred $X^3$ substituents include F, Cl, and Br, preferred $X^4$ groups include Cl, Br, —$CO_2$—$Pg^2$. Reduction of the nitro group can be affected by hydrogenation at 1-6 atm $H_2$ with a metal catalyst such as palladium on carbon or Raney nickel in a protic solvent such as MeOH or EtOH or aprotic solvent such as DMF, THF or EtOAc. Alternatively, the nitro group may be reduced with iron, zinc, $SnCl_2$ or other suitable metal in an acidic media such as 1N HCl, AcOH or aqueous $NH_4Cl$ in THF to provide compounds of general structure 32 (Scheme 8a). Compounds such as 33 may be acylated by acyl halides by standard fashion or by carboxylates via standard amide coupling protocols to provide compounds 34. Reduction to compounds 35 may be performed under standard conditions with reducing agents such as LAH or $BH_3$-THF or $BH_3$-DMS (Scheme 8b).

Scheme 8 a)

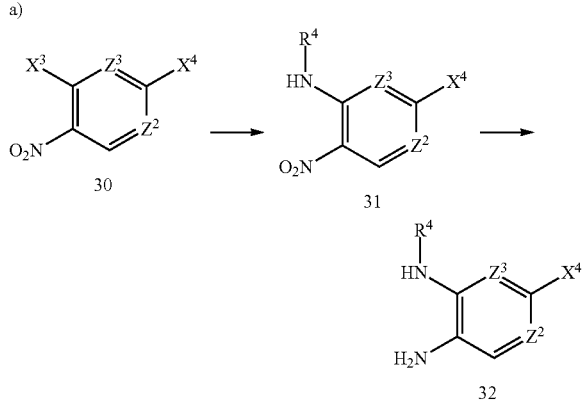

b)

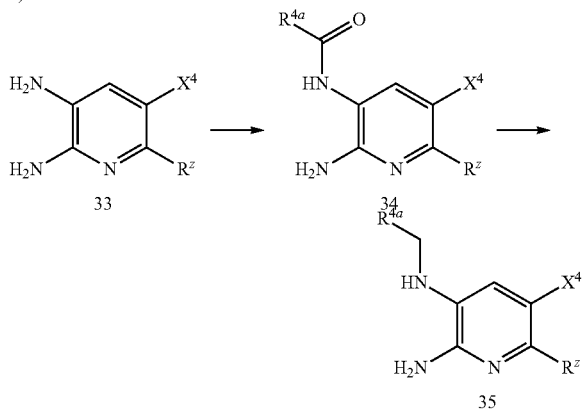

Diamine compounds 32 and 35 prepared via methods described in Schemes 8a and 8b, collectively designated as diamine 37 (Scheme 9), may be acylated with acids of general structure 29 under standard amide coupling protocols to deliver amines 38 which will exist as a mixture from 100% 38a to 100% 38b. This mixture of amines 38 may be cyclized to deliver compounds of general structure 39 by a variety of methods. Amines 38 may be heated with a dehydrating agent such as $T_3P®$ or an alkyl alcohol such as n-butanol under microwave conditions (10-60 min at 120-180° C.) to deliver compounds 39. Alternatively, the mixture of compounds 38 may be heated under acidic conditions such as AcOH from 60-100° C. or under basic conditions such as aqueous NaOH or KOH in 1,4-dioxane from 60-100° C. to provide 39. Compounds of general structure 39 ($X^4$=Cl, Br or I) can be converted to esters of structure 40 by palladium-catalyzed carbonylation under a 15-100 psi carbon monoxide atmosphere at a temperature from 20-100 at a temperature from 20-100° C. with an appropriate alcohol such as MeOH or EtOH or other alkyl alcohol. Hydrolysis of ester 40 can be performed as described in Scheme 7 to provide acids 41. For compounds 38 where $X^4$=$CO_2$—$Pg^2$ conversion to ester 40 proceeds under similar conditions as described previously except for use of the basic cyclization method where compound 41 may be isolated directly from the reaction mixture. For compounds 40 where $X^4$ is $CO_2{}^tBu$, deprotection to acid 41 can be performed under acidic conditions described in Scheme 7.

Scheme 9

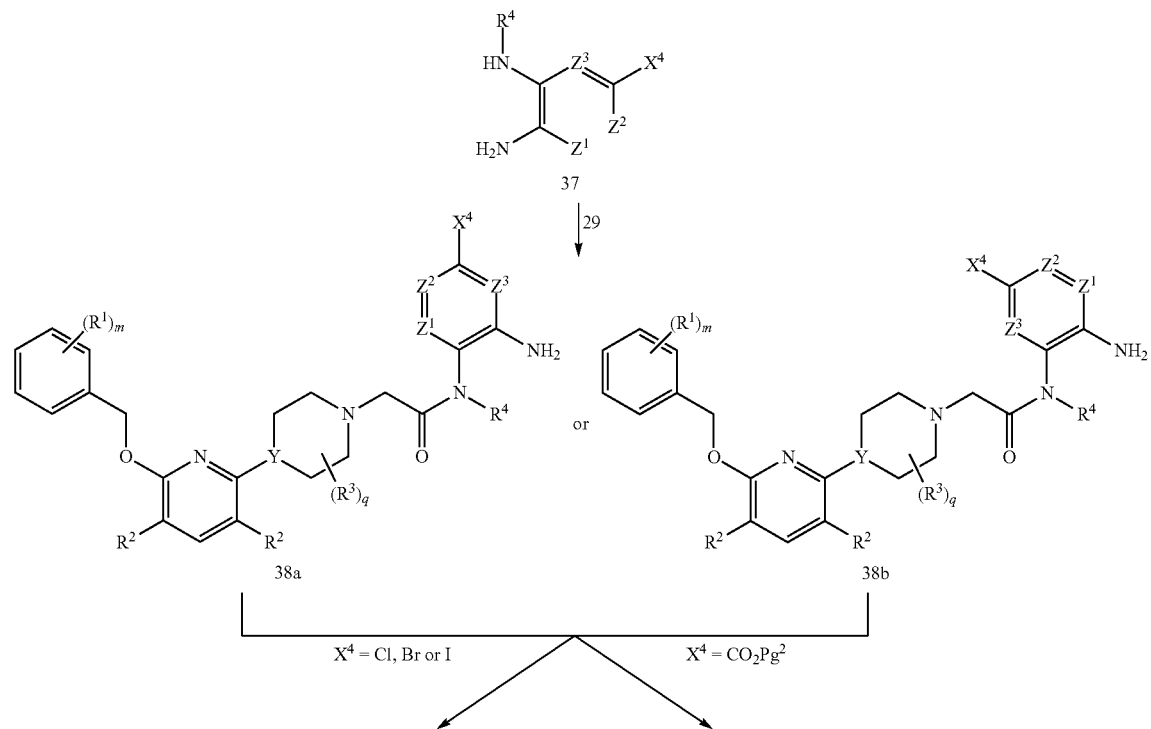

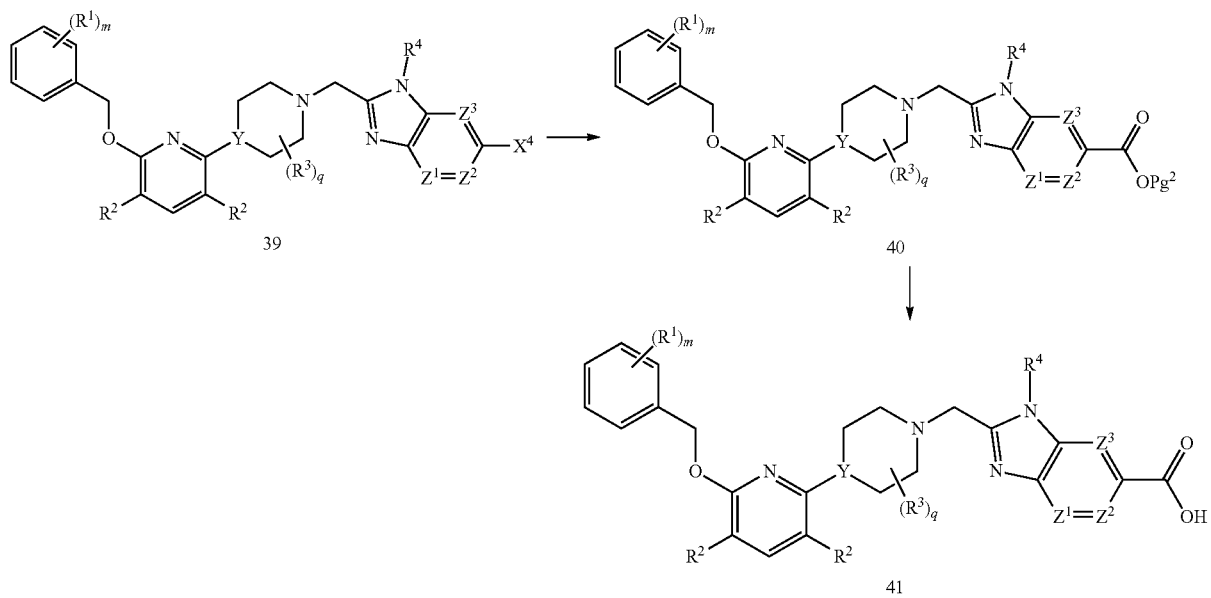

Additionally, diamine 37 may be converted to the 2-chloromethyl benzimidazole 42 (Scheme 10) by several methods. Treatment with 2-chloroacetyl chloride in an aprotic solvent such as 1,4-dioxane followed by heating at 40-100° C. for 2-18 h can deliver the desired benzimidazole 42 where $Z^1$, $Z^2$ and $Z^3$ are CH. In the cases where $Z^1$, $Z^2$ and $Z^3$ are not all $CR^z$, after treatment with 2-chloroacetyl chloride in an aprotic solvent such as 1,4-dioxane for 30 min to 4 h, the solvent is exchanged for an acidic media such as AcOH or TFA followed by heating at 40-100° C. for 2-18 h to provide the desired compound 42. Diamine 37 can also be treated with chloroacetic anhydride at a temperature between 0 and 80° C. in an aprotic solvent such as, but not limited to 1,4-dioxane, THF or MeCN, followed by heating for 2 to 18 h at 60-100° C. to deliver the desired compound 42. In addition, diamine 37 can be treated with 2-chloro-1,1,1-trimethoxyethane in an aprotic solvent such as, but not limited to 1,4-dioxane, THF or MeCN, or a protic solvent, e.g., MeOH or EtOH, in the presence of an acid catalyst, e.g., pTSA, at 20-100° C. Alternatively, diamines 37 may be heated 100-180° C. with 2-hydroxyacetic acid in an aprotic solvent, such as but not limited to mesitylene, to provide a hydroxymethyl intermediate. Conversion of the hydroxymethyl group to the chloromethyl compound 42 may be accomplished by standard methods, including treatment with $SOCl_2$ in an aprotic solvent. Compounds of general structure 42 can be reacted with compounds 27 in the presence of bases such as sodium-, potassium-, or cesium carbonate, -bicarbonate, NaH or an organic amine base such as $Et_3N$, DIPEA, DBU, and the like in a polar aprotic solvent, such as but not limited to THF, MeCN, DMF, DMAc, DMSO or NMP, to deliver compounds 39 ($X^4$=Cl, Br, I) or compounds 40 ($X^4$=$CO_2$—$Pg^2$) that are then used to obtain compounds 41 via methods described in Scheme 9.

Scheme 10

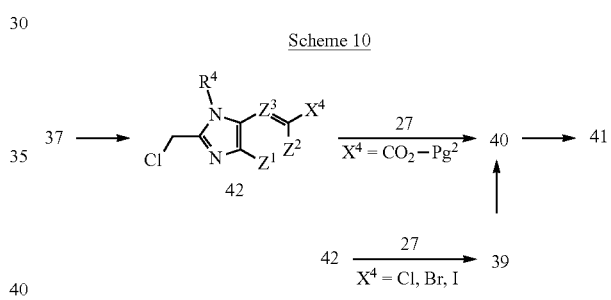

Alternatively, compounds of general structure 42 can be reacted with appropriately substituted and protected piperazines to provide compounds 43 (Scheme 11). Removal of $Pg^1$ could be effected with many methods described in literature to provide amines 44. Conversion to compounds of general structure 39 ($X^4$=Cl, Br or I) or 40 ($X^4$=$CO_2$—$Pg^2$) can be accomplished by such manner as a Buchwald-Hartwig C—N coupling between compounds of the general structures 10 and as described previously in Scheme 4. Compounds of general structure 39 or 40 can then be used to obtain compounds of structure 41 via methods described in Scheme 9.

Scheme 11

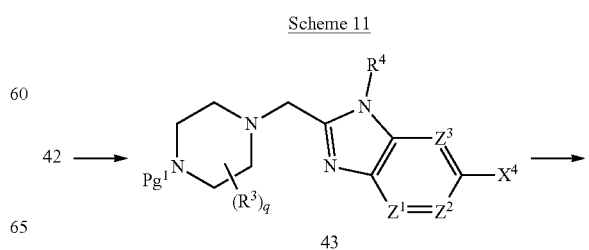

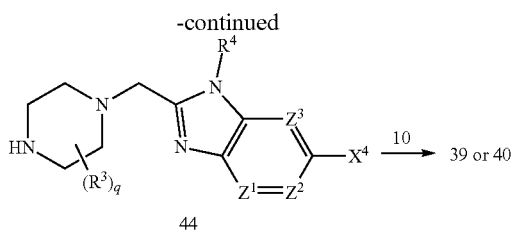

EXAMPLES

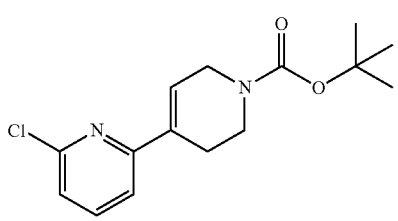 [SMILES: CC(C)(C)OC(=O)N1CC=C(c2cccc(Cl)n2)CC1]

Intermediate 1 tert-Butyl 6-chloro-3',6'-dihydro-[2,4'-bipyridine]-1' (2'H)-carboxylate

A reaction vessel equipped with a reflux condenser was charged with of tert-butyl 4-(4,4,5,5-tetramethyl-1,3,2-dioxaborolan-2-yl)-3,6-dihydropyridine-1(2H)-carboxylate (1.5 g, 4.9 mmol), 2,6-dichloropyridine (1.4 g, 9.7 mmol), Pd(dppf)Cl$_2$ (0.34 g, 0.49 mmol), and cesium carbonate (3.5 g, 11 mmol). A sparged solution of 1,4-dioxane (15 mL) and water (3 mL) was added and the mixture was heated to 90° C. under N$_2$ (g). After 7 h, the mixture was allowed to cool to RT and filtered through a pad of Celite® with EtOAc (50 mL). The mixture was diluted with water (20 mL), the aq. layer was extracted with EtOAc (3×50 mL), and the combined organic layers were dried over anhydrous Na$_2$SO$_4$, filtered, and the solvent removed under reduced pressure. The crude material was purified using column chromatography eluting with 10% EtOAc in heptane to obtain Intermediate 1 as a colorless oil (1.1 g, 75%). $^1$H NMR (CDCl$_3$) δ: 7.57 (t, 1H), 7.23 (d, 1H), 7.14 (d, 1H), 6.66 (br s, 1H), 4.11 (br s, 2H), 3.61 (br s, 2H), 2.57 (br s, 2H), 1.43-1.52 (m, 9H).

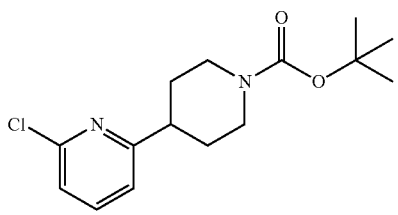 [SMILES: CC(C)(C)OC(=O)N1CCC(c2cccc(Cl)n2)CC1]

Intermediate 2 tert-Butyl 4-(6-chloropyridin-2-yl)piperidine-1-carboxylate

To a stirred solution of Intermediate 1 (0.55 g, 1.9 mmol) in MeOH (19 mL) was added PtO$_2$ (0.042 g, 0.19 mmol).

The solution was subject to a hydrogen atmosphere (30 PSI) at RT. After 3 h, the solution was filtered through a Celite® plug, washed with MeOH (2×15 mL) and concentrated under reduced pressure. The crude material was purified using column chromatography eluting with 30% EtOAc in heptane to obtain Intermediate 2 (0.22 g, 40%) as a colorless oil. $^1$H NMR (CDCl$_3$) δ: 7.57 (t, 1H), 7.15 (d, 1H), 7.05 (d, 1H), 4.23 (br s, 2H), 2.80 (d, 3H), 1.89 (d, 2H), 1.60-1.73 (m, 2H), 1.45 (s, 9H).

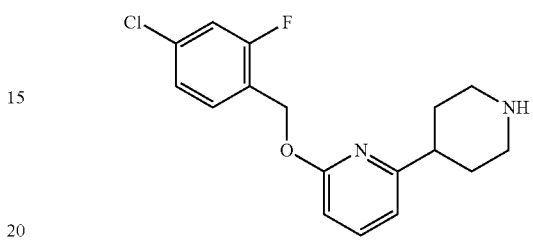

Intermediate 3

2-((4-Chloro-2-fluorobenzyl)oxy)-6-(piperidin-4-yl) pyridine bis(4-methylbenzenesulfonate)

Step 1

A reaction vessel equipped with a reflux condenser was charged with Intermediate 2 (6.5 g, 22 mmol), (4-chloro-2-fluorophenyl)methanol (3.5 g, 22 mmol), Pd$_2$(dba)$_3$ (1.0 g, 1.1 mmol), BINAP (1.4 g, 2.2 mmol) and cesium carbonate (14 g, 44 mmol). Toluene (73 mL) was added and the mixture was heated to 100° C. After 16 h, the mixture was allowed to cool to RT, filtered through Celite® with EtOAc (100 mL) and concentrated under reduced pressure. The crude material was purified using column chromatography eluting with 10% EtOAc in PE to obtain tert-butyl 4-(6-((4-chloro-2-fluorobenzyl)oxy)pyridin-2-yl)piperidine-1-carboxylate as a yellow oil (7.6 g, 82%). $^1$H NMR (CDCl$_3$) δ: 7.51 (dd, 1H), 7.39-7.47 (m, 1H), 7.06-7.18 (m, 2H), 6.73 (d, 1H), 6.62 (d, 1H), 5.40 (s, 2H), 4.22 (br s, 2H), 2.83 (m, 2H), 2.73 (tt, 1H), 1.81-1.94 (m, 2H), 1.64-1.79 (m, 2H), 1.50 (s, 9H).

Step 2

To a stirred solution of tert-butyl 4-(6-((4-chloro-2-fluorobenzyl)oxy)pyridin-2-yl)piperidine-1-carboxylate (50 g, 120 mmol) in EtOAc (700 mL) was added pTSA.H$_2$O (59 g, 310 mmol). The mixture was heated to 60° C. After 30 min, the solution was allowed to cool to RT. The resultant solid precipitate was slurried for 16 h, collected by filtration and then dried under reduced pressure to obtain Intermediate 3 as a solid (81 g, quant). $^1$H NMR (600 MHz, DMSO-d6) δ: 8.55 (br s, 1H), 8.28 (d, 1H), 7.68 (t, 1H), 7.60 (t, 1H), 7.48 (d, 4H), 7.32 (d, 1H), 7.12 (d, 4H), 6.89 (d, 1H), 6.74 (d, 1H), 5.38 (s, 2H), 3.37 (d, 2H), 2.98-3.09 (m, 2H), 2.87-2.96 (m, 1H), 2.29 (s, 6H), 1.96-2.01 (m, 2H), 1.80-1.94 (m, 2H).

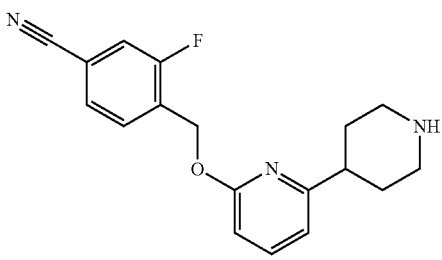

Intermediate 4

3-Fluoro-4-(((6-(piperidin-4-yl)pyridin-2-yl)oxy)methyl)benzonitrile bis(4-methylbenzenesulfonate)

Step 1

To a solution of diisopropylamine (92 mL, 656 mmol) in THF (350 mL) at −26° C. was added n-butyllithium in heptanes (2.6 M, 250 mL, 650 mmol) over 15 min. The mixture was cooled to −30° C. and a solution of 1-(tert-butyl) 4-methyl piperidine-1,4-dicarboxylate (156 g, 641 mmol) in THF (150 mL) added over 25 min. After 10 min, a solution of 2,6-dichloropyridine (94 g, 635 mmol) in THF (150 mL) was added over 2 min. The mixture was warmed to 25° C. for 2.5 h and then cooled to 8° C. and treated with 6 M HCl (125 mL) over 20 min to bring the pH of the mixture to ~7-8. The mixture was diluted with water (100 mL) and MTBE (150 mL) and the layers separated. The aq. layer was extracted with MTBE (150 mL) and the combined organic layers washed with brine (150 mL), dried over $MgSO_4$. The solvent was removed under reduced pressure to provide crude 1-(tert-butyl) 4-methyl 4-(6-chloropyridin-2-yl)piperidine-1,4-dicarboxylate (241 g) as a yellow oil, which was used in the next step without purification. $^1$H NMR of a purified sample (400 MHz, $CDCl_3$) δ: 7.62 (t, 1H), 7.21 (d, 2H), 3.83 (br s, 2H), 3.71 (s, 3H), 3.14 (br s, 2H), 2.41 (d, 2H), 2.08 (ddd, 2H), 1.45 (s, 9H).

Step 2

The crude 1-(tert-butyl) 4-methyl 4-(6-chloropyridin-2-yl)piperidine-1,4-dicarboxylate (241 g, assumed 635 mmol) was dissolved in MeOH (400 mL) at 43° C. and treated with 4 M aq. NaOH (300 mL) over 20 min. The mixture was warmed to 50° C. and stirred for 35 min. The mixture was then cooled to 11° C. and the pH adjusted to ~2 by addition of 6 M HCl (200 mL) over 25 min while continuing to cool to 5° C., after which a solid precipitate formed. The slurry was diluted with water (300 mL) and stirred for 40 min, after which the solid was collected by filtration, washed with water and then dried under vacuum at 50° C. to provide a white solid (224 g). The solid was triturated in heptane (750 mL) at 45° C. for 45 min. The mixture was cooled to 16° C. and the solid collected by filtration, washed with heptane and dried to provide 1-(tert-butoxycarbonyl)-4-(6-chloropyridin-2-yl)piperidine-4-carboxylic acid (187 g, 549 mmol, 86% for two steps) as a white solid.

Step 3

A solution of 1-(tert-butoxycarbonyl)-4-(6-chloropyridin-2-yl)piperidine-4-carboxylic acid (187 g, 549 mmol) in DCE (900 mL) was heated at 82° C. overnight and then cooled to 20° C. The mixture was treated with Magnesol® (30 g) for 40 min. The slurry was filtered through a pad of Magnesol® (30 g) and the solids washed with 1:1 MTBE:heptane (300 mL). The filtrate was concentrated under reduced pressure to give a pale yellow solid, which was triturated in heptane (250 mL) at 50° C. The mixture was cooled to 12° C. and the solid collected by filtration, washed with heptane and dried under vacuum at 45° C. to provide tert-butyl 4-(6-chloropyridin-2-yl)piperidine-1-carboxylate (143 g, 481 mmol, 88%) as a solid. $^1$H NMR (600 MHz, $CDCl_3$) δ: 7.58 (t, 1H), 7.17 (d, 1H), 7.06 (d, 1H), 4.25 (br s, 2H), 2.66-2.93 (m, 3H), 1.91 (d, 2H), 1.69 (qd, 2H), 1.47 (s, 9H).

Step 4

A mixture of tert-butyl 4-(6-chloropyridin-2-yl)piperidine-1-carboxylate (100 g, 337 mmol), 3-fluoro-4-(hydroxymethyl)benzonitrile (53.9 g, 357 mmol) and $Cs_2CO_3$ (170 g, 522 mmol) in dioxane (900 mL) was deoxygenated with 5 vacuum/nitrogen fill cycles. JohnPhos ([1,1'-biphenyl]-2-yl-di-tert-butylphosphine, 2.02 g, 6.77 mmol) and $Pd_2(dba)_3$ (3.10 g, 3.39 mmol) were added and 2 further vacuum/nitrogen fill cycles applied. The mixture was then heated at 95° C. for 3 h. Additional JohnPhos (660 mg, 2.21 mmol) and $Pd_2(dba)_3$ (990 mg, 1.08 mmol) were added and heating continued overnight. The mixture was cooled to 20° C. and filtered through a pad of Celite®, washing with MTBE (250 mL). The filtrate was concentrated under reduced pressure to give a red-orange oil (174 g). This material was dissolved in 30% MTBE/hexane (600 mL), stirred with Magnesol® (20 g) and Darco® G-60 (10 g) for 70 min and then filtered through a pad of silica (100 g), washing with 50% MTBE/hexane (600 mL). The filtrate was concentrated under reduced pressure and azeotroped with EtOAc (100 mL) to provide tert-butyl 4-(6-((4-cyano-2-fluorobenzyl)oxy)pyridin-2-yl)piperidine-1-carboxylate as an oil (147 g), which was used without further purification. $^1$H NMR of a purified sample (600 MHz, $CDCl_3$) δ: 7.62 (t, 1H), 7.53 (t, 1H), 7.44 (d, 1H), 7.37 (d, 1H), 6.75 (d, 1H), 6.65 (d, 1H), 5.49 (s, 2H), 4.20 (br s, 2H), 2.81 (br s, 2H), 2.70 (tt, 1H), 1.82 (d, 2H), 1.67 (d, 2H), 1.49 (s, 9H).

Step 5

To a stirred solution of tert-butyl 4-(6-((4-cyano-2-fluorobenzyl)oxy)pyridin-2-yl)piperidine-1-carboxylate (147 g, assumed 337 mmol) in EtOAc (1.8 L) at RT was added pTSA.$H_2O$ (161 g, 846 mmol). The mixture was heated to 60° C., which resulted in gas evolution and solid formation. The mixture was stirred for 1.5 h, after which additional pTSA.$H_2O$ (12 g, 63 mmol) added, and stirring continued for 45 min. The slurry was cooled to 17° C. and the solids collected by filtration, washed with EtOAc (200 mL), and dried to provide 205 g of solid. This material was dissolved in MeOH (500 mL) at 55° C. and diluted with EtOAc (1 L). The resulting slurry was cooled to 20° C. and the solids collected by filtration, washed with 9:1 EtOAc:MeOH (100 mL) and EtOAc (250 mL) and dried to provide Intermediate 4 (176.6 g, 269 mmol, 80% for two steps) as a white solid. $^1$H NMR (600 MHz, DMSO-d6) δ: 8.53 (br s, 1H), 8.26 (br s, 1H), 7.89 (d, 1H), 7.67-7.78 (m, 3H), 7.48 (d, 4H), 7.11 (d, 4H), 6.90 (d, 1H), 6.79 (d, 1H), 5.48 (s, 2H), 3.35 (d, 2H), 2.96-3.09 (m, 2H), 2.79-2.96 (m, 1H), 2.29 (s, 6H), 1.93-2.03 (m, 2H), 1.77-1.90 (m, 2H).

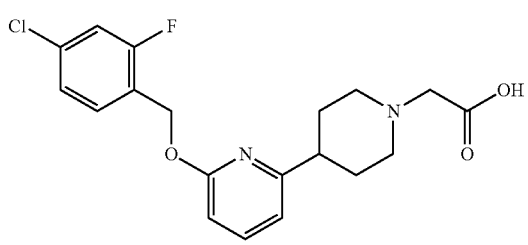 [SMILES: O=C(O)CN1CCC(c2cccc(OCc3ccc(Cl)cc3F)n2)CC1]

Intermediate 5

2-(4-(6-((4-Chloro-2-fluorobenzyl)oxy)pyridin-2-yl) piperidin-1-yl)acetic acid

Step 1

To a mixture of Intermediate 3 (70.0 g, 209 mmol) and K$_2$CO$_3$ (118 g, 863 mmol) in DMF (800 mL) was added ethyl 2-bromoacetate (39.9 g, 236 mmol) portionwise. The mixture was stirred at 30° C. for 1 h. The mixture was diluted with water (500 mL), and extracted with EtOAc (400 mL×3). The organic layers were combined, dried over Na$_2$SO$_4$, filtered and concentrated under reduced pressure. The crude product was purified by flash chromatography (silica gel column, 10:1 PE/EtOAc) to afford 74 g of ethyl 2-(4-(6-((4-chloro-2-fluorobenzyl)oxy)pyridin-2-yl)piperidin-1-yl)acetate (84%) as a yellow oil. $^1$H NMR (400 MHz, CDCl$_3$) δ 7.51 (t, 1H), 7.45 (t, 1H), 7.09-7.17 (m, 2H), 6.75 (d, 1H), 6.61 (d, 1H), 5.41 (s, 2H), 4.22 (q, 2H), 3.27 (s, 2H), 3.07 (d, 2H), 2.54-2.65 (m, 1H), 2.32 (td, 2H), 1.93-2.07 (m, 2H), 1.85-1.92 (m, 2H), 1.30 (t, 3H).

Step 2

To a solution of ethyl 2-(4-(6-((4-chloro-2-fluorobenzyl) oxy)pyridin-2-yl)piperidin-1-yl)acetate (73 g, 179 mmol) in EtOH (270 mL) was added 5 M NaOH (156 mL, 780 mmol). The solution was stirred at 25° C. for 2 h. The mixture was acidified to pH ~3.5 with 1 M HCl. The resulting precipitate was collected by filtration. The solids were washed with water and dried under vacuum to afford 54 g of Intermediate 5 (78%) as a pale yellow solid. $^1$H NMR (400 MHz, DMSO-d6) δ 7.65-7.72 (m, 1H), 7.62 (t, 1H), 7.47 (dd, 1H), 7.32 (dd, 1H), 6.92 (d, 1H), 6.73 (d, 1H), 5.40 (s, 2H), 4.13 (s, 2H), 3.58 (d, 2H), 3.16-3.26 (m, 2H), 2.89 (br s, 1H), 2.00-2.19 (m, 4H); LC-MS=378.8.

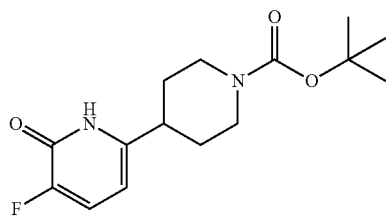 [SMILES: CC(C)(C)OC(=O)N1CCC(c2ccc(F)c(=O)[nH]2)CC1]

Intermediate 6 tert-Butyl 4-(5-fluoro-6-oxo-1,6-dihydropyridin-2-yl)piperidine-1-carboxylate

Step 1

To a solution of 2-bromo-5-fluoropyridine (20 g, 110 mmol) and tert-butyl 4-(4,4,5,5-tetramethyl-1,3,2-dioxaborolan-2-yl)-3,6-dihydropyridine-1(2H)-carboxylate (35.1 g, 114 mmol) in THF (240 mL) was added Pd(PPh$_3$)$_4$(13.1 g, 11.4 mmol), and Na$_2$CO$_3$ (24.1 g, 227 mmol). The resulting yellow reaction mixture was stirred at 90° C. for 48 h. The reaction was cooled to RT, diluted with water (100 mL) and extracted with EtOAc (3×200 mL). The combined organic extracts were washed with brine (100 mL), dried over Na$_2$SO$_4$, filtered and concentrated under reduced pressure. The crude product was purified by flash chromatography (1-20% EtOAc/PE gradient) to deliver tert-butyl 5-fluoro-3',6'-dihydro-[2,4'-bipyridine]-1'(2'H)-carboxylate (31 g, 98%) as a colorless oil. $^1$H NMR (CDCl$_3$) δ 8.41 (t, 1H), 7.37 (dd, 2H), 6.52 (br s, 1H), 4.13 (d, 2H), 3.65 (m, 2H), 2.57-2.70 (m, 2H), 1.49 (s, 9H).

Step 2

To a colorless solution of tert-butyl 5-fluoro-3',6'-dihydro-[2,4'-bipyridine]-1'(2'H)-carboxylate (31 g, 110 mmol) in EtOAc (300 mL) was added 10% wet Pd/C (1.2 g, 5.6 mmol). The black mixture was stirred at 25° C. under H$_2$ (15 psi) for 16 h. The mixture was filtered through a Celite® pad and concentrated under reduced pressure to deliver tert-butyl 4-(5-fluoropyridin-2-yl)piperidine-1-carboxylate (31 g, 99%) as a colorless oil. $^1$H NMR (CDCl$_3$) δ 8.39 (d, 1H), 7.34 (td, 1H), 7.15 (dd, 1H), 4.25 (br s, 2H), 2.74-2.93 (m, 3H), 1.89 (d, 2H), 1.69 (qd, 2H), 1.48 (s, 9H).

Step 3

To a solution of deliver tert-butyl 4-(5-fluoropyridin-2-yl)piperidine-1-carboxylate (31 g, 110 mmol) in DCM (400 mL) was added m-CPBA (47.7 g, 276 mmol) at 0° C. The resulting reaction mixture was stirred at RT for 16 h. The white suspension was filtered, and the filtrate then quenched with aq. Na$_2$SO$_3$ (200 mL). The aq. layer was separated and then extracted with DCM (3×200). The combined organic layers were washed with brine (50 mL), dried over anhydrous Na$_2$SO$_4$, filtered, and concentrated under reduced pressure. The crude product was purified by flash chromatography (0.5-4% MeOH/DCM gradient) to deliver 2-(1-(tert-butoxycarbonyl)piperidin-4-yl)-5-fluoropyridine 1-oxide (20 g, 61%) as a solid. $^1$H NMR (CDCl$_3$) δ 8.21 (dd, 1H), 7.11-7.18 (m, 1H), 7.02-7.09 (m, 1H), 4.26 (br s, 2H), 3.58 (m, 1H), 2.89 (br s, 2H), 2.02 (d, 2H), 1.43-1.52 (m, 11H).

Step 4

To a solution of 2-(1-(tert-butoxycarbonyl)piperidin-4-yl)-5-fluoropyridine 1-oxide (10 g, 34 mmol) in THF (150 mL) at 0° C. was added Et$_3$N (6.83 g, 67.5 mmol), and TFAA (70.9 g, 337 mmol), dropwise. The mixture was stirred at 0° C. for 1 h, and RT for 16 h. The light yellow solution was quenched with aq. NaHCO$_3$ (400 mL). The pH was adjusted to ~4 with TFA and the mixture extracted with EtOAc (3×200 mL). The combined organic extracts were washed with brine (50 mL), dried over anhydrous Na$_2$SO$_4$, filtered, and concentrated under reduced pressure. The crude product was purified by flash chromatography (4-80% EtOAc in PE) to give Intermediate 6 (5.4 g, 54%) as a solid. $^1$H NMR (CDCl$_3$) δ 12.92 (br s, 1H), 7.17 (dd, 1H), 5.97 (dd, 1H), 4.25 (br s, 2H), 2.86 (br s, 2H), 2.72 (t, 1H), 1.95 (d, 2H), 1.56 (qd, 2H), 1.48 (s, 9H).

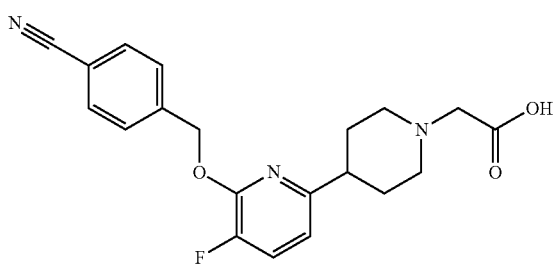 [SMILES: N#Cc1ccc(COc2nc(C3CCN(CC(=O)O)CC3)ccc2F)cc1]

Intermediate 7

2-(4-(6-((4-Cyanobenzyl)oxy)-5-fluoropyridin-2-yl)piperidin-1-yl)acetic acid

Step 1

To a solution of Intermediate 6 (2.0 g, 6.8 mmol), 4-cyanobenzyl alcohol (1.35 g, 10.1 mmol) and 1,1'-(azodicarbonyl)dipiperidine (2.55 g, 10.1 mmol) in PhCH$_3$ (30 mL) was added tri-n-butylphosphine (2.05 g, 10.1 mmol), dropwise, under a N$_2$ atmosphere. The resulting light yellow solution was stirred at 80° C. under N$_2$ atmosphere for 48 h. The mixture was diluted with EtOAc (100 mL) and washed with water (100 mL). The organic phase was dried over Na$_2$SO$_4$, filtered and concentrated under reduced pressure. The crude product was purified by flash chromatography (0-15% EtOAc/PE) to give tert-butyl 4-(6-((4-cyanobenzyl)oxy)-5-fluoropyridin-2-yl)piperidine-1-carboxylate (1.72 g, 62% yield) as a colorless oil. $^1$H NMR (CDCl$_3$) δ 7.67 (d, 2H), 7.58 (d, 2H), 7.29 (dd, 1H), 6.71 (dd, 1H), 5.51 (s, 2H), 4.20 (br s, 2H), 2.81 (t, 2H), 2.69 (dt, 1H), 1.81 (d, 2H), 1.65 (br s, 2H), 1.49 (s, 9H).

Step 2

To a solution of tert-butyl 4-(6-((4-cyanobenzyl)oxy)-5-fluoropyridin-2-yl)piperidine-1-carboxylate (1.72 g, 4.18 mmol) in DCM (15 mL) was added, dropwise, TFA (5 mL). The resulting light yellow solution was stirred at 25° C. for 2 h. The mixture was concentrated under reduced pressure to give 4-(((3-fluoro-6-(piperidin-4-yl)pyridin-2-yl)oxy)methyl)benzonitrile trifluoroacetate (1.3 g, quant.) as a light yellow solid. $^1$H NMR (CD$_3$OD) δ 7.74 (d, 2H), 7.63 (d, 2H), 7.46 (dd, 1H), 6.89 (dd, 1H), 5.56 (s, 2H), 3.42-3.53 (m, 2H), 3.11 (td, 2H), 2.96 (tt, 1H), 2.03-2.13 (m, 2H), 1.87-2.02 (m, 2H).

Step 3

To a colorless solution of 4-(((3-fluoro-6-(piperidin-4-yl)pyridin-2-yl)oxy)methyl)benzonitrile trifluoroacetate (1.3 g, 4.2 mmol) and ethyl 2-bromoacetate (767 mg, 4.59 mmol) in MeCN (20 mL) was added K$_2$CO$_3$ (2.89 g, 20.9 mmol). The resulting white suspension was stirred at 60° C. for 3 h and left at RT for 16 h. The mixture was filtered and concentrated under reduced pressure. The crude product was purified by flash chromatography (0-33% EtOAc in PE) to give ethyl 2-(4-(6-((4-cyanobenzyl)oxy)-5-fluoropyridin-2-yl)piperidin-1-yl)acetate (1.07 g, 65%) as light yellow solid. $^1$H NMR (CDCl$_3$) δ 7.67 (d, 2H), 7.58 (d, 2H), 7.28 (dd, 1H), 6.72 (dd, 1H), 5.52 (s, 2H), 4.21 (m, 2H), 3.26 (s, 2H), 3.06 (d, 2H), 2.55 (tt, 1H), 2.29 (dt, 2H), 1.94 (dq, 2H), 1.77-1.86 (m, 2H), 1.30 (m, 3H).

Step 4

To a solution of ethyl 2-(4-(6-((4-cyanobenzyl)oxy)-5-fluoropyridin-2-yl)piperidin-1-yl)acetate (1.07 g, 2.69 mmol) in MeOH (10 mL) was added, dropwise, a solution of NaOH (162 mg, 4.04 mmol) in water (2 mL). The resulting colorless solution was stirred at 25° C. for 3 h. The mixture was diluted with water (30 mL), extracted with MTBE (30 mL). The organic phase was acidified to pH ~7 with 2 M HCl and lyophilized for 16 h. The crude product was purified by flash chromatography (0-5% MeOH/DCM gradient) to give Intermediate 7 (850 mg, 86% yield) as a solid. $^1$H NMR (400 MHz, CD$_3$OD) δ 7.75 (d, 2H), 7.67 (d, 2H), 7.46 (dd, 1H), 6.92 (dd, 1H), 5.59 (s, 2H), 3.71-3.80 (m, 2H), 3.35 (s, 2H), 3.10-3.27 (m, 2H), 2.90-3.06 (m, 1H), 2.11-2.29 (m, 2H), 2.01-2.10 (m, 2H), LC-MS(ES+): 369.9 (M+H).

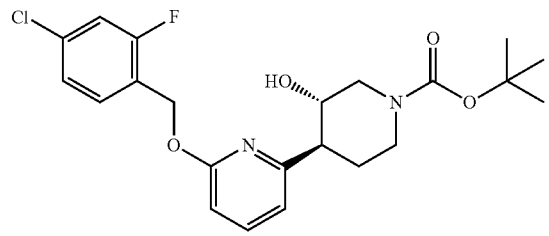 [SMILES: CC(C)(C)OC(=O)N1CC[C@@H](c2cccc(OCc3ccc(Cl)cc3F)n2)[C@H](O)C1]

Intermediate 8 rac-tert-Butyl (3R,4R)-4-(6-((4-chloro-2-fluorobenzyl)oxy)pyridin-2-yl)-3-hydroxypiperidine-1-carboxylate To a solution of Intermediate 1 (800 mg, 1.9 mmol) in THF (15 mL) at 0° C. under a nitrogen atmosphere was added borane-THF complex (1 M in THF, 2.1 mL, 2.1 mmol). The reaction mixture was stirred at 0° C. for 10 min and then warmed to 30° C. for 30 min. The reaction vessel was then cooled to 0° C., opened to the air, and a solution of NaOH (190 mg, 4.8 mmol) in water (5 mL) and hydrogen peroxide (30 wt % in water, 0.86 mL, 9.6 mmol) was added slowly. The mixture was then warmed to 26° C. and stirred for 16 h. Aqueous Na$_2$SO$_3$ (15 mL) and NaHCO$_3$ (15 mL) were added to the resulting white suspension and the mixture was extracted with DCM (3×50 mL). The combined organic layers were washed with brine (50 mL), dried over anhydrous Na$_2$SO$_4$ and concentrated under reduced pressure. The crude material was purified using column chromatography eluting with EtOAc in PE (10% to 30% to 60% gradient) to obtain Intermediate 8 as a colorless oil (320 mg, 38%). LC-MS(ES+): 437 (M+H), 459 (M+Na).

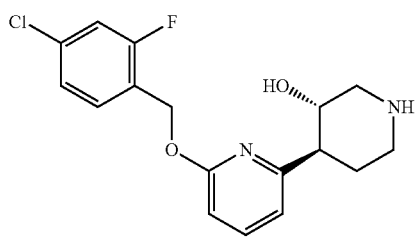 [SMILES: O[C@@H]1CNCC[C@H]1c1cccc(OCc2ccc(Cl)cc2F)n1]

Intermediate 9 rac-(3R,4R)-4-(6-((4-Chloro-2-fluorobenzyl)oxy)pyridin-2-yl)piperidin-3-ol trifluoroacetate To a solution of Intermediate 8 (60 mg, 0.14 mmol) in DCM (2 mL) was added TFA (0.5 mL) at RT, and the mixture stirred for 1 h. The reaction mixture was concentrated under reduced pressure to obtain crude Intermediate 9 as a light yellow oil, which was used without purification. LC-MS(ES+): 337 (M+H).

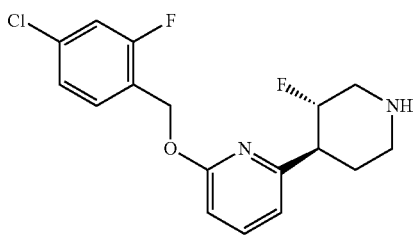 [SMILES: Fc1cc(Cl)ccc1COc1cccc([C@@H]2CCNC[C@H]2F)n1]

Intermediate 10 rac-2-((4-Chloro-2-fluorobenzyl)oxy)-6-((3R,4R)-3-fluoropiperidin-4-yl)pyridine hydrochloride To a solution of Intermediate 8 (60 mg, 0.14 mmol) in DCM (6 mL) 0° C. under a nitrogen atmosphere was added DAST (diethylaminosulfur trifluoride, 38 mg, 0.23 mmol). The resulting mixture was stirred at 0° C. for 10 min and then at RT for 2 h. Water was then added to the solution and the mixture extracted with EtOAc (3×100 mL). The combined organic solution was washed with brine and then concentrated under reduced pressure. The crude product was purified by prep-TLC (PE:EtOAc=10:1) to give rac-tert-butyl (3R,4R)-4-(6-((4-chloro-2-fluorobenzyl)oxy)pyridin-2-yl)-3-fluoropiperidine-1-carboxylate (80 mg), which was used without further purification. The material was dissolved in DCM (2 mL) at RT and 4 M HCl in EtOAc (1 mL) added, dropwise. The mixture was stirred for 1 h before being concentrated under reduced pressure to give Intermediate 10 as a white solid. 1H NMR (400 MHz, CD$_3$OD) δ 7.65-7.77 (m, 1H), 7.51 (t, 1H), 7.18-7.32 (m, 2H), 7.00 (d, 1H), 6.81 (d, 1H), 5.45 (s, 2H), 5.09-5.33 (m, 1H), 3.72 (ddd, 1H), 3.40-3.49 (m, 1H), 3.40-3.49 (m, 1H), 3.32-3.38 (m, 1H), 3.13-3.25 (m, 1H), 2.08-2.39 (m, 2H). Note: the stereochemistry of the piperidine substituents was assigned as trans by analogy to published precedent (see, for example, WO 2010/022055), but was not confirmed experimentally.

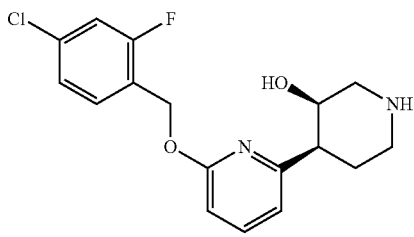 [SMILES: O[C@H]1CNCC[C@H]1c1cccc(OCc2ccc(Cl)cc2F)n1]

Intermediate 11 rac-(3R,4S)-4-(6-((4-Chloro-2-fluorobenzyl)oxy)pyridin-2-yl)piperidin-3-ol hydrochloride

Step 1

To a solution of Intermediate 8 (170 mg, 0.39 mmol) in DCM (5 mL) 0° C. was added Et$_3$N (0.16 mL, 1.2 mmol) and MsCl (58 mg, 0.51 mmol) and the mixture stirred for 2 h. The mixture was diluted with DCM (30 mL), washed with saturated aq. NH$_4$Cl and brine, dried over Na$_2$SO$_4$ and then concentrated under reduced pressure to afford a yellow oil. This material was dissolved in DMSO (1.5 mL) and added to a suspension of cesium formate (140 mg, 0.78 mmol) in DMSO (1 mL). The mixture was stirred at 120° C. for 4 h and 25° C. for 14 h. The mixture was poured into water (15 mL) and extracted with EtOAc (3×15 mL). The combined organic solution was washed with brine, dried over Na$_2$SO$_4$ and concentrated under reduced pressure. The crude product was purified by prep-TLC (PE:EtOAc=4:1) to afford a colorless oil (60 mg).

The oil was dissolved in MeOH (2 mL) at RT, K$_2$CO$_3$ was added and the mixture stirred for 1 h. The mixture was diluted with EtOAc, washed with brine, dried over Na$_2$SO$_4$ and concentrated under reduced pressure to give a crude product. The product was purified by preparative SFC to afford rac-tert-butyl (3R,4S)-4-(6-((4-chloro-2-fluorobenzyl)oxy)pyridin-2-yl)-3-hydroxypiperidine-1-carboxylate as a yellow gum (20 mg, 12%). LC-MS(ES+): 437 (M+H), 459 (M+Na) SFC Method: Column: OJ (250 mm×30 mm, 5 μm); Mobile phase: CO$_2$ w/15% iPrOH (0.1% NH$_4$OH); Flow rate: 60 ml/min; Wavelength: 220 nm. Retention time=3.65 min.

Step 2

To a solution of rac-tert-butyl (3R,4S)-4-(6-((4-chloro-2-fluorobenzyl)oxy)pyridin-2-yl)-3-hydroxypiperidine-1-carboxylate (20 mg, 0.046 mmol) in EtOAc (4 mL) at 0° C. was added 4 M HCl in EtOAc (4 mL), and the mixture stirred for 2 h. The mixture was then concentrated under reduced pressure to afford crude example Intermediate 11 as a light yellow oil, which was used without purification. LC-MS(ES+): 337 (M+H).

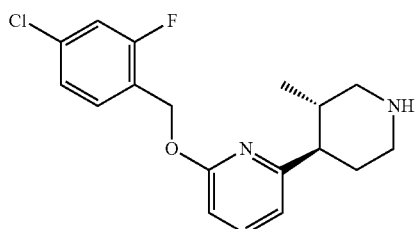

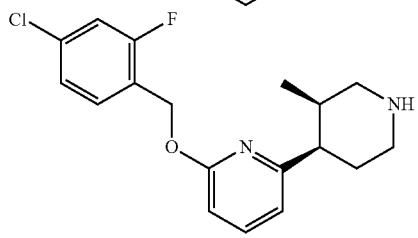

Intermediate 12a rac-2-((4-Chloro-2-fluorobenzyl)oxy)-6-((3R,4S)-3-methylpiperidin-4-yl)pyridine trifluoroacetate

Intermediate 12b rac-2-((4-Chloro-2-fluorobenzyl)oxy)-6-((3R,4R)-3-methylpiperidin-4-yl)pyridine trifluoroacetate

Step 1 rac-tert-butyl (3R,4S)-4-(6-chloropyridin-2-yl)-3-methylpiperidine-1-carboxylate and rac-tert-butyl (3R,4R)-4-(6-chloropyridin-2-yl)-3-methylpiperidine-1-carboxylate were prepared using a route analogous to that described for Intermediates 1 and 2, using tert-butyl 3-methyl-4-(4,4,5,5-tetramethyl-1,3,2-dioxaborolan-2-yl)-3,6-dihydropyridine-1(2H)-carboxylate in the Suzuki reaction. The mixture of cis and trans isomers was separated by column chromatography eluting with EtOAc in PE (0-15% gradient). The trans (rac-3R,4S)-isomer eluted first.

rac-tert-butyl (3R,4S)-4-(6-chloropyridin-2-yl)-3-methylpiperidine-1-carboxylate: $^1$H NMR (400 MHz, CDCl$_3$) δ 7.56 (t, 1H), 7.71 (d, 1H), 7.04 (d, 1H), 4.22 (br s, 2H), 2.76 (br s, 1H), 2.43-2.39 (m, 2H), 2.02-1.92 (m, 1H), 1.79-1.71 (m, 2H), 1.48 (s, 9H), 0.70 (d, 3H).

rac-tert-butyl (3R,4R)-4-(6-chloropyridin-2-yl)-3-methylpiperidine-1-carboxylate: $^1$H NMR (400 MHz, CDCl$_3$) δ 7.59 (t, 1H), 7.16 (d, 1H), 6.99 (d, 1H), 4.36 (br s, 1H), 4.01 (br s, 1H), 3.05 (dt, 2H), 2.79 (br s, 1H), 2.33 (q, 1H), 2.07-2.01 (m, 1H), 1.71 (d, 1H), 1.46 (s, 9H), 0.66 (d, 3H).

Step 2

Intermediates 12a and 12b were prepared from the respective separated chloropyridine isomers by etherification in a manner analogous to Intermediate 3, step 1, and deprotection in a manner analogous to Intermediate 9, and used without purification.

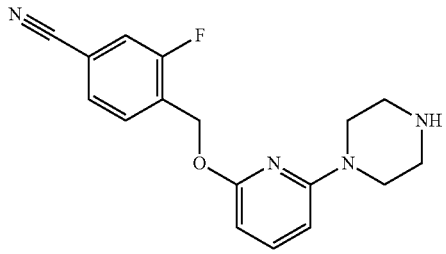 [SMILES: N#Cc1ccc(COc2cccc(N3CCNCC3)n2)c(F)c1]

Intermediate 13

3-Fluoro-4-(((6-(piperazin-1-yl)pyridin-2-yl)oxy)methyl)benzonitrile bis hydrochloride

Step 1

The reaction was carried out in two parallel batches; example batch preparation follows: To a stirred suspension of KOtBu (313 g, 2.79 mol) in THF (4.0 L) was added 4-cyano-2-fluorobenzyl alcohol (281 g, 1.86 mol) portionwise between 10-15° C. The mixture was stirred at 15° C. for 45 min and 2,6-dichloropyridine (230 g, 1.55 mol) was added in several portions to the reaction mixture at 15° C. and the mixture was stirred at 15° C. for 18 h. The mixture was poured into sat. aq. NH$_4$Cl (10 L). EtOAc (10 L) was added and the mixture was stirred for 15 min. The mixture was filtered through a pad of Celite®. The organic layer was separated and the aq. layer extracted with EtOAc (2×6.0 L). The combined organic layers were washed with brine (5.0 L), dried over Na$_2$SO$_4$, filtered and concentrated under reduced pressure. The crude product was purified by column chromatography on silica gel (PE/EtOAc 10-15% gradient) to give 4-(((6-chloropyridin-2-yl)oxy)methyl)-3-fluorobenzonitrile as a light yellow solid. The combined batches yielded 550 g (67%). $^1$H NMR (CDCl$_3$) δ 7.67 (t, 1H), 7.58 (t, 1H), 7.48 (dd, 1H), 7.40 (dd, 1H), 6.97 (d, 1H), 6.75 (d, 1H), 5.49 (s, 2H).

Step 2

To a stirred solution of 4-(((6-chloropyridin-2-yl)oxy)methyl)-3-fluorobenzonitrile (180 g, 0.685 mol) and tert-butyl piperazine-1-carboxylate (140 g, 0.754 mol) in PhCH$_3$ (2.0 L) was added Cs$_2$CO$_3$ (446 g, 1.37 mol), BINAP (42.6 g, 0.0685 mol) and Pd$_2$(dba)$_3$ (31.4 g, 0.0343 mol) under N$_2$ at 15° C. The mixture was degassed and refilled with N$_2$ three times. The resulting mixture was heated to 120° C. under N$_2$ for 18 h. The reaction mixture was cooled to 80° C. and filtered through a pad of Celite®. The filter cake was washed with EtOAc (4×1.0 L) and the combined organic layers were concentrated under reduced pressure. The crude product was purified by column chromatography on silica gel (PE/EtOAc 10-15% gradient). The product was triturated with PE (1.0 L) with stirring at 10° C. for 2 h. The solids were collected by filtration to yield tert-butyl 4-(6-(((4-cyano-2-fluorobenzyl)oxy)pyridin-2-yl)piperazine-1-carboxylate (168 g, 76%) as an off-white solid. $^1$H NMR (CDCl$_3$) δ 7.62 (t, 1H), 7.41-7.49 (m, 2H), 7.38 (dd, 1H), 6.20 (dd, 2H), 5.45 (s, 2H), 3.37-3.57 (m, 8H), 1.49 (s, 9H).

Step 3

To a solution of EtOH (2.8 mL, 48 mmol) in EtOAc (20 mL) was added acetyl chloride (2.0 ml, 28 mmol), dropwise. After stirring for 1 h at 40° C., tert-butyl 4-(6-((4-cyano-2-fluorobenzyl)oxy)pyridin-2-yl)piperazine-1-carboxylate (1.75 g, 4.24 mmol) was added in one portion and the mixture was then stirred at 40° C. for 2 h. The reaction was allowed to cool to RT and stirred for 1 h. EtOAc (10 mL) was added to the white suspension and the resultant slurry was stirred vigorously at RT for 1 h. The solid was collected by filtration to provide the bis HCl salt of the desired product Intermediate 13 (1.45 g, 89%) as a solid. $^1$H NMR (600 MHz, DMSO-d6) δ 9.45 (br s, 2H), 7.89 (d, 1H), 7.65-7.73 (m, 2H), 7.55 (m, 1H), 6.44 (d, 1H), 6.22 (d, 1H), 5.42 (s, 2H), 3.61-3.74 (m, 4H), 3.09 (br s, 4H).

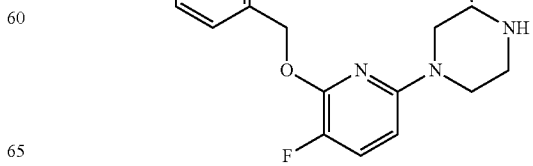

Intermediate 14

(S)-1-(6-((4-Chloro-2-fluorobenzyl)oxy)-5-fluoro-pyridin-2-yl)-3-methylpiperazine hydrochloride

Step 1

To a solution of 2,3,5-trifluoropyridine (1.5 g, 11 mmol) and 4-chloro-2-fluorobenzyl alcohol (1.81 g, 11.3 mmol) in NMP (20 mL) was added $K_2CO_3$ (4.67 g, 33.8 mmol) at 25° C. and the mixture was stirred at 100° C. for 16 h. The mixture was poured into water (30 mL) and then extracted with EtOAc (3×50 mL). The combined organic extracts were washed with brine (3×40 mL), dried over $Na_2SO_4$, filtered and concentrated under reduced pressure. The crude product was purified by flash chromatography (0 to 5% EtOAc/PE gradient) to give 2-((4-chloro-2-fluorobenzyl)oxy)-3,6-difluoropyridine (2.45 g, 80%) as a colorless oil. $^1$H NMR (CDCl$_3$) δ 7.41-7.54 (m, 2H), 7.11-7.20 (m, 2H), 6.47 (ddd, 1H), 5.44 (s, 2H).

Step 2

To a solution of 2-((4-chloro-2-fluorobenzyl)oxy)-3,6-difluoropyridine (200 mg, 0.731 mmol) and tert-butyl (S)-2-methylpiperazine-1-carboxylate (161 mg, 0.804 mmol) in DMSO (3 mL) was added $K_2CO_3$ (303 mg, 2.19 mmol) at RT. The reaction was stirred at 120° C. for 18 h. The mixture was poured into water (10 mL) and then extracted with EtOAc (3×20 mL). The combined organic extracts were washed with brine (3×20 mL), dried over $Na_2SO_4$, filtered and concentrated under reduced pressure. The crude product was purified by Prep-TLC (15% EtOAc/PE) to give tert-butyl (S)-4-(6-((4-chloro-2-fluorobenzyl)oxy)-5-fluoropyridin-2-yl)-2-methylpiperazine-1-carboxylate (60 mg, 18%) as a colorless oil. LC-MS(ES+): 397.9 (M+H-tBu).

Step 3

To a solution of (S)-4-(6-((4-chloro-2-fluorobenzyl)oxy)-5-fluoropyridin-2-yl)-2-methylpiperazine-1-carboxylate (60 mg, 0.13 mmol) in DCM (3 mL) was added HCl/EtOAc (3 mL). The solution was stirred at 30° C. for 0.5 h. The suspension was concentrated under reduced pressure to deliver Intermediate 14 (50 mg, 89%) as a solid. LC-MS(ES+): 353.9 (M+H).

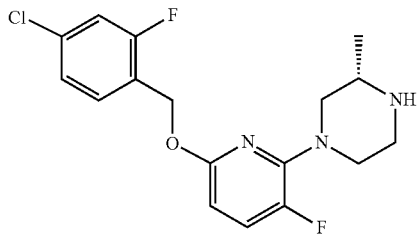 [SMILES: C[C@H]1CN(c2nc(OCc3ccc(Cl)cc3F)ccc2F)CCN1]

Intermediate 15

(S)-1-(6-((4-Chloro-2-fluorobenzyl)oxy)-3-fluoro-pyridin-2-yl)-3-methylpiperazine hydrochloride

Step 1

To a solution of 2,3,5-trifluoropyridine (500 mg, 3.76 mmol) and tert-butyl piperazine-1-carboxylate (753 mg, 3.76 mmol) in MeCN (8 mL) was added $Et_3N$ (1.14 g, 11.3 mmol) at 30° C. and the reaction was heated and then stirred at 70° C. for 16 h. The reaction mixture was poured into water (20 mL) and extracted with EtOAc (3×30 mL). The combined organic extracts were washed with brine (2×20 mL), dried over $Na_2SO_4$, filtered and concentrated under reduced pressure. The crude product was purified by flash chromatography (0 to 5% EtOAc/PE) to give tert-butyl (S)-4-(3,6-difluoropyridin-2-yl)-2-methylpiperazine-1-carboxylate (870 mg, 74%) as a pale brown oil. $^1$H NMR (CDCl$_3$) δ 7.24-7.34 (m, 1H), 6.22 (ddd, 1H), 4.31 (br s, 1H), 4.09 (ddt, 1H), 3.92 (dt, 2H), 3.22 (td, 1H), 3.13 (dd, 1H), 2.93 (td, 1H), 1.49 (s, 9H), 1.23 (d, 3H).

Step 2

To a solution of 4-chloro-2-fluorobenzyl alcohol (102 mg, 0.638 mmol) in DMF (2 mL) was added NaH (44.7 mg, 1.12 mmol, 60% in mineral oil). The yellow mixture was stirred at 30° C. for 15 min. Then a solution of tert-butyl (S)-4-(3,6-difluoropyridin-2-yl)-2-methylpiperazine-1-carboxylate (100 mg, 0.319 mmol) in DMF (2 mL) was added at RT. The reaction mixture was stirred at 90° C. for 18 h. The reaction mixture were poured into water (30 mL) and then extracted with EtOAc (3×30 mL). The combined organic extracts were washed with brine (3×20 mL), dried over $Na_2SO_4$, filtered and concentrated under reduced pressure. The crude product was purified by Prep-TLC (EtOAc:PE 5:1) to give tert-butyl (S)-4-(6-((4-chloro-2-fluorobenzyl)oxy)-3-fluoropyridin-2-yl)-2-methylpiperazine-1-carboxylate (136 mg, 47%) as a colorless oil. LC-MS(ES+): 397.9 (M+H-tBu).

Step 3

To a solution of tert-butyl (S)-4-(6-((4-chloro-2-fluorobenzyl)oxy)-3-fluoropyridin-2-yl)-2-methylpiperazine-1-carboxylate (136 mg, 0.300 mmol) in DCM (4 mL) was added HCl/EtOAc (4 mL). The solution was stirred at 30° C. for 2 h. The suspension was concentrated under reduced pressure to give Intermediate 15 (132 mg, quant.) as a pale yellow solid. LC-MS(ES+): 354.1 (M+H).

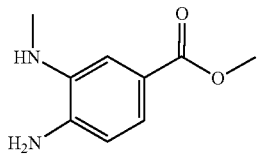

Methyl 4-amino-3-(methylamino)benzoate

Step 1

To a solution of methyl 3-fluoro-4-nitrobenzoate (5.10 g, 25.6 mmol) in THF (60 mL) was added methylamine (38.4 mL, 76.8 mmol, 2 M in THF), dropwise, over 10 min. The pale yellow solution turned deep orange immediately upon addition and was stirred 2 h at RT. The mixture was diluted with $Et_2O$ (100 mL) and the separated organic layer washed with water (50 mL) and brine (50 mL). The organic layer was dried over $Na_2SO_4$, filtered and concentrated under reduced pressure to yield 5.26 g of methyl 3-(methylamino)-4-nitrobenzoate (98%) as a deep orange solid. $^1$H NMR (400

MHz, CDCl₃) δ 8.21 (d, 1H), 7.99 (br s, 1H), 7.54 (d, 1H), 7.23 (dd, 1H), 3.94 (s, 3H), 3.08 (d, 3H); LC-MS(ES+): 211.1 (M+H).

Step 2

Methyl 3-(methylamino)-4-nitrobenzoate (5.26 g, 25.0 mmol) was dissolved in EtOH (150 mL). The solution was added to 500 mL Parr® bottle previously charged with 1 g 10% Pd/C (50% water). The mixture was shaken under 50 psi H₂ atmosphere for 1 h at RT. The mixture was filtered and the filtercake rinsed with EtOH (100 mL). The colorless filtrate was concentrated under reduced pressure to yield 4.38 g of Intermediate 16 (97%) as an off-white solid. ¹H NMR (400 MHz, CDCl₃) δ 7.47 (dd, 1H), 7.35 (d, 1H), 6.69 (d, 1H), 3.88 (s, 3H), 3.75 (br s, 2H), 3.22 (br s, 1H), 2.92 (s, 3H); MS(APCl+): 181.1 (M+H).

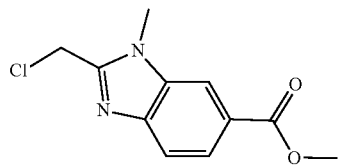 [SMILES: COC(=O)c1ccc2nc(CCl)n(C)c2c1]

Intermediate 17

Methyl 2-(chloromethyl)-1-methyl-1H-benzo[d]imidazole-6-carboxylate

Intermediate 16 (206 mg, 1.14 mmol) was dissolved in dioxane (11.5 mL) and treated with chloroacetyl chloride (109 µL, 1.37 mmol). The mixture was stirred at 100° C. for 3 h and cooled to RT. Et₃N (0.8 mL, 7 mmol) and heptane (10 mL) were added and filtered. The filtrate was concentrated under reduced pressure and the crude product was purified by flash chromatography (silica gel column, 40% EtOAc/heptanes) to afford 120 mg of Intermediate 17 (44%). ¹H NMR (400 MHz, CDCl₃) δ 8.14 (s, 1H), 8.01 (d, 1H), 7.78 (d, 1H), 4.87 (s, 2H), 3.97 (s, 3H), 3.94 (s, 3H); LC-MS(ES+): 239.1 (M+H).

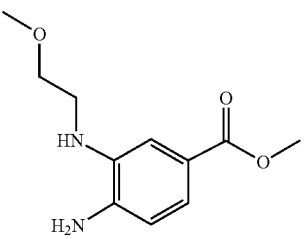

Intermediate 18

Methyl 4-amino-3-((2-methoxyethyl)amino)benzoate

Step 1

To a colorless solution of methyl 3-fluoro-4-nitrobenzoate (50 g, 250 mmol) in THF (400 mL) was added Et₃N (40.7 g, 402 mmol, 55.8 mL) followed by addition of 2-methoxyethylamine (30.2 g, 402 mmol) in THF (100 mL), dropwise, at RT. The resultant yellow solution was stirred at 55° C. for 18 h. The solution was cooled to RT and concentrated under reduced pressure to remove THF. The resultant yellow solid was dissolved in EtOAc (800 mL) and washed with sat. aq. NH₄Cl (250 mL). The aq. phase was separated and extracted with EtOAc (200 mL). The combined organic layers were washed with brine (3×250 mL), dried over Na₂SO₄, filtered and concentrated under reduced pressure to yield methyl 3-((2-methoxyethyl)amino)-4-nitrobenzoate (60.2 g, 94%) as a yellow solid. ¹H NMR (CDCl₃) δ 8.23 (d, 1H), 8.17 (br s, 1H), 7.58 (d, 1H), 7.25 (dd, 1H), 3.95 (s, 3H), 3.69-3.73 (m, 2H), 3.56 (m, 2H), 3.45 (s, 3H); LC-MS(ES+): 255.4 (M+H).

Step 2

To solution of methyl 3-((2-methoxyethyl)amino)-4-nitrobenzoate (30 g, 118 mmol) in MeOH (500 mL) was added Pd/C (10 g, 94 mmol). This reaction was stirred at RT under 15 psi H₂ for 18 h. The black suspension was filtered through Celite® and the filtercake washed with MeOH (500 mL). The combined filtrates were concentrated under vacuum to give Intermediate 18 (26.5 g, quant.) as a brown oil which solidified on standing. ¹H NMR (400 MHz, CDCl₃) δ 7.48 (dd, 1H), 7.36 (d, 1H), 6.69 (d, 1H), 3.87 (s, 3H), 3.77 (br.s, 2H), 3.68 (t, 2H), 3.41 (s, 3H), 3.32 (t, 2H); LC-MS(ES+): 224.7 (M+H).

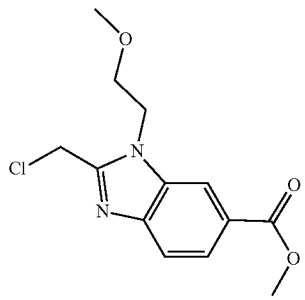 [SMILES: COCCn1c(CCl)nc2ccc(C(=O)OC)cc21]

Intermediate 19

Methyl 2-(chloromethyl)-1-(2-methoxyethyl)-1H-benzo[d]imidazole-6-carboxylate hydrochloride A solution of Intermediate 18 (5.0 g, 24 mmol) in dioxane (100 mL) was heated to 100° C., a solution of chloroacetic anhydride (4.1 g, 24.5 mmol) in dioxane (60 mL) was added via addition funnel over a period of 10 h, and then stirred for another 12 h at 100° C. The following day, the reaction was cooled to RT and the dioxane was removed under reduced pressure. The crude reaction mixture was dissolved in EtOAc and washed with saturated NaHCO₃ solution. The EtOAc layer was separated and dried over Na₂SO₄ and filtered. A solution of 4 M HCl in dioxane (1.1 equiv.) was added to the EtOAc solution of the product with constant stirring. The HCl salt of desired product precipitated out as a pale yellow solid. The suspension was stirred for 1 h and the product then collected by filtration to obtain Intermediate 19 as a yellow solid (6.1 g 86%). ¹H NMR (600 MHz, CD₃OD) δ 8.64 (s, 1H), 8.30 (d, 1H), 7.92 (d, 1H), 5.32 (s, 2H), 4.84 (m, 2H), 3.99 (s, 3H), 3.83 (t, 2H), 3.31 (s, 3H). LC-MS(ES+): 283.2 (M+H).

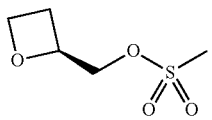

Intermediate 20

(S)-Oxetan-2-ylmethyl methanesulfonate

Step 1

To a solution of potassium t-butoxide (670 g, 5.98 mol) in t-BuOH (5 L) was added trimethylsulfoxonium iodide (1.32 kg, 5.98 mol) at 25° C. The mixture was heated to 60° C. and stirred for 30 min, then (S)-2-((benzyloxy)methyl)oxirane (500 g, 2.99 mol) was added. The mixture was heated to 80° C. for 2 h. The mixture was cooled to 25° C. and filtered through Celite®. The solids were washed with PE (3×2 L). The filtrate was treated with water (10 L) and extracted with PE (2×5 L). The organic layer was washed with brine, dried, filtered and concentrated in vacuo. The crude product was purified by column chromatography (PE/EtOAc gradient from 15:1 to 10:1) to deliver (S)-2-((benzyloxy)methyl) oxetane (280 g, 52.6%) as a clear oil. $^1$H NMR (400 MHz, CDCl$_3$) δ 7.15-7.34 (m, 5H), 4.90 (tdd, 1H), 4.44-4.67 (m, 4H), 3.49-3.63 (m, 2H), 2.44-2.66 (m, 2H).

Step 2

The reaction was carried out in two parallel batches; an example batch follows: To a solution of (S)-2-((benzyloxy) methyl)oxetane (140 g, 780 mmol) in THF (1.4 L) was added Pd(OH)$_2$ (14 g) under a blanket of nitrogen. The mixture was heated to 45° C. and stirred under H$_2$ (50 psi) for 16 h. The mixture was cooled to 25° C. and filtered through Celite® to deliver the desired compound (S)-oxetan-2-ylmethanol as a solution in THF. A small aliquot was checked by $^1$H NMR and the remaining solution used directly in the next step. $^1$H NMR (400 MHz, DMSO-d6) δ 4.76-4.90 (m, 1H), 4.66 (tdd, 1H), 4.46 (ddd, 1H), 4.37 (td, 1H), 3.47 (dd, 2H), 2.32-2.58 (m, 2H).

Step 3

The reaction was carried out in two parallel batches; an example batch follows: To a solution of (S)-oxetan-2-yl-methanol (from Step 2, assumed 69 g, 780 mmol) in THF (1.4 L) was added Et$_3$N (197 g, 1.95 mol) at 0° C. Methanesulfonic anhydride (204 g, 1.17 mol) was added, dropwise, keeping the internal temperature below 10° C. The mixture was stirred at 25° C. for 2 h. The two batches were combined and the mixture was treated with water (1 L) and the layers separated. The aq. phase was extracted with DCM (3×2 L). The combined organic solution was dried, filtered and concentrated under reduced pressure. The crude product was purified by column chromatography (EtOAc/PE 50-100% gradient) to yield Intermediate 20 (250 g, 96% for two steps) as a yellow oil. $^1$H NMR (400 MHz, CDCl$_3$) δ 4.98-5.09 (m, 1H), 4.69 (ddd, 1H), 4.59 (td, 1H), 4.37 (d, 2H), 3.11 (s, 3H), 2.72-2.82 (m, 1H), 2.64 (tdd, 1H).

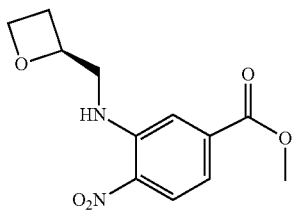 [SMILES: COC(=O)c1ccc([N+](=O)[O-])c(NC[C@@H]2CCO2)c1]

Intermediate 21

Methyl (S)-4-nitro-3-((oxetan-2-ylmethyl)amino) benzoate

Step 1

To a solution of (S)-oxetan-2-ylmethyl methanesulfonate (180 g, 1.08 mol) in DMF (1.2 L) was added sodium azide (105 g, 1.62 mol). The mixture was heated to 80° C. and stirred for 16 h. The mixture was cooled to 0° C. and treated with diethyl ether (1.5 L) and the resultant suspension was stirred for 30 min. The solids were removed by filtration and the filter cake was washed with diethyl ether (2×200 mL). The diethyl ether was removed under vacuum at 25° C. to deliver a solution of (S)-2-(azidomethyl)oxetane in DMF (~1.2 L), which was used directly in the next step.

Step 2

The reaction was carried out in three parallel batches; an example batch follows: To a solution of (S)-2-(azidomethyl) oxetane (assumed 41 g, 360 mmol) in DMF (~400 mL) and THF (1 L) was added 10% Pd/C (50 wt % wet, 13 g) under a blanket of nitrogen. The mixture was stirred at 25° C. under H$_2$ (50 psi) for 16 h. The solution was filtered through Celite®, 10% Pd/C (dry, 4.0 g) added and the mixture stirred at 40° C. under H$_2$ (50 psi) for 3 h, after which TLC analysis indicated complete reaction. The mixture was cooled to 0° C. and all three batches were combined. The mixture was filtered through Celite® to obtain a solution of (S)-2-(aminomethyl)oxetane in DMF (~1.4 L) and THF (~2.6 L), which was used directly in the next step.

Step 3

To a solution of (S)-2-(aminomethyl)oxetane (assumed 94 g, 1.08 mol) in DMF (~1.4 L) and THF (~2.6 L) were added Et$_3$N (327 g, 3.24 mol) and methyl 3-fluoro-4-nitrobenzoate (200 g, 1.0 mol) at 25° C. The mixture was stirred at 25° C. for 16 h. The mixture was concentrated under reduced pressure to remove THF and the remaining solution was diluted with water (1 L). The mixture was extracted with EtOAc (2×1.5 L). The combined organic extracts were washed with brine (2×), dried and concentrated under reduced pressure. The crude product was purified by column chromatography (EtOAc/PE=10-50% gradient) to deliver Intermediate 21 (158 g, 55%) as a yellow solid. $^1$H NMR (600 MHz, CDCl$_3$) δ 8.38 (br s, 1H), 8.25 (d, 1H), 7.64 (s, 1H), 7.27 (d, 1H), 5.13-5.20 (m, 1H), 4.70-4.82 (m, 1H), 4.64 (td, 1H), 3.95 (s, 3H), 3.57-3.71 (m, 2H), 2.71-2.86 (m, 1H), 2.55-2.70 (m, 1H); MS(ES+)=266.7.

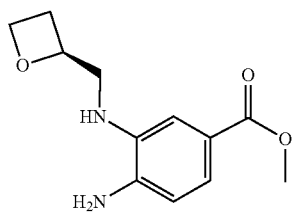

Intermediate 22

Methyl (S)-4-amino-3-((oxetan-2-ylmethyl)amino)benzoate

Intermediate 21 (15 g, 56 mmol) was dissolved in THF (100 mL) in a Parr® reactor. Pd/C (10% w/w, 1.5 g) was added to the reactor and the mixture was shaken at RT under 50 psi H₂ for 4 h. The mixture was filtered through Celite® and the filtrate was concentrated under reduced pressure to deliver Intermediate 22 (12.3 g, 92%) as a tan solid. ¹H NMR (600 MHz, CDCl₃) δ 7.49 (dd, 1H), 7.39 (d, 1H), 6.70 (d, 1H), 5.05-5.18 (m, 1H), 4.76 (ddd, 1H), 4.62 (dt, 1H), 3.87 (s, 3H), 3.42-3.50 (m, 1H), 3.34-3.40 (m, 1H), 2.71-2.82 (m, 1H), 2.60 (ddt, 1H).

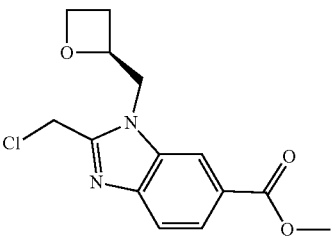 [SMILES: COC(=O)c1ccc2nc(CCl)n(C[C@@H]3CCO3)c2c1]

Intermediate 23

Methyl (S)-2-(chloromethyl)-1-(oxetan-2-ylmethyl)-1H-benzo[d]imidazole-6-carboxylate To a solution of Intermediate 22 (127 g, 0.54 mol) in MeCN (500 mL) was added 2-chloro-1,1,1-trimethoxy ethane (76.2 ml, 0.57 mol) and pTSA.H₂O (5.12 g, 26.9 mmol). The mixture was heated to 60° C. for 1 h. The reaction was cooled to RT and concentrated under reduced pressure. The resultant crude product was triturated in 50% EtOAc/heptane. The solids were collected by filtration to deliver Intermediate 23 (79 g, 50%) as a tan solid. ¹H NMR (600 MHz, CDCl₃) δ 8.12 (s, 1H), 8.00 (d, 1H), 7.79 (d, 1H), 5.16-5.26 (m, 1H), 5.03 (s, 2H), 4.57-4.66 (m, 2H), 4.48-4.56 (m, 1H), 4.33 (m, 1H), 3.95 (s, 3H), 2.71-2.81 (m, 1H), 2.36-2.47 (m, 1H).

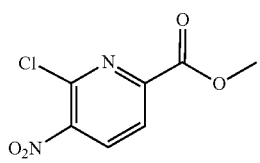

Intermediate 24

Methyl 6-chloro-5-nitropicolinate

Step 1

2-Chloro-6-methyl-3-nitropyridine (97 g, 560 mmol) was slowly added to a flask previously charged with 18 M H₂SO₄ (400 mL) with stirring. Chromium trioxide (169 g, 1.69 mol) was added to the reaction mixture in small portions keeping the temperature below 50° C. The reaction mixture was stirred at 15° C. for 20 h. The resultant green gum was poured into 2 Kg of ice and the resultant solids collected by filtration and dried under vacuum to yield 6-chloro-5-nitropicolinic acid (103 g, 90%) as a pale solid. ¹H NMR (400 MHz, DMSO-d6) δ 8.70 (d, 1H), 8.24 (d, 1H).

Step 2

To a suspension 6-chloro-5-nitropicolinic acid (103 g, 508.51 mmol) in CH₂Cl₂ (1 L) was added oxalyl chloride (129 g, 1.02 mol) and DMF (6 mL) at 0° C. The reaction mixture was stirred at 15° C. for 1 h. MeOH (60 mL) was added to the reaction mixture at 15° C. The solution was stirred at 15° C. for an additional 10 min. The yellow solution was concentrated under reduced pressure and the resultant crude product was purified by column chromatography (EtOAc/PE: 0-20% gradient) to deliver Intermediate 24 (106 g, 96%) as a solid. ¹H NMR (400 MHz, CD₃OD) δ 8.55 (d, 1H), 8.27 (d, 1H), 4.01 (s, 3H).

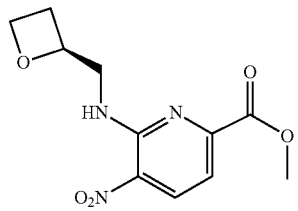 [SMILES: COC(=O)c1ccc([N+](=O)[O-])c(NC[C@@H]2CCO2)n1]

Intermediate 25

Methyl (S)-5-nitro-6-((oxetan-2-ylmethyl)amino)picolinate

Step 1

A solution of (S)-2-(aminomethyl)oxetane (assumed 152 g, 1.7 mol) in DMF (3 L) and THF (3 L) was prepared from Intermediate 20 as described for Intermediate 21 (steps 1 and 2). Intermediate 24 (270 g, 1.25 mol) and Et₃N (500 g, 5.1 mol) were added to a solution of Intermediate 20 (152 g, 1.7 mol) in DMF (3 L) and THF (3 L) at 25° C. The mixture was stirred at 25° C. for 16 h. The mixture was concentrated under reduced pressure to remove the THF and water (5 L) added. The mixture was extracted with EtOAc (2×5 L) and the combined organic solutions were washed with brine (2×), dried and concentrated under reduced pressure. The crude material was combined with a second batch of crude product from a similar experiment (70 g) and the solids triturated with PE:EtOAc (4:1, 500 mL) for 2 h. The solids were collected by filtration and dried to provide Intermediate 25 (304 g, 52%) as a yellow solid. ¹H NMR (400 MHz, CDCl₃) δ 8.58 (br s, 1H), 8.56 (d, 1H), 7.39 (d, 1H), 5.08-5.18 (m, 1H), 4.73 (ddd, 1H), 4.61 (td, 1H), 4.06-4.16 (m, 1H), 3.98 (s, 3H), 3.88-3.97 (m, 1H), 2.68-2.80 (m, 1H), 2.55 (tdd, 1H).

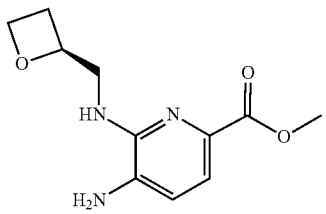 [SMILES: COC(=O)c1ccc(N)c(NC[C@@H]2CCO2)n1]

Intermediate 26

Methyl (S)-5-amino-6-((oxetan-2-ylmethyl)amino)picolinate

Intermediate 25 (10 g, 37 mmol) was suspended in MeOH (150 mL) and treated with 10% Pd/C (1.0 g) and the mixture was stirred at RT under 50 psi H₂ for 4 h. The mixture was filtered through Celite® and the filtrate was concentrated under reduced pressure to yield Intermediate 26 (8.4 g, 95%) as a yellow oil which solidified on standing. $^1$H NMR (600 MHz, CDCl₃) δ 7.49 (d, 1H), 6.86 (d, 1H), 5.06-5.15 (m, 1H), 4.68-4.77 (m, 1H), 4.53-4.63 (m, 2H), 3.91 (s, 3H), 3.80-3.86 (m, 2H), 3.72 (br s, 2H), 2.68-2.78 (m, 1H), 2.52-2.61 (m, 1H).

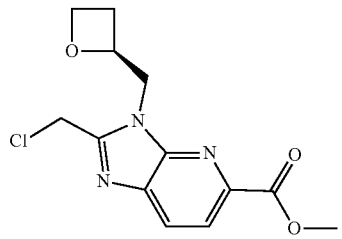 [SMILES: COC(=O)c1ccc2nc(CCl)n(C[C@@H]3CCO3)c2n1]

Intermediate 27

Methyl (S)-2-(chloromethyl)-3-(oxetan-2-ylmethyl)-3H-imidazo[4,5-b]pyridine-5-carboxylate In a 2 L, 3 neck flask equipped with a mechanical overhead stirrer Intermediate 26 (43.0 g, 181 mmol) was taken up in THF (780 mL). The resultant pale pink suspension was treated with a solution of chloroacetic anhydride (33.5 g, 190 mmol in 100 mL THF) via addition funnel over 30 min. The resultant light amber solution was stirred at RT for 2 h and then heated at 60° C. for 7 h. The reaction mixture was cooled to RT. Approximately 400 mL of solvent from the reaction was removed under reduced pressure on a rotary evaporator. The resulting solution was diluted with EtOAc, (500 mL) and treated with sat. aq. NaHCO₃ (200 mL). The biphasic mixture was stirred at RT for 30 min. The organic layer was separated and the aq. layer was extracted with EtOAc (500 mL). The combined organic layers were washed with brine (500 mL), dried over Na₂SO₄, filtered and concentrated under reduced pressure to yield Intermediate 27 (52.5 g, 98%) as a yellowish brown solid. $^1$H NMR (600 MHz, CDCl₃) δ 8.14 (d, 2H), 5.19-5.28 (m, 1H), 4.99-5.16 (m, 2H), 4.70-4.88 (m, 2H), 4.55-4.67 (m, 1H), 4.24-4.44 (m, 1H), 4.01 (s, 3H), 2.70-2.88 (m, 1H), 2.37-2.53 (m, 1H); LC-MS(ES+): 296.4 (M+H).

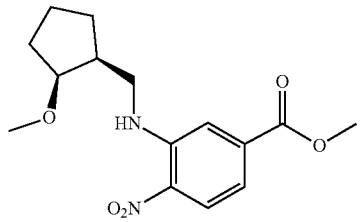

Intermediate 28 cis (+/−) Methyl 3-(((2-methoxycyclopentyl)methyl)amino)-4-nitrobenzoate

Step 1

To a flask containing cis (+/−)-2-(aminomethyl)cyclopentan-1-ol (300 mg, 2.60 mmol), methyl 3-fluoro-4-nitrobenzoate (571 mg, 2.87 mmol) and Et₃N (1.1 mL, 7.8 mmol) was added DMF and the mixture was stirred overnight. The reaction mixture was diluted with water and extracted with EtOAc. The organic extract was concentrated under reduced pressure and the crude product was purified by flash chromatography (EtOAc/heptanes) to deliver cis (+/−) methyl 3-(((-2-hydroxycyclopentyl)methyl)amino)-4-nitrobenzoate (493 mg, 64%). 1H NMR (CDCl₃) δ 8.21 (br s, 1H), 8.19 (d, 1H), 7.62 (s, 1H), 7.20 (d, 1H), 4.38 (br s, 1H), 3.94 (s, 3H), 3.60 (ddd, 1H), 3.38-3.50 (m, 1H), 2.13-2.25 (m, 1H), 1.84-2.01 (m, 3H), 1.57-1.78 (m, 4H).

Step 2

To a flask containing solution of cis (+/−) methyl 3-(((2-hydroxycyclopentyl)methyl)amino)-4-nitrobenzoate (0.48 g, 1.6 mmol) in DCM (50 mL) was added 1,8-bis(dimethylamino)naphthalene (0.35 g, 1.6 mmol). The solution was stirred for 5 min and then trimethyloxonium tetrafluoroborate (0.48 g, 3.3 mmol) was added in portions over 10 min. The reaction mixture was then stirred an additional 18 h at RT. Water was added to the flask and the resulting mixture was extracted with DCM. The combined organic layers were filtered and the solution was concentrated under reduced pressure. The crude mixture was purified by flash chromatography (EtOAc/heptanes) to obtain Intermediate 28 (0.4 g, 80%). $^1$H NMR (600 MHz, CDCl₃) δ 8.19 (d, 1H), 7.61 (s, 1H), 7.20-7.12 (m, 1H), 3.93 (s, 3H), 3.57-3.50 (m, 1H), 3.43 (dd, 6.3 Hz, 1H), 3.30 (s, 3H), 2.22 (d, 1H), 1.89-1.43 (m, 7H).

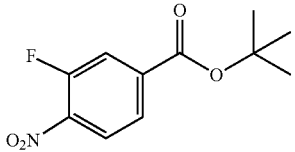 [SMILES: CC(C)(C)OC(=O)c1ccc([N+](=O)[O-])c(F)c1]

Intermediate 29 tert-Butyl 3-fluoro-4-nitrobenzoate

3-Fluoro-nitrobenzoic acid (2.60 g, 14.0 mmol) was dissolved in THF (30 mL), the mixture treated with Boc anhydride (6.13 g, 28.1 mmol) and DMAP (525 mg, 4.21 mmol), and then stirred at RT. A thick slurry quickly formed and was then stirred for 3 h at 40° C. during which time the slurry became a tan solution. After concentrating the reaction mixture under reduced pressure, the residue was dissolved in EtOAc, adsorbed onto silica gel and then eluted through a short pad of silica gel with 50% EtOAc/Heptane. The filtrate was concentrated under reduced pressure to yield Intermediate 29 (8.88 g, 68%) as a yellow solid. $^1$H NMR (600 MHz, CDCl$_3$) δ 8.05-8.09 (m, 1H), 7.86-7.90 (m, 2H), 1.61 (s, 9H).

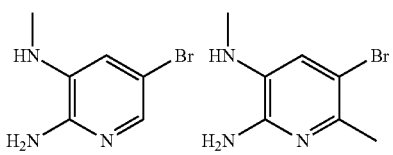

Intermediate 30

5-Bromo-N$^3$-methylpyridine-2,3-diamine

Intermediate 31

5-Bromo-N$^3$,6-dimethylpyridine-2,3-diamine

Intermediate 30 was synthesized according to the literature procedure (Choi, J. Y. et al. *J. Med. Chem.* 2012, 55, 852-870). Intermediate 31 was synthesized using the same method.

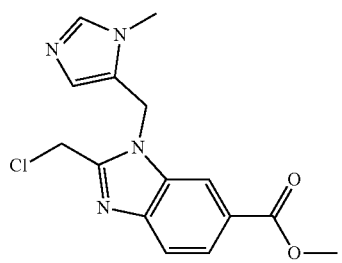 [SMILES: COC(=O)c1ccc2nc(CCl)n(Cc3cncn3C)c2c1]

Intermediate 32

Methyl 2-(chloromethyl)-1-((1-methyl-1H-imidazol-5-yl)methyl)-1H-benzo[d]imidazole-6-carboxylate

Step 1

To a colorless solution of methyl 3-fluoro-4-nitrobenzoate (1.0 g, 5.0 mmol) in DMF (10 mL) was added (1-methyl-1H-imidazol-5-yl)methanamine (670 mg, 6.0 mmol) and Et$_3$N (762 mg, 7.53 mmol), slowly. The solution was stirred at 60° C. for 16 h. The reaction mixture was poured into H$_2$O (30 mL) and extracted with DCM (3×30 mL). The combined organic extracts were dried over Na$_2$SO$_4$, filtered and concentrated under reduced pressure. The crude product was purified by flash chromatography (20% MeOH/DCM). The obtained yellow solid was triturated with 30:1 PE/EtOAc to deliver methyl 3-(((1-methyl-1H-imidazol-5-yl)methyl)amino)-4-nitrobenzoate (1.2 g, 82%) as a yellow solid. $^1$H NMR (CDCl$_3$) δ 8.26 (d, 1H), 7.96 (br s, 1H), 7.71 (d, 1H), 7.50 (s, 1H), 7.35 (dd, 1H), 7.13 (s, 1H), 4.55 (d, 2H), 3.97 (s, 3H), 3.68 (s, 3H).

Step 2

To a yellow suspension of methyl 3-(((1-methyl-1H-imidazol-5-yl)methyl)amino)-4-nitrobenzoate (5.46 g, 18.8 mmol) in MeOH (160 mL) was added wet 10% Pd/C (1 g). The mixture was stirred under 1 atm H$_2$ for 36 h at 20° C. The reaction mixture was filtered and the filter cake rinsed with MeOH (200 mL). The filtrate was concentrated under reduced pressure to deliver methyl 4-amino-3-(((1-methyl-1H-imidazol-5-yl)methyl)amino)benzoate (4.8 g, 98%) as a brown solid. $^1$H NMR (DMSO-d6) δ 7.56 (s, 1H), 7.18 (d, 1H), 7.13 (s, 1H), 6.87 (s, 1H), 6.55 (d, 1H), 5.50 (s, 2H), 4.84 (t, 1H), 4.23 (d, 2H), 3.73 (s, 3H), 3.63 (s, 3H).

Step 3

A red mixture of methyl 4-amino-3-(((1-methyl-1H-imidazol-5-yl)methyl)amino)benzoate (780 mg, 3.00 mmol) and 2-hydroxyacetic acid (342 mg, 4.49 mmol) in mesitylene (8 mL) was stirred at 140° C. under N$_2$ for 14 h and at 25° C. for 48 h. The clear yellow solution was decanted off to give a brown residue that was dissolved in MeOH (50 mL) and concentrated under reduced pressure. The crude product was purified by flash chromatography (20% MeOH/DCM) to give methyl 2-(hydroxymethyl)-1-((1-methyl-1H-imidazol-5-yl)methyl)-1H-benzo[d]imidazole-6-carboxylate (318 mg, 35%) as a yellow foam. $^1$H NMR (DMSO-d6) δ 8.13 (d, 1H), 7.83 (dd, 1H), 7.71 (d, 1H), 7.60 (s, 1H), 6.59 (s, 1H), 5.69 (s, 2H), 4.76 (s, 2H), 3.91 (s, 1H), 3.84 (s, 3H), 3.53 (s, 3H).

Step 4

To a yellow suspension of 2-(hydroxymethyl)-1-((1-methyl-1H-imidazol-5-yl)methyl)-1H-benzo[d]imidazole-6-carboxylate (500 mg, 1.66 mmol) in DCM (10 mL) and DMF (3 mL) was added SOCl$_2$ (990 mg, 0.60 mL, 8.32 mmol), dropwise, at RT. The reaction mixture was stirred at RT for 1 h, concentrated under reduced pressure and the resultant brown residue was triturated with DCM (10 mL). The solids were collected by filtration, rinsed with DCM (5 mL) and dried under vacuum to give Intermediate 32 (431 mg, 73%) as an off-white solid. $^1$H NMR (400 MHz, DMSO-d6) δ 9.17 (s, 1H), 8.31 (s, 1H), 7.91-7.99 (m, 1H), 7.77-7.87 (m, 1H), 7.11 (s, 1H), 5.92 (s, 2H), 5.13 (s, 2H),) 3.87 (s, 3H), 3.86 (s, 3H); MS(ES+): 319.0 (M+H).

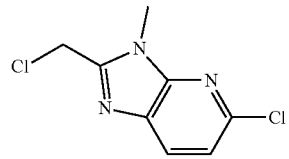

Intermediate 33

5-Chloro-2-(chloromethyl)-3-methyl-3H-imidazo[4,5-b]pyridine

Step 1

To a suspension of 2,6-dichloro-3-nitropyridine (200 g, 1.04 mol) and $Na_2CO_3$ (132 g, 1.24 mol) in EtOH (1 L) was added 2.0 M $MeNH_2$ in THF (622 mL, 1.24 mol), dropwise, at 0° C. via syringe. After the addition, the reaction mixture was stirred at 18° C. for 6 h. The yellow mixture was filtered and the filtrate concentrated under reduced pressure to give a yellow solid. The crude product was purified by flash chromatography (PE/EtOAc 0-5%) to afford 6-chloro-N-methyl-3-nitropyridin-2-amine (158 g, 81% yield) as a yellow solid. $^1$H NMR (DMSO-d6) δ 8.72 (br s, 1H), 8.41 (d, 1H), 6.76 (d, 1H), 3.00 (d, 3H).

Step 2

To a mixture of 6-chloro-N-methyl-3-nitropyridin-2-amine (15.8 g, 84.2 mmol) in AcOH (100 mL) was added iron powder (15.4 g, 276 mmol). The yellow mixture was stirred at 80° C. for 3 h. The reaction was cooled to RT and filtered. The filtercake was washed with EtOAc (2×100). The combined organic layers were concentrated under reduced pressure and the crude product was purified by flash chromatography (120 g silica gel, 50% EtOAc/PE) to afford 3-amino-6-chloro-2-methylaminopyridine (8.40 g, 63% yield) as a brown solid. $^1$H NMR ($CDCl_3$) δ 6.80 (d, 1H), 6.50 (d, 1H), 3.39 (br s, 2H), 3.01 (s, 3H).

Step 3

To a solution of 3-amino-6-chloro-2-methylaminopyridine (50.0 g, 317 mmol) in dioxane (1.2 L) was added chloroacetyl chloride (55.5 mL, 698 mmol) and the mixture was stirred at 15° C. for 50 min. The brown mixture was concentrated under reduced pressure to give a brown solid which was taken up in TFA (1.2 L) and stirred at 80° C. for 60 h. The mixture was concentrated under reduced pressure to give a brown oil. The oil was diluted with EtOAc (1 L) and neutralized with sat. aq. $NaHCO_3$. When $CO_2$ evolution subsided the layers were separated and the aq. layer extracted with EtOAc (200 mL). The organic extracts were combined, dried over $Na_2SO_4$, filtered and concentrated under reduced pressure. The crude product was purified by flash chromatography (10-25% EtOAc/PE gradient) to afford Intermediate 33 (61.0 g, 79%) yield as a yellow solid. $^1$H NMR (400 MHz, DMSO-d6) δ 8.13 (d, 1H), 7.37 (d, 1H), 5.11 (s, 2H), 3.84 (s,

Intermediate 34

Methyl 2-((4-(6-((4-chloro-2-fluorobenzyl)oxy)pyridin-2-yl)piperidin-1-yl)methyl)-1-(2-methoxyethyl)-1H-benzo[d]imidazole-6-carboxylate To a mixture of Intermediate 3 (13.0 g, 23.8 mmol) and Intermediate 19 (6.72 g, 23.8 mmol) and $K_2CO_3$ (16.4 g, 119 mmol) in MeCN (200 mL) was stirred at 50° C. for 12 h. The mixture was cooled to RT and poured into water (200 mL). The mixture was extracted with EtOAc (3×500 mL) and the combined organic layers were washed with brine (2×500 mL), dried over $Na_2SO_4$, filtered and concentrated under reduced pressure. The crude product was purified by flash chromatography (120 g, silica gel, 0-2% MeOH/DCM gradient) to deliver Intermediate 34 (12.5 g, 93%) as a pale yellow solid. $^1$H NMR (400 MHz, $CDCl_3$) δ 8.16 (s, 1H), 7.97 (d, 1H), 7.75 (d, 1H), 7.50 (t, 1H), 7.44 (t, 1H), 7.11 (m, 2H), 6.73 (d, 1H), 6.61 (d, 1H), 5.41 (s, 2H), 4.64 (t, 2H), 3.96 (s, 3H), 3.92 (s, 2H), 3.79 (t, 2H), 3.31 (s, 3H), 2.99 (d, 2H), 2.58-2.67 (m, 1H), 2.29 (t, 2H), 1.78-1.91 (m, 4H).

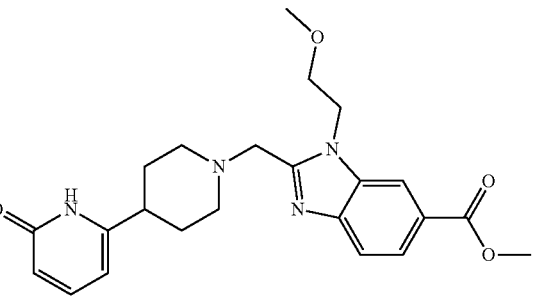

Intermediate 35

Methyl 1-(2-methoxyethyl)-2-((4-(6-oxo-1,6-dihydropyridin-2-yl)piperidin-1-yl)methyl)-1H-benzo[d]imidazole-6-carboxylate To a stirred suspension of Intermediate 34 (500 mg, 0.88 mmol) in MeOH (10 mL) was added 4 M HCl in dioxane (4.5 ml, 20 mmol). The reaction was heated to 70° C. and stirred for 18 h. The mixture was then cooled to RT and concentrated under reduced pressure. The residue was taken up in sat. aq. $NaHCO_3$ and extracted with DCM (3×). The combined organic extracts were washed with brine, dried over $Na_2SO_4$, filtered and concentrated under reduced pressure. The residue was dissolved in a minimum of DCM and PE was added slowly until precipitate formed. The mixture was stirred to granulate solids for 2 h. The solids were isolated by filtration and rinsed with PE to give Intermediate 35 (280 mg, 75%) as an off-white solid. $^1$H NMR (600 MHz, $CDCl_3$) δ 11.43 (br s, 1H), 8.13 (s, 1H), 7.96 (d, 1H), 7.73 (d, 1H), 7.36 (dd, 1H), 6.39 (d, 1H), 6.02 (d, 1H), 4.61 (t, 2H), 3.96 (s, 3H), 3.92 (s, 2H), 3.75 (t, 2H), 3.29 (s, 3H), 2.99 (d, 2H), 2.51 (t, 1H), 2.30 (t, 2H), 1.93 (d, 2H), 1.72 (qd, 2H).

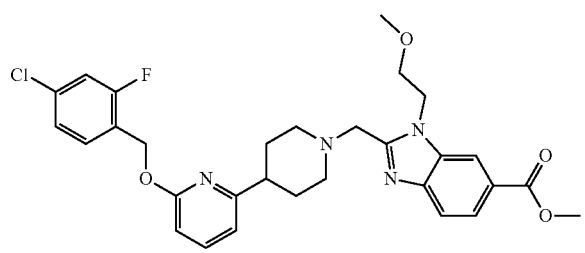 [SMILES: COCCn1c(CN2CCC(c3cccc(OCc4ccc(Cl)cc4F)n3)CC2)nc2ccc(C(=O)OC)cc21]

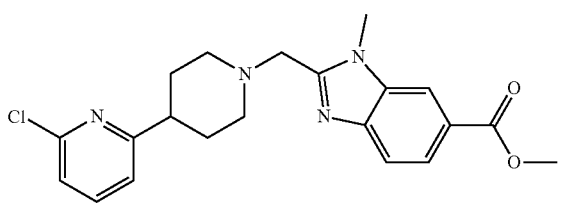 [SMILES: COC(=O)c1ccc2nc(CN3CCC(c4cccc(Cl)n4)CC3)n(C)c2c1]

Intermediate 36

Methyl 2-((4-(6-chloropyridin-2-yl)piperidin-1-yl)methyl)-1-methyl-1H-benzo[d]imidazole-6-carboxylate Step 1

To a colorless solution of Intermediate 2 (6.00 g, 20.2 mmol) in DCM (60 mL) was added 4 M HCl/EtOAc (60 mL) and the solution turned turbid. The suspension was stirred at 20° C. for 2 h, and then concentrated under reduced pressure to give 2-chloro-6-(piperidin-4-yl)pyridine hydrochloride (5.45 g, 99%) as a solid. $^1$H NMR (DMSO-d6) δ 9.32 (br s, 1H), 8.95 (br s, 1H), 7.83 (t, 1H), 7.37 (d, 1H), 7.31 (d, 1H), 3.31 (d, 2H), 2.89-3.06 (m, 3H), 1.85-2.04 (m, 4H).

Step 2

To a mixture of 2-chloro-6-(piperidin-4-yl)pyridine hydrochloride (5.45 g, 20.2 mmol) and $K_2CO_3$ (8.38 g, 60.6 mmol) in DMF (50 mL) was added ethyl 2-bromoacetate (4.05 g, 24.3 mmol). The mixture was stirred at 20° C. for 2 h and then diluted with EtOAc (300 mL) and washed with water (100 mL). The organic layer was washed with brine (200 mL), dried over $Na_2SO_4$, filtered and concentrated under reduced pressure. The crude product was purified by flash chromatography (EtOAc/PE 5-15% gradient) to afford ethyl 2-(4-(6-chloropyridin-2-yl)piperidin-1-yl)acetate (5.44 g, 95%) as a yellow oil. $^1$H NMR (CDCl$_3$) δ 7.59 (t, 1H), 7.16 (d, 1H), 7.11 (d, 1H), 4.21 (q, 2H), 3.26 (s, 2H), 3.08 (d, 2H), 2.72 (tt, 1H), 2.31 (dt, 2H), 1.82-2.02 (m, 4H), 1.29 (t, 3H).

Step 3

To a solution of ethyl 2-(4-(6-chloropyridin-2-yl)piperidin-1-yl)acetate (5.44 g, 19.2 mmol) in EtOH (50 mL) was added 5 M NaOH (11.5 mL, 57.5 mmol). The solution was stirred at 25° C. for 2 h. The reaction mixture was quenched with 1 M HCl and extracted with DCM/MeOH (10:1, 5×80 mL). The combined organic extracts were dried over $MgSO_4$, filtered and concentrated under reduced pressure to afford 2-(4-(6-chloropyridin-2-yl)piperidin-1-yl)acetic acid (4.50 g, 92%) as a yellow solid. $^1$H NMR (CD$_3$OD) δ 7.71 (t, 1H), 7.24 (d, 2H), 3.20 (d, 2H), 3.13 (br s, 2H), 2.70-2.83 (m, 1H), 2.29 (br s, 2H), 1.83-2.06 (m, 4H).

Step 4

To a yellow solution of 2-(4-(6-chloropyridin-2-yl)piperidin-1-yl)acetic acid (4.50 g, 17.7 mmol) and Intermediate 16 (3.50 g, 19.4 mmol) in DMF (50 mL) was added HATU (8.06 g, 21.2 mmol) at RT. The reaction mixture was stirred at 15° C. for 20 min, and then Et$_3$N (3.58 g, 35.3 mmol) was added. The yellow mixture was stirred at 50° C. for 2 h. The resulting brown mixture was poured into water (160 mL) and extracted with EtOAc (3×100 mL). The combined organic extracts were washed with brine (3×100 mL). The organic layer was dried over Na$_2$SO$_4$, filtered and concentrated under reduced pressure. The crude product was purified by flash chromatography (MeOH/DCM 0-5% gradient) to afford methyl 4-amino-3-(2-(4-(6-chloropyridin-2-yl)piperidin-1-yl)-N-methylacetamido)benzoate (7.37 g, quant.) as a yellow oil. LC-MS(ES+): 417.1 (M+H).

Step 5

A mixture of methyl 4-amino-3-(2-(4-(6-chloropyridin-2-yl)piperidin-1-yl)-N-methyl-acetamido)benzoate (7.37 g, 17.7 mmol) in AcOH (100 mL) was stirred at 60° C. for 16 h. The brown mixture was concentrated under reduced pressure to give a brown oil which was taken up in EtOAc (300 mL) and washed with sat. aq. NaHCO$_3$ (100 mL). The organic layer was washed with brine (3×100 mL), dried over MgSO$_4$, filtered and concentrated under reduced pressure. The crude product was purified by flash chromatography (EtOAc/PE 0-50% gradient) to afford Intermediate 36 (3.51 g, 50%) as a yellow solid. $^1$H NMR (CDCl$_3$) δ $^1$H NMR (400 MHz, CDCl3) δ 8.14 (s, 1H), 7.98 (d, 1H), 7.75 (d, 1H), 7.58 (t, 1H), 7.17 (d, 1H), 7.10 (d, 1H), 3.99 (s, 3H), 3.97 (s, 3H), 3.95 (br s, 2H), 3.09 (d, 2H), 2.77 (br s, 1H), 2.43 (br s, 2H), 1.83-2.04 (m, 4H); LC-MS(ES+): 399.1 (M+H).

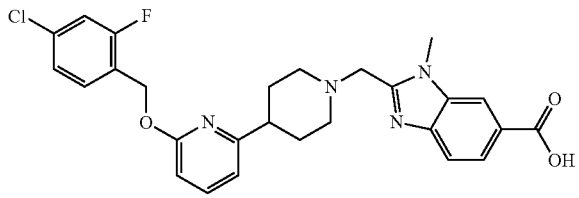 [SMILES: Cn1c(CN2CCC(c3cccc(OCc4ccc(Cl)cc4F)n3)CC2)nc2ccc(C(=O)O)cc21]

2-((4-(6-((4-Chloro-2-fluorobenzyl)oxy)pyridin-2-yl)piperidin-1-yl)methyl)-1-methyl-1H-benzo[d]imidazole-6-carboxylic acid hydrochloride Step 1

Intermediate 17 (115 mg, 0.482 mmol), Intermediate 3 (178 mg, 0.554 mmol) and K$_2$CO$_3$ (133 mg, 0.96 mmol) were combined in MeCN (4.8 mL) and the mixture was allowed to stir at 35° C. for 3 h. The reaction was cooled to RT, diluted with EtOAc and extracted with water. The organic layer was dried over MgSO$_4$, filtered and concentrated under reduced pressure. The resultant crude product was purified by flash chromatography (24 g silica, 0-100% EtOAc/heptane) to deliver 215 mg of methyl 2-((4-(6-((4-chloro-2-fluorobenzyl)oxy)pyridin-2-yl)piperidin-1-yl)methyl)-1-methyl-1H-benzo[d]imidazole-6-carboxylate (85%) as a white foam. $^1$H NMR (400 MHz, CDCl$_3$) δ 8.10 (br s, 1H), 7.95 (d, 1H), 7.72 (d, 1H), 7.51-7.36 (m, 2H), 7.07 (br s, 2H), 6.71 (br s, 1H), 6.57 (d, 1H), 5.38 (br s, 2H), 3.95 (s, 3H), 3.93 (s, 3H), 3.84 (br s, 2H), 2.97 (br s, 2H), 2.59 (br s, 1H), 2.27 (br s, 2H), 1.75-1.93 (m, 4H); LC-MS (ES+): 523.3 (M+H).

Step 2

Methyl 2-((4-(6-((4-chloro-2-fluorobenzyl)oxy)pyridin-2-yl)piperidin-1-yl)methyl)-1-methyl-1H-benzo[d]imidazole-6-carboxylate (215 mg, 0.411 mmol) was suspended in MeOH (4 mL) and treated with 2 M NaOH (820 μL, 1.64 mmol). The reaction was allowed to stir at 40° C. for 3 h and 14 h at RT. The reaction was heated back up to 40° C. and acidified with 1 M HCl (2.50 mL, 2.50 mmol). The mixture was allowed to cool to RT and as a precipitate began to form, a $N_2$ steam was blown over the reaction to remove approximately half of the MeOH. The solid was then collected by filtration, washed with $H_2O$ (2×2 mL), and then dried under $N_2$ to deliver Example 1A-01 (155 mg, 69%) as a solid. $^1H$ NMR (600 MHz, DMSO-d6) δ 12.74 (br s, 1H), 8.15 (s, 1H), 7.79 (d, 1H), 7.58-7.65 (m, 2H), 7.54 (t, 1H), 7.43 (d, 1H), 7.27 (d, 1H), 6.85 (d, 1H), 6.65 (d, 1H), 5.34 (s, 2H), 3.94 (s, 3H), 3.82 (s, 2H), 2.93 (d, 2H), 2.57 (t, 1H), 2.19 (t, 2H), 1.73-1.80 (m, 2H), 1.64-1.73 (m, 2H); LC-MS(ES+): 509.2 (M+H).

The compounds listed in Table 1 below were prepared using procedures analogous to those described above for the synthesis of Compound 1A-01 using the appropriate starting materials which are available commercially, prepared using preparations well-known to those skilled in the art, or prepared in a manner analogous to routes described above for other intermediates. The compounds were purified using methods well known to those skilled in the art and may include silica gel chromatography, HPLC, or crystallization from the reaction mixture. The final compounds may have been isolated as neutrals or acid or base salts.

TABLE 1

| Ex. # | Name | NMR data/LC-MS data |
|---|---|---|
| 1A-02 | 2-[(4-{6-[(4-chloro-2-fluorobenzyl)oxy]pyridin-2-yl}piperidin-1-yl)methyl]-1-(2-methoxyethyl)-1H-benzimidazole-6-carboxylic acid | $^1H$ NMR (400 MHz, $CD_3OD$) δ 8.30 (s, 1H), 7.99 (d, 1H), 7.71 (d, 1H), 7.60 (t, 1H), 7.50 (t, 1H), 7.17-7.25 (m, 2H), 6.86 (d, 1H), 6.67 (d, 1H), 5.42 (s, 2H), 4.68 (t, 2H), 4.25 (br s, 2H), 3.81 (t, 2H), 3.35 (s, 3H), 2.67-2.88 (m, 3H), 2.00 (br s, 4H). LC-MS(ES+): 556.3 (M + H). |
| 1A-03 | 2-{[(2S)-4-{6-[(4-cyano-2-fluorobenzyl)oxy]pyridin-2-yl}-2-methylpiperazin-1-yl]methyl}-1-(2-methoxyethyl)-1H-benzimidazole-6-carboxylic acid | $^1H$ NMR (400 MHz, $CD_3OD$) δ 8.41 (d, 1H), 8.12 (dd, 1H), 7.82 (d, 1H), 7.65 (m, 1H), 7.60-7.48 (m, 3H), 6.43 (d, 1H), 6.27 (d, 1H), 5.48 (s, 2H), 4.68 (m, 2H), 4.57 (d, 1H), 4.17-4.01 (m, 2H), 3.80 (m, 2H), 3.52 (m, 3H), 3.31 (s, 3H), 3.30-3.18 (m, 1H), 1.43 (d, 3H). LC-MS(ES+): 559.2 (M + H). |
| 1A-04 | 2-[(4-{6-[(4-chloro-2-fluorobenzyl)oxy]-5-fluoropyridin-2-yl}piperidin-1-yl)methyl]-1-(2-methoxyethyl)-1H-benzimidazole-6-carboxylic acid | $^1H$ NMR (600 MHz, $CD_3OD$) δ 8.32 (s, 1H), 7.99-8.11 (m, 1H), 7.73-7.84 (m, 1H), 7.50-7.57 (m, 1H), 7.43-7.49 (m, 1H), 7.19-7.29 (m, 2H), 6.89-6.99 (m, 1H), 5.29-5.65 (m, 2H), 4.78-4.81 (m, 2H), 4.63 (s, 2H), 3.83-3.96 (m, 2H), 3.72-3.78 (m, 2H), 3.35-3.46 (m, 2H), 3.30 (s, 3H), 2.95-3.13 (m, 1H), 2.21 (d, 4H). LC-MS(ES+): 570.0 (M + H). |
| 1A-05 | 2-[(4-{6-[(4-chloro-2-fluorobenzyl)oxy]-3-fluoropyridin-2-yl}piperazin-1-yl)methyl]-1-(2-methoxyethyl)-1H-benzimidazole-6-carboxylic acid | LCMS E(4-302) XBridge C18 2.1 × 50 mm, 5 μm; Mobile phase: 1.0% MeCN in water (0.1% TFA) to 5% MeCN in water (0.1% TFA) in 0.6 min; then from 5.0% MeCN in water (0.1% TFA) to 100% MeCN (0.1% TFA) in 3.4 min; then back to 1.0% MeCN in water (0.1% TFA) until 4.3 min, and hold 0.7 min. Flow rate: 0.8 ml/min. Retention time: 2.95 min. LC-MS(ES+): 572.2 (M + H). |
| 1A-06 | 2-{[(2S)-4-{6-[(4-chloro-2-fluorobenzyl)oxy]-3-fluoropyridin-2-yl}-2-methylpiperazin-1-yl]methyl}-1-(2-methoxyethyl)-1H-benzimidazole-6-carboxylic acid | $^1H$ NMR (400 MHz, $CD_3OD$) δ 8.43 (d, 1H), 8.13 (dd, 1H), 7.83 (d, 1H), 7.51-7.37 (m, 2H), 7.29-7.18 (m, 2H), 6.36 (dd, 1H), 5.38 (s, 2H), 4.69 (q, 2H), 4.56 (d, 1H), 3.97 (m, 2H), 3.80 (t, 2H), 3.56 (m, 3H), 3.29 (m, 1H), 1.44 (d, 3H). LC-MS(ES+): 586.0 (M + H). |
| 1A-07 | 2-{[(2S)-4-{6-[(4-chloro-2-fluorobenzyl)oxy]-5-fluoropyridin-2-yl}-2-methylpiperazin-1-yl]methyl}-1-(2-methoxyethyl)-1H-benzimidazole-6-carboxylic acid | $^1H$ NMR (400 MHz, $CD_3OD$) δ 8.43 (d, 1H), 8.13 (dd, 1H), 7.83 (d, 1H), 7.50 (m, 1H), 7.40 (dd, 1H), 7.29-7.20 (m, 2H), 6.38 (dd, 1H), 5.47 (s, 2H), 4.69 (m, 2H), 4.55 (d, 1H), 4.06 (dd, 2H), 3.80 (m, 2H), 3.55 (br s, 2H), 3.43 (d, 1H), 3.24 (m, 1H), 1.45 (d, 3H). LC-MS(ES+): 586.1 (M + H). |
| 1A-08 | 2-{[(2S)-4-{6-[(4-cyanobenzyl)oxy]-5-fluoropyridin-2-yl}-2-methylpiperazin-1-yl]methyl}-1-(2-methoxyethyl)-1H-benzimidazole-6-carboxylic acid | $^1H$ NMR (400 MHz, $CD_3OD$) δ 8.42 (d, 1H), 8.13 (dd, 1H), 7.82 (d, 1H), 7.77-7.69 (m, 2H), 7.62 (d, 2H), 7.42 (dd, 1H), 6.37 (dd, 1H), 5.52 (s, 2H), 4.69 (m, 2H), 4.52 (d, 1H), 3.99 (t, 2H), 3.80 (m, 2H), 3.56-3.32 (m, 3H), 3.32 (m, 2H), 3.27-3.10 (m, 2H), 1.41 (d, 3H). LC-MS(ES+): 559.2 (M + H). |
| 1A-09 | 2-{[4-(6-{[(4-cyano-2-fluorophenyl)(methyl-d2)]oxy}pyridin-2-yl)piperidin-1-yl]methyl}-1-[(2S)-oxetan-2-ylmethyl]-1H-benzimidazole-6-carboxylic acid | $^1H$ NMR (400 MHz, $CD_3OD$) δ 8.33 (d, 1H), 7.99 (dd, 1H), 7.73-7.49 (m, 5H), 6.86 (d, 1H), 6.70 (d, 1H), 5.30 (d, 1H), 4.81-4.71 (m, 1H), 4.66 (m, 1H), 4.50 (m, 1H), 4.08 (d, 1H), 3.97 (d, 1H), 3.11 (m, 1H), 3.00 (d, 1H), 2.83 (m, 1H), 2.67 (m, 1H), 2.56 (m, 1H), 2.36 (m, 2H), 1.86 (m, 4H). LC-MS(ES+): 558.2 (M + H). |
| 1A-10 | 2-({4-[6-(benzyloxy)pyridin-2-yl]piperidin-1-yl}methyl)-1-(2-methoxyethyl)-1H-benzimidazole-6-carboxylic acid | $^1H$ NMR (400 MHz, $CD_3OD$) δ 8.35 (dd, 1H), 8.05 (dd, 1H), 7.81 (dd, 1H), 7.67 (dd, 1H), 7.51-7.42 (m, 2H), 7.42-7.34 (m, 2H), 7.34-7.25 (m, 1H), 6.93 (d, 1H), 6.75 (dd, 1H), 5.43 (s, 2H), 4.82 (s, 2H), 4.64 (t, 2H), 3.91 (brs, 2H), 3.77 (m, 2H), 3.43 (t, 2H), 3.15-3.02 (m, 1H), 2.27 (m, 4H). LC-MS(ES+): 501.3 (M + H). |

TABLE 1-continued

| Ex. # | Name | NMR data/LC-MS data |
|---|---|---|
| 1A-11 | 2-[(4-{6-[(4-cyanobenzyl)oxy]pyridin-2-yl}piperazin-1-yl)methyl]-1-(2-methoxyethyl)-1H-benzimidazole-6-carboxylic acid | $^1$H NMR (400 MHz, CD$_3$OD) δ 8.41 (d, 1H), 8.11 (dd, 1H), 7.82 (d, 1H), 7.76-7.67 (m, 2H), 7.57 (dd, 3H), 6.43 (d, 1H), 6.30 (d, 1H), 5.44 (s, 2H), 4.68 (m, 4H), 3.78 (m, 6H), 3.37 (m, 4H), 3.31 (s, 3H). LC-MS(ES+): 527.2 (M + H). |
| 1A-12 | 2-[(4-{6-[(4-chloro-2-fluorobenzyl)oxy]pyridin-2-yl}-3,3-dimethylpiperazin-1-yl)methyl]-1-(2-methoxyethyl)-1H-benzimidazole-6-carboxylic acid | $^1$H NMR (400 MHz, CD$_3$OD) δ 8.46 (d, 1H), 8.15 (dd, 1H), 7.85 (d, 1H), 7.70 (t, 1H), 7.48 (t, 1H), 7.29-7.19 (m, 2H), 6.82 (d, 1H), 6.69 (d, 1H), 5.42 (s, 2H), 4.77 (t, 2H), 4.52 (s, 2H), 3.82 (m, 2H), 3.69 (m, 2H), 3.27 (m, 2H), 3.10 (m, 2H), 1.40 (s, 6H). LC-MS(ES+): 582.3 (M + H). |
| 1A-13 | 2-{[(3S)-4-{6-[(4-chloro-2-fluorobenzyl)oxy]pyridin-2-yl}-3-methylpiperazin-1-yl]methyl}-1-(2-methoxyethyl)-1H-benzimidazole-6-carboxylic acid | $^1$H NMR (400 MHz, CD$_3$OD) δ 8.43 (d, 1H), 8.13 (dd, 1H), 7.82 (d, 1H), 7.48 (m, 2H), 7.26-7.14 (m, 2H), 6.31 (d, 1H), 6.17 (d, 1H), 5.45-5.28 (m, 2H), 4.76 (m, 2H), 4.68 (m, 1H), 4.47-4.31 (m, 2H), 4.12 (m, 1H), 3.82 (m, 2H), 3.26 (m, 3H), 2.90 (m, 1H), 2.77 (m, 2H), 1.25 (d, 3H). LC-MS(ES+): 568.0 (M + H). |
| 1A-14 | 2-{[(3R)-4-{6-[(4-chloro-2-fluorobenzyl)oxy]pyridin-2-yl}-3-methylpiperazin-1-yl]methyl}-1-(2-methoxyethyl)-1H-benzimidazole-6-carboxylic acid | $^1$H NMR (400 MHz, CD$_3$OD) δ 8.45 (s, 1H), 8.14 (d, 1H), 7.83 (d, 1H), 7.55-7.42 (m, 2H), 7.27-7.16 (m, 2H), 6.32 (d, 1H), 6.18 (d, 1H), 5.45-5.29 (m, 2H), 4.79-4.64 (m, 3H), 4.50-4.38 (m, 2H), 4.14 (d, 1H), 3.82 (t, 2H), 3.00-2.78 (m, 3H), 1.27 (d, 3H). LC-MS(ES+): 568.3 (M + H). |
| 1A-15 | 2-{[(3R)-4-{6-[(4-chloro-2-fluorobenzyl)oxy]pyridin-2-yl}-3-(hydroxymethyl)piperazin-1-yl]methyl}-1-(2-methoxyethyl)-1H-benzimidazole-6-carboxylic acid | $^1$H NMR (400 MHz, CD$_3$OD) δ 8.45 (d, 1H), 8.14 (dd, 1H), 7.85 (d, 1H), 7.50 (m, 2H), 7.27-7.17 (m, 2H), 6.36 (d, 1H), 6.21 (d, 1H), 5.43-5.28 (m, 2H), 4.78-4.70 (m, 2H), 4.68 (m, 1H), 4.60 (s, 2H), 4.25 (m, 1H), 3.98 (dd, 1H), 3.90-3.76 (m, 4H), 3.62-3.45 (m, 2H), 3.11 (m, 2H). LC-MS(ES+): 584.3 (M + H). |
| 1A-16 | 2-[(4-{6-[(4-cyano-2-fluorobenzyl)oxy]pyridin-2-yl}piperidin-1-yl)methyl]-1-[(1-methyl-1H-imidazol-5-yl)methyl]-1H-benzimidazole-6-carboxylic acid | Column: Waters Atlantis dC18 4.6 × 50 mm, 5 μm; Mobile phase A: 0.05% TFA in water (v/v); Mobile phase B: 0.05% TFA in MeCN (v/v); Gradient: 95% H$_2$O/5% MeCN linear to 5% H$_2$O/95% MeCN in 4.0 min, hold at 5% H$_2$O/95% MeCN to 5.0 min. Flow: 2 mL/min. Retention time: 2.05 min. LC-MS(ES+): 580.4 (M + H). |
| 1A-17 | 2-[(4-{6-[(2,4-difluorobenzyl)oxy]pyridin-2-yl}piperidin-1-yl)methyl]-1-[(1-methyl-1H-imidazol-5-yl)methyl]-1H-benzimidazole-6-carboxylic acid | $^1$H NMR (400 MHz, CD$_3$OD) δ 9.01 (d, 1H), 8.31 (d, 1H), 8.09 (dd, 1H), 7.89 (d, 1H), 7.67 (t, 1H), 7.58 (m, 1H), 7.09 (d, 1H), 7.06-6.89 (m, 3H), 6.73 (d, 1H), 5.89 (s, 2H), 5.45 (s, 2H), 4.85 (s, 2H), 4.00 (m, 5H), 3.42 (m, 2H), 3.14-2.99 (m, 1H), 2.40-2.17 (m, 4H). LC-MS(ES+): 573.2 (M + H). |
| 1A-18 | 2-[(4-{6-[(4-chloro-2-fluorobenzyl)oxy]pyridin-2-yl}piperidin-1-yl)methyl]-1-[(4-propyl-4H-1,2,4-triazol-3-yl)methyl]-1H-benzimidazole-6-carboxylic acid | $^1$H NMR (400 MHz, CDCl$_3$) δ 8.13 (s, 1H), 8.09 (s, 1H), 7.95 (d, 1H), 7.74 (d, 1H), 7.49 (t, 1H), 7.42 (t, 1H), 7.09 (t, 2H), 6.71 (d, 1H), 6.60 (d, 1H), 5.93 (br s, 2H), 5.37 (s, 2H), 4.08 (br s, 1H), 3.87 (t, 2H), 3.50 (s, 1H), 3.20 (d, 2H), 2.66 (t, 1H), 2.47 (br s, 2H), 2.05 (s, 1H), 1.73-2.01 (m, 4H), 1.55 (sxt, 2H), 0.89 (t, 3H), 0.74 (t, 3H). LC-MS(ES+): 618.6 (M + H). |
| 1A-19 | 2-{[(2S)-4-{6-[(4-chloro-2-fluorobenzyl)oxy]pyridin-2-yl}-2-methylpiperazin-1-yl]methyl}-1-[(2S)-oxetan-2-ylmethyl]-1H-benzimidazole-6-carboxylic acid | $^1$H NMR (DMSO-d6) δ 12.74 (br s, 1H), 8.27 (s, 1H), 7.81 (d, 1H), 7.66 (d, 1H), 7.37-7.57 (m, 3H), 7.29 (d, 1H), 6.33 (d, 1H), 6.08 (d, 1H), 5.30 (s, 2H), 5.17 (br s, 1H), 4.77 (br s, 2H), 4.42-4.57 (m, 1H), 4.37 (d, 1H), 4.28 (d, 1H), 3.86 (d, 1H), 3.76 (d, 1H), 3.66 (d, 1H), 3.02 (t, 1H), 2.79-2.93 (m, 1H), 2.60-2.77 (m, 3H), 2.21-2.45 (m, 2H), 1.12 (d, 3H). LC-MS(ES+): 580.1 (M + H). |
| 1A-20 | 2-[(4-{6-[(4-cyano-2-fluorobenzyl)oxy]pyridin-2-yl}piperidin-1-yl)methyl]-1-[(4-methyl-4H-1,2,4-triazol-3-yl)methyl]-1H-benzimidazole-6-carboxylic acid | $^1$H NMR (400 MHz, CD$_3$CN) δ 8.39 (s, 1H), 8.24 (s, 1H), 8.08-7.96 (m, 1H), 7.83 (d, 1H), 7.80-7.63 (m, 2H), 7.55 (d, 2H), 6.92 (d, 1H), 6.75 (d, 1H), 5.78 (s, 2H), 5.60 (s, 2H), 4.72-4.49 (m, 2H), 3.89 (s, 3H), 3.72 (m, 2H), 3.29 (m, 2H), 3.03 (m, 1H), 2.21-2.11 (m, 4H). LC-MS(ES+): 581.3 (M + H). |
| 1A-21 | 2-[(4-{6-[(4-cyano-2-fluorobenzyl)oxy]pyridin-2-yl}piperidin-1-yl)methyl]-1-[(2S)-tetrahydrofuran-2-ylmethyl]-1H-benzimidazole-6-carboxylic acid | $^1$H NMR (600 MHz, CD$_3$OD) δ 8.33 (s, 1H), 8.02 (d, 1H), 7.78 (d, 1H), 7.68 (d, 2H), 7.58 (dd, 2H), 6.94 (d, 1H), 6.78 (d, 1H), 5.54 (s, 2H), 4.80-4.72 (m, 2H), 4.67 (d, 1H), 4.43 (dd, 1H), 4.22 (q, 1H), 3.89 (dt, 3H), 3.75 (q, 1H), 3.37 (d, 2H), 3.04 (t, 1H), 2.18 (d, 5H), 1.93 (dd, 2H), 1.67 (dd, 1H). LC-MS(ES+): 570.6 (M + H). |
| 1A-22 | rac 2-{[(3S,4S)-4-{6-[(4-chloro-2-fluorobenzyl)oxy]pyridin-2-yl}-3-fluoropiperidin-1-yl]methyl}-1-(2-methoxyethyl)-1H-benzimidazole-6-carboxylic acid | $^1$H NMR (400 MHz, CD$_3$OD) δ 8.46 (d, 1H), 8.15 (dd, 1H), 7.82 (d, 1H), 7.67 (dd, 1H), 7.52 (t, 1H), 7.30-7.19 (m, 2H), 6.96 (d, 1H), 6.76 (d, 1H), 5.45 (s, 2H), 4.76 (t, 2H), 4.44 (s, 2H), 3.83 (t, 2H), 3.59 (m, 1H), 3.31-3.20 (m, 1H), 3.04 (m, 1H), 2.92-2.73 (m, 2H), 2.32-1.89 (m, 3H). LC-MS(ES+): 571.1 (M + H). |

TABLE 1-continued

| Ex. # | Name | NMR data/LC-MS data |
|---|---|---|
| 1A-23 | rac-2-{[(3S,4S)-4-{6-[(4-chloro-2-fluorobenzyl)oxy]pyridin-2-yl}-3-hydroxypiperidin-1-yl] methyl}-1-(2-methoxyethyl)-1H-benzimidazole-6-carboxylic acid | $^1$H NMR (400 MHz, CD$_3$OD) δ 8.37 (d, 1H), 8.07 (dd, 1H), 7.81 (d, 1H), 7.68 (dd, 1H), 7.54 (t, 1H), 7.32-7.21 (m, 2H), 6.98 (d, 1H), 6.78 (d, 1H), 5.51-5.37 (m, 2H), 4.79 (s, 2H), 4.67 (t, 2H), 4.38 (m, 1H), 3.86-3.73 (m, 4H), 3.16 (m, 1H), 2.95 (s, 1H), 2.37-2.16 (m, 2H). LC-MS(ES+): 569.3 (M + H). |
| 1A-24 | rac-2-{[(3R,4S)-4-{6-[(4-chloro-2-fluorobenzyl)oxy]pyridin-2-yl}-3-hydroxypiperidin-1-yl] methyl}-1-(2-methoxyethyl)-1H-benzimidazole-6-carboxylic acid | $^1$H NMR (400 MHz, CD$_3$OD) δ 8.35 (dd, 1H), 8.02 (dd, 1H), 7.78 (dd, 1H), 7.71 (dd, 1H), 7.48 (t, 1H), 7.29-7.21 (m, 2H), 6.99 (dd, 1H), 6.81 (dd, 1H), 5.46-5.36 (m, 2H), 5.24 (d, 1H), 4.90 (m, 1H), 4.69 (m, 2H), 4.26 (m, 1H), 3.99 (dd, 1H), 3.94-3.81 (m, 3H), 3.78 (m, 2H), 3.63 (m, 1H), 3.30 (s, 3H), 2.56-2.40 (m, 2H). LC-MS(ES+): 569.1 (M + H). |
| 1A-25 | rac-2-{[(3R,4R)-4-{6-[(4-chloro-2-fluorobenzyl)oxy]pyridin-2-yl}-3-methylpiperidin-1-yl]methyl}-1-(2-methoxyethyl)-1H-benzimidazole-6-carboxylic acid | $^1$H NMR (400 MHz, CD$_3$OD) δ 8.32 (d, 1H), 8.00 (dd, 1H), 7.78 (d, 1H), 7.70 (dd, 1H), 7.46 (m, 1H), 7.26 (m, 2H), 6.94 (d, 1H), 6.81 (d, 1H), 5.37 (s, 2H), 4.82 (s, 2H), 4.64 (m, 2H), 4.03 (m, 1H), 3.88 (m, 1H), 3.75 (m, 2H), 3.67 (m, 1H), 3.54 (m, 1H), 3.27 (m, 4H), 2.58 (m, 1H), 2.34 (m, 2H), 0.84 (d, 3H). LC-MS(ES+): 567.1 (M + H). |
| 1A-26 | rac-2-{[(3S,4R)-4-{6-[(4-chloro-2-fluorobenzyl)oxy]pyridin-2-yl}-3-methylpiperidin-1-yl]methyl}-1-(2-methoxyethyl)-1H-benzimidazole-6-carboxylic acid | $^1$H NMR (400 MHz, CD$_3$OD) δ 8.36 (s, 1H), 8.06 (dd, 1H), 7.83 (d, 1H), 7.68 (t, 1H), 7.53 (t, 1H), 7.34-7.26 (m, 2H), 6.92 (d, 1H), 6.77 (d, 1H), 5.47 (q, 2H), 4.85 (s, 2H), 4.65 (t, 2H), 3.93 (d, 1H), 3.84 (d, 1H), 3.79 (t, 2H), 3.47 (m, 1H), 3.35 (s, 3H), 3.10 (t, 1H), 2.66 (dt, 1H), 2.54 (br. m., 1H), 2.32 (dq, 1H), 2.07 (dd, 1H), 0.77 (d, 3H), LC-MS(ES+): 567.1 (M + H). |
| 1A-27 | 2-[(4-{6-[(4-chloro-2-fluorobenzyl)oxy]pyridin-2-yl}piperidin-1-yl)methyl]-1-[(1R,2R)-2-methoxycyclopentyl]-1H-benzimidazole-6-carboxylic acid | $^1$H NMR (600 MHz, CD$_3$OD) δ 8.24 (s, 1H), 7.98 (d, 1H), 7.70 (d, 1H), 7.57 (t, 1H), 7.48 (t, 1H), 7.19 (ddd, 2H), 6.82 (d, 1H), 6.63 (d, 1H), 5.41 (s, 2H), 5.19 (q, 1H), 4.43 (q, 1H), 4.20 (d, 1H), 3.87 (d, 1H), 3.23 (s, 3H), 2.92 (d, 1H), 2.74-2.64 (m, 1H), 2.55-2.46 (m, 1H), 2.41-2.27 (m, 4H), 2.14-1.77 (m, 8H). LC-MS(ES+): 593.5 (M + H). |
| 1A-28 | 2-[(4-{6-[(4-chloro-2-fluorobenzyl)oxy]pyridin-2-yl}piperidin-1-yl)methyl]-1-[(cis-3-methoxycyclobutyl)methyl]-1H-benzimidazole-6-carboxylic acid | $^1$H NMR (600 MHz, CD$_3$OD) δ 8.32 (s, 1H), 8.01 (d, 1H), 7.78 (d, 1H), 7.65 (t, 1H), 7.51 (t, 1H), 7.26-7.19 (m, 2H), 6.93 (d, 1H), 6.73 (d, 1H), 5.45 (s, 2H), 4.80 (s, 2H), 4.45 (d, 2H), 3.92 (s, 2H), 3.79-3.72 (m, 1H), 3.43-3.36 (m, 2H), 3.21 (s, 3H), 3.08-3.02 (m, 1H), 2.46-2.17 (m, 7H), 1.75-1.70 (m, 2H). LC-MS(ES+): 593.6 (M + H). |
| 1A-29 | rac-2-[(4-{6-[(4-chloro-2-fluorobenzyl)oxy]pyridin-2-yl}piperidin-1-yl)methyl]-1-{[(1S,2S)-2-methoxycyclopentyl]methyl}-1H-benzimidazole-6-carboxylic acid | $^1$H NMR (600 MHz, CD$_3$OD) δ 8.36 (s, 1H), 8.01 (d, 1H), 7.78 (d, 1H), 7.65 (t, 1H), 7.51 (t, 1H), 7.23 (t, 2H), 6.92 (d, 1H), 6.73 (d, 1H), 5.45 (s, 2H), 4.78 (dd, 2H), 4.55 (dd, 1H), 4.38 (dd, 1H), 3.96-3.81 (m, 2H), 3.45-3.32 (m, 2H), 3.22 (s, 3H), 3.10-2.99 (m, 1H), 2.53-2.42 (m, 1H), 2.35-2.08 (m, 5H), 2.02-1.54 (m, 6H). LC-MS(ES+): 607.7 (M + H). |
| 1A-30 | 2-[(4-{6-[(4-chloro-2-fluorobenzyl)oxy]pyridin-2-yl}piperidin-1-yl)methyl]-1-{[(1R,2R)-2-(methoxymethyl)cyclopropyl]methyl}-1H-benzimidazole-6-carboxylic acid | $^1$H NMR (600 MHz, CD$_3$OD) δ 8.34 (s, 1H), 8.02 (d, 1H), 7.78 (d, 1H), 7.66 (t, 1H), 7.51 (t, 1H), 7.31-7.17 (m, 2H), 6.93 (d, 1H), 6.73 (d, 1H), 5.45 (s, 2H), 4.51-4.20 (m, 2H), 3.91 (d, 2H), 3.43-3.35 (m, 2H), 3.21 (s, 3H), 3.04 (m, 1H), 2.39-2.15 (m, 4H), 1.30 (d, 5H), 0.90 (t, 1H), 0.79 (dt, 1H), 0.64 (dd, 1H). LC-MS(ES+): 593.5 (M + H). |

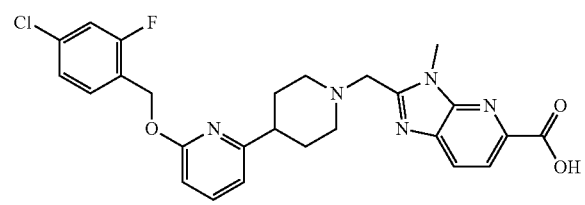 [SMILES: Cn1c(CN2CCC(c3cccc(OCc4ccc(Cl)cc4F)n3)CC2)nc2ccc(C(=O)O)nc21]

Example 2A-01

2-((4-(6-((4-Chloro-2-fluorobenzyl)oxy)pyridin-2-yl)piperidin-1-yl)methyl)-3-methyl-3H-imidazo[4,5-b]pyridine-5-carboxylic acid hydrochloride Step 1

A yellow mixture of Intermediate 3 (92.3 g, 119 mmol, 4 eq TFA salt), Intermediate 33 (25.9 g, 120 mmol) and K$_2$CO$_3$ (98.5 g, 713 mmol) in MeCN (300 mL) was stirred at 50° C. for 16 h. The yellow mixture was poured into water (300 mL) and extracted with EtOAc (3×500 mL). The combined organic layers were washed with brine (500 mL), dried over MgSO$_4$, filtered and concentrated under reduced pressure. The crude product was purified by flash chromatography (MeOH/DCM 0-5% gradient) to afford 5-chloro-2-((4-(6-((4-chloro-2-fluorobenzyl)oxy)pyridin-2-yl)piperidin-1-yl)methyl)-3-methyl-3H-imidazo[4,5-b]pyridine (59.0 g, 99%) as a yellow solid. $^1$H NMR (400 MHz, CDCl$_3$) δ 7.92 (d, 1H), 7.49 (m, 1H), 7.43 (m, 1H), 7.21 (d, 1H), 7.10-7.13 (m, 1H), 7.09 (d, 1H), 6.72 (d, 1H), 6.60 (d, 1H), 5.40 (s, 2H), 3.98 (s, 3H), 3.84 (s, 2H), 2.97 (d, 2H), 2.51-2.73 (m, 1H), 2.29 (m, 2H), 1.73-1.97 (m, 4H).

Step 2

A yellow solution of 5-chloro-2-((4-(6-((4-chloro-2-fluorobenzyl)oxy)pyridin-2-yl)piperidin-1-yl)methyl)-3-methyl-3H-imidazo[4,5-b]pyridine (59.0 g, 118 mmol), DPPP (6.80 g, 16.5 mmol), Pd(OAc)$_2$ (3.65 g, 16.3 mmol) and Et$_3$N (125 g, 1240 mmol) in MeOH (800 mL) and DMF (100 mL) was stirred at 80° C. under 50 psi CO for 16 h. The resulting orange solution was concentrated under reduced pressure to a brown oil, which was diluted with EtOAc (300 mL) and washed with water (200 mL). The organic layer was washed with brine (2×200 mL), dried over MgSO$_4$, filtered and concentrated under reduced pressure. The crude product was combined with product from a similar 11 g scale reaction and purified by flash chromatography (50-100% EtOAc/PE gradient) to afford methyl 2-((4-(6-((4-chloro-2-fluorobenzyl)oxy)pyridin-2-yl)piperidin-1-yl)methyl)-3-methyl-3H-imidazo[4,5-b]pyridine-5-carboxylate (62.6 g, 85%) as a pale yellow solid. $^1$H NMR (400 MHz, CDCl$_3$) δ 8.13 (d, 1H), 8.07 (d, 1H), 7.49 (t, 1H), 7.43 (t, 1H), 7.12 (t, 1H), 7.08-7.11 (m, 1H), 6.73 (d, 1H), 6.60 (d, 1H), 5.40 (s, 2H), 4.09 (s, 3H), 4.03 (s, 3H), 3.90 (s, 2H), 2.93-3.05 (m, 2H), 2.55-2.69 (m, 1H), 2.31 (dt, 2H), 1.79-1.97 (m, 4H).

Step 3

Methyl 2-((4-(6-((4-chloro-2-fluorobenzyl)oxy)pyridin-2-yl)piperidin-1-yl)methyl)-3-methyl-3H-imidazo[4,5-b]pyridine-5-carboxylate (57.0 g, 109 mmol) was suspended in MeOH (1 L) and treated with 2 M NaOH (218 mL). The slurry was stirred 5 min at RT and then heated at 85° C. for 3 h. The mixture was filtered through Celite® and the clear filtrate reheated to 70° C. The reaction was acidified with 2 M HCl (272 mL) and then allowed to cool to RT. Solid formed and the slurry was allowed to stir for 18 h at RT. The solids were collected by filtration to deliver Example 2A-01 (57.1 g, 96%) as an ivory white solid. $^1$H NMR (400 MHz, DMSO-d6) δ 13.20 (br s, 1H), 11.07 (br s, 1H), 8.27 (d, 1H), 8.07 (d, 1H), 7.57-7.78 (m, 2H), 7.47 (m, 1H), 7.32 (m, 1H), 6.92 (d, 1H), 6.74 (d, 1H), 5.40 (s, 2H), 4.84 (br s, 2H), 3.97 (s, 3H), 3.86 (br s, 2H), 3.37 (br s, 2H), 2.93 (br s, 1H), 1.85-2.36 (m, 4H); LC-MS(ES+): 510.2 (M+H).

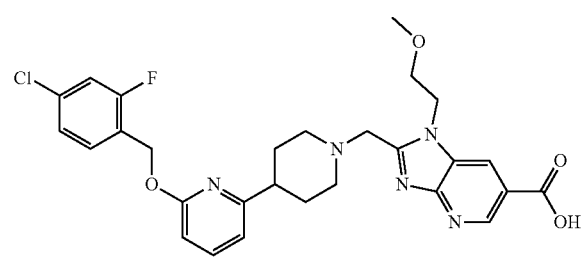 [SMILES: COCCn1c(CN2CCC(c3cccc(OCc4ccc(Cl)cc4F)n3)CC2)nc2ncc(C(=O)O)cc21]

2-((4-(6-((4-Chloro-2-fluorobenzyl)oxy)pyridin-2-yl)piperidin-1-yl)methyl)-1-(2-methoxyethyl)-1H-imidazo[4,5-b]pyridine-6-carboxylic acid hydrochloride Example 2A-02

Step 1

To a flask containing solution of methoxy acetic acid (1.00 g, 11.1 mmol) in DMF (30 mL) was added HATU (6.33 g, 16.7 mmol) and Et$_3$N (3.37 g, 33.3 mmol). After stirring for 20 min, 2,3-diamino-5-bromopyridine (2.3 g, 12 mmol) was added portion-wise, and the resulting reaction mixture stirred overnight. After 15 h, water was added, and the solution was extracted with EtOAc. The combined organic layers were dried, and the solvent removed under reduced pressure. The crude compound was purified by flash chromatography (0 to 80% EtOAc/heptane gradient) to yield N-(2-amino-5-bromopyridin-3-yl)-2-methoxyacetamide (2.3 g, 80%). $^1$H NMR (400 MHz, CDCl$_3$) δ 8.09 (s, 1H), 8.06 (d, 1H), 8.03 (s, 1H), 7.83 (d, 1H), 4.08 (s, 2H), 3.53 (s, 3H); LC-MS(ES+): 260.2 (M+H).

Step 2

To a solution of N-(2-amino-5-bromopyridin-3-yl)-2-methoxyacetamide (3.3 g, 13 mmol) in THF was added 1 M solution of BH$_3$ in THF (14 mL) over the period of 10 min, and stirred at RT overnight, Water was added to the reaction slowly to quench the excess borane, and the mixture then extracted with EtOAc. The EtOAc layer was dried and concentrated under reduced pressure. The crude product was dissolved in MeOH and HCl in dioxane (1.0 equiv) was added and stirred for 2 h. Excess methanol was removed under reduced pressure to obtain the crude product. The compound was purified by flash chromatography with a gradient ranging from 0 to 70% EtOAc in heptanes to obtain 5-bromo-N-(2-methoxyethyl)pyridine-2,3-diamine as a brown oil (1.1 g, 35%). $^1$H NMR (600 MHz, CDCl$_3$) δ 7.83 (d, 1H), 6.95 (d, 1H), 5.56 (s, 2H), 3.77 (t, 1H), 3.66 (t, 2H), 3.42 (s, 3H), 3.22 (q, 2H); LC-MS(ES+): 246.1.

Step 3

5-Bromo-N$^3$-(2-methoxyethyl)pyridine-2,3-diamine (400 mg, 1.63 mmol) was taken up in 8 mL dioxane (8 mL) and treated with chloroacetyl chloride (0.284 mL, 3.58 mmol) The mixture was stirred at RT. The solvent was removed under reduced pressure and the resultant residue was taken up in TFA (8 mL) and stirred at 80° C. for 18 h. The reaction was cooled to RT and concentrated under reduced pressure. The resultant brown oil was taken up in EtOAc (50 mL) and neutralized with sat. aq. NaHCO$_3$. After the CO$_2$ evolution had subsided, the layers were separated and the aq. layer extracted with additional EtOAc (20 mL). The organic extracts were combined, dried over Na$_2$SO$_4$, filtered and concentrated under reduced pressure. The resultant crude product was purified by flash chromatography (0-80% EtOAc/heptane gradient) to yield 6-bromo-2-(chloromethyl)-1-(2-methoxyethyl)-1H-imidazo[4,5-b]pyridine (176 mg, 36%) as a tan solid. $^1$H NMR (600 MHz, CDCl$_3$) δ 8.59 (s, 1H), 7.90 (s, 1H), 4.93 (s, 2H), 4.45 (m, 2H), 3.72 (m, 2H), 3.29 (s, 3H); LC-MS(ES+): 306.1 (M+H).

Step 4

A mixture of Intermediate 3 (294 mg, 0.97 mmol, free base), 6-bromo-2-(chloromethyl)-1-(2-methoxyethyl)-1H- imidazo[4,5-b]pyridine (341 mg, 1.06 mmol), KI (48 mg, 0.29 mmol) and N,N-diisopropylethyl amine (0.51 mL, 0.97 mmol) in MeCN (8 mL) was stirred at 60° C. for 16 h. The mixture was poured into water and extracted with EtOAc. The organic layer was dried, filtered and concentrated under reduced pressure. The crude product was purified by flash chromatography (0-100% EtOAc/heptane gradient) to afford to afford 6-bromo-2-((4-(6-((4-chloro-2-fluorobenzyl)oxy)pyridin-2-yl)piperidin-1-yl)methyl)-1-(2-methoxyethyl)-1H-imidazo[4,5-b]pyridine (406 mg, 71%) as a tan oil. $^1$H NMR (600 MHz, CDCl$_3$) δ 8.54 (s, 1H), 7.91 (s, 1H), 7.50 (m, 1H), 7.43 (m, 1H), 7.11 (m, 2H), 6.73 (d, 1H), 6.60 (d, 1H), 5.41 (s, 2H), 4.54 (m, 2H), 3.92 (s, 2H), 3.76 (m, 2H), 3.30 (s, 3H), 2.97 (d, 2H), 2.58-2.67 (m, 1H), 2.31 (m, 2H), 1.76-1.93 (m, 4H).

Step 5

To a mixture of 6-bromo-2-((4-(6-((4-chloro-2-fluorobenzyl)oxy)pyridin-2-yl)piperidin-1-yl)methyl)-1-(2-methoxyethyl)-1H-imidazo[4,5-b]pyridine (610 mg, 1.04 mmol), palladium(II) acetate (47 mg, 0.21 mmol), and dppp (128 mg, 0.31 mmol) was added DMF (4 mL), MeOH (16 mL) and trimethylamine (1.44 mL, 10.4 mmol). The reaction was heated at 80° C. with stirring under a 50 psi CO atmosphere for 20 h. The reaction mixture was cooled to RT and partitioned between water and EtOAc. The organic layer was separated and dried over MgSO$_4$, filtered and concentrated under reduced pressure. The crude material was purified by flash chromatography (0 to 5% MeOH in DCM gradient) to yield methyl 2-((4-(6-((4-chloro-2-fluorobenzyl)oxy)pyridin-2-yl)piperidin-1-yl)methyl)-1-(2-methoxyethyl)-1H-imidazo[4,5-b]pyridine-6-carboxylate (540 mg, 92%) as a tan gum. $^1$H NMR (600 MHz, CDCl$_3$) δ 9.18 (s, 1H), 8.39 (s, 1H), 7.49 (t, 1H), 7.43 (t, 1H), 7.10 (t, 2H), 6.73 (d, 1H), 6.60 (d, 1H), 5.40 (s, 2H), 4.64 (t, 2H), 4.00-3.90 (m, 5H), 3.78 (t, 2H), 3.29 (s, 3H), 2.99 (d, 2H), 2.62 (m, 1H), 2.27-2.40 (m, 2H), 1.79-1.91 (m, 4H).

Step 6

To a solution of methyl 2-((4-(6-((4-chloro-2-fluorobenzyl)oxy)pyridin-2-yl)piperidin-1-yl)methyl)-1-(2-methoxyethyl)-1H-imidazo[4,5-b]pyridine-6-carboxylate (2.0 g, 3.5 mmol) in MeOH (60 mL) was added 2 M NaOH (8.9 mL) and the mixture was heated at 60° C. for 1 h. The reaction was cooled to RT and acidified with 1 M HCl until pH ~4. The mixture was concentrated under reduced pressure to remove MeOH and the solid was collected by filtration and dried under vacuum to yield Example 2A-02 (1.7 g 82%) as a solid. $^1$H NMR (400 MHz, DMSO-d6) δ 13.35 (br s, 1H), 10.90 (br s, 1H), 9.01 (d, 1H), 8.70 (d, 1H), 7.69 (t, 1H), 7.63 (t, 1H), 7.47 (dd, 1H), 7.32 (dd, 1H), 6.93 (d, 1H), 6.73 (d, 1H), 5.40 (s, 2H), 4.86 (br s, 2H), 4.70 (br s, 2H), 3.81 (br s, 2H), 3.65 (m, 2H), 3.20 (s, 3H), 2.94 (br s, 1H), 2.08-2.25 (m, 4H); LC-MS(ES+): 554.2 (M+H).

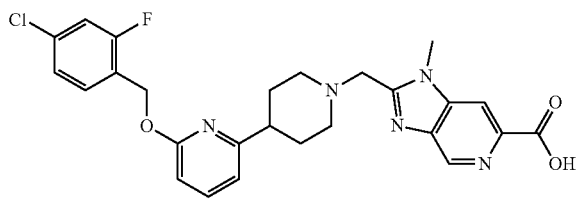 [SMILES: Cn1c(CN2CCC(c3cccc(OCc4ccc(Cl)cc4F)n3)CC2)nc2cnc(C(=O)O)cc21]

Example 2A-03

2-((4-(6-((4-Chloro-2-fluorobenzyl)oxy)pyridin-2-yl)piperidin-1-yl)methyl)-1-methyl-1H-imidazo[4,5-c]pyridine-6-carboxylic acid Step 1

To a stirred solution of 2,4-dibromo-5-nitropyridine (0.21 g, 0.72 mmol) in THF (4.1 mL) was added methyl amine in THF (2 M, 1.2 mL, 2.5 mmol). After 0.5 h, the solution was diluted with water (5 mL). The aq. phase was extracted with EtOAc (3×15 mL), the combined organic layers were washed with brine (20 mL), dried over anhydrous Na$_2$SO$_4$, filtered, and the solvent removed under reduced pressure. The crude material was purified using column chromatography (50% EtOAc/heptane) to obtain 2-bromo-N-methyl-5-nitropyridin-4-amine as a yellow solid (0.15 g, 90%). $^1$H NMR (CDCl$_3$) δ 8.99 (s, 1H), 6.95 (s, 1H), 3.08 (d, 3H).

Step 2

To a stirred solution of 2-bromo-N-methyl-5-nitropyridin-4-amine (0.22 g, 0.96 mmol) in AcOH (4.8 mL) was added Fe (0.053 g, 0.96 mmol). The solution was heated to 75° C. After 5 h, the solution was filtered through a Celite® plug, washed with EtOAc (10 mL) and then quenched with satd. Na$_2$CO$_3$. The aq. phase was extracted with EtOAc (2×10 mL), the combined organic layers were dried over anhydrous Na$_2$SO$_4$, filtered, treated with HCl in dioxane (4 M, 2.4 mL, 9.6 mmol) and the solvent removed under reduced pressure. The crude material was stirred in Et$_2$O/PE for 30 min, and the resultant solid was then collected by filtration, washed with PE and dried under reduced pressure to provide of 6-bromo-N$^4$-methylpyridine-3,4-diamine hydrochloride (0.20 g, 88%). $^1$H NMR (CD$_3$OD) δ 7.48 (s, 1H), 6.95 (s, 1H), 3.04 (s, 3H).

Step 3

To a stirred solution of 6-bromo-N$^4$-methylpyridine-3,4-diamine hydrochloride (0.15 g, 0.52 mmol) in DMF (2.4 mL) was added Intermediate 5 (0.18 g, 0.48 mmol) followed by DIPEA (0.25 mL, 1.4 mmol) and HBTU (0.18 g, 0.57 mmol). After 2 h, the solution was concentrated under reduced pressure, diluted with EtOAc (20 mL) and washed with satd. Na$_2$CO$_3$. The organic layer was dried over anhydrous Na$_2$SO$_4$, filtered and the solvent removed under reduced pressure. The crude amide N-(6-bromo-4-(methylamino)pyridin-3-yl)-2-(4-(6-((4-chloro-2-fluorobenzyl)oxy)pyridin-2-yl)piperidin-1-yl)acetamide was dissolved in 1,4-dioxane (5 mL), treated with NaOH (2 M, 2.4 mL, 4.8 mmol) and heated to 100° C. After 0.5 h, the solution was diluted with water (10 mL). The aq. phase was extracted with CH$_2$Cl$_2$ (3×10 mL), the combined organic layers were dried over anhydrous Na$_2$SO$_4$, filtered, and the solvent removed under reduced pressure. The crude material was purified using column chromatography eluting with EtOAc to obtain 6-bromo-2-((4-(6-((4-chloro-2-fluorobenzyl)oxy)pyridin-2-yl)piperidin-1-yl)methyl)-1-methyl-1H-imidazo[4,5-c]pyridine as a brown oil (0.19 g, 72%). $^1$H NMR (CDCl$_3$) δ 8.74 (s, 1H), 7.44-7.51 (m, 2H), 7.41 (t, 1H), 7.08 (t, 2H), 6.71 (d, 1H), 6.59 (d, 1H), 5.39 (s, 2H), 3.89 (s, 3H), 3.83 (s, 2H), 2.94 (d, 2H), 2.60 (ddd, 1H), 2.28 (t, 2H), 1.85-1.90 (m, 2H), 1.75-1.84 (m, 2H).

Step 4

To a vial containing 6-bromo-2-((4-(6-((4-chloro-2-fluorobenzyl)oxy)pyridin-2-yl)piperidin-1-yl)methyl)-1- methyl-1H-imidazo[4,5-c]pyridine (0.060 g, 0.11 mmol), DPPP (0.011 g, 0.028 mmol) and Pd(OAc)$_2$ (0.035 g, 0.015 mmol) was added DMF (0.4 mL) followed by MeOH (2.6 mL) and Et$_3$N (0.13 mL, 1.1 mmol). The solution was heated to 80° C. under CO (50 psi) atmosphere. After 16 h, the solution was diluted with brine (5 mL). The aq. phase was extracted with EtOAc (2×10 mL), the combined organic layers were dried over anhydrous MgSO$_4$, filtered, and the solvent removed under reduced pressure. The crude material was purified using column chromatography eluting with 5% MeOH in CH$_2$Cl$_2$ to obtain methyl 2-((4-(6-((4-chloro-2-fluorobenzyl)oxy)pyridin-2-yl)piperidin-1-yl)methyl)-1-methyl-1H-imidazo[4,5-c]pyridine-6-carboxylate as a yellow oil (0.060 g, quant.). $^1$H NMR (600 MHz, CDCl$_3$) δ 9.11 (s, 1H), 8.29 (s, 1H), 7.45-7.54 (m, 1H), 7.35-7.45 (m, 1H), 7.10 (t, 2H), 6.73 (d, 1H), 6.61 (d, 1H), 5.40 (s, 2H), 4.05 (s, 3H), 4.02 (s, 3H), 3.91 (s, 2H), 2.98 (d, 2H), 2.58-2.68 (m, 1H), 2.32 (t, 2H), 1.74-1.95 (m, 4H).

Step 5

To a stirred solution of methyl 2-((4-(6-((4-chloro-2-fluorobenzyl)oxy)pyridin-2-yl)piperidin-1-yl)methyl)-1-methyl-1H-imidazo[4,5-c]pyridine-6-carboxylate (0.041 g, 0.078 mmol) in MeOH (0.78 mL) was added a solution of NaOH in water (2 M, 0.14 mL) under stirring at 35° C. After 2 h, the solution was acidified to pH ~4 with HCl in water (1 M), cooled to 0° C., diluted with water (0.5 mL), and allowed to stand for 2 h. The resultant solid precipitate was slurried for 1 h, collected by filtration, washed with water (2×1 mL), and then dried under reduced pressure to provide Example 2A-03 as a solid (21 mg, 48%). $^1$H NMR (400 MHz, CD$_3$OD) δ: 9.10 (br s, 1H), 8.57 (br s, 1H), 7.67 (br. t, 1H), 7.52 (br. t, 1H), 7.13-7.33 (m, 2H), 6.95 (d, 1H), 6.75 (d, 1H), 5.46 (s, 2H), 4.92 (s, 2H), 3.92-4.18 (m, 5H), 3.45 (br s, 2H), 3.08 (br s, 1H), 2.11-2.46 (m, 4H). LC-MS(ES+): 510.3 (M+H).

The compounds listed in Table 2 below were prepared using procedures analogous to those described above for the synthesis of Examples 2A-01, 2A-02, and 2A-03 using the appropriate starting materials which are available commercially, prepared using preparations well-known to those skilled in the art, or prepared in a manner analogous to routes described above for other intermediates. The compounds were purified using methods well known to those skilled in the art and may include silica gel chromatography, HPLC, or crystallization from the reaction mixture. The final compounds may have been isolated as neutrals or acid or base salts.

TABLE 2

| Ex. # | Name | NMR data/LC-MS data |
|---|---|---|
| 2A-04 | 2-[(4-{6-[(4-chloro-2-fluorobenzyl)oxy]pyridin-2-yl}piperidin-1-yl)methyl]-1-methyl-1H-imidazo[4,5-b]pyridine-6-carboxylic acid | $^1$H NMR (600 MHz, CD$_3$OD) δ 9.04 (s, 1H), 8.52 (s, 1H), 7.70 (t, 1H), 7.46 (t, 1H), 7.27-7.04 (m, 2H), 6.82 (d, 1H), 6.62 (d, 1H), 5.38 (s, 2H), 4.11 (s, 2H), 4.02 (s, 3H), 3.21 (d, 2H), 2.77-2.45 (m, 3H), 2.07-1.78 (m, 4H). LC-MS(ES+): 510.3 (M + H). |
| 2A-05 | 2-[(4-{6-[(4-chloro-2-fluorobenzyl)oxy]pyridin-2-yl}piperidin-1-yl)methyl]-1-[(2S)-oxetan-2-ylmethyl]-1H-imidazo[4,5-c]pyridine-6-carboxylic acid | $^1$H NMR (400 MHz, CD$_3$OD) δ 8.92 (s, 1H), 8.50 (s, 1H), 7.60 (dd, 1H), 7.49 (m, 1H), 7.18 (m, 2H), 6.86 (d, 1H), 6.66 (d, 1H), 5.43 (s, 2H), 5.27 (d, 1H), 4.81 (m, 1H), 4.65 (m, 1H), 4.50 (m, 1H), 4.24 (d, 1H), 4.12 (d, 1H), 3.20 (m, 1H), 2.97-2.69 (m, 2H), 2.55 (m, 3H), 2.00 (m, 5H). LC-MS(ES+): 566.1 (M + H). |
| 2A-06 | 2-[(4-{6-[(4-chloro-2-fluorobenzyl)oxy]pyridin-2-yl}piperidin-1-yl)methyl]-1-(1,3-oxazol-2-ylmethyl)-1H-imidazo[4,5-c]pyridine-6-carboxylic acid | $^1$H NMR (400 MHz, CD$_3$OD) δ 9.14 (s, 1H), 8.63 (s, 1H), 8.00 (s, 1H), 7.68 (m, 1H), 7.53 (m, 1H), 7.24 (m, 3H), 6.95 (d, 1H), 6.76 (d, 1H), 5.96 (s, 2H), 5.47 (s, 2H), 4.98 (s, 2H), 3.97 (brs, 2H), 3.43 (m, 2H), 3.08 (m, 1H), 2.28 (m, 4H). LC-MS(ES+): 577.0 (M + H). |
| 2A-07 | 2-[(4-{6-[(4-chloro-2-fluorobenzyl)oxy]pyridin-2-yl}piperidin-1-yl)methyl]-1-(2-methoxyethyl)-1H-imidazo[4,5-c]pyridine-6-carboxylic acid | $^1$H NMR (400 MHz, DMSO-d6) δ 9.12 (d, 1H), 8.55 (d, 1H), 7.71 (t, 1H), 7.61 (t, 1H), 7.49 (dd, 1H), 7.33 (dd, 1H), 6.95 (d, 1H), 6.76 (d, 1H), 5.41 (s, 2H), 4.88 (s, 2H), 4.68 (d, 2H), 3.84 (s, 1H), 3.66 (t, 2H), 3.33 (s, 2H), 3.21 (s, 3H), 2.96 (s, 1H), 2.11 (s, 5H). LC-MS(ES+): 553.9 (M + H). |
| 2A-08 | 2-[(4-{6-[(4-chloro-2-fluorobenzyl)oxy]pyridin-2-yl}piperidin-1-yl)methyl]-7-fluoro-1-(2-methoxyethyl)-1H-benzimidazole-6-carboxylic acid | $^1$H NMR (400 MHz, CD$_3$OD) δ 7.86 (dd, 1H), 7.66 (dd, 1H), 7.58 (d, 1H), 7.51 (t, 1H), 7.19-7.28 (m, 2H), 6.94 (d, 1H), 6.74 (d, 1H), 5.45 (s, 2H), 4.80 (s, 2H), 4.67 (t, 2H), 3.91 (d, 2H), 3.80 (t, 3H), 3.34-3.47 (m, 2H), 3.32 (s, 3H), 3.06 (m, 1H), 2.16-2.35 (m, 4H). LC-MS(ES+): 571.2 (M + H). |
| 2A-09 | 2-[(4-{6-[(4-chloro-2-fluorobenzyl)oxy]pyridin-2-yl}piperidin-1-yl)methyl]-5-fluoro-1-methyl-1H-benzimidazole-6-carboxylic acid | $^1$H NMR (400 MHz, CDCl3) δ 7.88 (d, 1H), 7.59-7.50 (m, 1H), 7.45-7.33 (m, 2H), 7.14-7.04 (m, 2H), 6.77 (d, 1H), 6.67 (d, 1H), 5.36 (s, 2H), 4.76 (s, 2H), 4.04 (m, 5H), 3.37 (m, 2H), 2.98 (m, 1H), 2.31 (m, 4H). LC-MS(ES+): 527.1 (M + H). |
| 2A-10 | 2-[(4-{6-[(4-chloro-2-fluorobenzyl)oxy]pyridin-2-yl}piperidin-1-yl)methyl]-1-(2-methoxyethyl)-1H-imidazo[4,5-b]pyrazine-6-carboxylic acid | $^1$H NMR (600 MHz, CD$_3$OD) δ 9.28 (s, 1H), 7.61-7.71 (m, 1H), 7.45-7.57 (m, 1H), 7.23 (m, 2H), 6.85-7.03 (m, 1H), 6.61-6.81 (m, 1H), 5.46 (s, 2H), 5.00 (s, 2H), 4.65-4.74 (m, 2H), 3.91-4.10 (m, 2H), 3.70-3.86 (m, 2H), 3.42-3.59 (m, 2H), 3.33 (s, 3H), 3.03-3.18 (m, 1H), 2.31 (d, 2H), 2.18-2.26 (m, 2H). LC-MS(ES+): 554.0 (M + H). |

TABLE 2-continued

| Ex. # | Name | NMR data/LC-MS data |
|---|---|---|
| 2A-11 | 2-[(4-{6-[(4-chloro-2-fluorobenzyl)oxy]pyridin-2-yl}piperidin-1-yl)methyl]-1-(2-methoxyethyl)-7-methyl-1H-imidazo[4,5-b]pyridine-6-carboxylic acid | $^1$H NMR (400 MHz, CDCl3) δ: 8.79 (s, 1H), 7.70 (br s, 1H), 7.61 (t, 1H), 7.48 (d, 1H), 7.32 (d, 1H), 6.95 (br s, 1H), 6.74 (d, 1H), 5.41 (s, 2H), 4.73 (br s, 3H), 3.73 (br s, 4H), 3.22 (b s, 5H), 2.91 (b s, 4H), 2.09 (br s, 4H). LC-MS(ES+): 568.3 (M + H). |
| 2A-12 | 2-[(4-{6-[(4-chloro-2-fluorobenzyl)oxy]pyridin-2-yl}piperidin-1-yl)methyl]-1,5-dimethyl-1H-imidazo[4,5-b]pyridine-6-carboxylic acid | $^1$H NMR (600 MHz, DMSO-d6) δ 13.15 (s, 1H), 10.79 (s, 1H), 8.57 (s, 1H), 7.70 (t, 1H), 7.63 (t, 1H), 7.48 (dd, 1H), 7.33 (dd, 1H), 6.93 (s, 1H), 6.74 (d, 1H), 5.40 (s, 2H), 4.82 (s, 2H), 3.95 (s, 3H), 3.82 (m, 2H), 3.01-2.86 (m, 1H), 2.81 (s, 3H), 2.53-2.48 (m, 3H), 2.28-1.95 (m, 3H). LC-MS(ES+): 524.2 (M + H). |
| 2A-13 | 5-chloro-2-[(4-{6-[(4-chloro-2-fluorobenzyl)oxy]pyridin-2-yl}piperidin-1-yl)methyl]-1-methyl-1H-benzimidazole-6-carboxylic acid | $^1$H NMR (600 MHz, CD$_3$OD) δ: 8.07 (br s, 1H), 7.77 (br s, 1H), 7.63 (br s, 1H), 7.50 (br s, 1H), 7.14-7.31 (m, 2H), 6.90 (d, 1H), 6.71 (d, 1H), 5.43 (br s, 2H), 4.57 (br s, 2H), 3.94 (br s, 3H), 3.70 (d, 2H), 3.14 (br s, 2H), 2.95 (br s, 1H), 1.99-2.31 (m, 4H). LC-MS(ES+): 546.2 (M + H). |
| 2A-14 | 2-[(4-{6-[(4-cyanobenzyl)oxy]pyridin-2-yl}piperidin-1-yl)methyl]-5-fluoro-1-(2-methoxyethyl)-1H-benzimidazole-6-carboxylic acid | $^1$H NMR (400 MHz, CD$_3$OD) δ 8.25 (d, 1H), 7.79-7.59 (m, 5H), 7.54 (d, 1H), 6.95 (d, 1H), 6.80 (d, 1H), 5.53 (s, 2H), 4.81 (s, 2H), 4.60 (m, 2H), 3.93 (m, 1H), 3.78-3.70 (m, 2H), 3.41 (m, 3H), 3.06 (sm 1H), 2.21 (m, 4H). LC-MS(ES+): 544.3 (M + H). |
| 2A-15 | 2-[(4-{6-[(4-cyanobenzyl)oxy]pyridin-2-yl}piperidin-1-yl)methyl]-7-fluoro-1-(2-methoxyethyl)-1H-benzimidazole-6-carboxylic acid | $^1$H NMR (400 MHz, CD$_3$OD) δ 7.89 (dd, 1H), 7.80-7.56 (m, 6H), 6.95 (d, 1H), 6.80 (d, 1H), 5.53 (s, 2H), 4.81 (s, 2H), 4.67 (m, 2H), 3.92 (s, 2H), 3.81 (m, 2H), 3.41 (s, 2H), 3.07 (s, 1H), 2.21 (s, 4H). LC-MS(ES+): 544.3 (M + H). |
| 2A-16 | 2-[(4-{6-[(4-chloro-2-fluorobenzyl)oxy]pyridin-2-yl}piperidin-1-yl)methyl]-1-(2,2,2-trifluoroethyl)-1H-imidazo[4,5-b]pyridine-6-carboxylic acid | $^1$H NMR (600 MHz, CD$_3$OD) δ 9.18 (s, 1H), 8.80 (s, 1H), 7.67 (t, 1H), 7.51 (t, 1H), 7.23 (t, 2H), 6.94 (d, 1H), 6.74 (d, 1H), 5.47 (s, 2H), 5.45-5.39 (m, 2H), 4.94 (s, 2H), 4.03 (s, 2H), 3.44 (s, 2H), 3.09 (s, 1H), 2.44-2.12 (m, 4H). LC-MS(ES+): 578.4 (M + H). |
| 2A-17 | 2-[(4-{6-[(4-chloro-2-fluorobenzyl)oxy]pyridin-2-yl}piperidin-1-yl)methyl]-3-(2-methoxyethyl)-3H-imidazo[4,5-b]pyridine-5-carboxylic acid | $^1$H NMR (600 MHz, CD$_3$OD) δ 8.25-8.00 (m, 2H), 7.59 (t, 1H), 7.49 (t, 1H), 7.35-7.09 (m, 2H), 6.84 (d, 1H), 6.65 (d, 1H), 5.41 (s, 2H), 4.81 (t, 2H), 4.21 (s, 2H), 3.84 (t, 2H), 3.32 (s, 3H), 3.25 (d, 2H), 2.84-2.70 (m, 1H), 2.61 (t, 2H), 2.09-1.85 (m, 4H). LC-MS(ES+): 554.2 (M + H). |
| 2A-18 | 2-[(4-{6-[(4-chloro-2-fluorobenzyl)oxy]pyridin-2-yl}piperidin-1-yl)methyl]-3-(1,3-oxazol-2-ylmethyl)-3H-imidazo[4,5-b]pyridine-5-carboxylic acid | $^1$H NMR (400 MHz, CD$_3$OD) δ 8.31 (d, 1H), 8.24 (d, 1H), 7.99 (s, 1H), 7.72-7.63 (m, 1H), 7.53 (m, 1H), 7.31-7.19 (m, 2H), 7.16 (s, 1H), 6.95 (d, 1H), 6.75 (d, 1H), 5.99 (s, 2H), 5.47 (s, 2H), 3.96 (m, 2H), 3.52-3.34 (m, 2H), 3.08 (m, 1H), 2.25 (m, 5H). LC-MS(ES+): 577.0 (M + H). |
| 2A-19 | 2-[(4-{6-[(4-cyano-2-fluorobenzyl)oxy]pyridin-2-yl}piperidin-1-yl)methyl]-3-(1,3-oxazol-2-ylmethyl)-3H-imidazo[4,5-b]pyridine-5-carboxylic acid | $^1$H NMR (400 MHz, CD$_3$OD) δ 8.31 (d, 1H), 8.24 (d, 1H), 7.99 (s, 1H), 7.71 (m, 2H), 7.64-7.56 (m, 2H), 7.17 (s, 1H), 6.97 (d, 1H), 6.81 (d, 1H), 5.98 (s, 2H), 5.58 (s, 2H), 3.99 (d, 2H), 3.45 (m, 2H), 3.08 (m, 1H), 2.34-2.17 (m, 4H). LC-MS(ES+): 568.1 (M + H). |
| 2A-20 | 2-[(4-{6-[(2,4-difluorobenzyl)oxy]pyridin-2-yl}piperidin-1-yl)methyl]-3-[(2S)-oxetan-2-ylmethyl]-3H-imidazo[4,5-b]pyridine-5-carboxylic acid | $^1$H NMR (400 MHz, CD$_3$OD) δ 8.09 (q, 2H), 7.67-7.51 (m, 2H), 7.04-6.89 (m, 2H), 6.85 (d, 1H), 6.64 (d, 1H), 5.42 (s, 2H), 5.32 (m, 1H), 5.06 (dd, 1H), 4.64 (m, 1H), 4.47 (m, 1H), 4.23 (d, 1H), 4.12 (d, 1H), 3.28-3.09 (m, 2H), 2.87-2.66 (m, 2H), 2.62-2.42 (m, 3H), 2.06-1.85 (m, 4H). LC-MS(ES+): 550.1 (M + H). |
| 2A-21 | 2-{[(2S)-4-{6-[(4-cyano-2-fluorobenzyl)oxy]pyridin-2-yl}-2-methylpiperazin-1-yl]methyl}-3-(1,3-oxazol-2-ylmethyl)-3H-imidazo[4,5-b]pyridine-5-carboxylic acid | $^1$H NMR (400 MHz, CD$_3$OD) δ 8.33-8.19 (m, 2H), 7.98 (d, 1H), 7.77-7.48 (m, 4H), 7.17 (d, 1H), 6.45 (d, 1H), 6.30 (d, 1H), 5.98 (d, 2H), 5.48 (s, 2H), 5.09 (d, 1H), 4.73 (d, 1H), 4.06 (m, 2H), 3.74 (m, 2H), 3.61-3.46 (m, 2H), 3.38 (m, 1H), 1.50 (d, 3H). LC-MS(ES+): 583.1 (M + H) |
| 2A-22 | 2-[(4-{6-[(4-chloro-2-fluorobenzyl)oxy]pyridin-2-yl}piperidin-1-yl)methyl]-3-[(2R)-oxetan-2-ylmethyl]-3H-imidazo[4,5-b]pyridine-5-carboxylic acid | $^1$H NMR (400 MHz, CD$_3$OD) δ 8.14 (m, 2H), 7.66-7.57 (m, 1H), 7.51 (m, 1H), 7.22 (m, 2H), 6.87 (d, 1H), 6.68 (d, 1H), 5.44 (s, 2H), 5.32 (m, 1H), 5.02 (m, 1H), 4.71-4.59 (m, 1H), 4.52-4.42 (m, 1H), 4.38-4.21 (m, 2H), 3.28 (m, 1H), 2.87-2.74 (m, 2H), 2.66 (m, 1H), 2.62-2.50 (m, 1H), 2.00 (m, 4H). LC-MS(ES+): 566.1 (M + H) |

TABLE 2-continued

| Ex. # | Name | NMR data/LC-MS data |
|---|---|---|
| 2A-23 | 2-[(4-{6-[(4-chloro-2-fluorobenzyl)oxy]pyridin-2-yl}piperidin-1-yl)methyl]-3-[(2S)-oxetan-2-ylmethyl]-3H-imidazo[4,5-b]pyridine-5-carboxylic acid | $^1$H NMR (400 MHz, CD$_3$OD) δ 8.14 (d, 2H), 7.61 (t, 1H), 7.51 (t, 1H), 7.22 (m, 2H), 6.87 (d, 1H), 6.68 (d, 1H), 5.43 (s, 2H), 5.31 (m, 1H), 5.01 (m, 1H), 4.87 (d, 1H), 4.71-4.60 (m, 1H), 4.46 (m, 1H), 4.34 (m, 2H), 3.39 (m, 1H), 3.30 (m, 1H), 2.91-2.65 (m, 4H), 2.55 (m, 1H), 2.01 (m, 4H). LC-MS(ES+): 566.1 (M + H) |

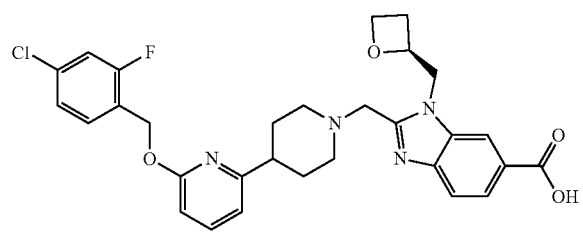 [SMILES: O=C(O)c1ccc2nc(CN3CCC(c4cccc(OCc5ccc(Cl)cc5F)n4)CC3)n(C[C@@H]3CCO3)c2c1]

Example 3A-01

2-[(4-{6-[(4-chloro-2-fluorobenzyl)oxy]pyridin-2-yl}piperidin-1-yl)methyl]-1-[(2S)-oxetan-2-ylmethyl]-1H-benzimidazole-6-carboxylic acid

Step 1

To a stirred solution of Intermediate 22 (49.8 g, 211 mmol) in MeCN (300 mL) was added 2-chloro-1,1,1-trimethoxyethane (30.0 mL, 223 mmol) followed by pTSA.H$_2$O (2.0 g, 10 mmol). After 1 h at 60° C., MeCN (400 mL), K$_2$CO$_3$ (116 g, 841 mmol) and Intermediate 3 (52.4 g, 90.2 mmol) were added. After 2 h, the solution was treated with water (1.6 L), allowed to cool to RT and stirred for 2 h. The resulting solid precipitate was collected by filtration, washed with water (2×300 mL) and dried under reduced pressure to provide methyl (S)-2-((4-(6-((4-chloro-2-fluorobenzyl)oxy)pyridin-2-yl)piperidin-1-yl)methyl)-1-(oxetan-2-ylmethyl)-1H-benzo[d]imidazole-6-carboxylate as a solid (102 g, 84%). $^1$H NMR (DMSO-d6) δ 8.30 (s, 1H), 7.82 (d, 1H), 7.67 (d, 1H), 7.62 (t, 1H), 7.55 (t, 1H), 7.45 (d, 1H), 7.29 (d, 1H), 6.87 (d, 1H), 6.67 (d, 1H), 5.37 (s, 2H), 5.04-5.16 (m, 1H), 4.82 (dd, 1H), 4.62-4.73 (m, 1H), 4.44-4.52 (m, 1H), 4.37 (dt, 1H), 3.96 (d, 1H), 3.87 (s, 3H), 3.78 (d, 1H), 3.00 (d, 1H), 2.85 (d, 1H), 2.66-2.76 (m, 1H), 2.54-2.64 (m, 1H), 2.38-2.49 (m, 1H), 2.24 (t, 2.11-2.21 (m, 1H), 1.60-1.88 (m, 4H).

Step 2

To a stirred solution of methyl (S)-2-((4-(6-((4-chloro-2-fluorobenzyl)oxy)pyridin-2-yl)piperidin-1-yl)methyl)-1-(oxetan-2-ylmethyl)-1H-benzo[d]imidazole-6-carboxylate (7.2 g, 12 mmol) in MeOH (50 mL) and THF (50 mL) was added 2 M NaOH (25 mL, 50 mmol). After 2 h at 45° C., the solution was allowed to cool to RT, diluted with water (100 mL) and acidified to pH ~6 with citric acid in water (1 M, 20 mL). The resultant solid precipitate was slurried for 1 h, collected by filtration, washed with water (100 mL) and then dried under reduced pressure to obtain Example 3A-01 as a solid (6.4 g, 91%). $^1$H NMR (DMSO-d6) δ 12.84 (br s, 1H), 8.27 (s, 1H), 7.80 (d, 1H), 7.59-7.67 (m, 2H), 7.55 (t, 1H), 7.45 (dd, 1H), 7.29 (dd, 1H), 6.86 (d, 1H), 6.67 (d, 1H), 5.37 (s, 2H), 5.06-5.17 (m, 1H), 4.80 (dd, 1H), 4.66 (dd, 1H), 4.44-4.53 (m, 1H), 4.38 (dt, 1H), 3.95 (d, 1H), 3.78 (d, 1H), 3.00 (d, 1H), 2.85 (d, 1H), 2.64-2.77 (m, 1H), 2.54-2.64 (m, 1H), 2.40-2.48 (m, 1H), 2.20-2.29 (m, 1H), 2.17 (t, 1H), 1.61-1.85 (m, 4H). LC-MS(ES+): 565.4 (M+H).

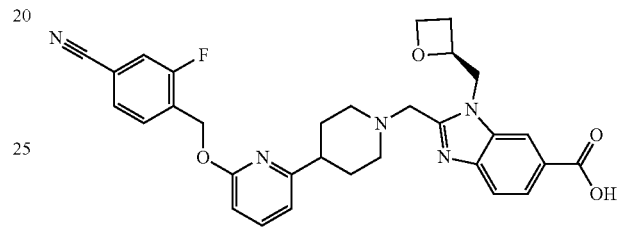

Example 4A-01

2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid

Step 1

To a stirred solution of Intermediate 22 (33.6 g, 142 mmol) in MeCN (285 mL) was added 2-chloro-1,1,1-trimethoxyethane (20.1 mL, 149 mmol) followed by pTSA.H$_2$O (1.35 g, 7.1 mmol). After 2 h at 50° C., MeCN (280 mL), K$_2$CO$_3$ (79 g, 570 mmol) and Intermediate 4 (93.2 g, 142 mmol) were added. After 2 h, the solution was treated with water (800 mL), allowed to cool to RT and stirred for 2 h. The resulting precipitate was collected by filtration, washed with 10% MeCN in water (150 mL), water (2×200 mL) and then dried under reduced pressure to provide methyl (S)-2-((4-(6-((4-cyano-2-fluorobenzyl)oxy)pyridin-2-yl)piperidin-1-yl)methyl)-1-(oxetan-2-ylmethyl)-1H-benzo[d]imidazole-6-carboxylate as a colorless solid (77 g, 95%). $^1$H NMR (600 MHz, DMSO-d6) δ 8.28 (s, 1H), 7.87 (d, 1H), 7.80 (d, 1H), 7.55-7.73 (m, 4H), 6.87 (d, 1H), 6.70 (d, 1H), 5.45 (s, 2H), 5.04-5.19 (m, 1H), 4.81 (dd, 1H), 4.66 (dd, 1H), 4.41-4.54 (m, 1H), 4.36 (dt, 1H), 3.94 (d, 1H), 3.86 (s, 3H), 3.76 (d, 1H), 2.97 (d, 1H), 2.82 (d, 1H), 2.63-2.77 (m, 1H), 2.49-2.63 (m, 1H), 2.37-2.46 (m, 1H), 2.18-2.29 (m, 1H), 2.05-2.18 (m, 1H), 1.47-1.82 (m, 4H).

Step 2

To a stirred solution of methyl (S)-2-((4-(6-((4-cyano-2-fluorobenzyl)oxy)pyridin-2-yl)piperidin-1-yl)methyl)-1-(oxetan-2-ylmethyl)-1H-benzo[d]imidazole-6-carboxylate (4 g, 7 mmol) in MeCN (70 mL) was added a solution of 1,5,7-triazabicyclo[4.4.0]dec-5-ene in water (0.97 M, 14.7 mL). After 20 h, the solution was acidified to pH ~6 with citric acid in water (2 M, 7 mL) and diluted with water (50 mL). The aq. phase was extracted with EtOAc (2×75 mL), the combined organic layers were dried over anhydrous $Na_2SO_4$, filtered, and the solvent removed under reduced pressure to give an off-white solid. The crude material was purified using column chromatography eluting with MeOH/DCM (0:100 to 8:92) to obtain Example 4A-01 as a solid (3.65 g, 90%). $^1$H NMR (400 MHz, DMSO-d6) δ 12.75 (br s, 1H), 8.27 (s, 1H), 7.89 (d, 1H), 7.80 (d, 1H), 7.68-7.72 (m, 2H), 7.60-7.67 (m, 2H), 6.89 (d, 1H), 6.72 (d, 1H), 5.47 (s, 2H), 5.11 (d, 1H), 4.74-4.86 (m, 1H), 4.62-4.72 (m, 1H), 4.43-4.53 (m, 1H), 4.35-4.42 (m, 1H), 3.95 (d, 1H), 3.77 (d, 1H), 2.98 (d, 1H), 2.84 (d, 1H), 2.65-2.77 (m, 1H), 2.53-2.64 (m, 1H), 2.37-2.45 (m, 1H), 2.10-2.28 (m, 2H), 1.57-1.84 (m, 4H). LC-MS(ES+): 556.6 (M+H).

Tris Salt of Example 4A-01

2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid tris salt To a stirred solution of Example 4A-01 (6.5 g, 11.7 mmol) in 1-propanol (275 mL) at 70° C. was added an aq. solution of tris (2.0 M, 6.1 mL, 12.2 mmol), dropwise, during which the solution remained homogeneous. After stirring for 5 min, seed crystals were added and the mixture was allowed to cool to RT over 2 h. After stirring overnight at RT, a solid had formed. The solid was collected by filtration, washed with 1-propanol (2×30 mL) and dried, first under a nitrogen stream and then in a vacuum oven at 45° C. for 15 h, to give the tris salt of Example 4A-01 (6.95 g, 88%) as a crystalline solid. $^1$H NMR (600 MHz, DMSO-d6) δ: 8.20 (s, 1H), 7.89 (d, 1H), 7.79 (d, 1H), 7.70 (br s, 2H), 7.64 (t, 1H), 7.56 (d, 1H), 6.89 (d, 1H), 6.72 (d, 1H), 5.47 (s, 2H), 5.11 (qd, 1H), 4.77 (dd, 1H), 4.64 (dd, 1H), 4.44-4.53 (m, 1H), 4.38 (dt, 1H), 3.93 (d, 1H), 3.76 (d, 1H), 3.35 (br s, 9H), 2.98 (d, 1H), 2.85 (d, 1H), 2.64-2.75 (m, 1H), 2.54-2.64 (m, 1H), 2.40-2.49 (m, 1H), 2.08-2.26 (m, 2H), 1.56-1.83 (m, 4H). mp=194° C.

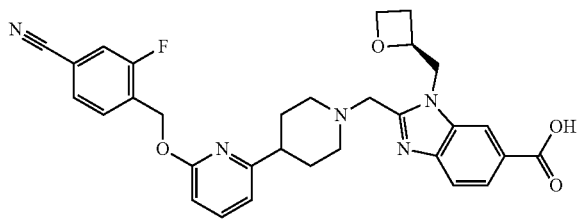 [SMILES: N#Cc1ccc(COc2cccc(C3CCN(Cc4nc5ccc(C(=O)O)cc5n4C[C@@H]4CCO4)CC3)n2)c(F)c1]

Example 5A-01

2-[(4-{6-[(4-Cyano-2-fluorobenzyl)oxy]pyridin-2-yl}piperazin-1-yl)methyl]-1-[(2S)-oxetan-2-ylmethyl]-1H-benzimidazole-6-carboxylic acid Step 1

A solution of Intermediate 13 (5 g, 14.4 mmol) in 5% MeOH:$CH_2Cl_2$ (60 mL) was treated with sat. aq. $Na_2CO_3$ (60 mL). The biphasic solution was stirred vigorously for 30 min and the organic layer was separated. The organic layer was dried, filtered and concentrated under reduced pressure to deliver 4-(((6-(4-piperazin-1-yl)pyridin-2-yl)oxy)methyl)-3-fluorobenzonitrile (4.4 g, quant.) as a semisolid.

Step 2

To a flask containing solution of 4-(((6-(4-piperazin-1-yl)pyridin-2-yl)oxy)methyl)-3-fluorobenzonitrile (1.58 grams, 5.06 mmol) in MeCN (15 mL) was added Intermediate 23 (1.40 g, 5.06 mmol) and $K_2CO_3$ (3.50 g, 25.3 mmol). The resulting suspension was stirred for 2 h at 50° C. After 2 h, the mixture was treated with water (30 mL), allowed to cool to RT and stirred for 2 h. The solid was collected by filtration, washed with water: MeCN (2:1) (2×30 mL) and dried under reduced pressure to provide methyl (S)-2-((4-(6-((4-cyano-2-fluorobenzyl)oxy)pyridin-2-yl)piperazin-1-yl)methyl)-1-(oxetan-2-ylmethyl)-1H-benzo[d]imidazole-6-carboxylate (2.47 g, 86%) as a solid. $^1$H NMR (600 MHz, $CDCl_3$) δ 8.16 (s, 1H), 7.98 (d, 1H), 7.76 (d, 1H), 7.59 (t, 1H), 7.42 (dt, 2H), 7.34 (d, 1H), 6.17 (dd, 2H), 5.42 (s, 2H), 5.23 (dd, 1H), 4.77-4.58 (m, 3H), 4.38 (dt, 1H), 4.05-3.95 (m, 2H), 3.95 (s, 3H), 3.46 (d, 4H), 2.80-2.69 (m, 1H), 2.62 (t, 4H), 2.50-2.38 (m, 1H).

Step 3

To a flask containing solution of methyl (S)-2-((4-(6-((4-cyano-2-fluorobenzyl)oxy)pyridin-2-yl)piperazin-1-yl)methyl)-1-(oxetan-2-ylmethyl)-1H-benzo[d]imidazole-6-carboxylate (2.5 g, 4.3 mmol) in 1:1 mixture of iPrOH and THF (140 mL) was added 1.4 equiv of LiOH (0.14 g, 6.1 mmol) and the resulting solution was heated at 45° C. for 15 h. The solution was allowed to cool to RT, diluted with water (50 mL) and acidified to pH ~6 with citric acid in water. The resulting solution was extracted with EtOAc. The EtOAc layer was dried and the solvent removed under reduced pressure to obtain the crude product. The crude product was purified by flash chromatography (10% MeOH in $CH_2Cl_2$) to obtain Example 5A-01 (0.86 g, 35%) as a solid. $^1$H NMR (600 MHz, $CDCl_3$) δ 8.23 (s, 1H), 8.06 (d, 1H), 7.83 (d, 1H), 7.59 (t, 1H), 7.46-7.39 (m, 2H), 7.34 (d, 1H), 6.18 (dd, 2H), 5.43 (s, 2H), 5.28-5.20 (m, 1H), 4.81-4.58 (m, 3H), 4.44-4.33 (m, 1H), 4.04 (d, 2H), 3.48 (m, 4H), 2.82-2.71 (m, 1H), 2.65 (m, 4H), 2.46 (dd, 1H). LC-MS(ES+): 557.2 (M+H).

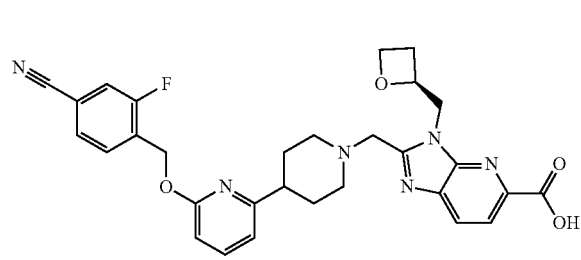 [SMILES: N#Cc1ccc(COc2cccc(C3CCN(Cc4nc5ccc(C(=O)O)nc5n4C[C@@H]4CCO4)CC3)n2)c(F)c1]

Example 6A-01

2-[(4-{6-[(4-cyano-2-fluorobenzyl)oxy]pyridin-2-yl}piperidin-1-yl)methyl]-3-[(2S)-oxetan-2-ylmethyl]-3H-imidazo[4,5-b]pyridine-5-carboxylic acid Step 1

To a 3-neck 3-L flask equipped with a mechanic stirrer, charged with Intermediate 4 (106 g, 161 mmol) was added MeCN (886 mL), $K_2CO_3$ (89.0 g, 644 mmol) and Intermediate 27 (52.4 g, 177 mmol). The mixture was stirred at 60° C. for 2 h. The reaction mixture was poured into a 4 L Erlenmeyer flask and diluted with 1.8 L water. The resulting suspension was stirred at RT for 4 h to give a light yellow suspension. The solids were collected by filtration and dried in a vacuum oven at 45° C. overnight to yield the desired methyl (S)-2-((4-(6-((4-cyano-2-fluorobenzyl)oxy)pyridin-2-yl)piperidin-1-yl)methyl)-3-(oxetan-2-ylmethyl)-3H-imidazo[4,5-b]pyridine-5-carboxylate (88.6 g, 96%) as a light yellow solid. $^1$H NMR (600 MHz, DMSO-d6) δ 8.16 (d, 1H), 8.01 (d, 1H), 7.87 (d, 1H), 7.61-7.74 (m, 3H), 6.88 (d, 1H), 6.71 (d, 1H), 5.46 (s, 2H), 5.11-5.26 (m, 1H), 4.85 (dd, 1H), 4.73 (dd, 1H), 4.43-4.60 (m, 1H), 4.37 (dt, 1H), 3.96-4.04 (m, 1H), 3.89-3.95 (m, 3H), 2.87-3.01 (m, 2H), 2.66-2.81 (m, 1H), 2.55-2.64 (m, 1H), 2.52 (br s, 3H), 2.24 (q, 2H), 1.64-1.81 (m, 3H); LC-MS(ES+): 571.5 (M+H).

Step 2

To a 1 L 3 neck flask equipped with a mechanic overhead stirrer was charged methyl (S)-2-((4-(6-((4-cyano-2-fluorobenzyl)oxy)pyridin-2-yl)piperidin-1-yl)methyl)-3-(oxetan-2-ylmethyl)-3H-imidazo[4,5-b]pyridine-5-carboxylate (35.5 g, 62.21 mmol). MeCN (350 mL) and water (70 mL) were added to the flask. The resulting mixture was stirred at RT for 30 min to form a thick suspension. LiOH.H$_2$O (2.92 g, 68.4 mmol) was slowly added as a solid. The resulting suspension was stirred at 40° C. for 1 h. The reaction mixture was cooled to RT and treated, dropwise, with 1.0 M citric acid (15.5 mL) until the pH of the suspension reached ~5. The resulting suspension was stirred at RT for 4 h. The resultant solids were collected by filtration, the solids were rinsed with ~20 ml water and then dried under a stream of N$_2$ for 4 h. The solids were dried for an additional 72 h at 40° C. in a vacuum oven to dry to yield Example 6A-01 (31.2 g, 90%.) as a solid. $^1$H NMR (600 MHz, DMSO-d6) δ 13.03 (br s, 1H), 8.15 (d, 1H), 8.00 (d, 1H), 7.87 (d, 1H), 7.67-7.73 (m, 2H), 7.64 (t, 1H), 6.88 (d, 1H), 6.71 (d, 1H), 5.45 (s, 2H), 4.93-5.03 (m, 1H), 4.87 (s, 1H), 4.70 (d, 1H), 4.36-4.45 (m, 1H), 4.23-4.35 (m, 1H), 4.05 (d, 1H), 3.79 (d, 1H), 2.93-3.06 (m, 1H), 2.76-2.88 (m, 1H), 2.54-2.69 (m, 1H), 2.34-2.46 (m, 1H), 2.25 (d, 2H), 2.05-2.21 (m, 1H), 1.73 (d, 3H), 1.47-1.67 (m, 1H); LC-MS (ES+): 557.6 (M+H).

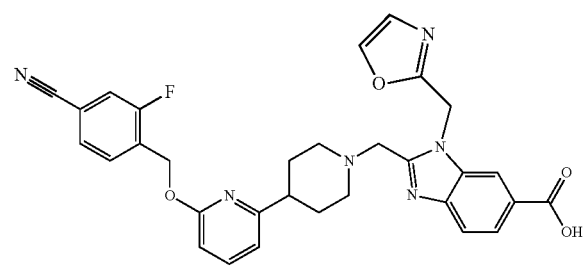

Example 7A-01

2-[(4-{6-[(4-cyano-2-fluorobenzyl)oxy]pyridin-2-yl}piperidin-1-yl)methyl]-1-(1,3-oxazol-2-ylmethyl)-1H-benzimidazole-6-carboxylic acid Step 1

To a suspension of the oxazol-2-ylmethanamine HCl salt (491 mg, 3.65 mmol) and Intermediate 29 (800 mg, 3.32 mmol) in DMF (5 mL) was added K$_2$CO$_3$ (1.04 g, 6.63 mmol). The reaction was stirred at 60° C. for 2 h. Additional oxazol-2-ylmethanamine HCl salt (100 mg, 1.0 mmol) was added and reaction stirred for an additional 30 min at 60° C. The reaction was cooled to RT then diluted with water (30 mL) and extracted with EtOAc (60 mL). The organic layer was washed with water, then brine, dried over Na$_2$SO$_4$, filtered and concentrated under reduced pressure. The orange residue was purified by flash chromatography (12 g silica gel, 0-50% EtOAc/heptane gradient) to deliver tert-butyl 4-nitro-3-((oxazol-2-ylmethyl)amino)benzoate (764 mg, 75%) as an orange solid. $^1$H NMR (CDCl$_3$) δ 8.48 (br s, 1H), 8.23 (d, 1H), 7.68 (d, 1H), 7.61 (d, 1H), 7.28 (dd, 1H), 7.15 (s, 1H), 4.72 (d, 2H), 1.60 (s, 9H).

Step 2

To a solution of tert-butyl 4-nitro-3-((oxazol-2-ylmethyl) amino)benzoate (15 g, 47 mmol) in THF (100 mL) was added 10% palladium on carbon (1.5 g, 10% w/w), and the mixture was then stirred under 50 psi H$_2$ at RT for 6 h. The reaction mixture was then filtered through Celite® to give a dark solution. The filtrate was filtered through second Celite® pad and the filtrate concentrated under reduced pressure to deliver tert-butyl 4-amino-3-((oxazol-2-ylmethyl)amino)benzoate (13.1 g, 92%) as a dark foam. $^1$H NMR (CDCl$_3$) δ 7.62 (s, 1H), 7.43 (dd, 1H), 7.35 (d, 1H), 7.08 (s, 1H), 6.66 (d, 1H), 4.44 (s, 2H), 1.56 (s, 9H).

Step 3

To a stirred solution of tert-butyl 4-amino-3-((oxazol-2-ylmethyl)amino)benzoate (13 g, 45 mmol) in MeCN (100 mL) was added 2-chloro-1,1,1-trimethoxy ethane (9.0 ml, 65 mmol) and pTSA.H$_2$O (400 mg, 2.1 mmol) and the mixture was heated at 60° C. for 3 h. The reaction was then cooled to RT and concentrated under reduced pressure. The crude product was purified by flash chromatography (120 g silica gel, 0-100% EtOAc/heptane gradient) to yield tert-butyl 2-(chloromethyl)-1-(oxazol-2-ylmethyl)-1H-benzo[d]imidazole-6-carboxylate (11.6 g, 74%) as a light yellow solid. $^1$H NMR (CDCl$_3$) δ 8.19 (d, 1H), 7.98 (dd, 1H), 7.77 (d, 1H), 7.64 (d, 1H), 7.12 (d, 1H), 5.64 (s, 2H), 5.00 (s, 2H), 1.62-1.66 (m, 9H).

Step 4

To a suspension of tert-butyl 2-(chloromethyl)-1-(oxazol-2-ylmethyl)-1H-benzo[d]imidazole-6-carboxylate (10.1 g, 29 mmol) and Intermediate 4 (11.2 g, 29.1 mmol) in MeCN (100 mL) was added K$_2$CO$_3$ (16.1 g, 116 mmol). The mixture was stirred at 60° C. for 2 h and then diluted with water (200 mL) and stirred for an additional 4 h at RT. The resulting solids were collected by filtration to deliver tert-butyl 2-((4-(6-((4-cyano-2-fluorobenzyl)oxy)pyridin-2-yl)piperidin-1-yl)methyl)-1-(oxazol-2-ylmethyl)-1H-benzo[d]imidazole-6-carboxylate (16.23 g, 89%) as a solid. $^1$H NMR (DMSO-d6) δ 8.13 (s, 1H), 8.04 (s, 1H), 7.88 (d, 1H), 7.78 (dd, 1H), 7.70 (br s, 2H), 7.66 (d, 1H), 7.62 (t, 1H), 7.13 (s, 1H), 6.79 (d, 1H), 6.69 (d, 1H), 5.91 (s, 2H), 5.44 (s, 2H), 3.84 (s, 2H), 2.80 (d, 2H), 2.46 (d, 1H), 2.05-2.13 (m, 2H), 1.64 (d, 1H), 1.55 (s, 9H), 1.35-1.43 (m, 2H).

Step 5

To a solution of tert-butyl 2-((4-(6-((4-cyano-2-fluorobenzyl)oxy)pyridin-2-yl)piperidin-1-yl)methyl)-1-(oxazol-2-ylmethyl)-1H-benzo[d]imidazole-6-carboxylate (31.1 g, 50.0 mmol) in DCE (300 mL) was added TFA (40 ml, 530 mmol). The mixture was heated to 70° C. for 4 h and then slowly cooled to RT and stirred overnight. The mixture was concentrated under reduced pressure and the residue was dissolved in MeOH (100 mL) and water (300 mL). Saturated aq. NaHCO$_3$ (85 mL) was added, dropwise, to bring the solution to pH ~7. The resulting solids were stirred to granulate for 3 h, and then collected by filtration to deliver Example 7A-01 (27.3 g, 96%) as a solid. $^1$H NMR (600 MHz, DMSO-d6) δ 12.93 (br s, 1H), 8.19 (s, 1H), 8.03 (s, 1H), 7.88 (d, 1H), 7.82 (d, 1H), 7.70 (br s, 2H), 7.65 (d, 1H), 7.62 (t, 1H), 7.12 (s, 1H), 6.80 (d, 1H), 6.66-6.71 (m, 1H), 5.90 (s, 2H), 5.43 (s, 2H), 3.84 (s, 2H), 2.81 (d, 2H), 2.46 (m, 1H), 2.10 (t, 2H), 1.64 (d, 2H), 1.36-1.46 (m, 2H); LC-MS (ES+): 568.3 (M+H).

TABLE 3

| Ex. # | Name | MW found | Ret. time (min) |
|---|---|---|---|
| 8A-02 | 2-((4-(6-((4-cyano-3-methylbenzyl)oxy)pyridin-2-yl)piperidin-1-yl)methyl)-1-(2-methoxyethyl)-1H-benzo[d]imidazole-6-carboxylic acid | 540.4 | 2.47 |
| 8A-03 | 2-((4-(6-((4-chloro-2,5-difluorobenzyl)oxy)pyridin-2-yl)piperidin-1-yl)methyl)-1-(2-methoxyethyl)-1H-benzo[d]imidazole-6-carboxylic acid | 571.4 | 2.70 |
| 8A-04 | 2-((4-(6-((4-chloro-2,6-difluorobenzyl)oxy)pyridin-2-yl)piperidin-1-yl)methyl)-1-(2-methoxyethyl)-1H-benzo[d]imidazole-6-carboxylic acid | 571.4 | 2.67 |

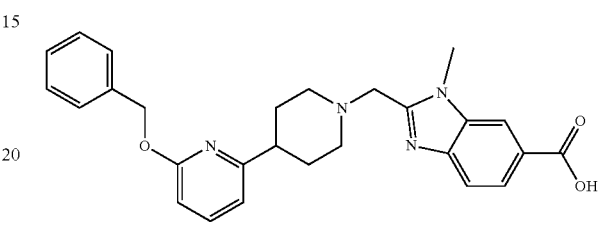

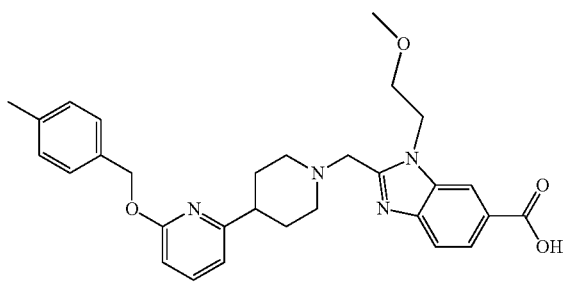 [SMILES: COCCn1c(CN2CCC(c3cccc(OCc4ccc(C)cc4)n3)CC2)nc2ccc(C(=O)O)cc21]

Example 8A-01

Ammonium 2-((4-(6-((4-Methylbenzyl)oxy)pyridin-2-yl)piperidin-1-yl)methyl)-1-(2-methoxyethyl)-1H-benzo[d]imidazole-6-carboxylate To a 1 dram vial was added Intermediate 35 (20 mg, 47 µmol) followed by 4-methylbenzyl alcohol (100 µmol). THF (500 µL) was added followed by Tsunoda Reagent (cyanomethylene tributyl phosphorane, 0.5 M in THF, 400 µL, 0.20 mmol) and the mixture was heated at 70° C. for 3 h. The reaction was cooled to RT and concentrated under reduced pressure. The residue was dissolved in MeOH (1 mL). 1 M NaOH (0.15 ml, 150 µmol) was added and the mixture heated at 60° C. for 3 h and then held at RT for 48 h. The mixture was concentrated under reduced pressure and the crude product purified by preparative SFC to deliver Example 8A-01 (10.7 mg, 45%). SFC Method (Column: Phenomenex Biphenyl 4.6×150 mm), 5 µm; Mobile phase A: CO$_2$ (v/v); Mobile phase B: Methanol w/ 0.2% NH$_4$OH (v/v) 85% CO$_2$/15% Methanol w/ 0.2% NH$_4$OH Linear in 8 min, HOLD at 70% CO$_2$/30% Methanol w/ 0.2% NH$_4$OH to 10 min. Flow: 75 mL/min. Back Pressure: 120 Bar; Retention time 2.56 min; LC-MS(ES+): 515.4 (M+H).

The compounds listed in Table 3 below were prepared using procedures analogous to those described above for the synthesis of Examples 8A-01 using the appropriate starting materials which are available commercially, prepared using preparations well-known to those skilled in the art, or prepared in a manner analogous to routes described above for other intermediates. The compounds were purified using methods well known to those skilled in the art and may include silica gel chromatography, HPLC, or crystallization from the reaction mixture. The final compounds may have been isolated as neutrals or acid or base salts.

Example 9A-01

2-((4-(6-(Benzyloxy)pyridin-2-yl)piperidin-1-yl)methyl)-1-methyl-1H-benzo[d]imidazole-6-carboxylic acid Step 1

A mixture of Intermediate 36 (100 mg, 0.251 mmol), benzyl alcohol (48.2 mg, 0.446 mmol), BINAP (23.2 mg, 0.0373 mmol), Pd$_2$(dba)$_3$ (15.2 mg, 0.0166 mmol) and Cs$_2$CO$_3$ (123 mg, 0.378 mmol) in PhMe (2 mL) was stirred at 100° C. for 14 h. The brown mixture was diluted with DCM (50 mL) and filtered. The filtrate was concentrated under reduced pressure to give a brown oil which was purified by prep-TLC (DCM:MeOH=20:1) to afford methyl 2-((4-(6-(benzyloxy)pyridin-2-yl)piperidin-1-yl)methyl)-1-methyl-1H-benzo[d]imidazole-6-carboxylate (99.7 mg, 84%) as a yellow solid. $^1$H NMR (CD$_3$OD) δ 8.32 (s, 1H), 8.02 (dd, 1H), 7.79 (d, 1H), 7.59-7.70 (m, 1H), 7.40-7.48 (m, 2H), 7.35 (m, 2H), 7.23-7.32 (m, 1H), 6.90 (d, 1H), 6.73 (d, 1H), 5.40 (s, 2H), 4.79 (s, 2H), 3.96 (s, 6H), 3.91 (d, 2H), 3.40 (m, 2H), 3.05 (br s, 1H), 2.14-2.38 (m, 4H).

Step 2

To a solution of methyl 2-((4-(6-(benzyloxy)pyridin-2-yl)piperidin-1-yl)methyl)-1-methyl-1H-benzo[d]imidazole-6-carboxylate (90.0 mg, 0.191 mmol) in MeOH (3 mL) was added 3.0 M NaOH (2.0 mL, 6.0 mmol). The mixture was stirred at 40° C. for 4 h. The reaction mixture was neutralized with 1 M HCl and the resultant slurry extracted with (DCM:MeOH 10:1, 2×40 mL). The combined organic extracts were dried over MgSO4, filtered and concentrated under reduced pressure to give a yellow solid. The yellow solid was purified by preparative HPLC (Column: Waters Xbridge Prep OBD C18 100×19 mm×5 µm; Mobile phase: from 5% MeCN in water [0.1% TFA] to 95% MeCN in water [0.1% TFA]; Wavelength: 220 nm; Flow rate: 25 ml/min) to deliver Example 9A-01 (33 mg, 28%) as a solid. Due to the purification solvent, the final compound was likely trifluoroacetate salt. $^1$H NMR (400 MHz, CD$_3$OD) δ 8.31 (s, 1H), 8.03 (dd, 1H), 7.78 (d, 1H), 7.65 (t, 1H), 7.40-7.46 (m, 2H), 7.35 (t, 2H), 7.25-7.31 (m, 1H), 6.90 (d, 1H), 6.73 (d, 1H), 5.40 (s, 2H), 4.79 (s, 2H), 3.96 (s, 3H), 3.90 (d, 2H), 3.40 (m, 2H), 3.05 (br s, 1H), 2.14-2.37 (m, 4H); LC-MS(ES+): 457.1 (M+H).

The compounds listed in Table 4 below were prepared using procedures analogous to those described above for the synthesis of Examples 9A-01 using the appropriate starting materials which are available commercially, prepared using preparations well-known to those skilled in the art, or prepared in a manner analogous to routes described above for other intermediates. The compounds were purified using HPLC. Due to the purification solvent, the final compounds isolated using methods PF-AB01 and PF-AB10 were likely trifluoroacetate salts, while compounds isolated using method PF-CD05 are likely ammonium salts.

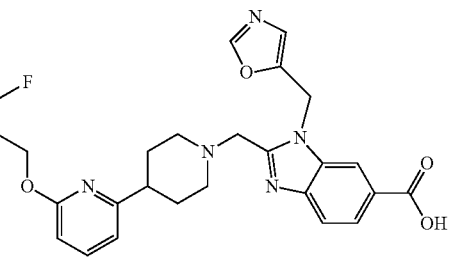

TABLE 4

| Ex. # | Name | *MW found | Ret. time (min) | **Method |
|---|---|---|---|---|
| 9A-02 | 2-{[4-(6-{[2-fluoro-4-(trifluoromethyl)benzyl]oxy}pyridin-2-yl)piperidin-1-yl]methyl}-1-methyl-1H-benzimidazole-6-carboxylic acid | 543 | 3.073 | PF-AB01 |
| 9A-03 | 2-[(4-{6-[(2,4-difluorobenzyl)oxy]pyridin-2-yl}piperidin-1-yl)methyl]-1-methyl-1H-benzimidazole-6-carboxylic acid | 493 | 2.897 | PF-AB01 |
| 9A-04 | 2-[(4-{6-[(2,6-difluorobenzyl)oxy]pyridin-2-yl}piperidin-1-yl)methyl]-1-methyl-1H-benzimidazole-6-carboxylic acid | 493 | 2.333 | PF-CD05 |
| 9A-05 | 2-[(4-{6-[(4-chlorobenzyl)oxy]pyridin-2-yl}piperidin-1-yl)methyl]-1-methyl-1H-benzimidazole-6-carboxylic acid | 491 | 2.934 | PF-AB01 |
| 9A-06 | 2-[(4-{6-[(2-fluorobenzyl)oxy]pyridin-2-yl}piperidin-1-yl)methyl]-1-methyl-1H-benzimidazole-6-carboxylic acid | 475 | 2.86 | PF-AB01 |
| 9A-07 | 2-[(4-{6-[(4-chlorobenzyl)oxy]pyridin-2-yl}piperidin-1-yl)methyl]-1-methyl-1H-benzimidazole-6-carboxylic acid | 491 | 2.9 | PF-AB01 |
| 9A-08 | 2-[(4-{6-[(2,3-difluorobenzyl)oxy]pyridin-2-yl}piperidin-1-yl)methyl]-1-methyl-1H-benzimidazole-6-carboxylic acid | 493 | 2.883 | PF-AB01 |
| 9A-09 | 1-methyl-2-{[4-(6-{[4-(trifluoromethoxy)benzyl]oxy}pyridin-2-yl)piperidin-1-yl]methyl}-1H-benzimidazole-6-carboxylic acid | 541 | 3.087 | PF-AB01 |
| 9A-10 | 1-methyl-2-{[4-(6-{[2-(trifluoromethoxy)benzyl]oxy}pyridin-2-yl)piperidin-1-yl]methyl}-1H-benzimidazole-6-carboxylic acid | 541 | 3.031 | PF-AB01 |
| 9A-11 | 1-methyl-2-[(4-{6-[(2-methylbenzyl)oxy]pyridin-2-yl}piperidin-1-yl)methyl]-1H-benzimidazole-6-carboxylic acid | 471 | 2.917 | PF-AB01 |
| 9A-12 | 2-[(4-{6-[(3-cyanobenzyl)oxy]pyridin-2-yl}piperidin-1-yl)methyl]-1-methyl-1H-benzimidazole-6-carboxylic acid | 482 | 2.681 | PF-AB01 |
| 9A-13 | 1-methyl-2-{[4-(6-{[4-(trifluoromethyl)benzyl]oxy}pyridin-2-yl)piperidin-1-yl]methyl}-1H-benzimidazole-6-carboxylic acid | 525 | 3.056 | PF-AB01 |
| 9A-14 | 2-[(4-{6-[(2,5-difluorobenzyl)oxy]pyridin-2-yl}piperidin-1-yl)methyl]-1-methyl-1H-benzimidazole-6-carboxylic acid | 493 | 2.897 | PF-AB01 |
| 9A-15 | 2-[(4-{6-[(4-cyanobenzyl)oxy]pyridin-2-yl}piperidin-1-yl)methyl]-1-methyl-1H-benzimidazole-6-carboxylic acid | 482 | 2.753 | PF-AB01 |

*MW found: MS(ES+): as (M + H)
**HPLC purification method PF-AB01: Mobile Phase A: 0.0375% TFA in H$_2$O. Mobile Phase B: 0.01875% TFA in MeCN. Initial conditions: B: 1%, A: 99%. Gradient: B: 1%, A: 99% to B: 5%, A: 95% from t = 0.00 min to 0.60 min, then to B: 100% from t = 0.60 min to 4.00 min, then to B: 1%, A: 99% from t = 4.00 min to 4.30 min, hold until t = 4.70 min. Flow rate = 0.8 mL/min, 2 μL injection volume.
**HPLC purification method PF-CD05: Mobile Phase A: 0.05% NH$_4$OH in H$_2$O Mobile Phase B: 100% MeCN. Initial conditions: B: 5%, A: 95%. Gradient: B: 5%, A: 95% to B: 100%, from t = 0.50 min to 3.40 min, hold until t = 4.20 min then to B: 5%, A: 95% from t = 4.21 min to 4.70 min, hold until t = 4.70 min. Flow rate = 0.8 mL/min, 2 μL injection volume.

Example 10A-01

2-[(4-{6-[(4-Chloro-2-fluorobenzyl)oxy]pyridin-2-yl}piperidin-1-yl)methyl]-1-(1,3-oxazol-5-ylmethyl)-1H-benzimidazole-6-carboxylic acid

Step 1

To a colorless solution of methyl 3-fluoro-4-nitrobenzoate (302 mg, 1.52 mmol) and oxazol-5-ylmethanamine (164 mg, 1.67 mmol) in DMF (5.0 mL) was added Et$_3$N (460 mg, 4.55 mmol) slowly at 20° C. The brown solution was stirred at 60° C. for 36 h. The mixture was diluted with EtOAc (50 mL) and washed with H$_2$O (50 mL). The organic phase was separated and the aq. phase extracted with EtOAc (2×50 mL). The combined organic extracts were dried over Na$_2$SO$_4$, filtered and concentrated under reduced pressure. The crude product was purified by flash chromatography (10-100% EtOAc/PE) to give methyl 4-nitro-3-((oxazol-5-ylmethyl)amino)benzoate (320 mg, 76%) as orange solid. $^1$H NMR (CDCl$_3$) δ 8.26 (d, 2H), 7.89 (s, 1H), 7.66 (d, 1H), 7.35 (dd, 1H), 7.11 (s, 1H), 4.68 (d, 2H), 3.96 (s, 3H).

Step 2

To a yellow suspension of methyl 4-nitro-3-((oxazol-5-ylmethyl)amino)benzoate (67 mg, 0.24 mmol) in MeOH (8 mL) was added 10% Pd/C (10.3 mg). The mixture was stirred under 1 atm H$_2$ at RT for 1 h. The solids were removed by filtration and rinsed with MeOH (20 mL). The combined organic layers were then concentrated under reduced pressure to give methyl 4-amino-3-((oxazol-5-ylmethyl)amino)benzoate (56 mg, 94%) as a white solid. LC-MS(ES+): 247.9 (M+H).

Step 3

To a yellow solution of Intermediate 5 (85 mg, 0.22 mmol), 4-amino-3-((oxazol-5-ylmethyl)amino)benzoate (55.5 mg, 0.224 mmol) and HATU (111 mg, 0.292 mmol) in DMF (2 mL) was added Et$_3$N (114 mg, 1.12 mmol, 0.15 mL). The yellow solution was stirred at 25° C. for 16 h. The mixture was then poured into H$_2$O (8 mL) and extracted with EtOAc (3×10 mL). The combined organic extracts were washed with brine (20 mL), dried over Na$_2$SO$_4$, filtered and concentrated under reduced pressure. The crude product was purified by prep-TLC (EtOAc) to give methyl 4-(2-(4-(6-((4-chloro-2-fluorobenzyl)oxy)pyridin-2-yl)piperidin-1-yl)acetamido)-3-((oxazol-5-ylmethyl)amino)benzoate (58 mg, 43%) as a yellow oil. LC-MS(ES+): 630.0 (M+Na).

Step 4

A yellow solution of methyl 4-(2-(4-(6-((4-chloro-2-fluorobenzyl)oxy)pyridin-2-yl)piperidin-1-yl)acetamido)-3-((oxazol-5-ylmethyl)amino)benzoate (58 mg, 0.095 mmol) in AcOH (0.5 mL) was stirred at 60° C. for 3 h and then at RT for 16 h. The yellow residue was neutralized with sat. aq. Na$_2$CO$_3$ and extracted with DCM (3×10 mL). The combined organic extracts was dried over Na$_2$SO$_4$, filtered and concentrated under reduced pressure to give methyl 2-((4-(6-((4-chloro-2-fluorobenzyl)oxy)pyridin-2-yl)piperidin-1-yl)methyl)-1-(oxazol-5-ylmethyl)-1H-benzo[d]imidazole-6-carboxylate (56 mg, 99%) as a yellow oil. LC-MS(ES+): 612.0 (M+Na).

Step 5

To a solution of methyl 2-((4-(6-((4-chloro-2-fluorobenzyl)oxy)pyridin-2-yl)piperidin-1-yl)methyl)-1-(oxazol-5-ylmethyl)-1H-benzo[d]imidazole-6-carboxylate (56 mg, 0.095 mmol) in THF (1 mL) and MeOH (0.2 mL) was added 2 M NaOH (0.0949 mL, 0.190 mmol). The yellow solution was stirred at 25° C. for 16 h and then stood for 48 h at 25° C. The yellow solution was concentrated under reduced pressure and the residue then dissolved in H$_2$O (5 mL), acidified to pH ~5 with 1 M HCl and extracted with DCM (5×10 mL). The combined organic extracts were concentrated under reduced pressure and the resultant crude product purified by preparative HPLC (Column: Waters Xbridge Prep OBD C18 150×30 mm×5 μm; Mobile phase: from 5% MeCN in water [0.1% TFA] to 95% MeCN in water [0.1% TFA]; Wavelength: 220 nm; Flow rate: 25 ml/min) to deliver Example 10A-01 (22 mg, 33%) as a solid. Due to the purification solvent, the final compound was likely isolated as the trifluoroacetate salt. $^1$H NMR (400 MHz, CD$_3$OD) δ 8.41 (s, 1H), 8.18 (s, 1H), 8.03 (dd, 1H), 7.80 (d, 1H), 7.61-7.70 (m, 1H), 7.52 (t, 1H), 7.36 (s, 1H), 7.20-7.30 (m, 2H), 6.94 (d, 1H), 6.74 (d, 1H), 5.78 (s, 2H), 5.45 (s, 2H), 4.91 (br s, 2H), 3.97 (d, 2H), 3.42 (br s, 2H), 3.07 (br s, 1H), 2.17-2.33 (m, 4H); LC-MS(ES+): 576.1 (M+H).

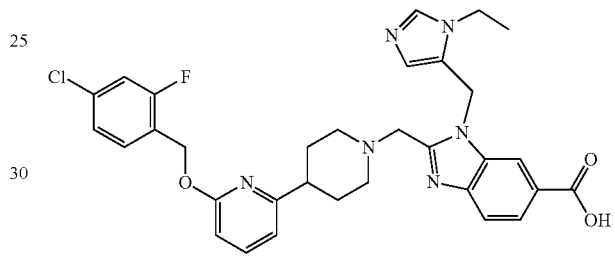

Example 10A-02

2-[(4-{6-[(4-chloro-2-fluorobenzyl)oxy]pyridin-2-yl}piperidin-1-yl)methyl]-1-[(1-ethyl-1H-imidazol-5-yl)methyl]-1H-benzimidazole-6-carboxylic acid

Step 1

To a solution of Intermediate 29 (200 mg, 0.829 mmol) in DMF (8 mL) was added (1-ethyl-1H-imidazol-5-yl)methanamine (104 mg, 0.829 mmol) and NaHCO$_3$ (348 mg, 4.15 mmol). The reaction mixture was stirred at 60° C. for 16 h. The reaction mixture was poured into water (10 mL) and then extracted with EtOAc (2×30 mL). The combined organic extracts were washed with brine (2×20 mL), dried over Na$_2$SO$_4$, filtered and concentrated under reduced pressure. The crude product was purified by flash chromatography (0 to 5% MeOH/DCM) to give tert-butyl 3-(((1-ethyl-1H-imidazol-5-yl)methyl)amino)-4-nitrobenzoate (105 mg, 37%) as a pale red oil. $^1$H NMR (CDCl$_3$) δ 8.23 (d, 1H), 7.96 (br s, 1H), 7.66 (d, 1H), 7.57 (s, 1H), 7.28 (dd, 1H), 7.12 (s, 1H), 4.54 (d, 2H), 4.00 (q, 2H), 1.62 (s, 9H), 1.47 (t, 3H).

Step 2

To a solution of tert-butyl 3-(((1-ethyl-1H-imidazol-5-yl)methyl)amino)-4-nitrobenzoate (105 mg, 0.303 mmol) in MeOH (3 mL) and H$_2$O (1 mL) was added Fe powder (59.2 mg, 1.06 mmol) and NH$_4$Cl (292 mg, 5.46 mmol). The reaction mixture was stirred at 80° C. for 50 min. The reaction mixture was poured into water (10 mL) and extracted with EtOAc (3×15 mL). The combined organic extracts were dried over Na₂SO₄, filtered and concentrated under reduced pressure to deliver tert-butyl 4-amino-3-(((1-ethyl-1H-imidazol-5-yl)methyl)amino)benzoate (93 mg, 97%) as a pale brown solid which was used directly in the next step.

Step 3

To a pale yellow solution of Intermediate 5 (55 mg, 0.15 mmol) and DMF (1 mL) was added HATU (66.2 mg, 0.174 mmol). The mixture was stirred at 30° C. for 10 min. A solution of tert-butyl 4-amino-3-(((1-ethyl-1H-imidazol-5-yl)methyl)amino)benzoate (45.9 mg, 0.145 mmol) and DIPEA (56.3 mg, 0.436 mmol) in DMF (1 mL) was added and the reaction was stirred at 30° C. for 16 h. The mixture was poured into water (10 mL) and then extracted with EtOAc (3×20 mL). The combined organic extracts were washed with aq NH₄Cl (3×20 mL), brine (2×20 mL), dried over Na₂SO₄, filtered and concentrated under reduced pressure. The crude product was purified by Prep-TLC (5% MeOH/DCM) to give tert-butyl 4-amino-3-(2-(4-(6-((4-chloro-2-fluorobenzyl)oxy)pyridin-2-yl)piperidin-1-yl)-N-((1-ethyl-1H-imidazol-5-yl)methyl)acetamido)benzoate (60 mg, 61%) as a pale brown gum. LC-MS(ES+): 699.4 (M+Na).

Step 4

A pale brown solution of give tert-butyl 4-amino-3-(2-(4-(6-((4-chloro-2-fluorobenzyl)oxy)pyridin-2-yl)piperidin-1-yl)-N-((1-ethyl-1H-imidazol-5-yl)methyl)acetamido)benzoate (60 mg, 0.089 mmol) in AcOH (2 mL) was stirred at 60° C. for 16 h. The reaction mixture was concentrated under vacuum to remove AcOH to deliver tert-butyl 2-((4-(6-((4-chloro-2-fluorobenzyl)oxy)pyridin-2-yl)piperidin-1-yl)methyl)-1-((1-ethyl-1H-imidazol-5-yl)methyl)-1H-benzo[d]imidazole-6-carboxylate (56 mg, 96%) as a pale brown gum which was used in the next step without further purification. LC-MS(ES+): 681.3 (M+Na).

Step 5

To a pale brown solution of tert-butyl 2-((4-(6-((4-chloro-2-fluorobenzyl)oxy)pyridin-2-yl)piperidin-1-yl)methyl)-1-((1-ethyl-1H-imidazol-5-yl)methyl)-1H-benzo[d]imidazole-6-carboxylate (56 mg, 0.085 mmol) in DCM (2 mL) was added TFA (1 mL). The reaction mixture was stirred at RT (10° C.) for 16 h. The reaction mixture was concentrated under reduced pressure and the crude product purified by preparative HPLC (Column: Waters Xbridge Prep OBD C18 150×30 mm×5 μm; Mobile phase: from 5% MeCN in water [0.1% TFA] to 95% MeCN in water [0.1% TFA]; Wavelength: 220 nm; Flow rate: 25 ml/min) to deliver Example 10A-02 (37 mg, 48%) as a beige solid. Due to the purification solvent, the compound was likely isolated as the trifluoroacetate salt. ¹H NMR (400 MHz, CD₃OD) δ 9.10 (d, 1H), 8.26 (s, 1H), 8.07 (dd, 1H), 7.88 (d, 1H), 7.66 (t, 1H), 7.52 (t, 1H), 7.19-7.28 (m, 2H), 7.08 (d, 1H), 6.93 (d, 1H), 6.73 (d, 1H), 5.88 (s, 2H), 5.45 (s, 2H), 4.84 (s, 2H), 4.36 (q, 2H), 3.98 (d, 2H), 3.41 (t, 2H), 3.06 (t, 1H), 2.14-2.40 (m, 4H), 1.58 (t, 3H); LC-MS(ES+): 603.1 (M+H).

The compounds listed in Table 5 below were prepared using procedures analogous to those described above for the synthesis of Examples 10A-01 or 10A-02 using the appropriate starting materials which are available commercially, prepared using preparations well-known to those skilled in the art, or prepared in a manner analogous to routes described above for other intermediates. The compounds were purified using methods well known to those skilled in the art and may include silica gel chromatography, HPLC, or crystallization from the reaction mixture. The final compounds may have been isolated as neutrals or acid or base salts.

TABLE 5

| Ex. # | Name | NMR data/LC-MS data |
|---|---|---|
| 10A-03 | 2-[(4-{6-[(4-chloro-2-fluorobenzyl)oxy]pyridin-2-yl}piperidin-1-yl)methyl]-1-[(4,4-dimethyloxetan-2-yl)methyl]-1H-benzimidazole-6-carboxylic acid, enantiomer 1 | Column: OD-H 4.6 × 100 mm, 5 μm Mobile phase A: CO₂; Mobile phase B: MeOH with 0.2% NH₄OH; 80:20 A/B Hold for 10 min, Column Temp: 40° C., Back Pressure: 150 Bar, Flow: 1.5 mL/min. Retention time = 4.53 min. LC-MS(ES+): 593.4 (M + H). |
| 10A-04 | 2-[(4-{6-[(4-chloro-2-fluorobenzyl)oxy]pyridin-2-yl}piperidin-1-yl)methyl]-1-[(4,4-dimethyloxetan-2-yl)methyl]-1H-benzimidazole-6-carboxylic acid, enantiomer 2 | Column: OD-H 4.6 × 100 mm, 5 μm; Mobile phase A: CO₂; Mobile phase B: MeOH with 0.2% NH₄OH; 80:20 A/B Hold for 10 min, Column Temp: 40° C., Back Pressure: 150 Bar, Flow: 1.5 mL/min. Retention time = 4.00 min. LC-MS(ES+): 593.4 (M + H). |
| 10A-05 | 2-[(4-{6-[(2,4-difluorobenzyl)oxy]pyridin-2-yl}piperidin-1-yl)methyl]-1-[(2S)-oxetan-2-ylmethyl]-1H-benzimidazole-6-carboxylic acid | ¹H NMR (400 MHz, CD₃OD) δ 8.35-8.28 (m, 1H), 7.97 (dd, 1H), 7.67 (dd, 1H), 7.62-7.46 (m, 2H), 7.01-6.89 (m, 2H), 6.86-6.77 (m, 1H), 6.62 (dd, 1H), 5.39 (s, 2H), 5.27 (m, 1H), 4.85 (m, 1H), 4.72 (dd, 1H), 4.63 (m, 1H), 4.47 (m, 1H), 4.14 (d, 1H), 4.02 (d, 1H), 3.18 (d, 1H), 3.07 (d, 1H), 2.86-2.65 (m, 2H), 2.60-2.38 (m, 3H), 1.92 (m, 4H). MS(ES+): 549.3 (M + H). |
| 10A-06 | 2-[(4-{6-[(4-chloro-2-fluorobenzyl)oxy]pyridin-2-yl}piperidin-1-yl)methyl]-1-{[4-(propan-2-yl)-4H-1,2,4-triazol-3-yl]methyl}-1H-benzimidazole-6-carboxylic acid | ¹H NMR (400 MHz, CD₃OD) δ 8.35-8.28 (m, 1H), 7.97 (dd, 1H), 7.67 (dd, 1H), 7.62-7.46 (m, 2H), 7.01-6.89 (m, 2H), 6.86-6.77 (m, 1H), 6.62 (dd, 1H), 5.39 (s, 2H), 5.27 (m, 1H), 4.85 (m, 1H), 4.72 (dd, 1H), 4.63 (m, 1H), 4.47 (m, 1H), 4.14 (d, 1H), 4.02 (d, 1H), 3.18 (d, 1H), 3.07 (m, 1H), 2.86-2.65 (m, 2H), 2.60-2.38 (m, 3H), 1.92 (m, 4H). MS(ES+): 549.3 (M + H). |

TABLE 5-continued

| Ex. # | Name | NMR data/LC-MS data |
|---|---|---|
| 10A-07 | 2-[(4-{6-[(4-chloro-2-fluorobenzyl)oxy]pyridin-2-yl}piperidin-1-yl)methyl]-1-[(4-ethyl-4H-1,2,4-triazol-3-yl)methyl]-1H-benzimidazole-6-carboxylic acid | $^1$H NMR (400 MHz, CD$_3$OD) δ 8.67 (s, 1H), 8.37 (d, 1H), 8.08 (dd, 1H), 7.86 (d, 1H), 7.67 (dd, 1H), 7.54 (t, 1H), 7.32-7.18 (m, 2H), 6.96 (d, 1H), 6.74 (d, 1H), 6.01 (s, 2H), 5.49 (s, 2H), 4.39 (q, 2H), 3.93 (s, 2H), 3.43 (d, 3H), 3.09 (s, 1H), 2.29 (m, 4H), 1.57 (t, 3H). MS(ES+): 604.3 (M + H). |
| 10A-08 | 2-[(4-{6-[(4-chloro-2-fluorobenzyl)oxy]pyridin-2-yl}piperazin-1-yl)methyl]-1-[(2S)-oxetan-2-ylmethyl]-1H-benzimidazole-6-carboxylic acid | $^1$H NMR (400 MHz, CD$_3$OD) δ 8.35 (d, 1H), 7.99 (dd, 1H), 7.69 (d, 1H), 7.46 (m, 2H), 7.20 (m, 2H), 6.29 (d, 1H), 6.12 (d, 1H), 5.35 (s, 2H), 5.29 (m, 1H), 4.93 (d, 2H), 4.75 (dd, 1H), 4.66 (m, 1H), 4.49 (m, 1H), 4.05 (d, 1H), 3.94 (d, 1H), 3.53 (t, 4H), 2.89-2.74 (m, 1H), 2.70-2.46 (m, 5H). MS(ES+): 566.1 (M + H). |
| 10A-09 | 2-{[(2S)-4-{6-[(4-cyano-2-fluorobenzyl)oxy]pyridin-2-yl}-2-methylpiperazin-1-yl]methyl}-3-[(2S)-oxetan-2-ylmethyl]-3H-imidazo[4,5-b]pyridine-5-carboxylic acid | $^1$H NMR (400 MHz, CD$_3$OD) δ 8.24-8.11 (m, 2H), 7.63 (t, 1H), 7.60-7.51 (m, 2H), 7.46 (m, 1H), 6.30 (d, 1H), 6.16 (d, 1H), 5.45 (s, 2H), 5.34 (m, 1H), 4.99 (d, 2H), 4.73-4.53 (m, 2H), 4.30 (m, 1H), 3.96-3.86 (m, 1H), 3.79 (dd, 2H), 3.10 (m, 1H), 2.91 (dd, 1H), 2.88-2.70 (m, 2H), 2.65 (m, 1H), 2.56-2.33 (m, 2H), 1.21 (d, 3H). MS(ES+): 572.1 (M + H). |
| 10A-10 | 2-{[(2S)-4-{6-[(4-chloro-2-fluorobenzyl)oxy]pyridin-2-yl}-2-methylpiperazin-1-yl]methyl}-3-[(2S)-oxetan-2-ylmethyl]-3H-imidazo[4,5-b]pyridine-5-carboxylic acid | $^1$H NMR (400 MHz, CD$_3$OD) δ 8.22-8.09 (m, 2H), 7.45 (m, 2H), 7.25-7.14 (m, 2H), 6.28 (d, 1H), 6.11 (d, 1H), 5.35 (m, 3H), 5.04-4.94 (m, 2H), 4.71-4.56 (m, 2H), 4.30 (m, 1H), 3.95 (d, 1H), 3.81 (dd, 2H), 3.17-3.07 (m, 1H), 2.94 (dd, 1H), 2.78 (m, 2H), 2.71-2.59 (m, 1H), 2.57-2.38 (m, 2H), 1.22 (d, 3H). MS(ES+): 581.0 (M + H). |
| 10A-11 | 2-[(4-{6-[(4-chloro-2-fluorobenzyl)oxy]pyridin-2-yl}piperidin-1-yl)methyl]-1-[2-(dimethylamino)ethyl]-1H-benzimidazole-6-carboxylic acid | $^1$H NMR (400 MHz, CD$_3$OD) δ 8.40 (d, 1H), 8.06 (dd, 1H), 7.82 (d, 1H), 7.66 (dd, 1H), 7.51 (t, 1H), 7.27-7.19 (m, 2H), 6.93 (d, 1H), 6.73 (d, 1H), 5.44 (s, 2H), 4.80 (brs, 2H), 3.89 (m, 2H), 3.63 (m, 2H), 3.05 (s, 6H), 2.22 (m, 5H). MS(ES+): 566.1 (M + H). |
| 10A-12 | 2-[(4-{6-[(4-chloro-2-fluorobenzyl)oxy]pyridin-2-yl}piperidin-1-yl)methyl]-1-[2-(2-oxopyrrolidin-1-yl)ethyl]-1H-benzimidazole-6-carboxylic acid | $^1$H NMR (400 MHz, CD$_3$OD) δ 8.30 (d, 1H), 8.01 (dd, 1H), 7.78 (d, 1H), 7.70-7.62 (m, 1H), 7.52 (m, 1H), 7.28-7.14 (m, 2H), 6.94 (d, 1H), 6.73 (d, 1H), 5.45 (s, 2H), 4.85 (s, 2H), 4.61 (t, 2H), 3.99 (m, 2H), 3.73 (t, 2H), 3.52 (t, 2H), 3.43 (m, 2H), 3.05 (m, 1H), 2.37-2.19 (m, 4H), 1.98 (m, 2H), 1.91-1.80 (m, 2H). MS(ES+): 606.0 (M + H). |
| 10A-13 | 2-{[(2S)-4-{6-[(4-chloro-2-fluorobenzyl)oxy]pyridin-2-yl}-2-methylpiperazin-1-yl]methyl}-1-(1,3-oxazol-4-ylmethyl)-1H-benzimidazole-6-carboxylic acid | $^1$H NMR (400 MHz, CD$_3$OD) δ 8.41 (d, 1H), 8.25 (d, 2H), 8.07 (dd, 1H), 7.80 (d, 1H), 7.55 (m, 1H), 7.47 (m, 1H), 7.29-7.15 (m, 2H), 6.43 (d, 1H), 6.24 (d, 1H), 5.78-5.59 (m, 2H), 5.39 (s, 2H), 5.17 (d, 1H), 4.74 (d, 1H), 4.08 (m, 2H), 3.74-3.41 (m, 4H), 1.55 (d, 3H). MS(ES+): 591.1 (M + H). |
| 10A-14 | 2-{[(2S)-4-{6-[(4-cyano-2-fluorobenzyl)oxy]pyridin-2-yl}-2-methylpiperazin-1-yl]methyl}-1-(1,3-oxazol-4-ylmethyl)-1H-benzimidazole-6-carboxylic acid | $^1$H NMR (400 MHz, CD$_3$OD) δ 8.42 (d, 1H), 8.27 (d, 2H), 8.08 (dd, 1H), 7.81 (d, 1H), 7.67 (m, 1H), 7.62-7.52 (m, 3H), 6.46 (d, 1H), 6.29 (d, 1H), 5.80-5.58 (m, 2H), 5.49 (s, 2H), 5.20 (d, 1H), 4.79 (d, 1H), 4.12 (m, 1H), 4.00 (m, 1H), 3.66 (m, 3H), 3.50 (s, 2H), 1.54 (d, 3H). MS(ES+): 582.1 (M + H). |
| 10A-15 | 2-{[(2S)-4-{6-[(4-cyano-2-fluorobenzyl)oxy]pyridin-2-yl}-2-methylpiperazin-1-yl]methyl}-1-(1,3-oxazol-2-ylmethyl)-1H-benzimidazole-6-carboxylic acid | $^1$H NMR (400 MHz, CD$_3$OD) δ 8.44-8.28 (m, 1H), 8.09 (dd, 1H), 7.97 (s, 1H), 7.83 (d, 1H), 7.71-7.51 (m, 4H), 7.20 (s, 1H), 6.43 (d, 1H), 6.28 (d, 1H), 5.90 (d, 2H), 5.48 (s, 2H), 5.02 (d, 1H), 4.62 (d, 1H), 4.03 (m, 2H), 3.59 (m, 2H), 3.47 (s, 1H), 3.24 (m, 1H), 1.47 (d, 3H). MS(ES+): 582.1 (M + H). |
| 10A-16 | 2-{[(2S)-4-{6-[(4-chloro-2-fluorobenzyl)oxy]pyridin-2-yl}-2-methylpiperazin-1-yl]methyl}-1-(1,3-oxazol-5-ylmethyl)-1H-benzimidazole-6-carboxylic acid | $^1$H NMR (400 MHz, CD$_3$OD) δ 8.51-8.40 (m, 1H), 8.20 (s, 1H), 8.09 (dd, 1H), 7.81 (d, 1H), 7.54 (t, 1H), 7.47 (t, 1H), 7.38 (s, 1H), 7.21 (m, 2H), 6.42 (d, 1H), 6.24 (d, 1H), 5.86 (d, 2H), 5.38 (s, 2H), 5.01 (d, 1H), 4.62 (d, 1H), 4.12 (m, 2H), 3.67-3.36 (m, 4H), 3.24 (s, 1H), 1.49 (d, 3H). MS(ES+): 591.1 (M + H). |
| 10A-17 | 2-{[(2S)-4-{6-[(4-cyano-2-fluorobenzyl)oxy]pyridin-2-yl}-2-methylpiperazin-1-yl]methyl}-1-(1,3-oxazol-5-ylmethyl)-1H-benzimidazole-6-carboxylic acid | $^1$H NMR (400 MHz, CD$_3$OD) δ 8.46 (d, 1H), 8.20 (s, 1H), 8.09 (dd, 1H), 7.82 (d, 1H), 7.66 (m, 1H), 7.63-7.54 (m, 3H), 7.38 (s, 1H), 6.44 (d, 1H), 6.28 (d, 1H), 5.86 (d, 2H), 5.48 (s, 2H), 5.01 (d, 1H), 4.63 (d, 1H), 4.25-3.88 (m, 2H), 3.59 (m, 2H), 3.50 (m, 1H), 3.25 (m, 2H), 1.47 (d, 3H). MS(ES+): 582.1 (M + H). |
| 10A-18 | 2-{[(2S)-4-{6-[(4-chloro-2-fluorobenzyl)oxy]pyridin-2-yl}-2-methylpiperazin-1-yl]methyl}-1-(1,3-oxazol-2-ylmethyl)-1H-benzimidazole-6-carboxylic acid | $^1$H NMR (400 MHz, CD$_3$OD) δ 8.38 (dd, 1H), 7.97 (s, 1H), 7.82 (d, 1H), 7.53 (t, 1H), 7.46 (t, 1H), 7.29-7.13 (m, 3H), 6.41 (d, 1H), 6.24 (d, 1H), 5.90 (d, 2H), 5.38 (s, 2H), 5.02 (d, 1H), 4.61 (d, 1H), 4.11 (d, 1H), 4.01 (d, 1H), 3.58 (m, 2H), 3.48 (m, 1H), 3.25 (m, 1H), 1.49 (d, 3H). MS(ES+): 591.1 (M + H). |

TABLE 5-continued

| Ex. # | Name | NMR data/LC-MS data |
|---|---|---|
| 10A-19 | 2-[(4-{6-[(4-chloro-2-fluorobenzyl)oxy]pyridin-2-yl}piperidin-1-yl)methyl]-1-[(1-methylazetidin-3-yl)methyl]-1H-benzimidazole-6-carboxylic acid | LCMS E(4-302) XBridge C18 2.1 × 50 mm, 5 μm; Mobile phase: 1.0% MeCN in water (0.1% TFA) to 5% MeCN in water (0.1% TFA) in 0.6 min; then from 5% MeCN in water (0.1% TFA) to 100% MeCN (0.1% TFA) in 3.4 min; then back to 1.0% ACN in water (0.1% TFA) till 4.3 min, and hold 0.7 min. Flow rate: 0.8 ml/min. Retention time = 2.541 min. MS(ES+): 578.2 (M + H). |
| 10A-20 | 2-[(4-{6-[(4-chloro-2-fluorobenzyl)oxy]pyridin-2-yl}piperidin-1-yl)methyl]-1-[(4,5-dimethyl-4H-1,2,4-triazol-3-yl)methyl]-1H-benzimidazole-6-carboxylic acid | Column: Waters Atlantis dC18 4.6 × 50 mm, 5 μm; Mobile phase A: 0.05% TFA in water (v/v); Mobile phase B: 0.05% TFA in MeCN (v/v); Gradient: 95% $H_2O$/5% MeCN linear to 5% $H_2O$/95% MeCN in 4.0 min, hold at 5% $H_2O$/95% MeCN to 5.0 min. Flow: 2 mL/min. Retention time = 2.62 min. MS(ES+): 604.4 (M + H). |
| 10A-21 | 2-{[(2S)-4-{6-[(4-chloro-2-fluorobenzyl)oxy]pyridin-2-yl}-2-methylpiperazin-1-yl]methyl}-1-[(4-ethyl-4H-1,2,4-triazol-3-yl)methyl]-1H-benzimidazole-6-carboxylic acid | $^1$H NMR (400 MHz $CD_3OD$) δ 8.72 (s, 1H), 8.42-8.35 (m, 1H), 8.10 (dd, 1H), 7.86 (dd, 1H), 7.54 (m, 1H), 7.47 (m, 1H), 7.27-7.18 (m, 2H), 6.43 (d, 1H), 6.25 (d, 1H), 6.03 (d, 2H), 5.38 (m, 2H), 5.08 (d, 1H), 4.71 (d, 1H), 4.38 (q, 2H), 4.15-3.91 (m, 2H), 3.81-3.50 (m, 3H), 3.45-3.34 (m, 2H), 1.58 (t, 3H), 1.52 (d, 3H). MS(ES+): 619.1 (M + H). |
| 10A-22 | 2-{[(2S)-4-{6-[(4-chloro-2-fluorobenzyl)oxy]pyridin-2-yl}-2-methylpiperazin-1-yl]methyl}-1-[(1-methyl-1H-1,2,3-triazol-5-yl)methyl]-1H-benzimidazole-6-carboxylic acid | $^1$H NMR (400 MHz, $CD_3OD$) δ 8.25-8.02 (m, 2H), 7.77 (d, 1H), 7.43 (m, 2H), 7.28-7.11 (m, 3H), 6.21 (d, 1H), 6.09 (d, 1H), 5.93 (s, 2H), 5.32 (s, 2H), 4.41 (d, 1H), 4.17 (s, 3H), 3.67 (m, 2H), 3.50 (m, 1H), 2.90-2.72 (m, 2H), 2.63-2.52 (m, 2H), 2.32 (m, 1H), 1.17 (d, 3H). MS(ES+): 605.3 (M + H). |
| 10A-23 | 2-{[(2S)-4-{6-[(4-cyano-2-fluorobenzyl)oxy]pyridin-2-yl}-2-methylpiperazin-1-yl]methyl}-1-[(1-methyl-1H-1,2,3-triazol-5-yl)methyl]-1H-benzimidazole-6-carboxylic acid | $^1$H NMR (400 MHz, $CD_3OD$) δ 8.16 (s, 1H), 8.04 (d, 1H), 7.76 (d, 1H), 7.50-7.66 (m, 3H), 7.42 (t, 1H), 7.12 (s, 1H), 6.21 (d, 1H), 6.12 (d, 1H), 5.91 (s, 2H), 5.41 (s, 2H), 4.60 (br s, 1H), 4.39 (d, 1H), 4.16 (s, 3H), 3.66 (d, 1H), 3.58 (d, 1H), 3.42 (br s, 1H), 2.68-2.80 (m, 2H), 2.46-2.61 (m, 2H), 2.22-2.31 (m, 1H), 1.14 (d, 3H). MS(ES+): 596.1 (M + H). |
| 10A-24 | 2-[(4-{6-[(4-cyano-2-fluorobenzyl)oxy]pyridin-2-yl}piperidin-1-yl)methyl]-3-(1,3-oxazol-5-ylmethyl)-3H-imidazo[4,5-b]pyridine-5-carboxylic acid | $^1$H NMR (400 MHz, $CD_3OD$) δ 8.35-8.14 (m, 3H), 7.78-7.67 (m, 2H), 7.67-7.55 (m, 2H), 7.38 (s, 1H), 6.98 (d, 1H), 6.82 (d, 1H), 5.88 (s, 2H), 5.59 (s, 2H), 4.98 (s, 2H), 4.01 (m, 2H), 3.46 (m, 2H), 3.09 (m, 1H), 2.27 (m, 4H). MS(ES+): 568.0 (M + H). |
| 10A-25 | 2-{[(2S)-4-{6-[(4-cyano-2-fluorobenzyl)oxy]pyridin-2-yl}-2-methylpiperazin-1-yl]methyl}-1-[(1-methyl-1H-imidazol-5-yl)methyl]-1H-benzimidazole-6-carboxylic acid | $^1$H NMR (600 MHz, DMSO-d6) δ 12.78 (br s, 1H), 8.07 (s, 1H), 7.87 (d, 1H), 7.82 (d, 1H), 7.77 (br s, 1H), 7.70 (d, 2H), 7.63 (t, 1H), 7.44 (t, 1H), 6.48 (br s, 1H), 6.29 (d, 1H), 6.10 (d, 1H), 5.74 (s, 2H), 5.38 (s, 2H), 4.28 (d, 1H), 3.65 (d, 2H), 3.62 (s, 3H), 3.55 (d, 1H), 2.86 (t, 1H), 2.76 (dd, 1H), 2.53-2.65 (m, 2H), 2.27 (t, 1H), 1.06 (d, 1H). MS(ES+): 595.6 (M + H). |
| 10A-26 | 2-[(4-{6-[(4-chloro-2-fluorobenzyl)oxy]pyridin-2-yl}piperidin-1-yl)methyl]-1-[(1-methoxycyclobutyl)methyl]-1H-benzimidazole-6-carboxylic acid | $^1$H NMR (400 MHz, $CD_3OD$) δ 8.43 (d, 1H), 8.03 (dd, 1H), 7.80 (d, 1H), 7.68 (m,1H), 7.53 (m, 1H), 7.33-7.17 (m, 2H), 6.95 (d, 1H), 6.75 (d, 1H), 5.47 (s, 2H), 4.83 (s, 2H), 4.65 (s, 2H), 3.92 (m, 2H), 3.42 (m, 2H), 3.36 (s, 3H), 3.16-2.96 (m, 1H), 2.51 (m, 2H), 2.27 (m, 4H), 2.06-1.91 (m, 1H), 1.87 (m, 4H). MS(ES+): 593.1 (M + H). |
| 10A-27 | 2-[(4-{6-[(4-chloro-2-fluorobenzyl)oxy]pyridin-2-yl}piperidin-1-yl)methyl]-1-[(3-methyloxetan-3-yl)methyl]-1H-benzimidazole-6-carboxylic acid | $^1$H NMR (400 MHz, $CD_3OD$) δ 8.11 (d, 1H), 8.02-7.91 (m, 1H), 7.67-7.55 (m, 2H), 7.50 (m, 1H), 7.29-7.15 (m, 2H), 6.83 (d, 1H), 6.64 (d, 1H), 5.44 (s, 2H), 4.86 (d, 2H), 4.72 (s, 2H), 4.41 (d, 2H), 3.85 (s, 2H), 3.00 (m, 2H), 2.66 (m, 1H), 2.33-2.23 (m, 2H), 2.04-1.77 (m, 4H), 1.41 (s, 3H). MS(ES+): 579.3 (M + H). |
| 10A-27 | 2-[(4-{6-[(4-cyanobenzyl)oxy]pyridin-2-yl}piperidin-1-yl)methyl]-1-(oxetan-3-ylmethyl)-1H-benzimidazole-6-carboxylic acid | $^1$H NMR (400 MHz, $CD_3OD$) δ 8.28 (d, 1H), 7.99 (dd, 1H), 7.75-7.55 (m, 6H), 6.84 (d, 1H), 6.69 (d, 1H), 5.48 (s, 2H), 4.87-4.72 (m, 6H), 3.92 (s, 2H), 3.87-3.76 (m, 1H), 3.06 (d, 2H), 2.66 (m, 1H), 2.34 (m, 2H), 1.96-1.80 (m, 4H). MS(ES+): 538.3 (M + H). |
| 10A-28 | 2-[(4-{6-[(4-chloro-2-fluorobenzyl)oxy]pyridin-2-yl}piperidin-1-yl)methyl]-1-[2-(5-methyl-1,3,4-oxadiazol-2-yl)ethyl]-1H-benzimidazole-6-carboxylic acid | $^1$H NMR (400 MHz, $CD_3OD$) δ 8.26 (d, 1H), 8.03 (dd, 1H), 7.80 (d, 1H), 7.69 (dd, 1H), 7.54 (m, 1H), 7.31-7.16 (m, 2H), 6.97 (d, 1H), 6.76 (d, 1H), 5.49 (s, 2H), 4.97 (s, 2H), 4.00 (m, 2H), 3.59 (m, 2H), 3.47 (m, 2H), 3.11 (m, 1H), 2.45 (s, 2H), 2.43-2.20 (m, 3H). MS(ES+): 605.2 (M + H). |
| 10A-29 | 2-[(4-{6-[(4-chloro-2-fluorobenzyl)oxy]pyridin-2-yl}piperidin-1-yl)methyl]-1- | $^1$H NMR (400 MHz, $CD_3OD$) δ 8.40 (s, 1H), 8.06 (d, 1H), 7.84 (d, 1H), 7.67 (t, 1H), 7.52 (t, 1H), 7.24 (t, 2H), 6.94 (d, 1H), 6.74 (d, 1H), 5.96 (s, 2H), 5.46 (s, |

TABLE 5-continued

| Ex. # | Name | NMR data/LC-MS data |
|---|---|---|
| | [(5-methyl-1,3,4-oxadiazol-2-yl)methyl]-1H-benzimidazole-6-carboxylic acid | 2H), 3.95 (br s, 2H), 3.36-3.51 (m, 2H), 3.07 (br s, 1H), 2.53 (s, 3H), 2.24 (br s, 4H). MS(ES+): 591.0 (M + H). |
| 10A-30 | 2-[(4-{6-[(4-chloro-2-fluorobenzyl)oxy]pyridin-2-yl}piperidin-1-yl)methyl]-1-[(1-methyl-1H-imidazol-4-yl)methyl]-1H-benzimidazole-6-carboxylic acid | $^1$H NMR (400 MHz, CD$_3$OD) δ 8.40 (d, 1H), 8.05 (dd, 1H), 7.90 (d, 1H), 7.80 (d, 1H), 7.70 (m, 1H), 7.59-7.50 (m, 2H), 7.29-7.20 (m, 2H), 6.99 (d, 1H), 6.78 (d, 1H), 5.70 (s, 2H), 5.50 (s, 2H), 3.81 (d, 2H), 3.72 (s, 3H), 3.44 (m, 1H), 3.21-3.07 (m, 1H), 2.27 (m, 4H). MS(ES+): 589.2 (M + H). |
| 10A-31 | 2-[(4-{6-[(2,4-difluorobenzyl)oxy]pyridin-2-yl}piperidin-1-yl)methyl]-1-(1,3-oxazol-2-ylmethyl)-1H-benzimidazole-6-carboxylic acid | $^1$H NMR (400 MHz, CD$_3$OD) δ 8.36 (d, 1H), 8.06 (dd, 1H), 7.99 (s, 1H), 7.84 (d, 1H), 7.68 (dd, 1H), 7.57 (m, 1H), 7.20 (s, 1H), 7.07-6.92 (m, 3H), 6.75 (d, 1H), 5.87 (s, 2H), 5.45 (s, 2H), 4.94 (s, 2H), 3.98 (m, 2H), 3.46 (m, 2H), 3.10 (m, 1H), 2.30 (m, 4H). MS(ES+): 589.2 (M + H). |
| 10A-32 | 2-[(4-{6-[(2,4-difluorobenzyl)oxy]pyridin-2-yl}piperidin-1-yl)methyl]-1-[(1-ethyl-1H-imidazol-5-yl)methyl]-1H-benzimidazole-6-carboxylic acid | $^1$H NMR (400 MHz, CD$_3$OD) δ 8.86 (s, 1H), 8.23 (s, 1H), 8.06 (dd, 1H), 7.83 (d, 1H), 7.63 (dd, 1H), 7.50-7.59 (m, 1H), 6.93-7.03 (m, 3H), 6.87 (d, 1H), 6.69 (d, 1H), 5.88 (s, 2H), 5.41 (s, 2H), 4.51 (br s, 2H), 4.32 (q, 2H), 3.61 (d, 2H), 2.82-3.12 (m, 3H), 1.94-2.21 (m, 4H), 1.52 (t, 3H). MS(ES+): 587.2 (M + H). |
| 10A-33 | 2-[(4-{6-[(4-chloro-2-fluorobenzyl)oxy]pyridin-2-yl}piperazin-1-yl)methyl]-1-(1,3-oxazol-2-ylmethyl)-1H-benzimidazole-6-carboxylic acid | $^1$H NMR (400 MHz, CD$_3$OD) δ 8.36 (d, 1H), 8.07 (dd, 1H), 7.95 (d, 1H), 7.81 (d, 1H), 7.50 (m, 2H), 7.28-7.12 (m, 3H), 6.38 (d, 1H), 6.22 (d, 1H), 5.91 (s, 2H), 5.37 (s, 2H), 4.57 (s, 2H), 3.69 (s, 4H), 3.22 (s, 4H). MS(ES+): 577.1 (M + H). |
| 10A-34 | 2-[(4-{6-[(4-cyano-2-fluorobenzyl)oxy]pyridin-2-yl}piperazin-1-yl)methyl]-1-(1,3-oxazol-2-ylmethyl)-1H-benzimidazole-6-carboxylic acid | $^1$H NMR (400 MHz, CD$_3$OD) δ 8.39 (d, 1H), 8.09 (dd, 1H), 7.98 (d, 1H), 7.84 (d, 1H), 7.67 (m, 1H), 7.63-7.53 (m, 3H), 7.21 (d, 1H), 6.45 (d, 1H), 6.30 (d, 1H), 5.89 (s, 2H), 5.49 (s, 2H), 4.81 (s, 2H), 3.80 (brs, 4H), 3.48 (brs, 4H). MS(ES+): 568.2 (M + H). |
| 10A-35 | 2-[(4-{6-[(4-cyano-2-fluorobenzyl)oxy]pyridin-2-yl}piperazin-1-yl)methyl]-1-[(1-ethyl-1H-imidazol-5-yl)methyl]-1H-benzimidazole-6-carboxylic acid | $^1$H NMR (400 MHz, CD$_3$OD) δ 9.07 (d, 1H), 8.26 (dd, 1H), 8.09 (dd, 1H), 7.85 (dd, 1H), 7.66 (dd, 1H), 7.62-7.47 (m, 3H), 7.10 (d, 1H), 6.35 (d, 1H), 6.24 (d, 1H), 5.96-5.85 (m, 2H), 5.45 (s, 2H), 4.43-4.29 (m, 4H), 3.53 (m, 4H), 3.00 (m, 4H), 1.58 (t, 3H). MS(ES+): 595.1 (M + H). |
| 10A-36 | 2-[(4-{6-[(4-chloro-2-fluorobenzyl)oxy]pyridin-2-yl}piperazin-1-yl)methyl]-1-[(1-methyl-1H-imidazol-5-yl)methyl]-1H-benzimidazole-6-carboxylic acid | $^1$H NMR (400 MHz, CD$_3$OD) δ 8.21-8.13 (m, 1H), 8.02 (dd, 1H), 7.78-7.65 (m, 2H), 7.45 (m, 2H), 7.27-7.12 (m, 2H), 6.67 (s, 1H), 6.25 (d, 1H), 6.12 (d, 1H), 5.80 (s, 2H), 5.41-5.28 (m, 2H), 3.91 (s, 2H), 3.67 (s, 3H), 3.44-3.34 (m, 4H), 2.55 (m, 4H). MS(ES+): 590.0 (M + H). |
| 10A-37 | 2-[(4-{6-[(4-cyano-2-fluorobenzyl)oxy]pyridin-2-yl}piperazin-1-yl)methyl]-1-[(1-methyl-1H-imidazol-5-yl)methyl]-1H-benzimidazole-6-carboxylic acid | $^1$H NMR (400 MHz, CD$_3$OD) δ 8.17 (dd, 1H), 8.02 (dd, 1H), 7.76-7.70 (m, 2H), 7.68-7.62 (m, 1H), 7.56 (m, 2H), 7.45 (t, 1H), 6.66 (d, 1H), 6.26 (d, 1H), 6.15 (d, 1H), 5.80 (d, 2H), 5.43 (s, 2H), 3.90 (s, 2H), 3.67 (s, 3H), 2.53 (t, 4H). MS(ES+): 581.1 (M + H). |
| 10A-38 | 2-[(4-{6-[(4-chloro-2-fluorobenzyl)oxy]pyridin-2-yl}piperidin-1-yl)methyl]-1-[(1-methyl-1H-imidazol-2-yl)methyl]-1H-benzimidazole-6-carboxylic acid | $^1$H NMR (400 MHz, CD$_3$OD) δ 6.75 (d, 1H), 6.52-6.44 (m, 1H), 6.26 (dd, 1H), 6.09 (m, 1H), 5.92 (m, 1H), 5.73 (d, 1H), 5.65 (m, 2H), 5.55 (dd, 1H), 5.37 (dd, 1H), 5.17 (dd, 1H), 4.40 (brs, 2H), 3.89 (m, 2H), 3.23 (s, 2H), 2.48 (m, 3H), 2.21 (m, 2H), 1.85-1.67 (m, 2H), 1.54-1.42 (m, 1H), 0.60 (m, 4H). MS(ES+): 589.1 (M + H). |
| 10A-39 | 2-[(4-{6-[(4-chloro-2-fluorobenzyl)oxy]pyridin-2-yl}piperidin-1-yl)methyl]-1-ethyl-1H-benzimidazole-6-carboxylic acid | $^1$H NMR (400 MHz, CD$_3$OD) δ 8.32 (s, 1H), 8.03 (dd, 1H), 7.79 (d, 1H), 7.71-7.62 (m, 1H), 7.52 (m, 1H), 7.29-7.19 (m, 2H), 6.94 (d, 1H), 6.74 (d, 1H), 5.45 (s, 2H), 4.81 (s, 2H), 4.44 (q, 2H), 3.94 (m, 2H), 3.37 (m, 2H), 3.06 (m, 1H), 2.25 (m, 4H), 1.49 (t, 3H). MS(ES+): 523.2 (M + H). |
| 10A-40 | 2-[(4-{6-[(4-chloro-2-fluorobenzyl)oxy]pyridin-2-yl}piperidin-1-yl)methyl]-1-(propan-2-yl)-1H-benzimidazole-6-carboxylic acid | $^1$H NMR (400 MHz, CD$_3$OD) δ 8.48-8.39 (m, 1H), 8.03 (dd, 1H), 7.81 (d, 1H), 7.69 (dd, 1H), 7.54 (m, 1H), 7.31-7.23 (m, 2H), 6.96 (d, 1H), 6.76 (d, 1H), 5.48 (s, 2H), 4.86 (s, 2H), 3.96 (m, 2H), 3.40 (m, 2H), 3.07 (m, 1H), 2.41-2.18 (m, 4H), 1.76 (d, 6H). MS(ES+): 536.9 (M + H). |

TABLE 5-continued

| Ex. # | Name | NMR data/LC-MS data |
|---|---|---|
| 10A-41 | 2-[(4-{6-[(4-chloro-2-fluorobenzyl)oxy]pyridin-2-yl}piperidin-1-yl)methyl]-1-(1,3-oxazol-4-ylmethyl)-1H-benzimidazole-6-carboxylic acid | ¹H NMR (400 MHz, CD₃OD) δ 8.37 (d, 1H), 8.22 (s, 2H), 8.03 (dd, 1H), 7.78 (d, 1H), 7.71-7.62 (m, 1H), 7.52 (m, 1H), 7.30-7.19 (m, 2H), 6.94 (d, 1H), 6.74 (d, 1H), 5.69 (s, 2H), 5.46 (s, 2H), 4.80 (s, 2H), 3.76 (m, 2H), 3.24 (m, 2H), 3.02 (m, 1H), 2.19 (m, 4H). MS(ES+): 576.2 (M + H). |
| 10A-42 | 2-[(4-{6-[(4-chloro-2-fluorobenzyl)oxy]pyridin-2-yl}piperidin-1-yl)methyl]-1-(1,3-oxazol-2-ylmethyl)-1H-benzimidazole-6-carboxylic acid | ¹H NMR (400 MHz, CD₃OD) δ 8.36 (d, 1H), 8.06 (dd, 1H), 7.98 (d, 1H), 7.83 (d, 1H), 7.68 (dd, 1H), 7.53 (m,1H), 7.30-7.14 (m, 3H), 6.95 (d, 1H), 6.75 (d, 1H), 5.88 (s, 2H), 5.47 (s, 2H), 3.90 (m, 2H), 3.06 (m, 1H), 2.25 (m, 4H). MS(ES+): 576.2 (M + H). |
| 10A-43 | 2-[(4-{6-[(4-cyano-2-fluorobenzyl)oxy]pyridin-2-yl}piperidin-1-yl)methyl]-1-(1,3-oxazol-5-ylmethyl)-1H-benzimidazole-6-carboxylic acid | ¹H NMR (400 MHz, CD₃OD) δ 8.42 (d, 1H), 8.19 (s, 1H), 8.05 (dd, 1H), 7.82 (d, 1H), 7.72 (m, 2H), 7.66-7.57 (m, 2H), 7.38 (s, 1H), 6.98 (d, 1H), 6.81 (d, 1H), 5.79 (s, 2H), 5.58 (s, 2H), 4.94 (s, 2H), 3.99 (m, 2H), 3.45 (m, 2H), 3.09 (m, 1H), 2.27 (m, 5H). MS(ES+): 567.1 (M + H). |
| 10A-44 | 2-[(4-{6-[(2,4-difluorobenzyl)oxy]pyridin-2-yl}piperidin-1-yl)methyl]-1-(1,3-oxazol-5-ylmethyl)-1H-benzimidazole-6-carboxylic acid | ¹H NMR (400 MHz, CD₃OD) δ 8.42 (dd, 1H), 8.20 (s, 1H), 8.06-8.01 (m, 1H), 7.82 (dd, 1H), 7.68 (dd, 1H), 7.61-7.53 (m, 1H), 7.38 (s, 1H), 7.07-6.92 (m, 3H), 6.75 (dd, 1H), 5.80 (s, 2H), 5.46 (s, 2H), 4.94 (s, 2H), 4.01 (m, 2H), 3.47 (m, 2H), 3.17-3.04 (m, 1H), 2.41-2.20 (m, 4H). MS(ES+): 560.1 (M + H). |
| 10A-45 | 2-[(4-{6-[(4-chloro-2-fluorobenzyl)oxy]pyridin-2-yl}piperazin-1-yl)methyl]-1-(1,3-oxazol-5-ylmethyl)-1H-benzimidazole-6-carboxylic acid | ¹H NMR (400 MHz, CD₃OD) δ 8.44 (d, 1H), 8.18 (s, 1H), 8.07 (dd, 1H), 7.80 (d, 1H), 7.54 (t, 1H), 7.47 (t, 1H), 7.36 (s, 1H), 7.21 (t, 1H), 6.42 (d, 1H), 6.24 (d, 1H), 5.82 (s, 2H), 5.37 (s, 2H), 4.75 (s, 2H), 3.82 (br s, 4H), 3.43 (br s, 4H). MS(ES+): 577.1 (M + H). |
| 10A-46 | 1-[(4-tert-butyl-4H-1,2,4-triazol-3-yl) methyl]-2-[(4-{6-[(4-chloro-2-fluorobenzyl)oxy]pyridin-2-yl}piperidin-1-yl)methyl]-1H-benzimidazole-6-carboxylic acid | ¹H NMR (400 MHz, CD₃OD) δ 8.71 (s, 1H), 8.18 (d, 1H), 8.06 (dd, 1H), 7.86 (d, 1H), 7.67 (dd, 1H), 7.54 (m, 1H), 7.31-7.18 (m, 2H), 6.95 (d, 1H), 6.74 (d, 1H), 6.11 (s, 2H), 5.47 (s, 2H), 4.84 (s, 2H), 3.96 (m, 2H), 3.41 (d, 2H), 3.09 (m, 1H), 2.28 (m, 4H), 1.90 (s, 9H). MS(ES+): 632.3 (M + H). |
| 10A-47 | 2-{[(2S)-4-{6-[(4-cyano-2-fluorobenzyl)oxy]pyridin-2-yl}-2-methylpiperazin-1-yl]methyl}-1-[(2S)-oxetan-2-ylmethyl]-1H-benzimidazole-6-carboxylic acid | ¹H NMR (400 MHz, DMSO-d6) δ 12.75 (br s, 1H), 8.26 (d, 1H), 7.87 (dd, 1H), 7.80 (dd, 1H), 7.58-7.73 (m, 3H), 7.46 (t, 1H), 6.33 (d, 1H), 6.11 (d, 1H), 5.39 (s, 2H), 5.09-5.21 (m, 1H), 4.71-4.80 (m, 2H), 4.43-4.52 (m, 1H), 4.35 (d, 1H), 4.27 (dt, 1H), 3.81 (d, 1H), 3.72 (d, 1H), 3.64 (d, 1H), 2.98 (t, 1H), 2.80 (dd, 1H), 2.63-2.73 (m, 2H), 2.57 (br s, 1H), 2.24-2.42 (m, 2H), 1.09 (d, 3H). MS(ES+): 571.7 (M + H). |
| 10A-48 | 2-[(4-{6-[(4-chloro-2-fluorobenzyl)oxy]pyridin-2-yl}piperazin-1-yl)methyl]-1-[(2R)-oxetan-2-ylmethyl]-1H-benzimidazole-6-carboxylic acid | ¹H NMR (400 MHz, CD₃OD) δ 8.21 (d, 1H), 7.96 (dd, 1H), 7.61 (d, 1H), 7.46 (m, 2H), 7.25-7.16 (m, 2H), 6.29 (d, 1H), 6.12 (d, 1H), 5.35 (s, 2H), 5.34-5.26 (m, 1H), 4.74 (dd, 1H), 4.65 (m, 1H), 4.48 (m, 1H), 4.04 (d, 1H), 3.94 (d, 1H), 3.53 (t, 4H), 2.87-2.74 (m, 1H), 2.69-2.49 (m, 5H). MS(ES+): 566.1 (M + H). |
| 10A-49 | 2-{[(2S)-4-{6-[(4-cyanobenzyl)oxy]pyridin-2-yl}-2-methylpiperazin-1-yl]methyl}-1-[(2S)-oxetan-2-ylmethyl]-1H-benzimidazole-6-carboxylic acid | ¹H NMR (400 MHz, CD₃OD 4) δ 8.35 (s, 1H), 8.00 (d, 1H), 7.71 (dd, 3H), 7.58 (d, 2H), 7.46 (m, 1H), 6.29 (d, 1H), 6.16 (d, 1H), 5.40 (s, 2H), 5.31 (m, 1H), 4.84-4.74 (m, 1H), 4.70-4.49 (m, 3H), 4.41-4.30 (m, 1H), 3.78 (m, 3H), 3.09 (m, 1H), 2.92 (m, 1H), 2.77 (d, 2H), 2.64 (m, 1H), 2.44 (m, 2H), 1.20 (d, 3H). MS(ES+): 553.1 (M + H). |
| 10A-50 | 2-[(4-{6-[(4-chloro-2-fluorobenzyl)oxy]pyridin-2-yl}piperidin-1-yl)methyl]-1-(2-hydroxyethyl)-1H-benzimidazole-6-carboxylic acid | ¹H NMR (400 MHz, CD₃OD) δ 8.36 (d, 1H), 8.07 (dd, 1H), 7.83 (d, 1H), 7.67 (dd, 1H), 7.52 (m, 1H), 7.31-7.19 (m, 2H), 6.93 (d, 1H), 6.74 (d, 1H), 5.45 (s, 2H), 4.83 (s, 2H), 4.64 (m, 2H), 3.99 (m, 2H), 3.86 (m, 2H), 3.41 (m, 2H), 3.14-3.01 (m, 1H), 2.28-2.14 (m, 4H). MS(ES+): 539.2 (M + H). |
| 10A-51 | 2-[(4-{6-[(4-chloro-2-fluorobenzyl)oxy]pyridin-2-yl}piperidin-1-yl)methyl]-1-[(5-ethyl-1,2,4-oxadiazol-3-yl)methyl]-1H-benzimidazole-6-carboxylic acid | ¹H NMR (400 MHz, CD₃OD) δ 8.35 (d, 1H), 8.05 (dd, 1H), 7.83 (d, 1H), 7.69 (dd, 1H), 7.53 (m, 1H), 7.33-7.20 (m, 2H), 6.96 (d, 1H), 6.76 (d, 1H), 5.81 (s, 2H), 5.47 (s, 2H), 4.96 (s, 2H), 3.99 (m, 2H), 3.49 (m, 2H), 3.10 (m, 1H), 2.92 (q, 2H), 2.29 (m, 4H), 1.32 (t, 3H). MS(ES+): 605.1 (M + H). |
| 10A-52 | 2-[(4-{6-[(4-chloro-2-fluorobenzyl)oxy]pyridin-2-yl}piperidin-1-yl)methyl]-1-[(3-ethyl-1,2,4-oxadiazol-5-yl)methyl]-1H-benzimidazole-6-carboxylic acid | ¹H NMR (400 MHz, CD₃OD) δ 8.32 (d, 1H), 8.05 (dd, 1H), 7.84 (d, 1H), 7.66 (dd, 1H), 7.51 (m, 1H), 7.30-7.18 (m, 2H), 6.93 (d, 1H), 6.74 (d, 1H), 6.01 (s, 2H), 5.44 (s, 2H), 3.95 (m, 2H), 3.41 (m, 3H), 3.06 (m, 1H), 2.70 (q, 2H), 2.34-2.16 (m, 5H), 1.23 (t, 3H). MS(ES+): 605.1 (M + H). |

TABLE 5-continued

| Ex. # | Name | NMR data/LC-MS data |
|---|---|---|
| 10A-53 | 2-[(4-{6-[(4-chloro-2-fluorobenzyl)oxy]pyridin-2-yl}piperidin-1-yl)methyl]-1-[(2-methyloxetan-2-yl)methyl]-1H-benzimidazole-6-carboxylic acid | ¹H NMR (400 MHz, CD₃OD) δ 8.35 (d, 1H), 8.00 (dd, 1H), 7.71 (d, 1H), 7.60 (dd, 1H), 7.50 (m, 1H), 7.21 (m, 2H), 6.85 (d, 1H), 6.70-6.62 (m, 1H), 5.43 (d, 2H), 4.88-4.81 (m, 1H), 4.66 (d, 2H), 4.48-4.37 (m, 1H), 4.19 (d, 1H), 4.12-4.02 (m, 2H), 3.12 (d, 2H), 2.70 (m, 1H), 2.50 (m, 3H), 1.90 (m, 4H), 1.55 (s, 3H). MS(ES+): 579.1 (M + H). |
| 10A-54 | 2-[(4-{6-[(4-cyano-2-fluorobenzyl)oxy]-5-fluoropyridin-2-yl}piperidin-1-yl)methyl]-1-[(2S)-oxetan-2-ylmethyl]-1H-benzimidazole-6-carboxylic acid | ¹H NMR (400 MHz, CD₃OD) δ 8.32 (d, 1H), 7.98 (dd, 1H), 7.72 (t, 1H), 7.70-7.55 (m, 3H), 7.42 (dd, 1H), 6.86 (dd, 1H), 5.61 (s, 2H), 5.30 (m, 1H), 4.75 (dd, 1H), 4.70-4.60 (m, 1H), 4.50 (dt, 1H), 4.07 (d, 1H), 3.95 (d, 1H), 3.09 (d, 1H), 2.99 (d, 1H), 2.88-2.75 (m, 1H), 2.65 (m, 1H), 2.56 (m, 1H), 2.33 (ddd, 2H), 1.94-1.73 (m, 5H). MS(ES+): 574.1 (M + H). |
| 10A-55 | 2-[(4-{6-[(4-cyanobenzyl)oxy]-5-fluoropyridin-2-yl}piperidin-1-yl)methyl]-1-[(2S)-oxetan-2-ylmethyl]-1H-benzimidazole-6-carboxylic acid | ¹H NMR (400 MHz, DMSO-d6) δ 8.27 (d, 1H), 7.90-7.83 (m, 2H), 7.80 (dd, 1H), 7.69-7.55 (m, 4H), 6.91 (dd, 1H), 5.53 (s, 2H), 5.16-5.05 (m, 1H), 4.80 (dd, 1H), 4.66 (dd, 1H), 4.47 (m, 1H), 4.38 (m, 1H), 3.94 (d, 1H), 3.78 (d, 1H), 2.98 (d, 1H), 2.85 (m, 1H), 2.77-2.53 (m, 2H), 2.48-2.31 (m, 1H), 2.19 (m, 2H), 1.71 (m, 4H). MS(ES+): 556.1 (M + H). |
| 10A-56 | 2-{[(2S)-4-{6-[(2,4-difluorobenzyl)oxy]-5-fluoropyridin-2-yl}-2-methylpiperazin-1-yl]methyl}-1-[(2S)-oxetan-2-ylmethyl]-1H-benzimidazole-6-carboxylic acid | ¹H NMR (400 MHz, CD₃OD) δ 8.35 (d, 1H), 8.00 (dd, 1H), 7.70 (d, 1H), 7.59-7.45 (m, 1H), 7.29 (m, 1H), 7.03-6.91 (m, 2H), 6.22 (dd, 1H), 5.41 (s, 2H), 5.35-5.25 (m, 1H), 4.95 (m, 1H), 4.79 (dd, 1H), 4.68-4.53 (m, 2H), 4.36 (m, 1H), 3.85 (d, 1H), 3.72 (t, 2H), 3.07 (m, 1H), 2.90 (dd, 1H), 2.86-2.72 (m, 2H), 2.72-2.60 (m, 1H), 2.53-2.37 (m, 2H), 1.23 (d, 3H). MS(ES+): 582.1 (M + H). |
| 10A-57 | 2-{[(2S)-4-{6-[(2,4-difluorobenzyl)oxy]-5-fluoropyridin-2-yl}-2-methylpiperazin-1-yl]methyl}-1-[(2R)-oxetan-2-ylmethyl]-1H-benzimidazole-6-carboxylic acid | ¹H NMR (400 MHz, CD₃OD) δ 8.35 (d, 1H), 8.00 (dd, 1H), 7.70 (d, 1H), 7.58-7.46 (m, 1H), 7.31 (dd, 1H), 7.07-6.92 (m, 2H), 6.24 (dd, 1H), 5.42 (s, 2H), 5.27 (q, 1H), 5.09 (dd, 1H), 4.77-4.61 (m, 3H), 4.56 (dt, 1H), 4.01-3.90 (m, 1H), 3.82 (d, 1H), 3.64 (d, 1H), 3.03 (t, 1H), 2.93-2.74 (m, 3H), 2.74-2.55 (m, 2H), 2.44 (t, 1H), 1.35 (d, 3H). MS(ES+): 582.1 (M + H). |
| 10A-58 | 2-{[(2S)-4-{6-[(2,4-difluorobenzyl)oxy]pyridin-2-yl}-2-methylpiperazin-1-yl]methyl}-1-[(2S)-oxetan-2-ylmethyl]-1H-benzimidazole-6-carboxylic acid | ¹H NMR (400 MHz, CD₃OD) δ 8.41-8.28 (m, 1H), 8.00 (dd, 1H), 7.70 (dd, 1H), 7.60-7.39 (m, 2H), 7.05-6.86 (m, 2H), 6.28 (d, 1H), 6.10 (d, 1H), 5.33 (s, 3H), 4.80 (dd, 1H), 4.67-4.52 (m, 2H), 4.37 (dt, 1H), 3.93 (d, 1H), 3.82 (d, 1H), 3.71 (d, 1H), 3.15-3.04 (m, 1H), 2.96 (dd, 1H), 2.86-2.73 (m, 2H), 2.72-2.61 (m, 1H), 2.56-2.35 (m, 2H), 1.23 (d, 3H). MS(ES+): 564.0 (M + H). |
| 10A-59 | 2-{[(2S)-4-{6-[(4-cyano-2-fluorobenzyl)oxy]pyridin-2-yl}-2-methylpiperazin-1-yl]methyl}-1-[(3R)-tetrahydrofuran-3-ylmethyl]-1H-benzimidazole-6-carboxylic acid | ¹H NMR (400 MHz, CD₃OD) δ 8.45 (d, 1H), 8.14 (dd, 1H), 7.84 (d, 1H), 7.66 (m, 1H), 7.62-7.48 (m, 3H), 6.42 (d, 1H), 6.27 (d, 1H), 5.48 (s, 2H), 4.55-4.36 (m, 3H), 4.19-3.96 (m, 3H), 3.81 (m, 1H), 3.70 (m, 1H), 3.58 (m, 1H), 3.42 (s, 2H), 3.26 (m, 1H), 3.11 (m, 1H), 2.98 (m, 1H), 2.20-2.05 (m, 1H), 1.83 (m, 1H), 1.43 (d, 3H). MS(ES+): 585.1 (M + H). |
| 10A-60 | 2-[(4-{6-[(4-chloro-2-fluorobenzyl)oxy]pyridin-2-yl}piperidin-1-yl)methyl]-1-[(3R)-tetrahydrofuran-3-yl]-1H-benzimidazole-6-carboxylic acid | ¹H NMR (400 MHz, CD₃OD) δ 8.62 (s, 1H), 8.03 (d, 1H), 7.81 (d, 1H), 7.68 (t, 1H), 7.54 (t, 1H), 7.29-7.22 (m, 2H), 6.96 (d, 1H), 6.76 (d, 1H), 5.48 (s, 2H), 5.46-5.39 (m, 1H), 4.92 (s, 2H), 4.48 (td, 1H), 4.32 (dd, 1H), 4.10 (dd, 1H), 4.03-3.92 (m, 2H), 3.90-3.79 (m, 1H), 3.46 (t, 2H), 3.13-3.07 (m, 1H), 2.77-2.67 (m, 1H), 2.39-2.19 (m, 5H). MS(ES+): 565.4 (M + H). |
| 10A-61 | 2-[(4-{6-[(4-cyano-2-fluorobenzyl)oxy]pyridin-2-yl}piperazin-1-yl)methyl]-1-(1,3-oxazol-5-ylmethyl)-1H-benzimidazole-6-carboxylic acid | ¹H NMR (400 MHz, CD₃OD) δ 8.44 (dd, 1H), 8.19 (s, 1H), 8.08 (d, 1H), 7.81 (dd, 1H), 7.67 (m, 1H), 7.62-7.51 (m, 3H), 7.36 (s, 1H), 6.43 (d, 1H), 6.28 (d, 1H), 5.85 (s, 2H), 5.48 (s, 2H), 4.65 (s, 2H), 3.76 (brs, 4H). MS(ES+): 568.1 (M + H). |
| 10A-62 | 2-[(4-{6-[(4-cyano-2-fluorobenzyl)oxy]pyridin-2-yl}piperazin-1-yl)methyl]-1-[(1-ethyl-1H-1,2,3-triazol-5-yl)methyl]-1H-benzimidazole-6-carboxylic acid | ¹H NMR (400 MHz, CD₃OD) δ 8.27 (d, 1H), 8.11 (dd, 1H), 7.87 (d, 1H), 7.66 (t, 1H), 7.63-7.49 (m, 3H), 7.24 (s, 1H), 6.38 (d, 1H), 6.26 (d, 1H), 5.92 (s, 2H), 5.46 (s, 2H), 4.57-4.47 (m, 4H), 3.62 (s, 4H), 3.19 (s, 4H), 1.54 (t, 3H). MS(ES+): 596.1 (M + H). |
| 10A-63 | 2-{[(2S)-4-{6-[(4-cyano-2-fluorobenzyl)oxy]pyridin-2-yl}-2-methylpiperazin-1-yl]methyl}-1-[(1-ethyl-1H-imidazol-5-yl)methyl]-1H-benzimidazole-6-carboxylic acid | ¹H NMR (400 MHz, CD₃OD) δ 9.09 (d, 1H), 8.25 (d, 1H), 8.09 (dd, 1H), 7.85 (d, 1H), 7.72-7.41 (m, 4H), 7.08 (d, 1H), 6.36 (d, 1H), 6.24 (d, 1H), 5.93 (d, 2H), 5.56-5.39 (m, 2H), 4.77 (d, 1H), 4.49-4.21 (m, 3H), 3.87 (dd, 2H), 3.23-3.11 (m, 1H), 2.97 (m, 1H), 1.61 (t, 3H), 1.37 (d, 3H). MS(ES+): 609.2 (M + H). |

TABLE 5-continued

| Ex. # | Name | NMR data/LC-MS data |
|---|---|---|
| 10A-64 | 2-[(4-{6-[(4-chloro-2-fluorobenzyl)oxy]pyridin-2-yl}piperidin-1-yl)methyl]-1-(1,2-oxazol-5-ylmethyl)-1H-benzimidazole-6-carboxylic acid | $^1$H NMR (400 MHz, CD$_3$OD) δ 8.38 (dd, 2H), 8.06 (dd, 1H), 7.84 (d, 1H), 7.71-7.64 (m, 1H), 7.53 (m, 1H), 7.32-7.18 (m, 2H), 6.95 (d, 1H), 6.76 (d, 1H), 6.56 (d, 1H), 5.90 (s, 2H), 5.47 (s, 2H), 3.96 (m, 2H), 3.41 (s, 2H), 3.11 (m, 1H); 2.27 (m, 4H). MS(ES+): 576.1 (M + H). |
| 10A-65 | 2-[(4-{6-[(4-cyano-2-fluorobenzyl)oxy]pyridin-2-yl}piperidin-1-yl)methyl]-1-(1,2-oxazol-3-ylmethyl)-1H-benzimidazole-6-carboxylic acid | $^1$H NMR (400 MHz, CD$_3$OD) δ 8.72 (d, 1H), 8.35 (s, 1H), 8.05 (d, 1H), 7.84 (d, 1H), 7.71 (m, 2H), 7.61 (m, 2H), 6.97 (d, 1H), 6.81 (d, 1H), 6.62 (d, 1H), 5.81 (s, 2H), 5.58 (s, 2H), 3.97 (m, 2H), 3.42 (m, 3H), 3.07 (m, 1H), 2.25 (d, 4H). MS(ES+): 567.1 (M + H). |
| 10A-66 | 2-[(4-{6-[(4-cyano-2-fluorobenzyl)oxy]pyridin-2-yl}piperidin-1-yl)methyl]-1-[(1-ethyl-1H-imidazol-5-yl)methyl]-1H-benzimidazole-6-carboxylic acid | $^1$H NMR (400 MHz, CD$_3$OD) δ 9.11 (d, 1H), 8.27 (d, 1H), 8.09 (dd, 1H), 7.90 (d, 1H), 7.76-7.66 (m, 2H), 7.66-7.56 (m, 2H), 7.09 (d, 1H), 6.96 (d, 1H), 6.80 (d, 1H), 5.89 (d, 2H), 5.57 (s, 2H), 4.85 (s, 2H), 4.37 (m, 2H), 3.97 (d, 2H), 3.40 (d, 2H), 3.11-2.98 (m, 1H), 2.23 (m, 4H), 1.60 (t, 3H). MS(ES+): 594.1 (M + H). |
| 10A-67 | 2-{[(2S)-4-{6-[(4-chloro-2-fluorobenzyl)oxy]pyridin-2-yl}-2-methylpiperazin-1-yl]methyl}-1-[(1-ethyl-1H-imidazol-5-yl)methyl]-1H-benzimidazole-6-carboxylic acid | $^1$H NMR (400 MHz, CD$_3$OD) δ 9.11 (d, 1H), 8.26 (s, 1H), 8.10 (dd, 1H), 7.87 (d, 1H), 7.52 (m, 1H), 7.45 (d, 1H), 7.26-7.15 (m, 2H), 7.10 (m, 1H), 6.38 (d, 1H), 6.28-6.15 (m, 1H), 5.92 (s, 2H), 5.36 (s, 2H), 4.39 (m, 3H), 4.00 (m, 2H), 3.48 (m, 4H), 3.15 (m, 1H), 1.62 (t, 3H), 1.44 (m, 3H). MS(ES+): 618.1 (M + H). |
| 10A-68 | 2-[(4-{6-[(4-chloro-2-fluorobenzyl)oxy]pyridin-2-yl}piperidin-1-yl)methyl]-1-(1,2-oxazol-4-ylmethyl)-1H-benzimidazole-6-carboxylic acid | $^1$H NMR (400 MHz, CD$_3$OD) δ 8.77 (s, 1H), 8.47 (s, 1H), 8.30 (s, 1H), 8.03 (dd, 1H), 7.80 (d, 1H), 7.68-7.59 (m, 1H), 7.51 (m, 1H), 7.29-7.17 (m, 2H), 6.91 (d, 1H), 6.71 (d, 1H), 5.59 (s, 2H), 5.45 (s, 2H), 4.66 (brs, 2H), 3.76 (m, 2H), 3.32-3.04 (m, 2H), 2.97 (m, 1H), 2.17 (m, 5H). MS(ES+): 576.2 (M + H). |
| 10A-69 | 2-[(4-{6-[(4-cyano-2-fluorobenzyl)oxy]pyridin-2-yl}piperidin-1-yl)methyl]-1-[(1-ethyl-1H-1,2,3-triazol-5-yl)methyl]-1H-benzimidazole-6-carboxylic acid | $^1$H NMR (400 MHz, CD$_3$OD) δ 8.24 (d, 1H), 8.08 (dd, 1H), 7.89 (d, 1H), 7.76-7.67 (m, 2H), 7.67-7.55 (m, 2H), 7.25 (s, 1H), 6.96 (d, 1H), 6.81 (d, 1H), 5.89 (s, 2H), 5.58 (s, 2H), 4.78 (s, 2H), 4.53 (q, 2H), 3.95 (m, 2H), 3.04 (m, 1H), 2.23 (m, 4H), 1.54 (t, 3H). MS(ES+): 595.3 (M + H). |
| 10A-70 | 2-[(4-{6-[(4-chloro-2-fluorobenzyl)oxy]pyridin-2-yl}piperidin-1-yl)methyl]-1-(1,2,4-oxadiazol-3-ylmethyl)-1H-benzimidazole-6-carboxylic acid | LCMS Ultimate XB-C18, 3 µm, 3.0 × 50 mm; Mobile phase: A: H$_2$O (0.1% TFA), Mobile phase B: MeCN (0.1% TFA). Gradient: 1% B to 5% B in 1 min; then from 5% B to 100% B in 5 min; hold at 100% B for 2 min; back to 1.0% B at 8.01 min, hold two min. Flow rate: 1.2 ml/min. Retention time = 3.93 min. MS(ES+): 577.2 (M + H) |
| 10A-71 | 2-[(4-{6-[(4-chloro-2-fluorobenzyl)oxy]pyridin-2-yl}piperidin-1-yl)methyl]-1-[(3S)-tetrahydrofuran-3-yl]-1H-benzimidazole-6-carboxylic acid | $^1$H NMR (400 MHz, CD$_3$OD) δ 8.62 (s, 1H), 8.04 (dd, 1H), 7.81 (d, 1H), 7.69 (dd, 1H), 7.54 (t, 1H), 7.33-7.20 (m, 2H), 6.96 (d, 1H), 6.76 (d, 1H), 5.48 (s, 2H), 5.45-5.35 (m, 1H), 4.92 (s, 2H), 4.49 (td, 1H), 4.32 (dd, 1H), 4.09 (dd, 1H), 4.03-4.92 (m, 2H), 3.90-3.79 (m, 1H), 3.46 (t, 2H), 3.19-3.00 (m, 1H), 2.76-2.64 (m, 1H), 2.40-2.18 (m, 5H). MS(ES+): 565.4 (M + H). |
| 10A-72 | 2-[(4-{6-[(4-chloro-2-fluorobenzyl)oxy]pyridin-2-yl}piperidin-1-yl)methyl]-1-[(3R)-tetrahydrofuran-3-ylmethyl]-1H-benzimidazole-6-carboxylic acid | $^1$H NMR (CD$_3$OD) δ: 8.35 (s, 1H), 8.03 (d, 1H), 7.81 (d, 1H), 7.67 (t, 1H), 7.52 (t, 1H), 7.24 (t, 2H), 6.94 (d, 1H), 6.74 (d, 1H), 5.46 (s, 2H), 4.83 (br s, 2H), 4.37 (qd, 2H), 4.05 (q, 1H), 3.95 (br s, 2H), 3.79 (q, 1H), 3.63-3.73 (m, 1H), 3.54 (dd, 1H), 3.42 (br s, 2H), 3.07 (br s, 1H), 2.91 (br s, 1H), 2.30 (d, 2H), 2.19-2.26 (m, 2H), 2.09 (td, 1H), 1.79 (td, 1H). MS(ES+): 579.4 (M + H). |
| 10A-73 | 2-[(4-{6-[(4-chloro-2-fluorobenzyl)oxy]pyridin-2-yl}piperidin-1-yl)methyl]-1-[(2S)-tetrahydrofuran-2-ylmethyl]-1H-benzimidazole-6-carboxylic acid | $^1$H NMR (600 MHz, CD$_3$OD) δ 8.34 (s, 1H), 8.03 (d, 1H), 7.80 (d, 1H), 7.67 (t, 1H), 7.51 (t, 1H), 7.19-7.29 (m, 2H), 6.94 (d, 1H), 6.75 (d, 1H), 5.45 (s, 2H), 4.84 (q, 2H), 4.69 (d, 1H), 4.45 (dd, 1H), 4.16-4.28 (m, 1H), 3.86-3.99 (m, 3H), 3.77 (q, 1H), 3.43 (d, 2H), 3.08 (br s, 1H), 2.16-2.35 (m, 5H), 1.87-2.00 (m, 2H), 1.63-1.74 (m, 1H). MS(ES+): 579.4 (M + H). |
| 10A-74 | 2-[(4-{6-[(4-chloro-2-fluorobenzyl)oxy]pyridin-2-yl}piperazin-1-yl)methyl]-3-[(2S)-oxetan-2-ylmethyl]-3H-imidazo[4,5-b]pyridine-5-carboxylic acid | $^1$H NMR (400 MHz, CD$_3$OD) δ 8.21-8.12 (m, 2H), 7.46 (m, 2H), 7.26-7.15 (m, 2H), 6.30 (d, 1H), 6.13 (d, 1H), 5.41-5.26 (m, 3H), 5.06 (dd, 1H), 4.64 (m, 1H), 4.46 (m, 1H), 4.17 (d, 1H), 4.08 (d, 1H), 3.57 (t, 4H), 2.86-2.73 (m, 1H), 2.70 (d, 4H), 2.61-2.49 (m, 1H). MS(ES+): 567.0 (M + H). |

TABLE 5-continued

| Ex. # | Name | NMR data/LC-MS data |
|---|---|---|
| 10A-75 | 2-[(4-{6-[(4-cyano-2-fluorobenzyl)oxy]pyridin-2-yl}piperidin-1-yl)methyl]-3-[(1-ethyl-1H-imidazol-5-yl)methyl]-3H-imidazo[4,5-b]pyridine-5-carboxylic acid | $^1$H NMR (400 MHz, CD$_3$OD) δ 9.06 (d, 1H), 8.40-8.17 (m, 2H), 7.79-7.66 (m, 2H), 7.66-7.57 (m, 2H), 7.48 (d, 1H), 6.96 (d, 1H), 6.81 (d, 1H), 5.90 (s, 2H), 5.58 (s, 2H), 4.86 (s, 2H), 4.55 (q, 2H), 4.10-3.81 (m, 1H), 3.04 (m, 1H), 2.23 (m, 4H), 1.54 (t, 3H). MS(ES+): 595.1 (M + H). |
| 10A-76 | 2-[(4-{6-[(4-cyano-2-fluorobenzyl)oxy]pyridin-2-yl}piperidin-1-yl)methyl]-3-[(1-methyl-1H-imidazol-5-yl)methyl]-3H-imidazo[4,5-b]pyridine-5-carboxylic acid | $^1$H NMR (400 MHz, CD$_3$OD) δ 8.93 (s, 1H), 8.37-8.13 (m, 2H), 7.78-7.66 (m, 2H), 7.66-7.55 (m, 2H), 7.47 (s, 1H), 6.96 (d, 1H), 6.80 (d, 1H), 5.88 (s, 2H), 5.58 (s, 2H), 4.81 (s, 2H), 4.13 (s, 3H), 3.88 (d, 2H), 3.02 (s, 1H), 2.18 (m, 4H). MS(ES+): 581.1 (M + H). |
| 10A-77 | 2-[(4-{6-[(4-cyano-2-fluorobenzyl)oxy]pyridin-2-yl}piperazin-1-yl)methyl]-3-[(2S)-oxetan-2-ylmethyl]-3H-imidazo[4,5-b]pyridine-5-carboxylic acid | $^1$H NMR (400 MHz, CD$_3$OD) δ 8.11 (q, 2H), 7.65 (m, 1H), 7.56 (m, 2H), 7.47 (m, 1H), 6.31 (d, 1H), 6.16 (d, 1H), 5.46 (s, 2H), 5.32 (s, 1H), 5.06 (dd, 1H), 4.92 (d, 1H), 4.64 (m, 1H), 4.46 (m, 1H), 4.12 (d, 1H), 4.03 (d, 1H), 3.52 (m, 4H), 2.80 (m, 1H), 2.69-2.46 (m, 5H). MS(ES+): 558.1 (M + H). |
| 10A-78 | 2-[(4-{6-[(4-cyanobenzyl)oxy]pyridin-2-yl}piperidin-1-yl)methyl]-1-[(2S)-oxetan-2-ylmethyl]-1H-benzimidazole-6-carboxylic acid | $^1$H NMR (400 MHz, CD$_3$OD) δ 8.34 (d, 1H), 8.00 (dd, 1.4 Hz, 1H), 7.78-7.67 (m, 3H), 7.67-7.52 (m, 3H), 6.86 (d, 1H), 6.70 (d, 1H), 5.49 (s, 2H), 5.33-5.21 (m, 1H), 4.86 (m, 1H), 4.74 (m, 1H), 4.69-4.57 (m, 1H), 4.48 (m, 1H), 4.21-3.97 (m, 2H), 3.13 (m, 2H), 2.89-2.77 (m, 1H), 2.69 (m, 1H), 2.60-2.40 (m, 3H), 1.89 (m, 4H). MS(ES+): 538.3 (M + H). |
| 10A-79 | 2-[(4-{6-[(4-chloro-2-fluorobenzyl)oxy]pyridin-2-yl}piperidin-1-yl)methyl]-1-[(1-methylazetidin-2-yl)methyl]-1H-benzimidazole-6-carboxylic acid | $^1$H NMR (400 MHz, CD$_3$OD) δ: 8.30 (s, 1H), 8.00 (d, 1H), 7.68 (d, 1H), 7.56-7.64 (m, 1H), 7.48 (t, 1H), 7.16-7.28 (m, 2H), 6.86 (d, 1H), 6.67 (d, 1H), 5.41 (s, 2H), 4.77 (d, 2H), 4.27 (t, 1H), 4.06 (d, 2H), 3.82 (td, 1H), 3.33-3.43 (m, 1H), 3.19 (d, 2H), 2.71-2.85 (m, 1H), 2.47-2.57 (m, 1H), 2.43 (s, 3H), 2.34-2.41 (m, 1H), 2.18-2.30 (m, 1H), 1.80-2.01 (m, 4H). MS(ES+): 578.0 (M + H). |

The compounds listed in Table 6 below were prepared by parallel synthesis using procedures analogous to those described above for the synthesis of Examples 10A-01 using the appropriate starting materials which are available commercially, prepared using preparations well-known to those skilled in the art, or prepared in a manner analogous to routes described above for other intermediates. The compounds were purified using HPLC. Due to the purification solvent, the final compounds isolated using methods PF-AB01 and PF-AB10 were likely trifluoroacetate salts, while compounds isolated using method PF-CD05 are likely ammonium salts.

TABLE 6

| Ex. # | Name | *MW found | Ret. time (min) | **Method |
|---|---|---|---|---|
| 11A-01 | 2-[(4-{6-[(4-chloro-2-fluorobenzyl)oxy]pyridin-2-yl}piperidin-1-yl)methyl]-1-[2-(1-methyl-1H-imidazol-4-yl)ethyl]-1H-benzimidazole-6-carboxylic acid | 603 | 2.716 | PF-AB01 |
| 11A-02 | 2-[(4-{6-[(4-chloro-2-fluorobenzyl)oxy]pyridin-2-yl}piperidin-1-yl)methyl]-1-[(5-chloropyridin-2-yl)methyl]-1H-benzimidazole-6-carboxylic acid | 620 | 2.637 | PF-CD05 |
| 11A-03 | 2-[(4-{6-[(4-chloro-2-fluorobenzyl)oxy]pyridin-2-yl}piperidin-1-yl)methyl]-1-[(1-ethylpyrrolidin-3-yl)methyl]-1H-benzimidazole-6-carboxylic acid | 606 | 2.568 | PF-AB10 |
| 11A-04 | 2-[(4-{6-[(4-chloro-2-fluorobenzyl)oxy]pyridin-2-yl}piperidin-1-yl)methyl]-1-[(1-methylpiperidin-3-yl)methyl]-1H-benzimidazole-6-carboxylic acid | 606 | 2.549 | PF-AB10 |
| 11A-05 | 2-[(4-{6-[(4-chloro-2-fluorobenzyl)oxy]pyridin-2-yl}piperidin-1-yl)methyl]-1-[2-(tetrahydro-2H-pyran-2-yl)ethyl]-1H-benzimidazole-6-carboxylic acid | 607 | 2.962 | PF-AB10 |
| 11A-06 | 2-[(4-{6-[(4-chloro-2-fluorobenzyl)oxy]pyridin-2-yl}piperidin-1-yl)methyl]-1-{[3-(propan-2-yl)-1,2-oxazol-5-yl]methyl}-1H-benzimidazole-6-carboxylic acid | 618 | 3.041 | PF-AB10 |
| 11A-07 | 2-[(4-{6-[(4-chloro-2-fluorobenzyl)oxy]pyridin-2-yl}piperidin-1-yl)methyl]-1-[2-(1-methylpiperidin-4-yl)ethyl]-1H-benzimidazole-6-carboxylic acid | 620 | 2.602 | PF-AB10 |
| 11A-08 | 2-[(4-{6-[(4-chloro-2-fluorobenzyl)oxy]pyridin-2-yl}piperidin-1-yl)methyl]-1-[(1-methylpiperidin-4-yl)methyl]-1H-benzimidazole-6-carboxylic acid | 606 | 2.559 | PF-AB10 |

TABLE 6-continued

| Ex. # | Name | *MW found | Ret. time (min) | **Method |
|---|---|---|---|---|
| 11A-09 | 2-[(4-{6-[(4-chloro-2-fluorobenzyl)oxy]pyridin-2-yl}piperidin-1-yl)methyl]-1-[2-(1-methylpyrrolidin-2-yl)ethyl]-1H-benzimidazole-6-carboxylic acid | 606 | 2.369 | PF-AB10 |
| 11A-10 | 2-[(4-{6-[(4-chloro-2-fluorobenzyl)oxy]pyridin-2-yl}piperidin-1-yl)methyl]-1-[(1-methylpiperidin-2-yl)methyl]-1H-benzimidazole-6-carboxylic acid | 606 | 2.56 | PF-AB10 |
| 11A-11 | 2-[(4-{6-[(4-chloro-2-fluorobenzyl)oxy]pyridin-2-yl}piperidin-1-yl)methyl]-1-[2-(4-methylmorpholin-2-yl)ethyl]-1H-benzimidazole-6-carboxylic acid | 622 | 2.333 | PF-AB10 |
| 11A-12 | 2-[(4-{6-[(4-chloro-2-fluorobenzyl)oxy]pyridin-2-yl}piperidin-1-yl)methyl]-1-{[1-(2-methoxyethyl)piperidin-4-yl]methyl}-1H-benzimidazole-6-carboxylic acid | 650 | 2.552 | PF-AB10 |
| 11A-13 | 2-[(4-{6-[(4-chloro-2-fluorobenzyl)oxy]pyridin-2-yl}piperidin-1-yl)methyl]-1-{[1-(2-methoxyethyl)piperidin-3-yl]methyl}-1H-benzimidazole-6-carboxylic acid | 650 | 2.572 | PF-AB10 |
| 11A-14 | 2-[(4-{6-[(4-chloro-2-fluorobenzyl)oxy]pyridin-2-yl}piperidin-1-yl)methyl]-1-[(3-methyltetrahydrofuran-3-yl)methyl]-1H-benzimidazole-6-carboxylic acid | 593 | 2.901 | PF-AB10 |
| 11A-15 | 2-[(4-{6-[(4-chloro-2-fluorobenzyl)oxy]pyridin-2-yl}piperidin-1-yl)methyl]-1-(1H-pyrazol-4-ylmethyl)-1H-benzimidazole-6-carboxylic acid | 575 | 2.37 | PF-CD05 |
| 11A-16 | 2-[(4-{6-[(4-chloro-2-fluorobenzyl)oxy]pyridin-2-yl}piperidin-1-yl)methyl]-1-(cyclobutylmethyl)-1H-benzimidazole-6-carboxylic acid | 563 | 3.029 | PF-AB10 |
| 11A-17 | 2-[(4-{6-[(4-chloro-2-fluorobenzyl)oxy]pyridin-2-yl}piperidin-1-yl)methyl]-1-[2-(1H-1,2,4-triazol-1-yl)ethyl]-1H-benzimidazole-6-carboxylic acid | 590 | 2.926 | PF-AB01 |
| 11A-18 | 2-[(4-{6-[(4-chloro-2-fluorobenzyl)oxy]pyridin-2-yl}piperidin-1-yl)methyl]-1-(2-ethoxypropyl)-1H-benzimidazole-6-carboxylic acid | 581 | 2.831 | PF-AB10 |
| 11A-19 | 2-[(4-{6-[(4-chloro-2-fluorobenzyl)oxy]pyridin-2-yl}piperidin-1-yl)methyl]-1-{[4-(2-methoxyethyl)-4H-1,2,4-triazol-3-yl]methyl}-1H-benzimidazole-6-carboxylic acid | 634 | 2.368 | PF-CD05 |
| 11A-20 | 2-[(4-{6-[(4-chloro-2-fluorobenzyl)oxy]pyridin-2-yl}piperidin-1-yl)methyl]-1-[2-(2-oxo-1,3-oxazolidin-3-yl)ethyl]-1H-benzimidazole-6-carboxylic acid | 608 | 2.382 | PF-CD05 |
| 11A-21 | 2-[(4-{6-[(4-chloro-2-fluorobenzyl)oxy]pyridin-2-yl}piperidin-1-yl)methyl]-1-[(1-methyl-1H-pyrazol-5-yl)methyl]-1H-benzimidazole-6-carboxylic acid | 589 | 3.002 | PF-AB01 |
| 11A-22 | 2-[(4-{6-[(4-chloro-2-fluorobenzyl)oxy]pyridin-2-yl}piperidin-1-yl)methyl]-1-(2-methoxy-2-methylpropyl)-1H-benzimidazole-6-carboxylic acid | 581 | 3.003 | PF-AB10 |
| 11A-23 | 2-[(4-{6-[(4-chloro-2-fluorobenzyl)oxy]pyridin-2-yl}piperidin-1-yl)methyl]-1-(1H-1,2,3-triazol-4-ylmethyl)-1H-benzimidazole-6-carboxylic acid | 576 | 2.236 | PF-CD05 |
| 11A-24 | 2-[(4-{6-[(4-chloro-2-fluorobenzyl)oxy]pyridin-2-yl}piperidin-1-yl)methyl]-1-(1H-pyrazol-3-ylmethyl)-1H-benzimidazole-6-carboxylic acid | 575 | 2.409 | PF-CD05 |
| 11A-25 | 2-[(4-{6-[(4-chloro-2-fluorobenzyl)oxy]pyridin-2-yl}piperidin-1-yl)methyl]-1-(4H-1,2,4-triazol-3-ylmethyl)-1H-benzimidazole-6-carboxylic acid | 576 | 2.302 | PF-CD05 |
| 11A-26 | 2-[(4-{6-[(4-chloro-2-fluorobenzyl)oxy]pyridin-2-yl}piperidin-1-yl)methyl]-1-(tetrahydrofuran-3-yl)-1H-benzimidazole-6-carboxylic acid | 565 | 2.829 | PF-AB01 |
| 11A-27 | 2-[(4-{6-[(4-chloro-2-fluorobenzyl)oxy]pyridin-2-yl}piperidin-1-yl)methyl]-1-(2,2-difluoropropyl)-1H-benzimidazole-6-carboxylic acid | 573 | 2.773 | PF-AB10 |
| 11A-28 | 2-[(4-{6-[(4-chloro-2-fluorobenzyl)oxy]pyridin-2-yl}piperidin-1-yl)methyl]-1-[2-(1H-pyrazol-1-yl)ethyl]-1H-benzimidazole-6-carboxylic acid | 589 | 2.862 | PF-AB01 |
| 11A-29 | 2-[(4-{6-[(4-chloro-2-fluorobenzyl)oxy]pyridin-2-yl}piperidin-1-yl)methyl]-1-[2-(3-methyl-1,2,4-oxadiazol-5-yl)ethyl]-1H-benzimidazole-6-carboxylic acid | 605 | 3.069 | PF-AB01 |
| 11A-30 | 2-[(4-{6-[(4-chloro-2-fluorobenzyl)oxy]pyridin-2-yl}piperidin-1-yl)methyl]-1-[2-(2-oxo-1,3-oxazinan-3-yl)ethyl]-1H-benzimidazole-6-carboxylic acid | 622 | 2.779 | PF-AB10 |

TABLE 6-continued

| Ex. # | Name | *MW found | Ret. time (min) | **Method |
|---|---|---|---|---|
| 11A-31 | 2-[(4-{6-[(4-chloro-2-fluorobenzyl)oxy]pyridin-2-yl}piperidin-1-yl)methyl]-1-[2-(3-methyl-1H-pyrazol-1-yl)ethyl]-1H-benzimidazole-6-carboxylic acid | 603 | 2.899 | PF-AB10 |
| 11A-32 | 2-[(4-{6-[(4-chloro-2-fluorobenzyl)oxy]pyridin-2-yl}piperidin-1-yl)methyl]-1-[2-(1-methyl-1H-pyrazol-4-yl)ethyl]-1H-benzimidazole-6-carboxylic acid | 603 | 3.001 | PF-AB01 |
| 11A-33 | 2-[(4-{6-[(4-chloro-2-fluorobenzyl)oxy]pyridin-2-yl}piperidin-1-yl)methyl]-1-[(1-methyl-1H-1,2,4-triazol-5-yl)methyl]-1H-benzimidazole-6-carboxylic acid | 590 | 2.986 | PF-AB01 |
| 11A-34 | 2-[(4-{6-[(4-chloro-2-fluorobenzyl)oxy]pyridin-2-yl}piperidin-1-yl)methyl]-1-{[(2R)-1-methylpyrrolidin-2-yl]methyl}-1H-benzimidazole-6-carboxylic acid | 592 | 2.397 | PF-AB10 |
| 11A-35 | 2-[(4-{6-[(4-chloro-2-fluorobenzyl)oxy]pyridin-2-yl}piperidin-1-yl)methyl]-1-[(5-methyl-1,2-oxazol-3-yl)methyl]-1H-benzimidazole-6-carboxylic acid | 590 | 2.94 | PF-AB01 |
| 11A-36 | 2-[(4-{6-[(4-chloro-2-fluorobenzyl)oxy]pyridin-2-yl}piperidin-1-yl)methyl]-1-[(1-methyl-1H-1,2,3-triazol-4-yl)methyl]-1H-benzimidazole-6-carboxylic acid | 590 | 2.84 | PF-AB01 |
| 11A-37 | 2-[(4-{6-[(4-chloro-2-fluorobenzyl)oxy]pyridin-2-yl}piperidin-1-yl)methyl]-1-(1H-imidazol-5-ylmethyl)-1H-benzimidazole-6-carboxylic acid | 575 | 2.354 | PF-CD05 |
| 11A-38 | 2-[(4-{6-[(4-chloro-2-fluorobenzyl)oxy]pyridin-2-yl}piperidin-1-yl)methyl]-1-(3-methoxypropyl)-1H-benzimidazole-6-carboxylic acid | 567 | 2.703 | PF-AB10 |
| 11A-39 | 2-[(4-{6-[(4-chloro-2-fluorobenzyl)oxy]pyridin-2-yl}piperidin-1-yl)methyl]-1-[(1-ethyl-1H-imidazol-2-yl)methyl]-1H-benzimidazole-6-carboxylic acid | 603 | 2.455 | PF-CD05 |
| 11A-40 | 2-[(4-{6-[(4-chloro-2-fluorobenzyl)oxy]pyridin-2-yl}piperidin-1-yl)methyl]-1-(tetrahydro-2H-pyran-3-ylmethyl)-1H-benzimidazole-6-carboxylic acid | 593 | 2.907 | PF-AB10 |
| 11A-41 | 2-[(4-{6-[(4-chloro-2-fluorobenzyl)oxy]pyridin-2-yl}piperidin-1-yl)methyl]-1-[2-(1H-imidazol-4-yl)ethyl]-1H-benzimidazole-6-carboxylic acid | 589 | 2.695 | PF-AB01 |
| 11A-42 | 2-[(4-{6-[(4-chloro-2-fluorobenzyl)oxy]pyridin-2-yl}piperidin-1-yl)methyl]-1-[(1-methyl-5-oxopyrrolidin-3-yl)methyl]-1H-benzimidazole-6-carboxylic acid | 606 | 2.974 | PF-AB01 |
| 11A-43 | 2-[(4-{6-[(4-chloro-2-fluorobenzyl)oxy]pyridin-2-yl}piperidin-1-yl)methyl]-1-[(1-methyl-1H-pyrazol-4-yl)methyl]-1H-benzimidazole-6-carboxylic acid | 589 | 2.808 | PF-AB01 |
| 11A-44 | 2-[(4-{6-[(4-chloro-2-fluorobenzyl)oxy]pyridin-2-yl}piperidin-1-yl)methyl]-1-[2-(1-methyl-1H-1,2,3-triazol-4-yl)ethyl]-1H-benzimidazole-6-carboxylic acid | 604 | 2.801 | PF-AB01 |
| 11A-45 | 2-[(4-{6-[(4-chloro-2-fluorobenzyl)oxy]pyridin-2-yl}piperidin-1-yl)methyl]-1-[(2S)-1-methoxypropan-2-yl]-1H-benzimidazole-6-carboxylic acid | 567 | 2.721 | PF-AB10 |
| 11A-46 | 2-[(4-{6-[(4-chloro-2-fluorobenzyl)oxy]pyridin-2-yl}piperidin-1-yl)methyl]-1-[(2R)-1-methoxypropan-2-yl]-1H-benzimidazole-6-carboxylic acid | 567 | 2.723 | PF-AB10 |
| 11A-47 | 2-[(4-{6-[(4-chloro-2-fluorobenzyl)oxy]pyridin-2-yl}piperidin-1-yl)methyl]-1-[(3-methyl-1,2-oxazol-5-yl)methyl]-1H-benzimidazole-6-carboxylic acid | 590 | 2.481 | PF-CD05 |
| 11A-48 | 2-[(4-{6-[(4-chloro-2-fluorobenzyl)oxy]pyridin-2-yl}piperidin-1-yl)methyl]-1-(tetrahydro-2H-pyran-2-ylmethyl)-1H-benzimidazole-6-carboxylic acid | 590 | 2.481 | PF-CD05 |
| 11A-49 | 2-[(4-{6-[(4-chloro-2-fluorobenzyl)oxy]pyridin-2-yl}piperidin-1-yl)methyl]-1-(tetrahydro-2H-pyran-4-ylmethyl)-1H-benzimidazole-6-carboxylic acid | 593 | 2.87 | PF-AB10 |
| 11A-50 | 2-[(4-{6-[(4-chloro-2-fluorobenzyl)oxy]pyridin-2-yl}piperidin-1-yl)methyl]-1-[2-(morpholin-4-yl)ethyl]-1H-benzimidazole-6-carboxylic acid | 608 | 2.775 | PF-AB01 |
| 11A-51 | 2-[(4-{6-[(4-chloro-2-fluorobenzyl)oxy]pyridin-2-yl}piperidin-1-yl)methyl]-1-[(3,3-difluorocyclobutyl)methyl]-1H-benzimidazole-6-carboxylic acid | 599 | 2.853 | PF-AB10 |

TABLE 6-continued

| Ex. # | Name | *MW found | Ret. time (min) | **Method |
|---|---|---|---|---|
| 11A-52 | 2-[(4-{6-[(4-chloro-2-fluorobenzyl)oxy]pyridin-2-yl}piperidin-1-yl)methyl]-1-[1-(4-methyl-4H-1,2,4-triazol-3-yl)ethyl]-1H-benzimidazole-6-carboxylic acid | 604 | 2.964 | PF-AB01 |
| 11A-53 | 2-[(4-{6-[(4-chloro-2-fluorobenzyl)oxy]pyridin-2-yl}piperidin-1-yl)methyl]-1-[2-(4-methyl-4H-1,2,4-triazol-3-yl)ethyl]-1H-benzimidazole-6-carboxylic acid | 604 | 2.762 | PF-AB01 |
| 11A-54 | 2-[(4-{6-[(4-chloro-2-fluorobenzyl)oxy]pyridin-2-yl}piperidin-1-yl)methyl]-1-{[(2R)-1-ethylpyrrolidin-2-yl]methyl}-1H-benzimidazole-6-carboxylic acid | 606 | 2.599 | PF-AB10 |
| 11A-55 | 2-[(4-{6-[(4-chloro-2-fluorobenzyl)oxy]pyridin-2-yl}piperidin-1-yl)methyl]-1-[(2,5-dimethyl-1,3-oxazol-4-yl)methyl]-1H-benzimidazole-6-carboxylic acid | 604 | 2.492 | PF-CD05 |
| 11A-56 | 2-[(4-{6-[(4-chloro-2-fluorobenzyl)oxy]pyridin-2-yl}piperidin-1-yl)methyl]-1-[2-(4-methoxypiperidin-1-yl)ethyl]-1H-benzimidazole-6-carboxylic acid | 636 | 2.742 | PF-AB01 |
| 11A-57 | 2-[(4-{6-[(4-chloro-2-fluorobenzyl)oxy]pyridin-2-yl}piperidin-1-yl)methyl]-1-[2-(3,5-dimethyl-1H-pyrazol-1-yl)ethyl]-1H-benzimidazole-6-carboxylic acid | 617 | 2.934 | PF-AB10 |
| 11A-58 | 2-[(4-{6-[(4-chloro-2-fluorobenzyl)oxy]pyridin-2-yl}piperidin-1-yl)methyl]-1-[(3-methyl-1H-pyrazol-5-yl)methyl]-1H-benzimidazole-6-carboxylic acid | 589 | 2.428 | PF-CD05 |
| 11A-59 | 2-[(4-{6-[(4-chloro-2-fluorobenzyl)oxy]pyridin-2-yl}piperidin-1-yl)methyl]-1-[(3-methyl-1H-1,2,4-triazol-5-yl)methyl]-1H-benzimidazole-6-carboxylic acid | 590 | 2.347 | PF-CD05 |
| 11A-60 | 2-[(4-{6-[(4-chloro-2-fluorobenzyl)oxy]pyridin-2-yl}piperidin-1-yl)methyl]-1-[1-(2-methyl-2H-1,2,3-triazol-4-yl)ethyl]-1H-benzimidazole-6-carboxylic acid | 604 | 2.471 | PF-CD05 |
| 11A-61 | 2-[(4-{6-[(4-chloro-2-fluorobenzyl)oxy]pyridin-2-yl}piperidin-1-yl)methyl]-1-[(6-methylpyridin-3-yl)methyl]-1H-benzimidazole-6-carboxylic acid | 600 | 2.583 | PF-AB10 |
| 11A-62 | 2-[(4-{6-[(4-chloro-2-fluorobenzyl)oxy]pyridin-2-yl}piperidin-1-yl)methyl]-1-{[3-(methoxymethyl)-1H-pyrazol-5-yl]methyl}-1H-benzimidazole-6-carboxylic acid | 619 | 2.413 | PF-CD05 |
| 11A-63 | 2-[(4-{6-[(4-chloro-2-fluorobenzyl)oxy]pyridin-2-yl}piperidin-1-yl)methyl]-1-[(4-methylmorpholin-2-yl)methyl]-1H-benzimidazole-6-carboxylic acid | 608 | 2.745 | PF-AB01 |
| 11A-64 | 2-[(4-{6-[(4-chloro-2-fluorobenzyl)oxy]pyridin-2-yl}piperidin-1-yl)methyl]-1-[(5-cyclopropyl-1H-1,2,4-triazol-3-yl)methyl]-1H-benzimidazole-6-carboxylic acid | 616 | 2.401 | PF-CD05 |
| 11A-65 | 2-[(4-{6-[(4-chloro-2-fluorobenzyl)oxy]pyridin-2-yl}piperidin-1-yl)methyl]-1-[2-(tetrahydro-2H-pyran-4-yl)ethyl]-1H-benzimidazole-6-carboxylic acid | 607 | 2.912 | PF-AB10 |
| 11A-66 | 2-[(4-{6-[(4-chloro-2-fluorobenzyl)oxy]pyridin-2-yl}piperidin-1-yl)methyl]-1-[2-(3-methyl-1H-1,2,4-triazol-5-yl)ethyl]-1H-benzimidazole-6-carboxylic acid | 604 | 2.305 | PF-CD05 |
| 11A-67 | 2-[(4-{6-[(4-chloro-2-fluorobenzyl)oxy]pyridin-2-yl}piperidin-1-yl)methyl]-1-[1-(5-methyl-1H-1,2,4-triazol-3-yl)ethyl]-1H-benzimidazole-6-carboxylic acid | 604 | 2.379 | PF-CD05 |
| 11A-68 | 2-[(4-{6-[(4-chloro-2-fluorobenzyl)oxy]pyridin-2-yl}piperidin-1-yl)methyl]-1-[(2R)-tetrahydrofuran-2-ylmethyl]-1H-benzimidazole-6-carboxylic acid | 579 | 2.924 | PF-AB10 |
| 11A-69 | 2-[(4-{6-[(4-chloro-2-fluorobenzyl)oxy]pyridin-2-yl}piperidin-1-yl)methyl]-1-(1,2-oxazol-3-ylmethyl)-1H-benzimidazole-6-carboxylic acid | 576 | 2.465 | PF-CD05 |
| 11A-70 | 2-[(4-{6-[(4-chloro-2-fluorobenzyl)oxy]pyridin-2-yl}piperidin-1-yl)methyl]-1-[(1-methyl-1H-imidazol-5-yl)methyl]-1H-benzimidazole-6-carboxylic acid | 589 | 2.378 | PF-CD05 |
| 11A-71 | 2-[(4-{6-[(4-chloro-2-fluorobenzyl)oxy]pyridin-2-yl}piperidin-1-yl)methyl]-1-[(4-methyl-4H-1,2,4-triazol-3-yl)methyl]-1H-benzimidazole-6-carboxylic acid | 590 | 2.73 | PF-AB01 |

TABLE 6-continued

| Ex. # | Name | *MW found | Ret. time (min) | **Method |
|---|---|---|---|---|
| 11A-72 | 2-[(4-{6-[(4-chloro-2-fluorobenzyl)oxy]pyridin-2-yl}piperidin-1-yl)methyl]-1-[(1-methyl-1H-1,2,3-triazol-5-yl)methyl]-1H-benzimidazole-6-carboxylic acid | 590 | 2.381 | PF-CD05 |
| 11A-73 | 2-[(4-{6-[(4-chloro-2-fluorobenzyl)oxy]pyridin-2-yl}piperidin-1-yl)methyl]-1-(3,3,3-trifluoropropyl)-1H-benzimidazole-6-carboxylic acid | 591 | 2.811 | PF-AB10 |
| 11A-74 | 2-[(4-{6-[(4-chloro-2-fluorobenzyl)oxy]pyridin-2-yl}piperidin-1-yl)methyl]-1-{[1-(methoxymethyl)cyclobutyl]methyl}-1H-benzimidazole-6-carboxylic acid | 607 | 2.757 | PF-AB10 |

*MW found: MS(ES+): as (M + H)
**HPLC purification method PF-AB01: Mobile Phase A: 0.0375% TFA in H₂O. Mobile Phase B: 0.01875% TFA in MeCN. Initial conditions: B: 1%, A: 99%. Gradient: B: 1%, A: 99% to B: 5%, A: 95% from t = 0.00 min to 0.60 min, then to B: 100% from t = 0.60 min to 4.00 min, then to B: 1%, A: 99% from t = 4.00 min to 4.30 min, hold until t = 4.70 min. Flow rate = 0.8 mL/min, 2 µL injection volume
**HPLC purification method PF-AB10: Mobile Phase A: 0.0375% TFA in H₂O. Mobile Phase B: 0.01875% TFA in MeCN. Initial conditions: B: 10%, A: 90%. Gradient: B: 10%, A: 90% from t = 0.00 min to 0.50 min, then to B: 100% from t = 0.60 min to 4.00 min, then to B: 10%, A: 90% from t = 4.00 min to 4.30 min, hold until t = 4.70 min. Flow rate = 0.8 mL/min, 2 µL injection volume
**HPLC purification method PF-CD05: Mobile Phase A: 0.05% NH₄OH in H₂O Mobile Phase B: 100% MeCN. Initial conditions: B: 5%, A: 95%. Gradient: B: 5%, A: 95% to B: 100%, from t = 0.50 min to 3.40 min, hold until t = 4.20 min then to B: 5%, A: 95% from t = 4.21 min to 4.70 min, hold until t = 4.70 min. Flow rate = 0.8 mL/min, 2 µL injection volume

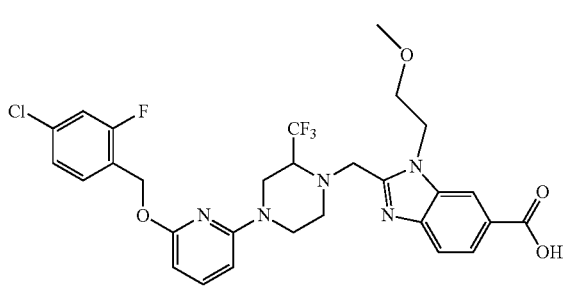 [SMILES: COCCn1c(CN2CCN(c3cccc(OCc4ccc(Cl)cc4F)n3)CC2C(F)(F)F)nc2ccc(C(=O)O)cc21]

Example 12A-01

2-((4-(6-((4-Chloro-2-fluorobenzyl)oxy)pyridin-2-yl)-2-(trifluoromethyl)piperazin-1-yl)methyl)-1-(2-methoxyethyl)-1H-benzo[d]imidazole-6-carboxylic acid, enantiomer 1

Example 12A-02

2-((4-(6-((4-Chloro-2-fluorobenzyl)oxy)pyridin-2-yl)-2-(trifluoromethyl)piperazin-1-yl)methyl)-1-(2-methoxyethyl)-1H-benzo[d]imidazole-6-carboxylic acid, enantiomer 2

Step 1

To a solution of 4-chloro-2-fluorobenzyl alcohol (15.0 g, 93.4 mmol) in DMF (250 mL) was added NaH (4.48 g, 112 mmol, 60% susp.) at 0° C. After stirring at 15° C. for 40 min, 2,6-dichloropyridine (16.6 g, 112 mmol) was added. The resulting mixture was stirred at 15° C. for 3 h. The mixture was poured into water (1 L) and extracted with EtOAc (2×200 mL). The combined organic layers were washed with sat. NH₄Cl (500 mL), brine (500 mL), dried over Na₂SO₄, filtered and concentrated under reduced pressure. The crude product was purified by flash chromatography (PE) to give 2-chloro-6-((4-chloro-2-fluorobenzyl)oxy)pyridine (19.2 g, 75%) as a solid. ¹H NMR (CDCl₃) δ 7.55 (t, 1H), 7.47 (t, 1H), 7.15 (t, 2H), 6.94 (d, 1H), 6.71 (d, 1H), 5.40 (s, 2H).

Step 2

To a solution of tert-butyl 3-(trifluoromethyl)piperazine-1-carboxylate (100 mg, 0.393 mmol) in MeCN (2 mL) was added Intermediate 19 (111 mg, 0.393 mmol), tetrabutylammonium iodide (145 mg, 0.39 mmol) and N,N-diisopropylethyl amine (152 mg, 1.18 mmol). The reaction mixture was stirred at 150° C. for 1 h under microwave conditions. The reaction mixture was concentrated under reduced pressure and purified by prep-TLC (33% EtOAc/PE) to deliver methyl 2-((4-(tert-butoxycarbonyl)-2-(trifluoromethyl)piperazin-1-yl)methyl)-1-(2-methoxyethyl)-1H-benzo[d]imidazole-6-carboxylate (100 mg, 51%) as yellow oil. MS(ES+): 501.1 (M+H).

Step 3

To a solution of methyl 2-((4-(tert-butoxycarbonyl)-2-(trifluoromethyl)piperazin-1-yl)methyl)-1-(2-methoxyethyl)-1H-benzo[d]imidazole-6-carboxylate (100 mg, 0.2 mmol) in EtOAc (5 mL) was added HCl-EtOAc (5 mL). The reaction mixture was stirred at RT for 2 h. The reaction mixture was concentrated under reduced pressure. The crude product was dissolved in DCM (10 mL), washed with sat. aq K₂CO₃, dried over Na₂SO₄, filtered and concentrated under reduced pressure to give methyl 1-(2-methoxyethyl)-2-((2-(trifluoromethyl)piperazin-1-yl)methyl)-1H-benzo[d]imidazole-6-carboxylate (42 mg, 53%) as yellow oil. MS(ES+): 401.0 (M+H).

Step 4

To a solution of methyl 1-(2-methoxyethyl)-2-((2-(trifluoromethyl)piperazin-1-yl)methyl)-1H-benzo[d]imidazole-6-carboxylate (90 mg, 0.22 mmol) in PhCH₃ (2 mL) was added 2-chloro-6-((4-chloro-2-fluorobenzyl)oxy)pyridine (61.2 mg, 0.225 mmol), Pd₂(dba)₃ (20.6 mg, 0.1 mmol), BINAP (28 mg, 0.045 mmol) and Cs₂CO₃ (220 mg, 0.674 mmol). The reaction mixture was stirred at 100° C. for 16 h.

The reaction mixture was concentrated under reduced pressure and the crude product purified by preparative TLC (33% EtOAc/PE) to give the racemic product as a yellow oil. The racematic mixture was separated by preparative chiral SFC (Column: Whelk-01 250×30 mm×10 μm; Mobile phase: 45% isopropanol (1% NH₄OH)/CO₂ Flow rate: 50 mL/min) to deliver the separated enantiomers of methyl 2-((4-(6-((4-chloro-2-fluorobenzyl)oxy)pyridin-2-yl)-2-(trifluoromethyl)piperazin-1-yl)methyl)-1-(2-methoxyethyl)-1H-benzo[d]imidazole-6-carboxylate: Enantiomer 1: (28 mg, 20%); retention time (15.98 min); Enantiomer 2: (33 mg, 23%); retention time (20.92 min).

Step 5

To a solution of Step 4 Enantiomer 1 (28 mg, 0.044 mmol) in MeOH (5 mL) was added 2 M NaOH (1 mL). The reaction mixture was stirred at 50° C. for 2 h. The reaction mixture was cooled to 0° C. and acidified with 1 M HCl to pH ~4. The reaction mixture was extracted by EtOAc (3×10 mL), dried over Na₂SO₄, concentrated under reduced pressure. The crude product was purified by preparative HPLC (Column: Waters Xbridge Prep OBD C18 150×30 mm×5 μm; Mobile phase: from 55% MeOH in water [0.1% TFA] to 75% MeOH in water [0.1% TFA]; 10 min gradient; Wavelength: 220 nm; Flow rate: 25 ml/min) to deliver Example 12A-01 (12.2 mg, 37%) as a solid. Due to the purification solvent, the compound was likely isolated as the trifluoroacetate salt. Analytical LC-MS data: Xtimate C18 5×30 mm, 3 μm; Mobile phase: 1% MeCN in water (0.1% TFA) to 5% MeCN in water (0.1% TFA) in 1 min; then from 5% MeCN in water (0.1% TFA) to 100% MeCN (0.1% TFA) in 5 min; hold at 100% MeCN (0.1% TFA) for 2 min; back to 1.0% MeCN in water (0.1% TFA) at 8.01 min, and hold 2 min. Flow rate: 1.2 ml/min; Retention time 4.465 min, MS(ES+): 622.2 (M+H).

Example 12A-02 was prepared in a similar manner from Step 4, Enantiomer 2 (33 mg, 0.052 mmol) and purified using the same preparative HPLC method to deliver Example 12A-02 (9.8 mg, 28%) as a solid. Due to the purification solvent, the compound was likely isolated as the trifluoroacetate salt. Analytical LC-MS data: Retention time 4.469 min, MS(ES+): 622.2 (M+H).

The compounds listed in Table 7 below were prepared using procedures analogous to those described above for the synthesis of Examples 12A-01 and 12A-02 using the appropriate starting materials which are available commercially, prepared using preparations well-known to those skilled in the art, or prepared in a manner analogous to routes described above for other intermediates. The compounds were purified using methods well known to those skilled in the art and may include silica gel chromatography, HPLC, or crystallization from the reaction mixture. The final compounds may have been isolated as neutrals or acid or base salts.

TABLE 7

| Ex. # | Name | NMR data/LC-MS data |
|---|---|---|
| 12A-03 | 2-[(7-{6-[(4-chloro-2-fluorobenzyl)oxy]pyridin-2-yl}-4,7-diazaspiro[2.5]oct-4-yl)methyl]-1-(2-methoxyethyl)-1H-benzimidazole-6-carboxylic acid | ¹H NMR (400 MHz, CD₃CN) δ 8.48 (s, 1H), 8.20 (dd, 1H), 7.89 (d, 1H), 7.49 (m, 2H), 7.24 (m, 2H), 6.29 (d, 1H), 6.15 (d, 1H), 5.37 (s, 2H), 4.60 (m, 4H), 3.77 (m, 2H), 3.71-3.42 (m, 4H), 3.28 (s, 3H), 3.12 (t, 2H), 0.87 (d, 2H), 0.67 (t, 2H). MS(ES+): 580.0 (M + H). |
| 12A-04 | 2-{[(2S)-4-{6-[(4-chloro-2-fluorobenzyl)oxy]pyridin-2-yl}-2-cyclopropylpiperazin-1-yl]methyl}-1-(2-methoxyethyl)-1H-benzimidazole-6-carboxylic acid | ¹H NMR (400 MHz, CD₃OD) δ 8.43 (d, 1H), 8.13 (dd, 1H), 7.82 (d, 1H), 7.53 (t, 1H), 7.45 (t, 1H), 7.15-7.25 (m, 2H), 6.41 (d, 1H), 6.23 (d, 1H), 5.38 (d, 2H), 5.29 (d, 1H), 4.64-4.80 (m, 2H), 4.53 (d, 1H), 4.32 (d, 1H), 4.11 (d, 1H), 3.79 (t, 2H), 3.54 (d, 1H), 3.36-3.49 (m, 2H), 3.08 (t, 1H), 2.61 (br s, 1H), 0.98-1.10 (m, 1H), 0.73-0.89 (m, 2H), 0.57-0.72 (m, 1H), 0.37-0.50 (m, 1H). MS(ES+): 594.0 (M + H). |
| 12A-05 | 2-{[(2S)-4-{6-[(4-chloro-2-fluorobenzyl)oxy]pyridin-2-yl}-2-(propan-2-yl)piperazin-1-yl]methyl}-1-(2-methoxyethyl)-1H-benzimidazole-6-carboxylic acid | ¹H NMR (400 MHz, CD₃OD) δ 8.44 (d, 1H), 8.15 (dd, 1H), 7.84 (d, 1H), 7.55 (m, 1H), 7.45 (m, 1H), 7.27-7.15 (m, 2H), 6.40 (d, 1H), 6.24 (d, 1H), 5.46-5.35 (m, 2H), 4.99 (m, 1H), 4.71 (m, 2H), 4.51 (m, 1H), 4.32 (m, 1H), 4.06 (m, 1H), 3.80 (m, 2H), 3.48-3.37 (m, 3H), 3.31 (s, 3H), 3.17 (d, 2H), 2.41-2.28 (m, 1H), 1.16 (d, 3H), 1.09 (d, 3H). MS(ES+): 596.3 (M + H). |
| 12A-06 | 2-[(4-{6-[(4-chloro-2-fluorobenzyl)oxy]pyridin-2-yl}-2,2-dimethylpiperazin-1-yl)methyl]-1-(2-methoxyethyl)-1H-benzimidazole-6-carboxylic acid | ¹H NMR (400 MHz, CD₃OD) δ 8.46 (d, 1H), 8.17 (dd, 1H), 7.86 (d, 1H), 7.49 (m, 2H), 7.28-7.18 (m, 2H), 6.40 (d, 1H), 6.20 (d, 1H), 5.38 (s, 2H), 4.72 (m, 2H), 4.62 (m, 2H), 3.87-3.62 (m, 6H), 1.41 (s, 6H). MS(ES+): 582.3 (M + H). |
| 12A-07 | 2-{[(2S)-4-{6-[(4-chloro-2-fluorobenzyl)oxy]pyridin-2-yl}-2-ethylpiperazin-1-yl]methyl}-1-(2-methoxyethyl)-1H-benzimidazole-6-carboxylic acid | ¹H NMR (400 MHz, CD₃OD) δ 8.40 (s, 1H), 8.11 (dd, 1H), 7.81 (d, 1H), 7.53 (t, 1H), 7.44 (t, 1H), 7.14-7.25 (m, 2H), 6.41 (d, 1H), 6.23 (d, 1H), 5.38 (s, 2H), 4.56-4.74 (m, 3H), 4.07 (d, 1H), 3.91 (d, 1H), 3.78 (t, 2H), 3.49-3.73 (m, 3H), 3.37 (brs, 1H), 1.93 (br s, 1H), 1.71-1.84 (m, 1H), 1.08 (t, 3H). MS(ES+): 582.1 (M + H). |
| 12A-08 | 2-{[(2S)-4-{6-[(4-cyanobenzyl)oxy]pyridin-2-yl}-2-methylpiperazin-1-yl]methyl}-1-(2-methoxyethyl)-1H-benzimidazole-6-carboxylic acid | ¹H NMR (400 MHz, CD₃OD) δ 8.42 (d, 1H), 8.12 (dd, 1H), 7.82 (d, 1H), 7.71 (d, 2H), 7.62-7.51 (m, 3H), 6.42 (d, 1H), 6.29 (d, 1H), 5.44 (s, 2H), 4.68 (q, 2H), 4.53 (m, 1H), 4.07 (m, 2H), 3.79 (m, 2H), 3.30 (s, 3H), 3.18 (m, 1H), 1.40 (d, 3H). MS(ES+): 541.0 (M + H). |

TABLE 7-continued

| Ex. # | Name | NMR data/LC-MS data |
|---|---|---|
| 12A-09 | 2-{[(2R)-4-{6-[(4-chloro-2-fluorobenzyl)oxy]pyridin-2-yl}-2-(hydroxymethyl)piperazin-l-yl]methyl}-1-(2-methoxyethyl)-1H-benzimidazole-6-carboxylic acid | $^1$H NMR (CD$_3$OD) δ 8.41 (s, 1H), 8.10 (d, 1H), 7.80 (d, 1H), 7.51 (t, 1H), 7.45 (t, 1H), 7.13-7.25 (m, 2H), 6.39 (d, 1H), 6.20 (d, 1H), 5.36 (s, 2H), 5.02 (d, 2H), 4.66-4.81 (m, 2H), 4.49 (d, 1H), 4.20 (d, 1H), 4.10 (d, 1H), 4.00 (d, 1H), 3.69-3.92 (m, 4H), 3.38 (br s, 2H), 3.09-3.26 (m, 2H), 1.32 (t, 2H). MS(ES+): 584.2 (M + H). |
| 12A-10 | 2-{[(2S)-4-{6-[(4-chloro-2-fluorobenzyl)oxy]pyridin-2-yl}-2-methylpiperazin-1-yl]methyl}-1-(2-methoxyethyl)-1H-benzimidazole-6-carboxylic acid | Column: AD-H 4.6 × 100 mm, 5 μm; Mobile phase A: CO$_2$; Mobile phase B: Methanol with 0.2% NH$_4$OH; 60:40 A/B Hold for 5 min, Column Temp: 40° C., Back Pressure: 120 Bar, Flow: 1.5 mL/min. Retention time: 3.035. MS(ES+): 568.3 (M + H). |
| 12A-11 | 2-{[(2R)-4-{6-[(4-chloro-2-fluorobenzyl)oxy]pyridin-2-yl}-2-methylpiperazin-1-yl]methyl}-1-(2-methoxyethyl)-1H-benzimidazole-6-carboxylic acid | Column: AD-H 4.6 × 100 mm, 5 μm; Mobile phase A: CO$_2$; Mobile phase B: Methanol with 0.2% NH$_4$OH; 60:40 A/B Hold for 5 min, Column Temp: 40° C., Back Pressure: 120 Bar, Flow: 1.5 mL/min. Retention time: 3.035. MS(ES+): 568.3 (M + H). |

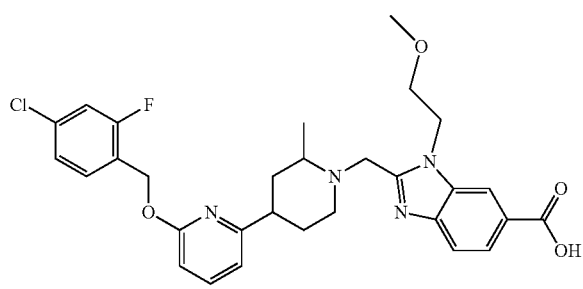 [SMILES: COCCn1c(CN2CCC(c3cccc(OCc4ccc(Cl)cc4F)n3)CC2C)nc2ccc(C(=O)O)cc21]

Examples 13A-01 and 13A-02 trans 2-{[4-{6-[(4-Chloro-2-fluorobenzyl)oxy]pyridin-2-yl}-2-methylpiperidin-1-yl]methyl}-1-(2-methoxyethyl)-1H-benzimidazole-6-carboxylic acid, enantiomers 1 and 2

Examples 13A-03 and 13A-04 cis 2-{[4-{6-[(4-Chloro-2-fluorobenzyl)oxy]pyridin-2-yl}-2-methylpiperidin-1-yl]methyl}-1-(2-methoxyethyl)-1H-benzimidazole-6-carboxylic acid, enantiomers 1 and 2

Step 1

A mixture of 2-[(4-chloro-2-fluorobenzyl)oxy]-6-(2-methylpiperidin-4-yl)pyridine (350 mg, 0.86 mmol) [prepared as a mixture of stereoisomers via a route similar to that used for Intermediate 3], Intermediate 19 (220 mg, 0.78 mmol) and K$_2$CO$_3$ (540 mg, 3.9 mmol) in MeCN (6 mL) was stirred at 60° C. for 16 h. The mixture was filtered and the filtrate concentrated under reduced pressure. The residue was purified using column chromatography eluting with EtOAc/PE (1:1) to obtain methyl 2-((4-(6-((4-chloro-2-fluorobenzyl)oxy)pyridin-2-yl)-2-methylpiperidin-1-yl)methyl)-1-(2-methoxyethyl)-1H-benzo[d]imidazole-6-carboxylate (250 mg, 55%, yellow oil) as a mixture of four stereoisomers. The mixture of stereoisomers was separated by SFC on a chiral column using condition 1 below to afford clean peaks 1, 3 and 4, along with peak 2 that was not pure. Peak 2 was repurified by SFC using condition 2. The retention times indicated refer to SFC condition 1. The relative stereochemistry was assigned by 2D NMR. The absolute configuration of each isomer was not assigned.

Peak 1 (retention time 5.6 min): trans methyl 2-((4-(6-((4-chloro-2-fluorobenzyl)oxy)pyridin-2-yl)-2-methylpiperidin-1-yl)methyl)-1-(2-methoxyethyl)-1H-benzo[d]imidazole-6-carboxylate enantiomer 1.

Peak 2 (retention time 5.8 min): trans methyl 2-((4-(6-((4-chloro-2-fluorobenzyl)oxy)pyridin-2-yl)-2-methylpiperidin-1-yl)methyl)-1-(2-methoxyethyl)-1H-benzo[d]imidazole-6-carboxylate enantiomer 2.

Peak 3 (retention time 6.4 min): cis methyl 2-((4-(6-((4-chloro-2-fluorobenzyl)oxy)pyridin-2-yl)-2-methylpiperidin-1-yl)methyl)-1-(2-methoxyethyl)-1H-benzo[d]imidazole-6-carboxylate enantiomer 1.

Peak 4 (retention time 6.9 min): cis methyl 2-((4-(6-((4-chloro-2-fluorobenzyl)oxy)pyridin-2-yl)-2-methylpiperidin-1-yl)methyl)-1-(2-methoxyethyl)-1H-benzo[d]imidazole-6-carboxylate enantiomer 2.

SFC condition 1: Column: AD (250 mm×30 mm, 5 μm); Mobile phase: CO$_2$ w/35% EtOH (0.1% NH$_4$OH); Flow rate: 70 ml/min; Wavelength: 220 nm.

SFC condition 2: Column: AD (250 mm×30 mm, 5 μm); Mobile phase: CO$_2$ w/40% iPrOH (0.1% NH$_4$OH); Flow rate: 60 ml/min; Wavelength: 220 nm

Step 2

The methyl esters from Step 1 were converted to the free acids by treatment with NaOH in MeOH as described previously to afford the four title examples.

Example 13A-01 (from trans methyl 2-((4-(6-((4-chloro-2-fluorobenzyl)oxy)pyridin-2-yl)-2-methylpiperidin-1-yl)methyl)-1-(2-methoxyethyl)-1H-benzo[d]imidazole-6-carboxylate enantiomer 1): $^1$H NMR (400 MHz, CD$_3$OD) δ: 8.32 (d, 1H), 8.01 (dd, 1H), 7.77 (d, 1H), 7.68 (dd, 1H), 7.49 (t, 1H), 7.17-7.31 (m, 2H), 6.97 (d, 1H), 6.76 (d, 1H), 5.37-5.50 (m, 2H), 4.75-4.86 (m, 2H), 4.62 (t, 2H), 4.19 (br s, 1H), 3.76 (t, 2H), 3.66 (d, 1H), 2.49 (ddd, 1H), 2.30 (m, 1H), 2.16-2.24 (m, 1H), 2.10 (dt, 1H), 1.62 (d, 2H); LC-MS (ES+): 567.1 (M+H).

Example 13A-02 (from trans methyl 2-((4-(6-((4-chloro-2-fluorobenzyl)oxy)pyridin-2-yl)-2-methylpiperidin-1-yl)methyl)-1-(2-methoxyethyl)-1H-benzo[d]imidazole-6-carboxylate enantiomer 2): $^1$H NMR (400 MHz, CD$_3$OD) δ 8.31 (d, 1H), 8.00 (dd, 1H), 7.76 (d, 1H), 7.67 (dd, 1H), 7.48 (t, 1H), 7.22 (m, 2H), 6.96 (d, 1H), 6.75 (d, 1H), 5.47-5.38 (m, 2H), 4.80 (m, 1H), 4.61 (m, 2H), 4.18 (m, 1H), 3.80-3.59

(m, 3H), 2.48 (m, 1H), 2.29 (m, 1H), 2.19 (m, 1H), 2.09 (m, 1H), 1.61 (d, 3H); LC-MS(ES+): 567.1 (M+H).

Example 13A-03 (from cis methyl 2-((4-(6-((4-chloro-2-fluorobenzyl)oxy)pyridin-2-yl)-2-methylpiperidin-1-yl)methyl)-1-(2-methoxyethyl)-1H-benzo[d]imidazole-6-carboxylate enantiomer 1): $^1$H NMR (400 MHz, CD$_3$OD) δ 8.34 (d, 1H), 8.05 (dd, 1H), 7.81 (d, 1H), 7.73-7.64 (m, 1H), 7.53 (m, 1H), 7.26 (m, 2H), 6.94 (d, 1H), 6.76 (d, 1H), 5.48 (s, 2H), 5.12 (d, 1H), 4.77 (d, 1H), 4.64 (m, 2H), 4.01-3.82 (m, 2H), 3.78 (m, 2H), 3.52-3.42 (m, 1H), 3.15 (m, 1H), 2.35-2.05 (m, 4H), 1.57 (d, 3H); LC-MS(ES+): 567.1 (M+H).

Example 13A-04 (from cis methyl 2-((4-(6-((4-chloro-2-fluorobenzyl)oxy)pyridin-2-yl)-2-methylpiperidin-1-yl)methyl)-1-(2-methoxyethyl)-1H-benzo[d]imidazole-6-carboxylate enantiomer 2): $^1$H NMR (400 MHz, CD$_3$OD) δ 8.34 (d, 1H), 8.05 (dd, 1H), 7.81 (d, 1H), 7.70-7.64 (m, 1H), 7.53 (t, 1H), 7.26 (m, 2H), 6.94 (d, 1H), 6.76 (d, 1H), 5.48 (s, 2H), 5.12 (d, 1H), 4.77 (d, 1H), 4.64 (t, 2H), 3.99-3.83 (m, 2H), 3.78 (t, 2H), 3.52-3.42 (m, 1H), 3.19-3.09 (m, 1H), 2.31-2.05 (m, 4H), 1.57 (d, 3H); LC-MS(ES+): 567.1 (M+H).

The methyl esters of the compounds listed in Table 8 below were prepared using procedures analogous to those described above for the synthesis of Examples 10A-01 using racemic 2-aminomethyltetrahydrofuran or 3-aminomethyltetrahydrofuran and other appropriate starting materials which are available commercially, prepared using preparations well-known to those skilled in the art, or prepared in a manner analogous to routes described above for other intermediates. The THF stereoisomers were separated by SFC to give the ester intermediates as single stereoisomers. The methyl esters were then hydrolyzed as described for example 10A-01 to provide the compounds listed in Table 8. Retention times and chromatography methods for the methyl ester intermediates are shown in the table. The stereochemistry of the THF stereocenter in each compound was not assigned.

TABLE 8

| Ex. # | Name | *Method | *Ret. time (min) | NMR data/LC-MS data |
|---|---|---|---|---|
| 14A-01 | 2-[(4-{6-[(4-cyanobenzyl)oxy]pyridin-2-yl}piperidin-1-yl)methyl]-1-(tetrahydrofuran-2-ylmethyl)-1H-benzimidazole-6-carboxylic acid, enantiomer 1 | A | 0.65 | $^1$H NMR (400 MHz, CD$_3$OD) δ 8.36 (d, 1H), 8.05 (dd, 1H), 7.82 (d, 1H), 7.77-7.73 (m, 2H), 7.69 (dd, 1H), 7.66-7.60 (m, 2H), 6.95 (d, 1H), 6.80 (d, 1H), 5.53 (s, 2H), 4.87-4.78 (m, 2H), 4.70 (dd, 1H), 4.44 (dd, 1H), 4.24 (m, 1H), 3.93 (m, 2H), 3.76 (m, 1H), 3.43 (m, 3H), 3.12-3.02 (m, 1H), 2.30-2.13 (m, 5H), 2.02-1.86 (m, 2H), 1.69 (m,1H). MS(ES+): 552.1 (M + H). |
| 14A-02 | 2-[(4-{6-[(4-cyanobenzyl)oxy]pyridin-2-yl}piperidin-1-yl)methyl]-1-(tetrahydrofuran-2-ylmethyl)-1H-benzimidazole-6-carboxylic acid, enantiomer 2 | A | 1.4 | $^1$H NMR (400 MHz, CD$_3$OD) δ 8.34 (d, 1H), 8.03 (dd, 1H), 7.80 (d, 1H), 7.73 (d, 2H), 7.64-7.70 (m, 1H), 7.61 (d, 2H), 6.93 (d, 1H), 6.78 (d, 1H), 5.51 (s, 2H), 4.82 (d, 2H), 4.68 (dd, 1H), 4.42 (dd, 1H), 4.17-4.27 (m, 1H), 3.83-3.97 (m, 3H), 3.70-3.81 (m, 1H), 3.35-3.45 (m, 2H), 2.98-3.11 (m, 1H), 2.13-2.28 (m, 5H), 1.87-2.00 (m, 2H), 1.61-1.74 (m, 1H). MS(ES+): 552.1 (M + H). |
| 14A-03 | 2-[(4-{6-[(4-cyanobenzyl)oxy]-5-fluoropyridin-2-yl}piperidin-1-yl)methyl]-1-(tetrahydrofuran-2-ylmethyl)-1H-benzimidazole-6-carboxylic acid, enantiomer 1 | B | 8.1 | $^1$H NMR (400 MHz, CD$_3$OD) δ 8.36 (d, 1H), 8.05 (dd, 1H), 7.82 (d, 1H), 7.80-7.73 (m, 2H), 7.65 (d, 2H), 7.51 (dd, 1H), 6.95 (dd, 1H), 5.60 (s, 2H), 4.86-4.78 (m, 2H), 4.70 (dd, 1H), 4.44 (dd, 1H), 4.31-4.17 (m, 1H), 3.93 (m, 3H), 3.76 (m, 1H), 3.41 (s, 2H), 3.06 (d, 1H), 2.32-2.09 (m, 5H), 1.94 (m, 2H), 1.69 (m, 1H). MS(ES+): 570.2 (M + H). |
| 14A-04 | 2-[(4-{6-[(4-cyanobenzyl)oxy]-5-fluoropyridin-2-yl}piperidin-1-yl)methyl]-1-(tetrahydrofuran-2-ylmethyl)-1H-benzimidazole-6-carboxylic acid, enantiomer 2 | B | 11.4 | $^1$H NMR (400 MHz, CD$_3$OD) δ 8.36 (d, 1H), 8.05 (dd, 1H), 7.82 (d, 1H), 7.79-7.73 (m, 2H), 7.65 (d, 2H), 7.51 (dd, 1H), 6.95 (dd, 1H), 5.60 (s, 2H), 4.86-4.77 (m, 2H), 4.70 (dd, 1H), 4.44 (dd, 1H), 4.24 (m, 1H), 3.93 (m, 2H), 3.76 (m, 1H), 3.40 (m, 3H), 3.05 (m, 1H), 2.29-2.12 (m, 5H), 1.94 (m, 2H), 1.69 (m, 1H). MS(ES+): 570.2 (M + H). |
| 14A-05 | 2-[(4-{6-[(4-cyanobenzyl)oxy]-5-fluoropyridin-2-yl}piperidin-1-yl)methyl]-1-(tetrahydrofuran-3-ylmethyl)-1H-benzimidazole-6-carboxylic acid, enantiomer 1 | C | 25.0 | $^1$H NMR (400 MHz, CD$_3$OD) δ 8.35 (d, 1H), 8.04 (dd, 1H), 7.81 (d, 1H), 7.78-7.72 (m, 2H), 7.65 (d, 2H), 7.49 (dd, 1H), 6.94 (dd, 1H), 5.60 (s, 2H), 4.82 (s, 2H), 4.43-4.29 (m, 2H), 4.05 (m, 1H), 3.94 (m, 2H), 3.79 (m, 1H), 3.67 (m, 1H), 3.53 (m, 1H), 3.38 (m, 2H), 3.09-2.83 (m, 2H), 2.19 (m, 4H), 2.09 (m, 1H), 1.78 (m, 1H). MS(ES+): 570.1 (M + H). |

TABLE 8-continued

| Ex. # | Name | *Method | *Ret. time (min) | NMR data/LC-MS data |
|---|---|---|---|---|
| 14A-06 | 2-[(4-{6-[(4-cyanobenzyl)oxy]-5-fluoropyridin-2-yl}piperidin-1-yl)methyl]-1-(tetrahydrofuran-3-ylmethyl)-1H-benzimidazole-6-carboxylic acid, enantiomer 2 | C | 29.2 | $^1$H NMR (400 MHz, CD$_3$OD) δ 8.37 (s, 1H), 8.05 (dd, 1H), 7.82 (d, 1H), 7.77 (d, 2H), 7.67 (d, 2H), 7.50 (dd, 1H), 6.95 (dd, 1H), 5.61 (s, 2H), 4.83 (s, 2H), 4.46-4.28 (m, 2H), 4.07 (m, 1H), 4.02-3.89 (m, 2H), 3.81 (m, 1H), 3.69 (dd, 1H), 3.55 (m, 1H), 3.39 (m, 2H), 3.11-2.98 (m, 1H), 2.92 (s, 1H), 2.30-2.06 (m, 5H), 1.80 (m, 1H). MS(ES+): 570.2 (M + H). |
| 14A-07 | 2-{[(2S)-4-{6-[(4-cyanobenzyl)oxy]pyridin-2-yl}-2-methylpiperazin-1-yl]methyl}-1-(tetrahydrofuran-2-ylmethyl)-1H-benzimidazole-6-carboxylic acid, diastereomer 1 | D | 8.7 | $^1$H NMR (400 MHz, CD$_3$OD) δ 8.40 (d, 1H), 8.09 (dd, 1H), 7.80 (d, 1H), 7.72-7.66 (m, 2H), 7.55 (dd, 3H), 6.40 (d, 1H), 6.27 (d, 1H), 5.42 (s, 2H), 4.72 (dd, 1H), 4.53 (d, 1H), 4.43 (dd, 1H), 4.25 (m, 1H), 4.04 (m, 2H), 3.89 (m, 1H), 3.50 (m, 3H), 3.16 (m, 1H), 2.23 (m, 1H), 2.01-1.89 (m, 2H), 1.69 (m, 1H), 1.39 (d, 3H). MS(ES+): 567.1 (M + H). |
| 14A-08 | 2-{[(2S)-4-{6-[(4-cyanobenzyl)oxy]pyridin-2-yl}-2-methylpiperazin-1-yl]methyl}-1-(tetrahydrofuran-2-ylmethyl)-1H-benzimidazole-6-carboxylic acid, diastereomer 2 | D | 14.8 | $^1$H NMR (400 MHz, CD$_3$OD) δ 8.40 (s, 1H), 8.06-8.12 (m, 1H), 7.79 (d, 1H), 7.68 (d, 2H), 7.57 (d, 2H), 7.53 (t, 1H), 6.39 (d, 1H), 6.26 (d, 1H), 5.42 (s, 2H), 4.67 (dd, 1H), 4.43-4.55 (m, 2H), 4.21-4.32 (m, 1H), 3.94-4.12 (m, 2H), 3.84-3.93 (m, 1H), 3.73 (q, 1H), 3.43 (br s, 3H), 3.12 (br s, 1H), 2.22 (dq, 1H), 1.88-2.00 (m, 2H), 1.69 (dq, 1H), 1.39 (d, 3H). MS(ES+): 567.1 (M + H). |
| 14A-09 | 2-[(4-{6-[(4-cyano-2-fluorobenzyl)oxy]pyridin-2-yl}piperidin-1-yl)methyl]-1-(tetrahydrofuran-3-ylmethyl)-1H-benzimidazole-6-carboxylic acid, enantiomer 1 | E | 5.25 | $^1$H NMR (400 MHz, CD$_3$OD) δ 8.37 (d, 1H), 8.05 (dd, 1H), 7.82 (d, 1H), 7.78-7.66 (m, 2H), 7.66-7.58 (m, 2H), 6.97 (d, 1H), 6.81 (d, 1H), 5.58 (s, 2H), 4.83 (s, 2H), 4.45-4.31 (m, 2H), 4.07 (m, 1H), 3.96 (d, 2H), 3.81 (m, 1H), 3.69 (dd, 1H), 3.55 (dd, 1H), 3.41 (m, 2H), 3.07 (m, 1H), 2.94 (m, 1H), 2.35-2.16 (m, 4H), 2.16-2.05 (m, 1H), 1.80 (m, 1H). MS(ES+): 570.2 (M + H). |
| 14A-10 | 2-[(4-{6-[(4-cyano-2-fluorobenzyl)oxy]pyridin-2-yl}piperidin-1-yl)methyl]-1-(tetrahydrofuran-3-ylmethyl)-1H-benzimidazole-6-carboxylic acid, enantiomer 2 | E | 6.0 | $^1$H NMR (400 MHz, CD$_3$OD) δ 8.37 (d, 1H), 8.05 (dd, 1H), 7.82 (d, 1H), 7.71 (m, 2H), 7.66-7.55 (m, 2H), 6.97 (d, 1H), 6.81 (d, 1H), 5.58 (s, 2H), 4.83 (s, 2H), 4.45-4.30 (m, 2H), 4.07 (m, 1H), 3.96 (m, 2H), 3.81 (m, 1H), 3.69 (m, 1H), 3.55 (m, 1H), 3.40 (m, 2H), 3.06 (d, 1H), 2.92 (d, 1H), 2.34-2.16 (m, 4H), 2.15-2.04 (m, 1H), 1.80 (m, 1H). MS(ES+): 570.2 (M + H) |
| 14A-11 | 2-{[(2S)-4-{6-[(4-cyano-2-fluorobenzyl)oxy]pyridin-2-yl}-2-methylpiperazin-1-yl]methyl}-1-(tetrahydrofuran-2-ylmethyl)-1H-benzimidazole-6-carboxylic acid, diastereomer 1 | F | 6.8 | $^1$H NMR (400 MHz, CD$_3$OD) δ 8.43 (d, 1H), 8.12 (dd, 1H), 7.82 (d, 1H), 7.65 (t, 1H), 7.61-7.49 (m, 3H), 6.43 (d, 1H), 6.28 (d, 1H), 5.48 (s, 2H), 4.70 (m, 1H), 4.63-4.43 (m, 2H), 4.28 (m, 1H), 4.07 (m, 2H), 3.90 (m, 1H), 3.75 (m, 1H), 3.51 (m, 3H), 3.22 (m, 1H), 2.24 (m, 1H), 2.03-1.88 (m, 2H), 1.71 (m, 1H), 1.43 (d, 3H). MS(ES+): 585.1 (M + H) |

TABLE 8-continued

| Ex. # | Name | *Method | *Ret. time (min) | NMR data/LC-MS data |
|---|---|---|---|---|
| 14A-12 | 2-{[(2S)-4-{6-[(4-cyano-2-fluorobenzyl)oxy]pyridin-2-yl}-2-methylpiperazin-1-yl]methyl}-1-(tetrahydrofuran-2-ylmethyl)-1H-benzimidazole-6-carboxylic acid, diastereomer 2 | F | 8.4 | $^1$H NMR (400 MHz, CD$_3$OD) δ 8.36 (d, 1H), 8.04 (dd, 1H), 7.74 (d, 1H), 7.64 (m, 1H), 7.60-7.42 (m, 3H), 6.35 (d, 1H), 6.21 (d, 1H), 5.46 (s, 2H), 4.77 (dd, 1H), 4.67 (d, 1H), 4.49 (m,1H), 4.33 (m, 1H), 4.11 (d, 1H), 4.01-3.82 (m, 3H), 3.75 (m, 1H), 3.30-3.23 (m, 1H), 3.18-2.99 (m, 3H), 2.77 (m, 1H), 2.19 (m, 1H), 2.00-1.86 (m, 2H), 1.71 (m, 1H), 1.31 (d, 3H). MS(ES+): 585.1 (M + H) |

*Separation methods and retention times for the methyl esters of examples:
Method A: Preparative method: Column: AD (250 mm × 30 mm, 10 μm); Mobile phase: CO$_2$ w/50% MeOH (0.1% NH$_4$OH); Flow rate: 80 ml/min; Wavelength: 220 nm. Analytical method: Column: AD (50 mm × 4.6 mm, 3 μm); Mobile phase as CO$_2$ w/40% EtOH (0.05% NHEt$_2$); Flow rate: 4 ml/min; Wavelength: 220 nm
Method B: Column: AD (250 mm × 30 mm, 10 μm); Mobile phase: CO$_2$ w/40% MeOH (0.1% NH$_4$OH); Flow rate: 80 ml/min; Wavelength: 220 nm
Method C: Column: IC (250 mm × 30 mm, 10 μm); Mobile phase: CO$_2$ w/50% MeOH (0.1% NH$_4$OH); Flow rate: 80 ml/min; Wavelength: 220 nm
Method D: Column: AD (250 mm × 30 mm, 10 μm); Mobile phase: CO$_2$ w/50% MeOH (0.1% NH$_4$OH); Flow rate: 80 ml/min; Wavelength: 220 nm
Method E: Column: OD (250 mm × 30 mm, 10 μm); Mobile phase: CO$_2$ w/45% EtOH (0.1% NH$_4$OH); Flow rate: 70 ml/min; Wavelength: 220 nm
Method F: Column: OJ (250 mm × 30 mm, 10 μm); Mobile phase: CO$_2$ w/30% EtOH (0.1 NH$_4$OH); Flow rate: 80 ml/min; Wavelength: 220 nm

CHO GLP-1R Clone H6—Assay 1

GLP-1R-mediated agonist activity was determined with a cell-based functional assay utilizing an HTRF (Homogeneous Time-Resolved Fluorescence) cAMP detection kit (cAMP HI Range Assay Kit; CisBio cat #62AM6PEJ) that measures cAMP levels in the cell. The method is a competitive immunoassay between native cAMP produced by the cells and exogenous cAMP labeled with the dye d2. The tracer binding is visualized by a mAb anti-cAMP labeled with Cryptate. The specific signal (i.e. energy transfer) is inversely proportional to the concentration of cAMP in either standard or experimental sample.

The human GLP-1R coding sequence (NCBI Reference Sequence NP_002053.3, including naturally-occurring variant Gly168Ser) was subcloned into pcDNA3 (Invitrogen) and a cell line stably expressing the receptor was isolated (designated Clone H6). Saturation binding analyses (filtration assay procedure) using $^{125}$I-GLP-1$_{7\text{-}36}$ (Perkin Elmer) showed that plasma membranes derived from this cell line express a high GLP-1R density (K$_d$: 0.4 nM, B$_{max}$: 1900 fmol/mg protein).

Cells were removed from cryopreservation, re-suspended in 40 mL of Dulbecco's Phosphate Buffered Saline (DPBS—Lonza Cat #17-512Q) and centrifuged at 800×g for 5 min at 22° C. The cell pellet was then re-suspended in 10 mL of growth medium [DMEM/F12 1:1 Mixture with HEPES, L-Gln, 500 mL (DMEM/F12 Lonza Cat #12-719F), 10% heat inactivated fetal bovine serum (Gibco Cat #16140-071), 5 mL of 100× Pen-Strep (Gibco Cat #15140-122), 5 mL of 100× L-Glutamine (Gibco Cat #25030-081) and 500 μg/mL Geneticin (G418) (Invitrogen #10131035)]. A 1 mL sample of the cell suspension in growth media was counted on a Becton Dickinson ViCell to determine cell viability and cell count per mL. The remaining cell suspension was then adjusted with growth media to deliver 2000 viable cells per well using a Matrix Combi Multidrop reagent dispenser, and the cells were dispensed into a white 384 well tissue culture treated assay plate (Corning 3570). The assay plate was then incubated for 48 hours at 37° C. in a humidified environment in 5% carbon dioxide.

Varying concentrations of each compound to be tested (in DMSO) were diluted in assay buffer (HBSS with Calcium/Magnesium (Lonza/BioWhittaker cat #10-527F)/0.1% BSA (Sigma Aldrich cat #A7409-1L)/20 mM HEPES (Lonza/BioWhittaker cat #17-737E) containing 100 μM 3-isobutyl-1-methylxanthin (IBMX; Sigma cat #15879). The final DMSO concentration is 1%.

After 48 hours, the growth media was removed from the assay plate wells, and the cells were treated with 20 μL of the serially diluted compound in assay buffer for 30 minutes at 37° C. in a humidified environment in 5% carbon dioxide. Following the 30 minute incubation, 10 μL of labeled d2 cAMP and 10 μL of anti-cAMP antibody (both diluted 1:20 in cell lysis buffer; as described in the manufacturer's assay protocol) were added to each well of the assay plate. The plates were then incubated at room temperature and after 60 minutes, changes in the HTRF signal were read with an Envision 2104 multi-label plate reader using excitation of 330 nm and emissions of 615 and 665 nm. Raw data were converted to nM cAMP by interpolation from a cAMP standard curve (as described in the manufacturer's assay protocol) and the percent effect was determined relative to a saturating concentration of the full agonist GLP-1$_{7\text{-}36}$ (1 μM) included on each plate. EC$_{50}$ determinations were made from agonist dose-response curves analyzed with a curve fitting program using a 4-parameter logistic dose response equation.

CHO GLP-1R Clone C6—Assay 2

GLP-1R-mediated agonist activity was determined with a cell-based functional assay utilizing an HTRF (Homogeneous Time-Resolved Fluorescence) cAMP detection kit (cAMP HI Range Assay Kit; Cis Bio cat #62AM6PEJ) that measures cAMP levels in the cell. The method is a competitive immunoassay between native cAMP produced by the cells and exogenous cAMP labeled with the dye d2. The tracer binding is visualized by a mAb ant-cAMP labeled with Cryptate. The specific signal (i.e. energy transfer) is inversely proportional to the concentration of cAMP in either a standard or an experimental sample.

The human GLP-1R coding sequence (NCBI Reference Sequence NP_002053.3, including naturally-occurring variant Leu260Phe) was subcloned into pcDNA5-FRT-TO and a clonal CHO cell line stably expressing a low receptor density was isolated using the Flp-In™ T-Rex™ System, as described by the manufacturer (ThermoFisher). Saturation binding analyses (filtration assay procedure) using $^{125}$I-GLP-1 (Perkin Elmer) showed that plasma membranes derived from this cell line (designated clone C6) express a low GLP-1R density ($K_d$: 0.3 nM, $B_{max}$: 240 fmol/mg protein), relative to the clone H6 cell line.

Cells were removed from cryopreservation, re-suspended in 40 mL of Dulbecco's Phosphate Buffered Saline (DPBS—Lonza Cat #17-512Q) and centrifuged at 800×g for 5 min at 22° C. The DPBS was aspirated, and the cell pellet was re-suspended in 10 mL of complete growth medium (DMEM:F12 1:1 Mixture with HEPES, L-Gln, 500 mL (DMEM/F12 Lonza Cat #12-719F), 10% heat inactivated fetal bovine serum (Gibco Cat #16140-071), 5 mL of 100× Pen-Strep (Gibco Cat #15140-122), 5 mL of 100× L-Glutamine (Gibco Cat #25030-081), 700 µg/mL Hygromycin (Invitrogen Cat #10687010) and 15 µg/mL Blasticidin (Gibco Cat #R21001). A 1 mL sample of the cell suspension in growth media was counted on a Becton Dickinson ViCell to determine cell viability and cell count per mL. The remaining cell suspension was then adjusted with growth media to deliver 1600 viable cells per well using a Matrix Combi Multidrop reagent dispenser, and the cells were dispensed into a white 384 well tissue culture treated assay plate (Corning 3570). The assay plate was then incubated for 48 h at 37° C. in a humidified environment (95% $O_2$, 5% $CO_2$)

Varying concentrations of each compound to be tested (in DMSO) were diluted in assay buffer [HBSS with Calcium/Magnesium (Lonza/BioWhittaker cat #10-527F)/0.1% BSA (Sigma Aldrich cat #A7409-1L)/20 mM HEPES (Lonza/BioWhittaker cat #17-737E)] containing 100 µM 3-isobutyl-1-methylxanthin (IBMX; Sigma cat #15879). The final DMSO concentration in the compound/assay buffer mixture is 1%.

After 48 h, the growth media was removed from the assay plate wells, and the cells were treated with 20 µL of the serially diluted compound in assay buffer for 30 min at 37° C. in a humidified environment (95% $O_2$, 5% $CO_2$). Following the 30 min incubation, 10 µL of labeled d2 cAMP and 10 µL of anti-cAMP antibody (both diluted 1:20 in cell lysis buffer; as described in the manufacturer's assay protocol) were added to each well of the assay plate. The plates were then incubated at room temperature and after 60 minutes, changes in the HTRF signal were read with an Envision 2104 multi-label plate reader using excitation of 330 nm and emissions of 615 and 665 nm. Raw data were converted to nM cAMP by interpolation from a cAMP standard curve (as described in the manufacturer's assay protocol) and the percent effect was determined relative to a saturating concentration of the full agonist GLP-1 (1 µM) included on each plate. $EC_{50}$ determinations were made from agonist dose response curves analyzed with a curve fitting program using a 4-parameter logistic dose response equation.

In Table 9, assay data are presented to two (2) significant figures as the geometric mean ($EC_{50}$s) and arithmetic mean (Emax) based on the number of replicates listed (Number). A blank cell means there was no data for that Example or the Emax was not calculated.

TABLE 9

| Example number | Assay 1 $EC_{50}$ (nM) | Assay 1 Emax (%) | Assay 1 Number | Assay 2 $EC_{50}$ (nM) | Assay 2 Emax (%) | Assay 2 Number |
|---|---|---|---|---|---|---|
| 1A-01 | 81 | 77 | 5 | 910 | 94 | 4 |
| 1A-02 | 16 | 85 | 6 | 320 | 88 | 11 |
| 1A-03 | 4.3 | 83 | 3 | 92 | 83 | 3 |
| 1A-04 | 21 | 79 | 3 | 350 | 82 | 3 |
| 1A-05 | 42 | 75 | 3 | 530 | 67 | 3 |
| 1A-06 | 29 | 84 | 3 | 350 | 70 | 3 |
| 1A-07 | 3.9 | 82 | 4 | 45 | 82 | 5 |
| 1A-08 | 7.1 | 81 | 3 | 120 | 85 | 3 |
| 1A-09 | 0.95 | 92 | 1 | 17 | 120 | 3 |
| 1A-10 | 930 | 86 | 3 | 9000 | 100 | 3 |
| 1A-11 | 19 | 76 | 3 | 530 | 97 | 3 |
| 1A-12 | 750 | 76 | 3 | | | |
| 1A-13 | 210 | 66 | 3 | | | |
| 1A-14 | 47 | 71 | 3 | 1600 | 81 | 3 |
| 1A-15 | >20000 | | 1 | | | |
| 1A-16 | 1.5 | 86 | 3 | 14 | 82 | 3 |
| 1A-17 | 2.4 | 87 | 3 | 45 | 95 | 3 |
| 1A-18 | 6.4 | 90 | 4 | 110 | 94 | 3 |
| 1A-19 | 0.28 | 84 | 5 | 3.2 | 84 | 4 |
| 1A-20 | 44 | 81 | 3 | 880 | 90 | 3 |
| 1A-21 | 4.9 | 77 | 7 | 75 | 83 | 3 |
| 1A-22 | 36 | 78 | 3 | 400 | 86 | 3 |
| 1A-23 | 50 | 83 | 3 | 1000 | 98 | 3 |
| 1A-24 | >11000 | 84 | 3 | | | |
| 1A-25 | 45 | 65 | 3 | 1000 | 84 | 3 |
| 1A-26 | 70 | 80 | 3 | 1800 | 85 | 3 |
| 1A-27 | 190 | 91 | 3 | 1400 | 47 | 3 |
| 1A-28 | 300 | 92 | 3 | 7700 | 100 | 3 |
| 1A-29 | 260 | 88 | 3 | 5600 | 86 | 3 |
| 1A-30 | 150 | 86 | 3 | 4100 | 110 | 3 |
| 2A-01 | 90 | 76 | 55 | 1800 | 89 | 43 |
| 2A-02 | 7.9 | 95 | 5 | 110 | 89 | 7 |
| 2A-03 | 150 | 74 | 3 | 1200 | 44 | 5 |
| 2A-04 | 36 | 84 | 6 | 150 | 92 | 3 |
| 2A-05 | 6 | 73 | 3 | 150 | 84 | 3 |
| 2A-06 | 9 | 82 | 3 | 170 | 85 | 3 |
| 2A-07 | 140 | 72 | 3 | 1600 | 46 | 3 |
| 2A-08 | 5.8 | 72 | 3 | 94 | 76 | 4 |
| 2A-09 | 120 | 76 | 4 | 2200 | 83 | 3 |
| 2A-10 | 43 | 82 | 3 | 680 | 110 | 4 |
| 2A-11 | 210 | 79 | 3 | | | |
| 2A-12 | 340 | 74 | 3 | | | |
| 2A-13 | 770 | 78 | 3 | >15000 | 100 | 3 |
| 2A-14 | 110 | 71 | 3 | 3000 | 92 | 3 |
| 2A-15 | 22 | 87 | 3 | 280 | 91 | 3 |
| 2A-16 | 370 | 75 | 3 | | | |
| 2A-17 | 24 | 76 | 5 | 1200 | 94 | 8 |
| 2A-18 | 6 | 80 | 3 | 78 | 88 | 3 |
| 2A-19 | 7.9 | 80 | 5 | 150 | 100 | 3 |
| 2A-20 | 0.96 | 80 | 5 | 14 | 95 | 2 |
| 2A-21 | 8.5 | 88 | 3 | 220 | 110 | 3 |
| 2A-22 | 14 | 72 | 4 | 190 | 83 | 3 |
| 2A-23 | 0.5 | 73 | 3 | 22 | 96 | 6 |
| 3A-01 | 0.94 | 83 | 15 | 12 | 98 | 21 |
| 4A-01 | 1.1 | 79 | 5 | 13 | 100 | 18 |
| 5A-01 | 0.34 | 78 | 6 | 7.4 | 94 | 6 |
| 6A-01 | 0.76 | 88 | 9 | 8.8 | 100 | 15 |
| 7A-01 | 3.2 | 84 | 7 | 55 | 86 | 11 |
| 8A-01 | 100 | 99 | 3 | 1100 | 90 | 3 |
| 8A-02 | 150 | 80 | 3 | | | |
| 8A-03 | 18 | 84 | 3 | 350 | 77 | 3 |
| 8A-04 | 120 | 79 | 3 | 1700 | 88 | 3 |
| 9A-01 | 1200 | 78 | 3 | | | |
| 9A-02 | 79 | 81 | 3 | 4000 | 75 | 3 |
| 9A-03 | 200 | 79 | 3 | | | |
| 9A-04 | 2900 | 89 | 3 | | | |
| 9A-05 | 2700 | 85 | 3 | | | |
| 9A-06 | 870 | 82 | 3 | | | |
| 9A-07 | 170 | 78 | 8 | 2100 | 71 | 3 |
| 9A-08 | 2400 | 87 | 3 | | | |
| 9A-09 | 880 | 59 | 3 | | | |
| 9A-10 | 4500 | 48 | 4 | | | |
| 9A-11 | 1600 | 83 | 3 | | | |
| 9A-12 | >17000 | 100 | 3 | | | |
| 9A-13 | 170 | 68 | 3 | | | |
| 9A-14 | 1800 | 93 | 3 | | | |

TABLE 9-continued

| Example number | Assay 1 EC$_{50}$ (nM) | Assay 1 Emax (%) | Assay 1 Number | Assay 2 EC$_{50}$ (nM) | Assay 2 Emax (%) | Assay 2 Number |
|---|---|---|---|---|---|---|
| 9A-15 | 180 | 78 | 8 | 3500 | 90 | 3 |
| 10A-01 | 3.2 | 77 | 3 | 43 | 84 | 3 |
| 10A-02 | 0.34 | 89 | 5 | 2.2 | 97 | 5 |
| 10A-03 | 1700 | 82 | 3 | | | |
| 10A-04 | 49 | 71 | 3 | 2100 | 90 | 3 |
| 10A-05 | 2.4 | 71 | 4 | 38 | 83 | 3 |
| 10A-06 | 68 | 77 | 3 | 1700 | 110 | 3 |
| 10A-07 | 2.8 | 82 | 3 | 68 | 81 | 3 |
| 10A-08 | 0.55 | 77 | 4 | 9.2 | 94 | 6 |
| 10A-09 | 0.99 | 95 | 4 | 10 | 120 | 7 |
| 10A-10 | 0.3 | 84 | 4 | 4.1 | 100 | 2 |
| 10A-11 | 75 | 69 | 3 | | | |
| 10A-12 | 110 | 68 | 3 | 4400 | 110 | 3 |
| 10A-13 | 4.1 | 67 | 3 | 170 | 75 | 3 |
| 10A-14 | 8.1 | 74 | 3 | 220 | 93 | 4 |
| 10A-15 | 1.3 | 72 | 4 | 27 | 87 | 3 |
| 10A-16 | 1.7 | 67 | 3 | 45 | 83 | 3 |
| 10A-17 | 1.8 | 77 | 3 | 59 | 85 | 3 |
| 10A-18 | 1.6 | 78 | 7 | 33 | 78 | 3 |
| 10A-19 | >19000 | 100 | 3 | | | |
| 10A-20 | >15000 | 98 | 3 | >20000 | | 1 |
| 10A-21 | 18 | 88 | 3 | 400 | 100 | 3 |
| 10A-22 | 5.7 | 67 | 3 | 100 | 79 | 3 |
| 10A-23 | 38 | 76 | 3 | 760 | 91 | 3 |
| 10A-24 | 5.7 | 78 | 3 | 130 | 94 | 3 |
| 10A-25 | 1.7 | 82 | 3 | 41 | 99 | 3 |
| 10A-26 | 7 | 59 | 3 | 190 | 80 | 3 |
| 10A-27 | 13 | 75 | 3 | 250 | 80 | 3 |
| 10A-27 | 50 | 81 | 3 | 870 | 83 | 3 |
| 10A-28 | 190 | 71 | 3 | | | |
| 10A-29 | 390 | 82 | 3 | | | |
| 10A-30 | 550 | 71 | 3 | | | |
| 10A-31 | 3.4 | 73 | 3 | 59 | 89 | 3 |
| 10A-32 | 0.47 | 77 | 5 | 5 | 94 | 6 |
| 10A-33 | 1.5 | 73 | 3 | 24 | 91 | 3 |
| 10A-34 | 1.5 | 80 | 7 | 29 | 95 | 5 |
| 10A-35 | 0.3 | 93 | 5 | 3.8 | 93 | 6 |
| 10A-36 | 0.33 | 82 | 3 | 13 | 110 | 7 |
| 10A-37 | 3.4 | 86 | 6 | 23 | 110 | 7 |
| 10A-38 | 130 | 72 | 3 | | | |
| 10A-39 | 170 | 69 | 3 | | | |
| 10A-40 | 1200 | 53 | 3 | | | |
| 10A-41 | 12 | 75 | 4 | 140 | 82 | 3 |
| 10A-42 | 2.7 | 73 | 4 | 29 | 74 | 5 |
| 10A-43 | 4 | 64 | 3 | 48 | 79 | 3 |
| 10A-44 | 6 | 73 | 3 | 99 | 81 | 3 |
| 10A-45 | 1 | 76 | 3 | 19 | 75 | 3 |
| 10A-46 | 1700 | 80 | 3 | | | |
| 10A-47 | 0.3 | 80 | 3 | 4.4 | 95 | 6 |
| 10A-48 | 8.6 | 64 | 3 | 140 | 76 | 3 |
| 10A-49 | 0.56 | 73 | 6 | 9.6 | 84 | 3 |
| 10A-50 | 290 | 64 | 3 | | | |
| 10A-51 | 390 | 72 | 3 | | | |
| 10A-52 | 1300 | 79 | 3 | | | |
| 10A-53 | 3.2 | 68 | 3 | 39 | 88 | 3 |
| 10A-54 | 0.71 | 81 | 5 | 11 | 100 | 6 |
| 10A-55 | 1.2 | 84 | 5 | 24 | 98 | 5 |
| 10A-56 | 0.5 | 78 | 3 | 16 | 86 | 5 |
| 10A-57 | 9.4 | 69 | 3 | 160 | 71 | 3 |
| 10A-58 | 0.52 | 70 | 4 | 8.5 | 78 | 4 |
| 10A-59 | 4.7 | 71 | 3 | 84 | 83 | 4 |
| 10A-60 | 31 | 81 | 3 | 460 | 66 | 3 |
| 10A-61 | 1.5 | 74 | 6 | 35 | 89 | 3 |
| 10A-62 | 2.9 | 96 | 4 | 28 | 97 | 3 |
| 10A-63 | 0.58 | 86 | 3 | 11 | 110 | 5 |
| 10A-64 | 2 | 82 | 3 | 32 | 79 | 3 |
| 10A-65 | 1.6 | 84 | 6 | 35 | 78 | 3 |
| 10A-66 | 0.39 | 84 | 4 | 3.4 | 100 | 4 |
| 10A-67 | 0.59 | 83 | 5 | 6.8 | 93 | 5 |
| 10A-68 | 140 | 76 | 4 | | | |
| 10A-69 | 2 | 84 | 3 | 20 | 87 | 3 |
| 10A-70 | 5 | 65 | 1 | 72 | 87 | 1 |
| 10A-71 | 190 | 62 | 3 | 5800 | 85 | 4 |
| 10A-72 | 3.4 | 79 | 4 | 53 | 68 | 5 |
| 10A-73 | 8.6 | 78 | 5 | 88 | 82 | 5 |
| 10A-74 | 0.9 | 94 | 3 | 9.7 | 100 | 3 |
| 10A-75 | 0.95 | 95 | 4 | 13 | 91 | 5 |
| 10A-76 | 2.9 | 79 | 4 | 51 | 95 | 3 |
| 10A-77 | 0.96 | 100 | 2 | 10 | 120 | 3 |
| 10A-78 | 1.6 | 83 | 6 | 28 | 88 | 4 |
| 10A-79 | 33 | 80 | 3 | 670 | 110 | 3 |
| 11A-01 | >10000 | 85 | 3 | | | |
| 11A-02 | >15000 | 100 | 3 | | | |
| 11A-03 | >16000 | 100 | 3 | | | |
| 11A-04 | >19000 | 100 | 3 | | | |
| 11A-05 | >20000 | | 1 | | | |
| 11A-06 | >20000 | | 1 | | | |
| 11A-07 | >20000 | | 1 | | | |
| 11A-08 | >20000 | | 1 | | | |
| 11A-09 | >20000 | | 1 | | | |
| 11A-10 | >20000 | | 1 | | | |
| 11A-11 | >20000 | | 1 | | | |
| 11A-12 | >20000 | | 1 | | | |
| 11A-13 | >20000 | | 1 | | | |
| 11A-14 | 8.1 | 64 | 3 | 230 | 77 | 3 |
| 11A-15 | 9.4 | 69 | 3 | 94 | 92 | 3 |
| 11A-16 | 11 | 71 | 4 | 410 | 75 | 3 |
| 11A-17 | 11 | 65 | 2 | 380 | 96 | 3 |
| 11A-18 | 14 | 80 | 3 | 270 | 92 | 1 |
| 11A-19 | 15 | 83 | 3 | 230 | 110 | 3 |
| 11A-20 | 15 | 83 | 4 | 270 | 88 | 3 |
| 11A-21 | 18 | 82 | 4 | 270 | 83 | 3 |
| 11A-22 | 21 | 82 | 6 | 200 | 81 | 3 |
| 11A-23 | 25 | 78 | 3 | 330 | 96 | 3 |
| 11A-24 | 28 | 80 | 3 | 450 | 89 | 3 |
| 11A-25 | 30 | 77 | 3 | 360 | 89 | 3 |
| 11A-26 | 36 | 73 | 3 | 1100 | 79 | 3 |
| 11A-27 | 44 | 72 | 3 | 490 | 98 | 2 |
| 11A-28 | 54 | 77 | 3 | 1200 | 82 | 3 |
| 11A-29 | 55 | 71 | 3 | 1700 | 99 | 3 |
| 11A-30 | 56 | 81 | 8 | 590 | 85 | 4 |
| 11A-31 | 72 | 76 | 3 | 1500 | 81 | 3 |
| 11A-32 | 87 | 83 | 3 | 3100 | 110 | 3 |
| 11A-33 | 96 | 86 | 6 | 1400 | 94 | 4 |
| 11A-34 | 110 | 70 | 5 | 3500 | 95 | 3 |
| 11A-35 | 110 | 74 | 6 | 2700 | 96 | 4 |
| 11A-36 | 110 | 79 | 6 | 2200 | 89 | 4 |
| 11A-37 | 120 | 93 | 3 | 1300 | 96 | 3 |
| 11A-38 | 120 | 80 | 6 | 1500 | 92 | 4 |
| 11A-39 | 130 | 80 | 3 | | | |
| 11A-40 | 170 | 77 | 3 | | | |
| 11A-41 | 190 | 74 | 5 | | | |
| 11A-42 | 190 | 86 | 3 | | | |
| 11A-43 | 190 | 80 | 5 | 3600 | 93 | 3 |
| 11A-44 | 210 | 77 | 3 | | | |
| 11A-45 | 290 | 74 | 3 | | | |
| 11A-46 | 300 | 66 | 3 | | | |
| 11A-47 | 320 | 79 | 3 | | | |
| 11A-48 | 350 | 71 | 3 | | | |
| 11A-49 | 380 | 68 | 3 | | | |
| 11A-50 | 380 | 75 | 3 | | | |
| 11A-51 | 390 | 69 | 2 | | | |
| 11A-52 | 440 | 86 | 3 | | | |
| 11A-53 | 450 | 71 | 3 | 5600 | 76 | 3 |
| 11A-54 | 500 | 69 | 3 | | | |
| 11A-55 | 520 | 80 | 3 | | | |
| 11A-56 | 1100 | 47 | 4 | | | |
| 11A-57 | 1100 | 65 | 1 | | | |
| 11A-58 | 1100 | 81 | 3 | | | |
| 11A-59 | 1400 | 97 | 3 | | | |
| 11A-60 | 1600 | 80 | 3 | | | |
| 11A-61 | 1900 | 79 | 3 | | | |
| 11A-62 | 2200 | 87 | 4 | | | |
| 11A-63 | 2500 | 71 | 3 | | | |
| 11A-64 | 2900 | 88 | 3 | | | |
| 11A-65 | 3100 | 51 | 3 | | | |
| 11A-66 | 4000 | 91 | 3 | | | |
| 11A-67 | 9300 | 100 | 3 | | | |
| 11A-68 | 63 | 78 | 3 | 2000 | 82 | 3 |
| 11A-69 | 5.3 | 76 | 3 | 21 | 84 | 3 |
| 11A-70 | 0.7 | 86 | 4 | 10 | 89 | 6 |
| 11A-71 | 30 | 73 | 4 | 570 | 93 | 8 |

TABLE 9-continued

| Example number | Assay 1 EC$_{50}$ (nM) | Assay 1 Emax (%) | Assay 1 Number | Assay 2 EC$_{50}$ (nM) | Assay 2 Emax (%) | Assay 2 Number |
|---|---|---|---|---|---|---|
| 11A-72 | 5 | 82 | 4 | 41 | 77 | 4 |
| 11A-73 | 150 | 68 | 3 | 5300 | 80 | 4 |
| 11A-74 | 560 | 72 | 3 | | | |
| 12A-01 | >20000 | | 1 | | | |
| 12A-02 | 36 | 71 | 3 | 1600 | 82 | 3 |
| 12A-03 | 600 | 70 | 3 | | | |
| 12A-04 | 250 | 64 | 4 | | | |
| 12A-05 | 1300 | 42 | 3 | | | |
| 12A-06 | 510 | 64 | 3 | | | |
| 12A-07 | 37 | 69 | 3 | 1200 | 83 | 3 |
| 12A-08 | 6.1 | 89 | 4 | 150 | 97 | 3 |
| 12A-09 | 21 | 79 | 3 | 540 | 80 | 3 |
| 12A-10 | 6.9 | 78 | 4 | 170 | 96 | 3 |
| 12A-11 | 54 | 81 | 4 | 2100 | 100 | 3 |
| 13A-01 | 1200 | 58 | 3 | | | |
| 13A-02 | 420 | 81 | 3 | | | |
| 13A-03 | 5.2 | 66 | 3 | 120 | 80 | 3 |
| 13A-04 | 46 | 66 | 4 | 1400 | 83 | 3 |
| 14A-01 | 5.6 | 80 | 3 | 200 | 89 | 3 |
| 14A-02 | 94 | 78 | 3 | 1500 | 69 | 3 |
| 14A-03 | 6.3 | 83 | 3 | 110 | 87 | 2 |
| 14A-04 | 100 | 78 | 3 | 1100 | 75 | 3 |
| 14A-05 | 28 | 82 | 3 | 350 | 70 | 3 |
| 14A-06 | 4.2 | 69 | 3 | 77 | 75 | 3 |
| 14A-07 | 1.9 | 63 | 3 | 55 | 75 | 3 |
| 14A-08 | 19 | 72 | 4 | 380 | 84 | 3 |
| 14A-09 | 3.3 | 73 | 4 | 54 | 81 | 3 |
| 14A-10 | 12 | 64 | 3 | 270 | 84 | 3 |
| 14A-11 | 7 | 65 | 3 | 140 | 71 | 3 |
| 14A-12 | 1.4 | 77 | 7 | 20 | 79 | 3 |

All patents, patent applications and references referred to herein are hereby incorporated by reference in their entirety.

What is claimed is:

1. A method for treating disease or disorder comprising administering to a mammal in need of such treatment a therapeutically effective amount of a compound of Formula II:

or a pharmaceutically acceptable salt thereof, wherein:
each $R^1$ is independently F, Cl, —CN, —CH$_3$, or —CF$_3$;
m is 0 or 1;
$R^2$ is F;
p is 0, or 1;
q is 0 or 1;
$R^3$ is F, —OH, —CN, —C$_{1-3}$alkyl, —OC$_{1-3}$alkyl, or —C$_{3-4}$cycloalkyl, or 2 $R^3$s may together cyclize to form —C$_{3-4}$spirocycloalkyl, wherein the alkyl of C$_{1-3}$alkyl and OC$_{1-3}$alkyl, cycloalkyl, or spirocycloalkyl may be substituted as valency allows with 0 to 3 F atoms and with 0 to 1 —OH;
Y is CH or N;
$R^4$ is —C$_{1-3}$alkyl, —C$_{0-3}$alkylene-C$_{3-6}$cycloalkyl, —C$_{0-3}$alkylene-R$^5$, or —C$_{1-3}$alkylene-R$^6$,
wherein said alkyl may be substituted as valency allows with 0 to 3 substituents independently selected from 0 to 3 F atoms and 0 to 1 substituent selected from —C$_{0-1}$alkylene-CN, —C$_{0-1}$alkylene-OR$^O$, and —N(R$^N$)$_2$, and
wherein said alkylene and cycloalkyl may be independently substituted as valency allows with 0 to 2 substituents independently selected from 0 to 2 F atoms and 0 to 1 substituent selected from —C$_{0-1}$alkylene-CN, —C$_{0-1}$alkylene-OR$^O$, and —N(R$^N$)$_2$;
$R^5$ is a 4- to 6-membered heterocycloalkyl, wherein said heterocycloalkyl may be substituted with 0 to 2 substituents as valency allows independently selected from:
0 to 1 oxo (=O),
0 to 1 —CN,
0 to 2 F atoms, and
0 to 2 substituents independently selected from —C$_{1-3}$alkyl and —OC$_{1-3}$alkyl, wherein the alkyl of C$_{1-3}$alkyl and OC$_{1-3}$alkyl may be substituted with 0 to 3 substituents as valency allows independently selected from:
0 to 3 F atoms,
0 to 1 —CN, and
0 to 1 —OR$^O$;
$R^6$ is a 5- to 6-membered heteroaryl, wherein said heteroaryl may be substituted with 0 to 2 substituents as valency allows independently selected from:
0 to 2 halogens,
0 to 1 substituent selected from —OR$^O$ and —N(R$^N$)$_2$, and
0 to 2 —C$_{1-3}$alkyl, wherein the alkyl may be substituted with 0 to 3 substituents as valency allows independently selected from:
0 to 3 F atoms, and
0 to 1 —OR$^O$;
each R$^O$ is independently H, or —C$_{1-3}$alkyl, wherein C$_{1-3}$alkyl may be substituted with 0 to 3 F atoms;
each R$^N$ is independently H, or —C$_{1-3}$alkyl;
$Z^1$ is CH or N;
$Z^3$ is —CR$^Z$ or N; and
each R$^Z$ is independently H, F, Cl, or —CH$_3$,
wherein the disease or disorder is selected from the group consisting of T2DM, pre-diabetes, malnutrition-related diabetes, gestational diabetes, hyperglycemia, insulin resistance, hepatic insulin resistance, impaired glucose tolerance, diabetic neuropathy, diabetic nephropathy, diabetic retinopathy, adipocyte dysfunction, obesity, eating disorders, weight gain from use of other agents, excessive sugar craving, dyslipidemia, hyperinsulinemia, NAFLD, NASH, fibrosis, NASH with fibrosis, cirrhosis, hepatocellular carcinoma, and a cardiovascular disease.

2. The method of claim 1, wherein $R^3$ is —F, —CH$_3$, —CH$_2$CH$_3$, —CH$_2$OH, —CF$_3$, isopropyl, or cyclopropyl.

3. The method of claim 1, wherein:
$R^3$ is —CH$_3$; and
$R^4$ is —CH$_2$CH$_2$OCH$_3$, C$_{1-3}$alkylene-R$^5$, or C$_{1-3}$alkylene-R$^6$.

4. The method of claim 1, wherein $R^4$ is —CH$_2$—R$^5$; $R^5$ is a 4- to 5-membered heterocycloalkyl, wherein said heterocycloalkyl may be substituted with 0 to 2 substituents as valency allows independently selected from:
0 to 2 F atoms, and
0 to 1 substituent selected from —OCH$_3$ and —CH$_2$OCH$_3$.

5. The method of claim 1, wherein $R^4$ is —CH$_2$—R$^5$; and the heterocycloalkyl of $R^5$ is a monovalent radical of

[Structures: oxetane, tetrahydrofuran, tetrahydropyran, azetidine (NH), pyrrolidine (NH), piperidine (NH), oxazolidine, imidazolidine, morpholine, 1,4-dioxane, 1,3-dioxane/morpholine variant (NH), hexahydropyrimidine (NH, NH),]

wherein the heterocycloalkyl may be substituted with 0 to 2 substituents as valency allows independently selected from:
 0 to 1 oxo (O═),
 0 to 1 —CN,
 0 to 2 F atoms, and
 0 to 2 substituents independently selected from —C$_{1-3}$alkyl and —OC$_{1-3}$alkyl, wherein the alkyl of C$_{1-3}$alkyl and OC$_{1-3}$alkyl may be independently substituted with 0 to 3 substituents as valency allows independently selected from:
  0 to 3 F atoms,
  0 to 1 —CN, and
  0 to 1 —OR$^O$.

6. The method of claim 1, wherein R$^4$ is —CH$_2$—R$^5$; the heterocycloalkyl of R$^5$ is a monovalent radical of

[Structures: oxetane, tetrahydrofuran, tetrahydropyran, azetidine (NH), pyrrolidine (NH), piperidine (NH), morpholine, or 1,4-dioxane,]

wherein the heterocycloalkyl may be substituted with 0 to 2 substituents as valency allows each independently selected from:
 0 to 1 —CN,
 0 to 2 F atoms, and
 0 to 2 substituents independently selected from —C$_{1-3}$alkyl and —OC$_{1-3}$alkyl, wherein the alkyl of C$_{1-3}$alkyl and OC$_{1-3}$alkyl may be independently substituted with 0 to 3 substituents as valency allows each independently selected from:
  0 to 3 F atoms,
  0 to 1 —CN, and
  0 to 1 —OR$^O$.

7. The method of claim 1, wherein R$^4$ is —CH$_2$—R$^5$; and the heterocycloalkyl of R$^5$ is a monovalent radical of

[Structures: oxetanes, tetrahydrofuran,]

-continued

[Structures: tetrahydrofuran, azetidine (NH), or oxazolidinone,]

and wherein the heterocycloalkyl may be substituted with 0 to 1 substituent as valency allows selected from:
 —CN,
 F atom, and
 0 to 1 substituent independently selected from —C$_{1-3}$alkyl and —OC$_{1-3}$alkyl, wherein the alkyl of C$_{1-3}$alkyl and OC$_{1-3}$alkyl may be substituted with 0 to 3 substituents as valency allows with:
  0 to 3 F atoms,
  0 to 1 —CN, or
  0 to 1 —OR$^O$.

8. The method of claim 1, wherein R$^4$ is —CH$_2$—R$^5$; and the heterocycloalkyl of R$^5$ is a monovalent radical of

[Structures: oxetane, tetrahydrofuran, or tetrahydrofuran variant,]

and wherein the heterocycloalkyl may be substituted as valency allows with 0 to 1 methyl, wherein said methyl may be substituted with 0 to 3 F atoms.

9. The method of claim 1, wherein the disease or disorder is selected from the group consisting of T2DM, obesity, NAFLD, NASH, and NASH with fibrosis, cirrhosis.

10. The method of claim 8, wherein the disease or disorder is selected from the group consisting of T2DM, obesity, NAFLD, NASH, and NASH with fibrosis, cirrhosis.

11. A method for treating disease or disorder comprising administering to a mammal in need of such treatment a therapeutically effective amount of a compound of Formula III:

[Structure of Formula III]

or a pharmaceutically acceptable salt thereof, wherein:
 each R$^1$ is independently F, Cl, —CN, —CH$_3$, or —CF$_3$;
 m is 0 or 1;
 R$^2$ is F;
 p is 0, or 1;
 R$^3$ is —C$_{1-2}$alkyl, wherein —C$_{1-2}$alkyl may be substituted as valency allows with 0 to 3 F atoms;

q is 0 or 1;
Y is CH or N;
R$^4$ is —C$_{1-3}$alkyl, —C$_{0-3}$alkylene-C$_{3-6}$cycloalkyl, —C$_{0-3}$alkylene-R$^5$, or —C$_{1-3}$alkylene-R$^6$,
wherein said alkyl may be substituted as valency allows with 0 to 3 substituents independently selected from 0 to 3 F atoms and 0 to 1 substituent selected from —C$_{0-1}$alkylene-CN, —C$_{0-1}$alkylene-OR$^O$, and —N(R$^N$)$_2$, and
wherein said alkylene and cycloalkyl may be independently substituted as valency allows with 0 to 2 substituents independently selected from 0 to 2 F atoms and 0 to 1 substituent selected from —C$_{0-1}$alkylene-CN, —C$_{0-1}$alkylene-OR$^O$, and —N(R$^N$)$_2$;
  R$^5$ is a 4- to 6-membered heterocycloalkyl, wherein said heterocycloalkyl may be substituted with 0 to 2 substituents as valency allows independently selected from:
  0 to 1 oxo (=O),
  0 to 1 —CN,
  0 to 2 F atoms, and
  0 to 2 substituents independently selected from —C$_{1-3}$alkyl and —OC$_{1-3}$alkyl, wherein the alkyl of C$_{1-3}$alkyl and OC$_{1-3}$alkyl may be substituted with 0 to 3 substituents as valency allows independently selected from:
    0 to 3 F atoms,
    0 to 1 —CN, and
    0 to 1 —OR$^O$;
  R$^6$ is a 5- to 6-membered heteroaryl, wherein said heteroaryl may be substituted with 0 to 2 substituents as valency allows independently selected from:
  0 to 2 halogens,
  0 to 1 substituent selected from —OR$^O$ and —N(R$^N$)$_2$, and
  0 to 2 —C$_{1-3}$alkyl, wherein the alkyl may be substituted with 0 to 3 substituents as valency allows independently selected from:
    0 to 3 F atoms, and
    0 to 1 —OR$^O$;
  each R$^O$ is independently H, or —C$_{1-3}$alkyl, wherein C$_{1-3}$alkyl may be substituted with 0 to 3 F atoms;
  each R$^N$ is independently H, or —C$_{1-3}$alkyl;
  Z$^1$ is CH or N;
  Z$^3$ is —CR$^Z$ or N; and
  each R$^Z$ is independently H, F, C, or —CH$_3$,
  wherein the disease or disorder is selected from the group consisting of T2DM, pre-diabetes, malnutrition-related diabetes, gestational diabetes, hyperglycemia, insulin resistance, hepatic insulin resistance, impaired glucose tolerance, diabetic neuropathy, diabetic nephropathy, diabetic retinopathy, adipocyte dysfunction, obesity, eating disorders, weight gain from use of other agents, excessive sugar craving, dyslipidemia, hyperinsulinemia, NAFLD, NASH, fibrosis, NASH with fibrosis, cirrhosis, hepatocellular carcinoma, and a cardiovascular disease.

12. The method of claim 11, wherein:
R$^3$ is —CH$_3$;
q is 0 or 1; and
R$^4$ is —CH$_2$CH$_2$OCH$_3$, C$_{1-3}$alkylene-R$^5$, or C$_{1-3}$alkylene-R$^6$.

13. The method of claim 11, wherein R$^4$ is —CH$_2$—R$^5$; and R$^5$ is a 4- to 5-membered heterocycloalkyl, wherein said heterocycloalkyl may be substituted with 0 to 2 substituents as valency allows independently selected from:

0 to 2 F atoms, and
0 to 1 substituent selected from —OCH$_3$ and —CH$_2$OCH$_3$.

14. The method of claim 11, wherein R$^4$ is —CH$_2$—R$^5$; and the heterocycloalkyl of R$^5$ is a monovalent radical of

[chemical structures]

wherein the heterocycloalkyl may be substituted with 0 to 2 substituents as valency allows independently selected from:
0 to 1 oxo (O=),
0 to 1 —CN,
0 to 2 F atoms, and
0 to 2 substituents independently selected from —C$_{1-3}$alkyl and —OC$_{1-3}$alkyl, wherein the alkyl of C$_{1-3}$alkyl and OC$_{1-3}$alkyl may be independently substituted with 0 to 3 substituents as valency allows independently selected from:
  0 to 3 F atoms,
  0 to 1 —CN, and
  0 to 1 —OR$^O$.

15. The method of claim 11, wherein R$^4$ is —CH$_2$—R$^5$; and the heterocycloalkyl of R$^5$ is a monovalent radical of

[chemical structures]

wherein the heterocycloalkyl may be substituted with 0 to 2 substituents as valency allows each independently selected from:
0 to 1 —CN,
0 to 2 F atoms, and
0 to 2 substituents independently selected from —C$_{1-3}$alkyl and —OC$_{1-3}$alkyl, wherein the alkyl of C$_{1-3}$alkyl and OC$_{1-3}$alkyl may be independently substituted with 0 to 3 substituents as valency allows each independently selected from:
  0 to 3 F atoms,
  0 to 1 —CN, and
  0 to 1 —OR$^O$.

16. The method of claim 11, wherein R$^4$ is —CH$_2$—R$^5$; and the heterocycloalkyl of R$^5$ is a monovalent radical of

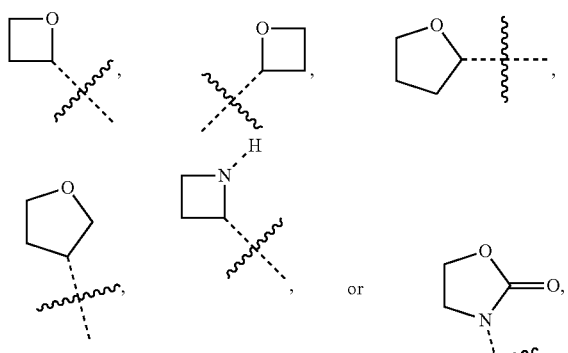

and wherein the heterocycloalkyl may be substituted with 0 to 1 substituent as valency allows selected from:
- —CN,
- F atom, and
- 0 to 1 substituent independently selected from —C$_{1-3}$alkyl and —OC$_{1-3}$alkyl, wherein the alkyl of C$_{1-3}$alkyl and OC$_{1-3}$alkyl may be substituted with 0 to 3 substituents as valency allows with:
  - 0 to 3 F atoms,
  - 0 to 1 —CN, or
  - 0 to 1 —OR$^O$.

17. The method of claim 11, wherein R$^4$ is —CH$_2$—R$^5$; and the heterocycloalkyl of R$^5$ is a monovalent radical of

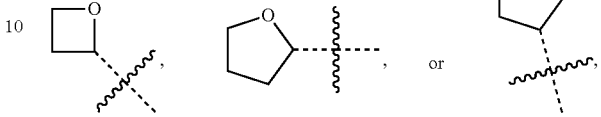

and wherein the heterocycloalkyl may be substituted as valency allows with 0 to 1 methyl, wherein said methyl may be substituted with 0 to 3 F atoms.

18. The method of claim 11, wherein the disease or disorder is selected from the group consisting of T2DM, obesity, NAFLD, NASH, and NASH with fibrosis, cirrhosis.

19. The method of claim 16, wherein the disease or disorder is selected from the group consisting of T2DM, obesity, NAFLD, NASH, and NASH with fibrosis, cirrhosis.

20. The method of claim 17, wherein the disease or disorder is selected from the group consisting of T2DM, obesity, NAFLD, NASH, and NASH with fibrosis, cirrhosis.

* * * * *